US012275964B2

(12) United States Patent
Doudna et al.

(10) Patent No.: US 12,275,964 B2
(45) Date of Patent: Apr. 15, 2025

(54) VARIANT TYPE V CRISPR/CAS EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Benjamin L. Oakes, El Cerrito, CA (US); Natalia Orlova, Carrboro, NC (US); Junjie Liu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 224 days.

(21) Appl. No.: 17/266,270

(22) PCT Filed: Aug. 21, 2019

(86) PCT No.: PCT/US2019/047488

§ 371 (c)(1),
(2) Date: Feb. 5, 2021

(87) PCT Pub. No.: WO2020/041456

PCT Pub. Date: Feb. 27, 2020

(65) Prior Publication Data

US 2021/0309981 A1 Oct. 7, 2021

Related U.S. Application Data

(60) Provisional application No. 62/721,528, filed on Aug. 22, 2018.

(51) Int. Cl.

| | |
|---|---|
| ***C12N 9/22*** | (2006.01) |
| ***A61K 9/127*** | (2006.01) |
| ***A61K 31/7088*** | (2006.01) |
| ***A61K 38/46*** | (2006.01) |
| ***C12N 15/11*** | (2006.01) |
| ***C12N 15/88*** | (2006.01) |
| ***C12N 15/90*** | (2006.01) |
| ***C12Q 1/6841*** | (2018.01) |
| ***C12Q 1/70*** | (2006.01) |

(52) U.S. Cl.

CPC ................ *C12N 9/22* (2013.01); *A61K 9/127* (2013.01); *A61K 31/7088* (2013.01); *A61K 38/465* (2013.01); *C12N 15/11* (2013.01); *C12N 15/88* (2013.01); *C12N 15/90* (2013.01); *C12N 15/907* (2013.01); *C12Q 1/6841* (2013.01); *C12Q 1/701* (2013.01); *C07K 2319/09* (2013.01); *C12N 2310/20* (2017.05); *C12N 2800/80* (2013.01)

(58) Field of Classification Search

CPC .............................. C12N 9/22; C12N 2310/20
See application file for complete search history.

(56) References Cited

U.S. PATENT DOCUMENTS

| | | | | |
|---|---|---|---|---|
| 10,570,415 B2 * | 2/2020 | Doudna | ................. | C12N 15/52 |
| 11,795,472 B2 * | 10/2023 | Doudna | ................. | C12N 15/62 |
| 2012/0252876 A1 | 10/2012 | Tenenbaum et al. | | |
| 2018/0148735 A1 | 5/2018 | Benson | | |
| 2018/0201921 A1 | 7/2018 | Excision | | |

FOREIGN PATENT DOCUMENTS

| | | | |
|---|---|---|---|
| WO | WO 2015/089486 | 6/2015 | |
| WO | WO 2016/183402 | 11/2016 | |
| WO | WO 2017/223538 | 12/2017 | |
| WO | WO 2018/064371 | 4/2018 | |
| WO | WO-2018064371 A1 * | 4/2018 | ............. C07K 19/00 |
| WO | WO 2018/107129 | 6/2018 | |
| WO | WO 2018/152418 | 8/2018 | |
| WO | WO 2020/247882 | 12/2020 | |
| WO | WO 2020/247883 | 12/2020 | |

OTHER PUBLICATIONS

Burstein et al., Feb. 9, 2017, “New CRISPR-Cas systems from uncultivated microbes” Nature, vol. 542, p. 237-243 and Extended Data (Year: 2017).*

Swarts et al., Apr. 20, 2017, “Structural Basis for Guide RNA Processing and Seed-Dependent DNA Targeting by CRISPR-Cas12a” Molecular Cell, 66, p. 221-233, Extended Data, and PDB Deposit documenting associated UniProt ID (Year: 2017).*

Yamano et al., May 5, 2016, “Crystal Structure of Cpf1 in Complex with Guide RNA and Target DNA” Cell, 165, p. 949-962, and PDB Deposit documenting associated UniProt ID (Year: 2016).*

Kim et al., Apr. 4, 2017, 2017, “Efficient Transcriptional Gene Repression by Type V-A CRISPR-Cpf1 from Eubacterium eligens”, ACS Synthetic Biology, 6, p. 1273-1282 (Year: 2017).*

Hajizadeh Dastjerdi, et al.; “The Expanding Class 2 CRISPR Toolbox: Diversity, Applicability, and Targeting Drawbacks”; BioDrugs; vol. 33, No. 4, pp. 503-513 (Aug. 5, 2019).

Liu, et al.; “CasX enzymes comprise a distinct family of RNA-guided genome editors”; Nature; vol. 566, pp. 218-223 (Feb. 14, 2019).

Yang, et al.; “CasX: a new and small CRISPR gene-editing protein”; Cell Research; vol. 29, pp. 345-346 (Apr. 16, 2019).

* cited by examiner

*Primary Examiner* — Jennifer Dunston
*Assistant Examiner* — Jenna L Persons
(74) *Attorney, Agent, or Firm* — Bozicevic, Field & Francis LLP

(57) ABSTRACT

The present disclosure provides variant type V CRISPR/Cas effector polypeptides, fusion polypeptides comprising the variant type V CRISPR/Cas effector polypeptides, and nucleic acids comprising nucleotide sequences encoding the variant polypeptides and fusion polypeptides. The present disclosure provides methods of binding, or binding and nicking, a target nucleic acid, using a variant type V CRISPR/Cas effector polypeptide of the present disclosure. The present disclosure provides methods of detecting a single-stranded DNA, using a variant type V CRISPR/Cas effector polypeptide of the present disclosure.

23 Claims, 55 Drawing Sheets

Specification includes a Sequence Listing.

Ternary complex with R-loop at State I 863 868 863

... Gln Ile Thr Tyr Tyr Asn Arg Tyr Lys Arg Gln ...

FIG. 12G

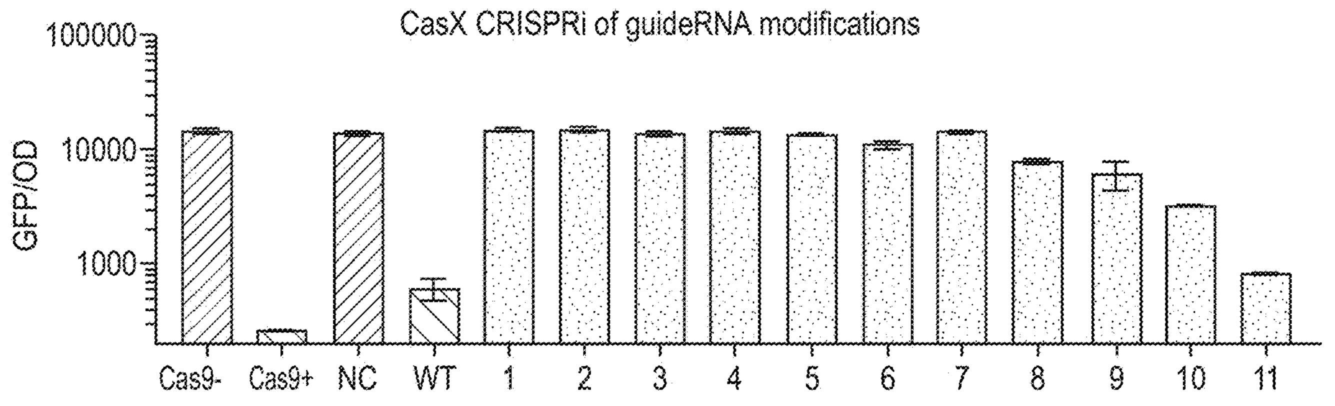

5'-GGCGCGTTTATTCCATTACTTTGGAGCCAGTCCCAGCGACTATGTCGTATGGACGAAGCGCTTATTTATCGGAGAGAAACCGATAAGTAAAACGCATCAAAGnnnnnnnnnnnnnnnnnnnn-3'

| tracr | loop | crRNA | spacer |
|---|---|---|---|

triplex triplex scaffold stem stretched stem triplex

1- GGCGCGTTTATTCCATTACTTTGGAGCCAGTCCCA--------------TGGACGAAGCGCTTATTTATCGGAGAGAAACCGATAAGTAAAACGCATCAAAG
2- GGCGCGTTTATTCCATTACTTTGGAGCCAGTCCCAGC---TAT---GTATGGACGAAGCGCTTATTTATCGGAGAGAAACCGATAAGTAAAACGCATCAAAG
3- GGCGCGTTTATTCCATTACTTTGGAGCCAGTCCCAGCGA-TAT-TCGTATGGACGAAGCGCTTATTTATCGGAGAGAAACCGATAAGTAAAACGCATCAAAG
4- GGCGCGTTTATTCCATTACTTTGGAGCCAGTCCAUGCGACTATGTCGTATGGACGAAGCGCTTATTTATCGGAGAGAAACCGATAAGTAAAACGCATCAAAG
5- GGCGCGTTTATTCCATTACTTTGGAGCCAGTCCCAGCGACTATGTCGTATGGACGAAGCGCTTATTTATCGGAGAGAAACCGATAAGTAAAACGCATCGGGG
6- GGCGCGTTTATTCCATTACTTTGGAGCCAGTCCCAGCGACTATGTCGTATGGACGAAGCGCTTATTTATCGGAGAGAAACCGATAAGTAAAACGCATCUUUG
7- GGCGCGTTTATTCCATTACTTTGGAGCCAGTCCCAGCGACTATGTCGTATGGACGAAGCGCTTATTTATCGGAGAGAAACCGATAAGTAAAACGCATCCCCG
8- GGCGCGCCCATTCCATTACCCCGGAGCCAGTCCCAGCGACTATGTCGTATGGACGAAGCGCTTATTTATCGGAGAGAAACCGATAAGTAAAACGCATCGGGG
9- GGCGCGTTTATTCCATTACTTTGGAGCCAGTCCCAGCGACTATGTCGTATGGACGAAGCGCTTAT-------AGAGAAA------AAGTAAAACGCATCAAAG
10- GGCGCGTTTATTCCATTACTTTGGAGCCAGTCCCAGCGACTATGTCGTATGGACGAAGCGCTTATTT-----AGAGAAA------AAGTAAAACGCATCAAAG
11- GGCGCGTTTATTCCATTACTTTGGAGCCAGTCCCAGCGACTATGTCGTATGGACGAAGCGCTTATTTAT---AGAGAAA---ATAAGTAAAACGCATCAAAG

State I
distance 43.8 Å

State II
distance 10.9 Å

FIG. 16

>CasX1
MEKRINKIRKKLSADNATKPVSRSGPMKTLLVRVMTDDLKKRLEKRRKKPEVMPQVISN
NAANNLRMLLDDYTKMKEAILQVYWQEFKDDHVGLMCKFAQPASKKIDQNKLKPEMDEK
GNLTTAGFACSQCGQPLFVYKLEQVSEKGKAYTNYFGRCNVAEHEKLILLAQLKPEKDS
DEAVTYSLGKFGQRALDFYSIHVTKESTHPVKPLAQIAGNRYASGPVGKALSDACMGTI
ASFLSKYQDIIIEHQKVVKGNQKRLESLRELAGKENLEYPSVTLPPQPHTKEGVDAYNE
VIARVRMWVNLNLWQKLKLSRDDAKPLLRLKGFPSFPVVERRENEVDWWNTINEVKKLI
DAKRDMGRVFWSGVTAEKRNTILEGYNYLPNENDHKKREGSLENPKKPAKRQFGDLLLY
LEKKYAGDWGKVFDEAWERIDKKIAGLTSHIEREEARNAEDAQSKAVLTDWLRAKASFV
LERLKEMDEKEFYACEIQLQKWYGDLRGNPFAVEAENRVVDISGFSIGSDGHSIQYRNL
LAWKYLENGKREFYLLMNYGKKGRIRFTDGTDIKKSGKWQGLLYGGGKAKVIDLTFDPD
DEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIG
EGYKEKQRAIQAAKEVEQRRAGGYSRKFASKSRNLADDMVRNSARDLFYHAVTHDAVLV
FENLSRGFGRQGKRTFMTERQYTKMEDWLTAKLAYEGLTSKTYLSKTLAQYTSKTCSNC
GFTITTADYDGMLVRLKKTSDGWATTLNNKELKAEGQITYYNRYKRQTVEKELSAELDR
LSEESGNNDISKWTKGRRDEALFLLKKRFSHRPVQEQFVCLDCGHEVHADEQAALNIAR
SWLFLNSNSTEFKSYKSGKQPFVGAWQAFYKRRLKEVWKPNA (SEQ ID NO: 1)

FIG. 17

>CasX2
MQEIKRINKIRRRLVKDSNTKKAGKTGPMKTLLVRVMTPDLRERLENLRKKPENIPQPI
SNTSRANLNKLLTDYTEMKKAILHVYWEEFQKDPVGLMSRVAQPAPKNIDQRKLIPVKD
GNERLTSSGFACSQCCQPLYVYKLEQVNDKGKPHTNYFGRCNVSEHERLILLSPHKPEA
NDELVTYSLGKFGQRALDFYSIHVTRESNHPVKPLEQIGGNSCASGPVGKALSDACMGA
VASFLTKYQDIILEHQKVIKKNEKRLANLKDIASANGLAFPKITLPPQPHTKEGIEAYN
NVVAQIVIWVNLNLWQKLKIGRDEAKPLQRLKGFPSFPLVERQANEVDWWDMVCNVKKL
INEKKEDGKVFWQNLAGYKRQEALLPYLSSEEDRKKGKKFARYQFGDLLLHLEKKHGED
WGKVYDEAWERIDKKVEGLSKHIKLEEERRSEDAQSKAALTDWLRAKASFVIEGLKEAD
KDEFCRCELKLQKWYGDLRGKPFAIEAENSILDISGFSKQYNCAFIWQKDGVKKLNLYL
IINYFKGGKLRFKKIKPEAFEANRFYTVINKKSGEIVPMEVNFNFDDPNLIILPLAFGK
RQGREFIWNDLLSLETGSLKLANGRVIEKTLYNRRTRQDEPALFVALTFERREVLDSSN
IKPMNLIGIDRGENIPAVIALTDPEGCPLSRFKDSLGNPTHILRIGESYKEKQRTIQAA
KEVEQRRAGGYSRKYASKAKNLADDMVRNTARDLLYYAVTQDAMLIFENLSRGFGRQGK
RTFMAERQYTRMEDWLTAKLAYEGLPSKTYLSKTLAQYTSKTCSNCGFTITSADYDRVL
EKLKKTATGWMTTINGKELKVEGQITYYNRYKRQNVVKDLSVELDRLSEESVNNDISSW
TKGRSGEALSLLKKRFSHRPVQEKFVCLNCGFETHADEQAALNIARSWLFLRSQEYKKY
QTNKTTGNTDKRAFVETWQSFYRKKLKEVWKPAV (SEQ ID NO: 2)

SEQUENCE LISTING

```
<160> NUMBER OF SEQ ID NOS: 114

<210> SEQ ID NO 1
<211> LENGTH: 986
<212> TYPE: PRT
<213> ORGANISM: Unknown
<220> FEATURE:
<223> OTHER INFORMATION: Synthetic sequence

<400> SEQUENCE: 1

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60
```

-continued

```
Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
```

-continued

```
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Arg Gln Gly Lys Arg Thr Phe Met
    770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
        835                 840                 845

Trp Ala Thr Thr Leu Asn Asn Lys Glu Leu Lys Ala Glu Gly Gln Ile
    850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
            900                 905                 910
```

Arg Phe Ser His Arg Pro Val Gln Glu Gln Phe Val Cys Leu Asp Cys
915 920 925

Gly His Glu Val His Ala Asp Glu Gln Ala Ala Leu Asn Ile Ala Arg
930 935 940

Ser Trp Leu Phe Leu Asn Ser Asn Ser Thr Glu Phe Lys Ser Tyr Lys
945 950 955 960

Ser Gly Lys Gln Pro Phe Val Gly Ala Trp Gln Ala Phe Tyr Lys Arg
965 970 975

Arg Leu Lys Glu Val Trp Lys Pro Asn Ala
980 985

<210> SEQ ID NO 2
<211> LENGTH: 978
<212> TYPE: PRT
<213> ORGANISM: Unknown
<220> FEATURE:
<223> OTHER INFORMATION: Synthetic sequence

<400> SEQUENCE: 2

Met Gln Glu Ile Lys Arg Ile Asn Lys Ile Arg Arg Arg Leu Val Lys
1 5 10 15

Asp Ser Asn Thr Lys Lys Ala Gly Lys Thr Gly Pro Met Lys Thr Leu
20 25 30

Leu Val Arg Val Met Thr Pro Asp Leu Arg Glu Arg Leu Glu Asn Leu
35 40 45

Arg Lys Lys Pro Glu Asn Ile Pro Gln Pro Ile Ser Asn Thr Ser Arg
50 55 60

Ala Asn Leu Asn Lys Leu Leu Thr Asp Tyr Thr Glu Met Lys Lys Ala
65 70 75 80

Ile Leu His Val Tyr Trp Glu Glu Phe Gln Lys Asp Pro Val Gly Leu
85 90 95

Met Ser Arg Val Ala Gln Pro Ala Pro Lys Asn Ile Asp Gln Arg Lys
100 105 110

Leu Ile Pro Val Lys Asp Gly Asn Glu Arg Leu Thr Ser Ser Gly Phe
115 120 125

Ala Cys Ser Gln Cys Cys Gln Pro Leu Tyr Val Tyr Lys Leu Glu Gln
130 135 140

Val Asn Asp Lys Gly Lys Pro His Thr Asn Tyr Phe Gly Arg Cys Asn
145 150 155 160

Val Ser Glu His Glu Arg Leu Ile Leu Leu Ser Pro His Lys Pro Glu
165 170 175

Ala Asn Asp Glu Leu Val Thr Tyr Ser Leu Gly Lys Phe Gly Gln Arg
180 185 190

Ala Leu Asp Phe Tyr Ser Ile His Val Thr Arg Glu Ser Asn His Pro
195 200 205

Val Lys Pro Leu Glu Gln Ile Gly Gly Asn Ser Cys Ala Ser Gly Pro
210 215 220

Val Gly Lys Ala Leu Ser Asp Ala Cys Met Gly Ala Val Ala Ser Phe
225 230 235 240

Leu Thr Lys Tyr Gln Asp Ile Ile Leu Glu His Gln Lys Val Ile Lys
245 250 255

Lys Asn Glu Lys Arg Leu Ala Asn Leu Lys Asp Ile Ala Ser Ala Asn
260 265 270

Gly Leu Ala Phe Pro Lys Ile Thr Leu Pro Pro Gln Pro His Thr Lys
275 280 285

-continued

```
Glu Gly Ile Glu Ala Tyr Asn Asn Val Val Ala Gln Ile Val Ile Trp
    290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
                325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
        355                 360                 365

Leu Ala Gly Tyr Lys Arg Gln Glu Ala Leu Leu Pro Tyr Leu Ser Ser
    370                 375                 380

Glu Glu Asp Arg Lys Lys Gly Lys Lys Phe Ala Arg Tyr Gln Phe Gly
385                 390                 395                 400

Asp Leu Leu Leu His Leu Glu Lys Lys His Gly Glu Asp Trp Gly Lys
                405                 410                 415

Val Tyr Asp Glu Ala Trp Glu Arg Ile Asp Lys Lys Val Glu Gly Leu
            420                 425                 430

Ser Lys His Ile Lys Leu Glu Glu Glu Arg Arg Ser Glu Asp Ala Gln
        435                 440                 445

Ser Lys Ala Ala Leu Thr Asp Trp Leu Arg Ala Lys Ala Ser Phe Val
    450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
                485                 490                 495

Ile Glu Ala Glu Asn Ser Ile Leu Asp Ile Ser Gly Phe Ser Lys Gln
            500                 505                 510

Tyr Asn Cys Ala Phe Ile Trp Gln Lys Asp Gly Val Lys Lys Leu Asn
        515                 520                 525

Leu Tyr Leu Ile Ile Asn Tyr Phe Lys Gly Gly Lys Leu Arg Phe Lys
    530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
                565                 570                 575

Asp Asp Pro Asn Leu Ile Ile Leu Pro Leu Ala Phe Gly Lys Arg Gln
            580                 585                 590

Gly Arg Glu Phe Ile Trp Asn Asp Leu Leu Ser Leu Glu Thr Gly Ser
        595                 600                 605

Leu Lys Leu Ala Asn Gly Arg Val Ile Glu Lys Thr Leu Tyr Asn Arg
    610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
                645                 650                 655

Gly Ile Asp Arg Gly Glu Asn Ile Pro Ala Val Ile Ala Leu Thr Asp
            660                 665                 670

Pro Glu Gly Cys Pro Leu Ser Arg Phe Lys Asp Ser Leu Gly Asn Pro
        675                 680                 685

Thr His Ile Leu Arg Ile Gly Glu Ser Tyr Lys Glu Lys Gln Arg Thr
    690                 695                 700
```

-continued

```
Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735

Asn Thr Ala Arg Asp Leu Leu Tyr Tyr Ala Val Thr Gln Asp Ala Met
            740                 745                 750

Leu Ile Phe Glu Asn Leu Ser Arg Gly Phe Gly Arg Gln Gly Lys Arg
        755                 760                 765

Thr Phe Met Ala Glu Arg Gln Tyr Thr Arg Met Glu Asp Trp Leu Thr
    770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Ser Ala Asp Tyr Asp Arg Val Leu Glu Lys Leu Lys Lys Thr
            820                 825                 830

Ala Thr Gly Trp Met Thr Thr Ile Asn Gly Lys Glu Leu Lys Val Glu
        835                 840                 845

Gly Gln Ile Thr Tyr Tyr Asn Arg Tyr Lys Arg Gln Asn Val Val Lys
    850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
                885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
        915                 920                 925

Ile Ala Arg Ser Trp Leu Phe Leu Arg Ser Gln Glu Tyr Lys Lys Tyr
    930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
                965                 970                 975

Ala Val


<210> SEQ ID NO 3
<211> LENGTH: 106
<212> TYPE: PRT
<213> ORGANISM: Artificial Sequence
<220> FEATURE:
<223> OTHER INFORMATION: Synthetic sequence

<400> SEQUENCE: 3

Cys Ser Asn Cys Gly Phe Thr Ile Thr Thr Ala Asp Tyr Asp Gly Met
1               5                   10                  15

Leu Val Arg Leu Lys Lys Thr Ser Asp Gly Trp Ala Thr Thr Leu Asn
            20                  25                  30

Asn Lys Glu Leu Lys Ala Glu Gly Gln Ile Thr Tyr Tyr Asn Arg Tyr
        35                  40                  45

Lys Arg Gln Thr Val Glu Lys Glu Leu Ser Ala Glu Leu Asp Arg Leu
    50                  55                  60

Ser Glu Glu Ser Gly Asn Asn Asp Ile Ser Lys Trp Thr Lys Gly Arg
65                  70                  75                  80

Arg Asp Glu Ala Leu Phe Leu Leu Lys Lys Arg Phe Ser His Arg Pro
```

```
                85                  90                  95

Val Gln Glu Gln Phe Val Cys Leu Asp Cys
            100                 105


<210> SEQ ID NO 4
<211> LENGTH: 880
<212> TYPE: PRT
<213> ORGANISM: Artificial Sequence
<220> FEATURE:
<223> OTHER INFORMATION: Synthetic sequence

<400> SEQUENCE: 4

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
```

```
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
            405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765
```

```
Glu Asn Leu Ser Arg Gly Phe Gly Arg Gln Gly Lys Arg Thr Phe Met
    770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Gly His Glu Val His Ala Asp Glu Gln Ala
            820                 825                 830

Ala Leu Asn Ile Ala Arg Ser Trp Leu Phe Leu Asn Ser Asn Ser Thr
        835                 840                 845

Glu Phe Lys Ser Tyr Lys Ser Gly Lys Gln Pro Phe Val Gly Ala Trp
    850                 855                 860

Gln Ala Phe Tyr Lys Arg Arg Leu Lys Glu Val Trp Lys Pro Asn Ala
865                 870                 875                 880


<210> SEQ ID NO 5
<211> LENGTH: 975
<212> TYPE: PRT
<213> ORGANISM: Artificial Sequence
<220> FEATURE:
<223> OTHER INFORMATION: Synthetic sequence

<400> SEQUENCE: 5

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255
```

```
Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670
```

```
Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Arg Gln Gly Lys Arg Thr Phe Met
    770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
        835                 840                 845

Trp Ala Thr Thr Leu Asn Asn Lys Glu Leu Lys Ala Glu Gly Thr Val
    850                 855                 860

Glu Lys Glu Leu Ser Ala Glu Leu Asp Arg Leu Ser Glu Glu Ser Gly
865                 870                 875                 880

Asn Asn Asp Ile Ser Lys Trp Thr Lys Gly Arg Arg Asp Glu Ala Leu
                885                 890                 895

Phe Leu Leu Lys Lys Arg Phe Ser His Arg Pro Val Gln Glu Gln Phe
            900                 905                 910

Val Cys Leu Asp Cys Gly His Glu Val His Ala Asp Glu Gln Ala Ala
        915                 920                 925

Leu Asn Ile Ala Arg Ser Trp Leu Phe Leu Asn Ser Asn Ser Thr Glu
    930                 935                 940

Phe Lys Ser Tyr Lys Ser Gly Lys Gln Pro Phe Val Gly Ala Trp Gln
945                 950                 955                 960

Ala Phe Tyr Lys Arg Arg Leu Lys Glu Val Trp Lys Pro Asn Ala
                965                 970                 975
```

<210> SEQ ID NO 6
<211> LENGTH: 11
<212> TYPE: PRT
<213> ORGANISM: Artificial Sequence
<220> FEATURE:
<223> OTHER INFORMATION: Synthetic sequence

<400> SEQUENCE: 6

```
Gln Ile Thr Tyr Tyr Asn Arg Tyr Lys Arg Gln
1               5                   10
```

<210> SEQ ID NO 7
<211> LENGTH: 91
<212> TYPE: PRT
<213> ORGANISM: Artificial Sequence
<220> FEATURE:
<223> OTHER INFORMATION: Synthetic sequence

<400> SEQUENCE: 7

-continued

```
Pro Ala Ser Lys Lys Ile Asp Gln Asn Lys Leu Lys Pro Glu Met Asp
1               5                   10                  15

Glu Lys Gly Asn Leu Thr Thr Ala Gly Phe Ala Cys Ser Gln Cys Gly
            20                  25                  30

Gln Pro Leu Phe Val Tyr Lys Leu Glu Gln Val Ser Glu Lys Gly Lys
        35                  40                  45

Ala Tyr Thr Asn Tyr Phe Gly Arg Cys Asn Val Ala Glu His Glu Lys
    50                  55                  60

Leu Ile Leu Leu Ala Gln Leu Lys Pro Glu Lys Asp Ser Asp Glu Ala
65                  70                  75                  80

Val Thr Tyr Ser Leu Gly Lys Phe Gly Gln Arg
                85                  90


<210> SEQ ID NO 8
<211> LENGTH: 895
<212> TYPE: PRT
<213> ORGANISM: Artificial Sequence
<220> FEATURE:
<223> OTHER INFORMATION: Synthetic sequence

<400> SEQUENCE: 8

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Ala Leu Asp Phe Tyr Ser Ile His Val Thr Lys Glu
            100                 105                 110

Ser Thr His Pro Val Lys Pro Leu Ala Gln Ile Ala Gly Asn Arg Tyr
        115                 120                 125

Ala Ser Gly Pro Val Gly Lys Ala Leu Ser Asp Ala Cys Met Gly Thr
    130                 135                 140

Ile Ala Ser Phe Leu Ser Lys Tyr Gln Asp Ile Ile Ile Glu His Gln
145                 150                 155                 160

Lys Val Val Lys Gly Asn Gln Lys Arg Leu Glu Ser Leu Arg Glu Leu
                165                 170                 175

Ala Gly Lys Glu Asn Leu Glu Tyr Pro Ser Val Thr Leu Pro Pro Gln
            180                 185                 190

Pro His Thr Lys Glu Gly Val Asp Ala Tyr Asn Glu Val Ile Ala Arg
        195                 200                 205

Val Arg Met Trp Val Asn Leu Asn Leu Trp Gln Lys Leu Lys Leu Ser
    210                 215                 220

Arg Asp Asp Ala Lys Pro Leu Leu Arg Leu Lys Gly Phe Pro Ser Phe
225                 230                 235                 240

Pro Val Val Glu Arg Arg Glu Asn Glu Val Asp Trp Trp Asn Thr Ile
                245                 250                 255

Asn Glu Val Lys Lys Leu Ile Asp Ala Lys Arg Asp Met Gly Arg Val
            260                 265                 270
```

```
Phe Trp Ser Gly Val Thr Ala Glu Lys Arg Asn Thr Ile Leu Glu Gly
        275                 280                 285

Tyr Asn Tyr Leu Pro Asn Glu Asn Asp His Lys Lys Arg Glu Gly Ser
    290                 295                 300

Leu Glu Asn Pro Lys Lys Pro Ala Lys Arg Gln Phe Gly Asp Leu Leu
305                 310                 315                 320

Leu Tyr Leu Glu Lys Lys Tyr Ala Gly Asp Trp Gly Lys Val Phe Asp
                325                 330                 335

Glu Ala Trp Glu Arg Ile Asp Lys Lys Ile Ala Gly Leu Thr Ser His
            340                 345                 350

Ile Glu Arg Glu Glu Ala Arg Asn Ala Glu Asp Ala Gln Ser Lys Ala
        355                 360                 365

Val Leu Thr Asp Trp Leu Arg Ala Lys Ala Ser Phe Val Leu Glu Arg
    370                 375                 380

Leu Lys Glu Met Asp Glu Lys Glu Phe Tyr Ala Cys Glu Ile Gln Leu
385                 390                 395                 400

Gln Lys Trp Tyr Gly Asp Leu Arg Gly Asn Pro Phe Ala Val Glu Ala
                405                 410                 415

Glu Asn Arg Val Val Asp Ile Ser Gly Phe Ser Ile Gly Ser Asp Gly
            420                 425                 430

His Ser Ile Gln Tyr Arg Asn Leu Leu Ala Trp Lys Tyr Leu Glu Asn
        435                 440                 445

Gly Lys Arg Glu Phe Tyr Leu Leu Met Asn Tyr Gly Lys Lys Gly Arg
    450                 455                 460

Ile Arg Phe Thr Asp Gly Thr Asp Ile Lys Lys Ser Gly Lys Trp Gln
465                 470                 475                 480

Gly Leu Leu Tyr Gly Gly Gly Lys Ala Lys Val Ile Asp Leu Thr Phe
                485                 490                 495

Asp Pro Asp Asp Glu Gln Leu Ile Ile Leu Pro Leu Ala Phe Gly Thr
            500                 505                 510

Arg Gln Gly Arg Glu Phe Ile Trp Asn Asp Leu Leu Ser Leu Glu Thr
        515                 520                 525

Gly Leu Ile Lys Leu Ala Asn Gly Arg Val Ile Glu Lys Thr Ile Tyr
    530                 535                 540

Asn Lys Lys Ile Gly Arg Asp Glu Pro Ala Leu Phe Val Ala Leu Thr
545                 550                 555                 560

Phe Glu Arg Arg Glu Val Val Asp Pro Ser Asn Ile Lys Pro Val Asn
                565                 570                 575

Leu Ile Gly Val Asp Arg Gly Glu Asn Ile Pro Ala Val Ile Ala Leu
            580                 585                 590

Thr Asp Pro Glu Gly Cys Pro Leu Pro Glu Phe Lys Asp Ser Ser Gly
        595                 600                 605

Gly Pro Thr Asp Ile Leu Arg Ile Gly Glu Gly Tyr Lys Glu Lys Gln
    610                 615                 620

Arg Ala Ile Gln Ala Ala Lys Glu Val Glu Gln Arg Arg Ala Gly Gly
625                 630                 635                 640

Tyr Ser Arg Lys Phe Ala Ser Lys Ser Arg Asn Leu Ala Asp Asp Met
                645                 650                 655

Val Arg Asn Ser Ala Arg Asp Leu Phe Tyr His Ala Val Thr His Asp
            660                 665                 670

Ala Val Leu Val Phe Glu Asn Leu Ser Arg Gly Phe Gly Arg Gln Gly
        675                 680                 685
```

```
Lys Arg Thr Phe Met Thr Glu Arg Gln Tyr Thr Lys Met Glu Asp Trp
    690                 695                 700

Leu Thr Ala Lys Leu Ala Tyr Glu Gly Leu Thr Ser Lys Thr Tyr Leu
705                 710                 715                 720

Ser Lys Thr Leu Ala Gln Tyr Thr Ser Lys Thr Cys Ser Asn Cys Gly
                725                 730                 735

Phe Thr Ile Thr Thr Ala Asp Tyr Asp Gly Met Leu Val Arg Leu Lys
            740                 745                 750

Lys Thr Ser Asp Gly Trp Ala Thr Thr Leu Asn Asn Lys Glu Leu Lys
        755                 760                 765

Ala Glu Gly Gln Ile Thr Tyr Tyr Asn Arg Tyr Lys Arg Gln Thr Val
    770                 775                 780

Glu Lys Glu Leu Ser Ala Glu Leu Asp Arg Leu Ser Glu Glu Ser Gly
785                 790                 795                 800

Asn Asn Asp Ile Ser Lys Trp Thr Lys Gly Arg Arg Asp Glu Ala Leu
                805                 810                 815

Phe Leu Leu Lys Lys Arg Phe Ser His Arg Pro Val Gln Glu Gln Phe
            820                 825                 830

Val Cys Leu Asp Cys Gly His Glu Val His Ala Asp Glu Gln Ala Ala
        835                 840                 845

Leu Asn Ile Ala Arg Ser Trp Leu Phe Leu Asn Ser Asn Ser Thr Glu
    850                 855                 860

Phe Lys Ser Tyr Lys Ser Gly Lys Gln Pro Phe Val Gly Ala Trp Gln
865                 870                 875                 880

Ala Phe Tyr Lys Arg Arg Leu Lys Glu Val Trp Lys Pro Asn Ala
                885                 890                 895


<210> SEQ ID NO 9
<211> LENGTH: 38
<212> TYPE: RNA
<213> ORGANISM: Artificial Sequence
<220> FEATURE:
<223> OTHER INFORMATION: Synthetic sequence

<400> SEQUENCE: 9

gcgcuuauuu aucggagaga aaccgauaag uaaaacgc                            38


<210> SEQ ID NO 10
<211> LENGTH: 84
<212> TYPE: PRT
<213> ORGANISM: Artificial Sequence
<220> FEATURE:
<223> OTHER INFORMATION: Synthetic sequence

<400> SEQUENCE: 10

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala
```

<210> SEQ ID NO 11
<211> LENGTH: 57
<212> TYPE: PRT
<213> ORGANISM: Artificial Sequence
<220> FEATURE:
<223> OTHER INFORMATION: Synthetic sequence

<400> SEQUENCE: 11

```
Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55
```

<210> SEQ ID NO 12
<211> LENGTH: 37
<212> TYPE: RNA
<213> ORGANISM: Artificial Sequence
<220> FEATURE:
<223> OTHER INFORMATION: Synthetic sequence

<400> SEQUENCE: 12
auuugaaggu aucuccgaua aguaaaacgc aucaaag 37

<210> SEQ ID NO 13
<211> LENGTH: 25
<212> TYPE: RNA
<213> ORGANISM: Artificial Sequence
<220> FEATURE:
<223> OTHER INFORMATION: Synthetic sequence

<400> SEQUENCE: 13
guuuacacac ucccucucau gaggu 25

<210> SEQ ID NO 14
<211> LENGTH: 25
<212> TYPE: RNA
<213> ORGANISM: Artificial Sequence
<220> FEATURE:
<223> OTHER INFORMATION: Synthetic sequence

<400> SEQUENCE: 14
guuuacacac ucccucucau agggu 25

<210> SEQ ID NO 15
<211> LENGTH: 25
<212> TYPE: RNA
<213> ORGANISM: Artificial Sequence
<220> FEATURE:
<223> OTHER INFORMATION: Synthetic sequence

<400> SEQUENCE: 15
uuuuacauac ccccucucau gggau 25

<210> SEQ ID NO 16
<211> LENGTH: 85
<212> TYPE: PRT
<213> ORGANISM: Artificial Sequence
<220> FEATURE:
<223> OTHER INFORMATION: Synthetic sequence

<400> SEQUENCE: 16

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85


<210> SEQ ID NO 17
<211> LENGTH: 76
<212> TYPE: PRT
<213> ORGANISM: Artificial Sequence
<220> FEATURE:
<223> OTHER INFORMATION: Synthetic sequence

<400> SEQUENCE: 17

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 18
<211> LENGTH: 76
<212> TYPE: PRT
<213> ORGANISM: Artificial Sequence
<220> FEATURE:
<223> OTHER INFORMATION: Synthetic sequence

<400> SEQUENCE: 18

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 19
<211> LENGTH: 72
<212> TYPE: PRT
<213> ORGANISM: Artificial Sequence
<220> FEATURE:
<223> OTHER INFORMATION: Synthetic sequence

<400> SEQUENCE: 19

Met Ala Gln Ile Asn Asn Met Ala Gln Gly Ile Gln Thr Leu Asn Pro
```

-continued

```
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70


<210> SEQ ID NO 20
<211> LENGTH: 69
<212> TYPE: PRT
<213> ORGANISM: Artificial Sequence
<220> FEATURE:
<223> OTHER INFORMATION: Synthetic sequence

<400> SEQUENCE: 20

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65


<210> SEQ ID NO 21
<211> LENGTH: 81
<212> TYPE: RNA
<213> ORGANISM: Artificial Sequence
<220> FEATURE:
<223> OTHER INFORMATION: Synthetic sequence

<400> SEQUENCE: 21

acaucuggcg cguuuauucc auuacuuugg agccaguccc agcgacuaug ucguauggac     60

gaagcgcuua uuuaucggag a                                               81


<210> SEQ ID NO 22
<211> LENGTH: 77
<212> TYPE: PRT
<213> ORGANISM: Artificial Sequence
<220> FEATURE:
<223> OTHER INFORMATION: Synthetic sequence

<400> SEQUENCE: 22

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
65                  70                  75
```

```
<210> SEQ ID NO 23
<211> LENGTH: 57
<212> TYPE: PRT
<213> ORGANISM: Artificial Sequence
<220> FEATURE:
<223> OTHER INFORMATION: Synthetic sequence

<400> SEQUENCE: 23

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55


<210> SEQ ID NO 24
<211> LENGTH: 65
<212> TYPE: PRT
<213> ORGANISM: Artificial Sequence
<220> FEATURE:
<223> OTHER INFORMATION: Synthetic sequence

<400> SEQUENCE: 24

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65


<210> SEQ ID NO 25
<211> LENGTH: 68
<212> TYPE: RNA
<213> ORGANISM: Artificial Sequence
<220> FEATURE:
<223> OTHER INFORMATION: Synthetic sequence

<400> SEQUENCE: 25

uuauuccauu acuuuggagc cagucccagc gacuaugucg uauggacgaa gcgcuuauuu      60

aucggaga                                                                68


<210> SEQ ID NO 26
<211> LENGTH: 72
<212> TYPE: PRT
<213> ORGANISM: Artificial Sequence
<220> FEATURE:
<223> OTHER INFORMATION: Synthetic sequence

<400> SEQUENCE: 26

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45
```

```
Cys Ala Ser Ser Trp Asn Ser Thr Ile Asn Gly Ala Ala Ala Thr Thr
    50                  55                  60

Asn Gly Ala Ser Ala Ala Ser Ser
65                  70


<210> SEQ ID NO 27
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 27

Gly Leu Phe Xaa Ala Leu Leu Xaa Leu Leu Xaa Ser Leu Trp Xaa Leu
1               5                   10                  15

Leu Leu Xaa Ala
            20


<210> SEQ ID NO 28
<211> LENGTH: 7
<212> TYPE: PRT
<213> ORGANISM: Artificial Sequence
<220> FEATURE:
<223> OTHER INFORMATION: Synthetic sequence

<400> SEQUENCE: 28

Pro Lys Lys Lys Arg Lys Val
1               5


<210> SEQ ID NO 29
<211> LENGTH: 16
<212> TYPE: PRT
<213> ORGANISM: Artificial Sequence
<220> FEATURE:
<223> OTHER INFORMATION: Synthetic sequence

<400> SEQUENCE: 29

Lys Arg Pro Ala Ala Thr Lys Lys Ala Gly Gln Ala Lys Lys Lys Lys
1               5                   10                  15


<210> SEQ ID NO 30
<211> LENGTH: 9
<212> TYPE: PRT
<213> ORGANISM: Artificial Sequence
<220> FEATURE:
<223> OTHER INFORMATION: Synthetic sequence

<400> SEQUENCE: 30

Pro Ala Ala Lys Arg Val Lys Leu Asp
```

1 5

<210> SEQ ID NO 31
<211> LENGTH: 11
<212> TYPE: PRT
<213> ORGANISM: Artificial Sequence
<220> FEATURE:
<223> OTHER INFORMATION: Synthetic sequence

<400> SEQUENCE: 31

Arg Gln Arg Arg Asn Glu Leu Lys Arg Ser Pro
1 5 10

<210> SEQ ID NO 32
<211> LENGTH: 38
<212> TYPE: PRT
<213> ORGANISM: Artificial Sequence
<220> FEATURE:
<223> OTHER INFORMATION: Synthetic sequence

<400> SEQUENCE: 32

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 33
<211> LENGTH: 42
<212> TYPE: PRT
<213> ORGANISM: Artificial Sequence
<220> FEATURE:
<223> OTHER INFORMATION: Synthetic sequence

<400> SEQUENCE: 33

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 34
<211> LENGTH: 8
<212> TYPE: PRT
<213> ORGANISM: Artificial Sequence
<220> FEATURE:
<223> OTHER INFORMATION: Synthetic sequence

<400> SEQUENCE: 34

Val Ser Arg Lys Arg Pro Arg Pro
1 5

<210> SEQ ID NO 35
<211> LENGTH: 8
<212> TYPE: PRT
<213> ORGANISM: Artificial Sequence
<220> FEATURE:
<223> OTHER INFORMATION: Synthetic sequence

<400> SEQUENCE: 35

Pro Gln Pro Lys Lys Lys Pro Leu
1 5

<210> SEQ ID NO 36
<211> LENGTH: 12
<212> TYPE: PRT
<213> ORGANISM: Artificial Sequence
<220> FEATURE:
<223> OTHER INFORMATION: Synthetic sequence

<400> SEQUENCE: 36

```
Ser Ala Leu Ile Lys Lys Lys Lys Lys Met Ala Pro
1               5                   10
```

<210> SEQ ID NO 37
<211> LENGTH: 5
<212> TYPE: PRT
<213> ORGANISM: Artificial Sequence
<220> FEATURE:
<223> OTHER INFORMATION: Synthetic sequence

<400> SEQUENCE: 37

```
Asp Arg Leu Arg Arg
1               5
```

<210> SEQ ID NO 38
<211> LENGTH: 7
<212> TYPE: PRT
<213> ORGANISM: Artificial Sequence
<220> FEATURE:
<223> OTHER INFORMATION: Synthetic sequence

<400> SEQUENCE: 38

```
Pro Lys Gln Lys Lys Arg Lys
1               5
```

<210> SEQ ID NO 39
<211> LENGTH: 10
<212> TYPE: PRT
<213> ORGANISM: Artificial Sequence
<220> FEATURE:
<223> OTHER INFORMATION: Synthetic sequence

<400> SEQUENCE: 39

```
Arg Lys Leu Lys Lys Lys Ile Lys Lys Leu
1               5                   10
```

<210> SEQ ID NO 40
<211> LENGTH: 20
<212> TYPE: PRT
<213> ORGANISM: Artificial Sequence
<220> FEATURE:
<223> OTHER INFORMATION: Synthetic sequence

<400> SEQUENCE: 40

```
Lys Arg Lys Gly Asp Glu Val Asp Gly Val Asp Glu Val Ala Lys Lys
1               5                   10                  15

Lys Ser Lys Lys
            20
```

<210> SEQ ID NO 41
<211> LENGTH: 17
<212> TYPE: PRT
<213> ORGANISM: Artificial Sequence
<220> FEATURE:
<223> OTHER INFORMATION: Synthetic sequence

<400> SEQUENCE: 41

```
Arg Lys Cys Leu Gln Ala Gly Met Asn Leu Glu Ala Arg Lys Thr Lys
```

-continued 1 5 10 15

Lys

<210> SEQ ID NO 42
<211> LENGTH: 108
<212> TYPE: RNA
<213> ORGANISM: Artificial Sequence
<220> FEATURE:
<223> OTHER INFORMATION: Synthetic sequence

<400> SEQUENCE: 42
acaucuggcg cguuuauucc auuacuuugg agccaguccc agcgacuaug ucguauggac 60
gaagcgcuua uuuaucggag agaaaccgau aaguaaaacg caucaaag 108

<210> SEQ ID NO 43
<211> LENGTH: 96
<212> TYPE: RNA
<213> ORGANISM: Artificial Sequence
<220> FEATURE:
<223> OTHER INFORMATION: Synthetic sequence

<400> SEQUENCE: 43
uuaucucauu acuuugagag ccaucaccag cgacuauguc guaugguaa agcgcuuauu 60 uaucgggaaa ucuccgauaa auaagaagca ucaaag 96

<210> SEQ ID NO 44
<211> LENGTH: 11
<212> TYPE: PRT
<213> ORGANISM: Artificial Sequence
<220> FEATURE:
<223> OTHER INFORMATION: Synthetic sequence

<400> SEQUENCE: 44

Tyr Gly Arg Lys Lys Arg Arg Gln Arg Arg Arg
1 5 10

<210> SEQ ID NO 45
<211> LENGTH: 12
<212> TYPE: PRT
<213> ORGANISM: Artificial Sequence
<220> FEATURE:
<223> OTHER INFORMATION: Synthetic sequence

<400> SEQUENCE: 45

Arg Arg Gln Arg Arg Thr Ser Lys Leu Met Lys Arg
1 5 10

<210> SEQ ID NO 46
<211> LENGTH: 27
<212> TYPE: PRT
<213> ORGANISM: Artificial Sequence
<220> FEATURE:
<223> OTHER INFORMATION: Synthetic sequence

<400> SEQUENCE: 46

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 47
<211> LENGTH: 33
<212> TYPE: PRT
<213> ORGANISM: Artificial Sequence
<220> FEATURE:
<223> OTHER INFORMATION: Synthetic sequence

<400> SEQUENCE: 47

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 48
<211> LENGTH: 16
<212> TYPE: PRT
<213> ORGANISM: Artificial Sequence
<220> FEATURE:
<223> OTHER INFORMATION: Synthetic sequence

<400> SEQUENCE: 48

Arg Gln Ile Lys Ile Trp Phe Gln Asn Arg Arg Met Lys Trp Lys Lys
1               5                   10                  15

<210> SEQ ID NO 49
<211> LENGTH: 9
<212> TYPE: PRT
<213> ORGANISM: Artificial Sequence
<220> FEATURE:
<223> OTHER INFORMATION: Synthetic sequence

<400> SEQUENCE: 49

Arg Lys Lys Arg Arg Gln Arg Arg Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic sequence

<400> SEQUENCE: 50

Arg Lys Lys Arg Arg Gln Arg Arg
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic sequence

<400> SEQUENCE: 51

Thr His Arg Leu Pro Arg Arg Arg Arg Arg Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic sequence

<400> SEQUENCE: 52

Gly Gly Arg Arg Ala Arg Arg Arg Arg Arg Arg
1               5                   10

```
<210> SEQ ID NO 53
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(5)
<223> OTHER INFORMATION: This stretch of amino acid residues may be
      repeated

<400> SEQUENCE: 53

Gly Ser Gly Gly Ser
1               5


<210> SEQ ID NO 54
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(6)
<223> OTHER INFORMATION: This stretch of amino acid residues may be
      repeated

<400> SEQUENCE: 54

Gly Gly Ser Gly Gly Ser
1               5


<210> SEQ ID NO 55
<211> LENGTH: 4
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(4)
<223> OTHER INFORMATION: This stretch of amino acid residues may be
      repeated

<400> SEQUENCE: 55

Gly Gly Gly Ser
1


<210> SEQ ID NO 56
<211> LENGTH: 4
<212> TYPE: PRT
<213> ORGANISM: Artificial Sequence
<220> FEATURE:
<223> OTHER INFORMATION: Synthetic sequence

<400> SEQUENCE: 56

Gly Gly Ser Gly
1


<210> SEQ ID NO 57
<211> LENGTH: 5
<212> TYPE: PRT
<213> ORGANISM: Artificial Sequence
<220> FEATURE:
<223> OTHER INFORMATION: Synthetic sequence

<400> SEQUENCE: 57

Gly Gly Ser Gly Gly
1               5
```

<210> SEQ ID NO 58
<211> LENGTH: 5
<212> TYPE: PRT
<213> ORGANISM: Artificial Sequence
<220> FEATURE:
<223> OTHER INFORMATION: Synthetic sequence

<400> SEQUENCE: 58

Gly Ser Gly Ser Gly
1 5

<210> SEQ ID NO 59
<211> LENGTH: 5
<212> TYPE: PRT
<213> ORGANISM: Artificial Sequence
<220> FEATURE:
<223> OTHER INFORMATION: Synthetic sequence

<400> SEQUENCE: 59

Gly Ser Gly Gly Gly
1 5

<210> SEQ ID NO 60
<211> LENGTH: 5
<212> TYPE: PRT
<213> ORGANISM: Artificial Sequence
<220> FEATURE:
<223> OTHER INFORMATION: Synthetic sequence

<400> SEQUENCE: 60

Gly Gly Gly Ser Gly
1 5

<210> SEQ ID NO 61
<211> LENGTH: 4
<212> TYPE: PRT
<213> ORGANISM: Artificial Sequence
<220> FEATURE:
<223> OTHER INFORMATION: Synthetic sequence

<400> SEQUENCE: 61

Gly Gly Gly Ser
1

<210> SEQ ID NO 62
<211> LENGTH: 5
<212> TYPE: PRT
<213> ORGANISM: Artificial Sequence
<220> FEATURE:
<223> OTHER INFORMATION: Synthetic sequence

<400> SEQUENCE: 62

Gly Ser Ser Ser Gly
1 5

<210> SEQ ID NO 63
<211> LENGTH: 68
<212> TYPE: RNA
<213> ORGANISM: Artificial Sequence
<220> FEATURE:
<223> OTHER INFORMATION: Synthetic sequence

<400> SEQUENCE: 63
uuauuccauu acuuuggagc cagucccagc gacuaugucg uauggacgaa gcgcuuauuu 60
aucggaga 68

<210> SEQ ID NO 64
<211> LENGTH: 65
<212> TYPE: RNA
<213> ORGANISM: Artificial Sequence
<220> FEATURE:
<223> OTHER INFORMATION: Synthetic sequence

<400> SEQUENCE: 64
uuauuccauu acuuuggagc cagucccagc gacuaugucg uauggacgaa gcgcuuauuu 60
aucgg 65

<210> SEQ ID NO 65
<211> LENGTH: 19
<212> TYPE: RNA
<213> ORGANISM: Artificial Sequence
<220> FEATURE:
<223> OTHER INFORMATION: Synthetic sequence

<400> SEQUENCE: 65
acaugaggau uacccaugu 19

<210> SEQ ID NO 66
<211> LENGTH: 10
<212> TYPE: PRT
<213> ORGANISM: Artificial Sequence
<220> FEATURE:
<223> OTHER INFORMATION: Synthetic sequence

<400> SEQUENCE: 66

Arg Glu Lys Lys Lys Phe Leu Lys Arg Arg
1 5 10

<210> SEQ ID NO 67
<211> LENGTH: 69
<212> TYPE: RNA
<213> ORGANISM: Artificial Sequence
<220> FEATURE:
<223> OTHER INFORMATION: Synthetic sequence

<400> SEQUENCE: 67
uuaucucauu acuuugagag ccaucaccag cgacuauguc guaugguaa agcgcuuauu 60 uaucggaga 69

<210> SEQ ID NO 68
<211> LENGTH: 66
<212> TYPE: RNA
<213> ORGANISM: Artificial Sequence
<220> FEATURE:
<223> OTHER INFORMATION: Synthetic sequence

<400> SEQUENCE: 68
uuaucucauu acuuugagag ccaucaccag cgacuauguc guaugguaa agcgcuuauu 60 uaucgg 66

<210> SEQ ID NO 69
<211> LENGTH: 43
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (24)..(43)
<223> OTHER INFORMATION: n is a, c, g, or u

<400> SEQUENCE: 69
ccgauaagua aaacgcauca aagnnnnnnn nnnnnnnnnn nnn 43

<210> SEQ ID NO 70
<211> LENGTH: 46
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (27)..(46)
<223> OTHER INFORMATION: n is a, c, g, or u

<400> SEQUENCE: 70
ucuccgauaa auaagaagca ucaaagnnnn nnnnnnnnnn nnnnnn 46

<210> SEQ ID NO 71
<211> LENGTH: 23
<212> TYPE: RNA
<213> ORGANISM: Artificial Sequence
<220> FEATURE:
<223> OTHER INFORMATION: Synthetic sequence

<400> SEQUENCE: 71
ccgauaagua aaacgcauca aag 23

<210> SEQ ID NO 72
<211> LENGTH: 26
<212> TYPE: RNA
<213> ORGANISM: Artificial Sequence
<220> FEATURE:
<223> OTHER INFORMATION: Synthetic sequence

<400> SEQUENCE: 72
ucuccgauaa auaagaagca ucaaag 26

<210> SEQ ID NO 73
<211> LENGTH: 25
<212> TYPE: RNA
<213> ORGANISM: Artificial Sequence
<220> FEATURE:
<223> OTHER INFORMATION: Synthetic sequence

<400> SEQUENCE: 73
guuuacacac ucccucucau ggggg 25

<210> SEQ ID NO 74
<211> LENGTH: 93
<212> TYPE: RNA
<213> ORGANISM: Artificial Sequence
<220> FEATURE:
<223> OTHER INFORMATION: Synthetic sequence

<400> SEQUENCE: 74
aaguaguaaa uuacaucugg cgcguuuauu ccauuacuuu ggagccaguc ccagcgacua 60
ugucguaugg acgaagcgcu uauuuaucgg aga 93

<210> SEQ ID NO 75
<211> LENGTH: 230
<212> TYPE: RNA
<213> ORGANISM: Artificial Sequence
<220> FEATURE:
<223> OTHER INFORMATION: Synthetic sequence

<400> SEQUENCE: 75
uaaauuuuuu gagcccuauc uccgcgagga agacagggcu cuuuucauga gaggaagcuu 60
uuauacccga ccgguaaucc ggucggggga uuggccguug aaacgauuuu aaagcggcca 120
augggccccu cuauauggau acuacuuaua uaaggagcuu ggggaagaag auagcuuaau 180
cccgcuaucu ugucaagggg uugggggagu aucaguaucc ggcaggcgcc 230

<210> SEQ ID NO 76
<211> LENGTH: 92
<212> TYPE: RNA
<213> ORGANISM: Artificial Sequence
<220> FEATURE:
<223> OTHER INFORMATION: Synthetic sequence

<400> SEQUENCE: 76
uuauuccauu acuuuggagc caguccagc gacuaugucg uauggacgaa gcgcuuauuu 60
aucgggaaac cgauaaguaa aacgcaucaa ag 92

<210> SEQ ID NO 77
<211> LENGTH: 8
<212> TYPE: PRT
<213> ORGANISM: Artificial Sequence
<220> FEATURE:
<223> OTHER INFORMATION: Synthetic sequence

<400> SEQUENCE: 77

Pro Pro Lys Lys Ala Arg Glu Asp
1               5

<210> SEQ ID NO 78
<211> LENGTH: 144
<212> TYPE: DNA
<213> ORGANISM: Artificial Sequence
<220> FEATURE:
<223> OTHER INFORMATION: Synthetic sequence

<400> SEQUENCE: 78
gaaattaata cgactcacta taggcgcgtt tattccatta ctttggagcc agtcccagcg 60
actatgtcgt atggacgaag cgcttattta tcggagagaa accgataagt aaaacgcatc 120
aaagtcctgc agcagaaaat caaa 144

<210> SEQ ID NO 79
<211> LENGTH: 20
<212> TYPE: PRT
<213> ORGANISM: Artificial Sequence
<220> FEATURE:
<223> OTHER INFORMATION: Synthetic sequence

<400> SEQUENCE: 79

Gly Leu Phe His Ala Leu Leu His Leu Leu His Ser Leu Trp His Leu
1               5                   10                  15

Leu Leu His Ala
            20

<210> SEQ ID NO 80
<211> LENGTH: 11
<212> TYPE: PRT
<213> ORGANISM: Artificial Sequence
<220> FEATURE:
<223> OTHER INFORMATION: Synthetic sequence

<400> SEQUENCE: 80

Tyr Ala Arg Ala Ala Ala Arg Gln Ala Arg Ala 1 5 10

<210> SEQ ID NO 81
<211> LENGTH: 20
<212> TYPE: DNA
<213> ORGANISM: Artificial Sequence
<220> FEATURE:
<223> OTHER INFORMATION: Synthetic sequence

<400> SEQUENCE: 81
cgggatttca tcctgcagca 20

<210> SEQ ID NO 82
<211> LENGTH: 45
<212> TYPE: DNA
<213> ORGANISM: Artificial Sequence
<220> FEATURE:
<223> OTHER INFORMATION: Synthetic sequence

<400> SEQUENCE: 82
gccctaaagt aggacgtcgt cttttagttt catattgcta tgtac 45

<210> SEQ ID NO 83
<211> LENGTH: 20
<212> TYPE: RNA
<213> ORGANISM: Artificial Sequence
<220> FEATURE:
<223> OTHER INFORMATION: Synthetic sequence

<400> SEQUENCE: 83
uccugcagca gaaaaucaaa 20

<210> SEQ ID NO 84
<211> LENGTH: 4
<212> TYPE: PRT
<213> ORGANISM: Artificial Sequence
<220> FEATURE:
<223> OTHER INFORMATION: Synthetic sequence

<400> SEQUENCE: 84

Cys Ser Asn Cys
1

<210> SEQ ID NO 85
<211> LENGTH: 4
<212> TYPE: PRT
<213> ORGANISM: Artificial Sequence
<220> FEATURE:
<223> OTHER INFORMATION: Synthetic sequence

<400> SEQUENCE: 85

Cys Leu Asp Cys
1

<210> SEQ ID NO 86
<211> LENGTH: 105
<212> TYPE: PRT
<213> ORGANISM: Artificial Sequence
<220> FEATURE:
<223> OTHER INFORMATION: Synthetic sequence

<400> SEQUENCE: 86

Cys Ser Asn Cys Gly Phe Thr Ile Thr Thr Ala Asp Tyr Asp Gly Met
1 5 10 15

Leu Val Arg Leu Lys Lys Thr Ser Asp Gly Trp Ala Thr Thr Leu Asn
20 25 30

```
Asn Lys Glu Leu Lys Ala Glu Gly Gln Ile Thr Tyr Tyr Asn Arg Tyr
        35                  40                  45

Lys Arg Gln Thr Val Glu Lys Glu Leu Ser Ala Glu Leu Asp Arg Leu
    50                  55                  60

Ser Glu Glu Ser Gly Asn Asn Asp Ile Ser Lys Trp Thr Lys Gly Arg
65                  70                  75                  80

Arg Asp Glu Ala Leu Phe Leu Leu Lys Lys Arg Phe Ser His Arg Pro
                85                  90                  95

Val Gln Glu Gln Phe Val Cys Leu Asp
            100                 105
```

```
<210> SEQ ID NO 87
<211> LENGTH: 122
<212> TYPE: RNA
<213> ORGANISM: Artificial Sequence
<220> FEATURE:
<223> OTHER INFORMATION: Synthetic sequence

<400> SEQUENCE: 87

ggcgcguuua uuccauuacu uuggagccag ucccagcgac uaugucguau ggacgaagcg     60

cuuauuuauc ggagagaaac cgauaaguaa aacgcaucaa aguccugcag cagaaaauca    120

aa                                                                   122
```

```
<210> SEQ ID NO 88
<211> LENGTH: 31
<212> TYPE: DNA
<213> ORGANISM: Artificial Sequence
<220> FEATURE:
<223> OTHER INFORMATION: Synthetic sequence

<400> SEQUENCE: 88

cgggatttcc atcctgcagc atccccgacc c                                    31
```

```
<210> SEQ ID NO 89
<211> LENGTH: 30
<212> TYPE: DNA
<213> ORGANISM: Artificial Sequence
<220> FEATURE:
<223> OTHER INFORMATION: Synthetic sequence

<400> SEQUENCE: 89

gccctaaagt aggacgtcgt cttttagttt                                     30
```

```
<210> SEQ ID NO 90
<211> LENGTH: 20
<212> TYPE: RNA
<213> ORGANISM: Artificial Sequence
<220> FEATURE:
<223> OTHER INFORMATION: Synthetic sequence

<400> SEQUENCE: 90

uccugcagca gaaaaucaaa                                                20
```

```
<210> SEQ ID NO 91
<211> LENGTH: 45
<212> TYPE: DNA
<213> ORGANISM: Artificial Sequence
<220> FEATURE:
<223> OTHER INFORMATION: Synthetic sequence

<400> SEQUENCE: 91

cgggatttca tcctgcagca tccccgaccc gtataacgat acatg                    45
```

<210> SEQ ID NO 92
<211> LENGTH: 45
<212> TYPE: DNA
<213> ORGANISM: Artificial Sequence
<220> FEATURE:
<223> OTHER INFORMATION: Synthetic sequence

<400> SEQUENCE: 92
gccctaaagt aggacgtcgt cttttagttt catattgcta tgtac 45

<210> SEQ ID NO 93
<211> LENGTH: 20
<212> TYPE: RNA
<213> ORGANISM: Artificial Sequence
<220> FEATURE:
<223> OTHER INFORMATION: Synthetic sequence

<400> SEQUENCE: 93
uccugcagca gaaaaucaaa 20

<210> SEQ ID NO 94
<211> LENGTH: 20
<212> TYPE: DNA
<213> ORGANISM: Artificial Sequence
<220> FEATURE:
<223> OTHER INFORMATION: Synthetic sequence

<400> SEQUENCE: 94
cgggatttca tcctgcagca 20

<210> SEQ ID NO 95
<211> LENGTH: 45
<212> TYPE: DNA
<213> ORGANISM: Artificial Sequence
<220> FEATURE:
<223> OTHER INFORMATION: Synthetic sequence

<400> SEQUENCE: 95
gccctaaagt aggacgtcgt cttttagttt catattgcta tgtac 45

<210> SEQ ID NO 96
<211> LENGTH: 20
<212> TYPE: RNA
<213> ORGANISM: Artificial Sequence
<220> FEATURE:
<223> OTHER INFORMATION: Synthetic sequence

<400> SEQUENCE: 96
uccugcagca gaaaaucaaa 20

<210> SEQ ID NO 97
<211> LENGTH: 55
<212> TYPE: DNA
<213> ORGANISM: Artificial sequence
<220> FEATURE:
<223> OTHER INFORMATION: synthetic sequence

<400> SEQUENCE: 97
gcttgtggcc gttcatcctg cagcagaaaa tcaaaaggat gggcaccacc ccggc 55

<210> SEQ ID NO 98
<211> LENGTH: 55
<212> TYPE: DNA
<213> ORGANISM: Artificial sequence
<220> FEATURE:

<223> OTHER INFORMATION: synthetic sequence

<400> SEQUENCE: 98
gccggggtgg tgcccatcct tttgattttc tgctgcagga tgaacggcca caagc 55

<210> SEQ ID NO 99
<211> LENGTH: 20
<212> TYPE: RNA
<213> ORGANISM: Artificial sequence
<220> FEATURE:
<223> OTHER INFORMATION: synthetic sequence

<400> SEQUENCE: 99
uccugcagca gaaaaucaaa 20

<210> SEQ ID NO 100
<211> LENGTH: 10
<212> TYPE: PRT
<213> ORGANISM: Artificial sequence
<220> FEATURE:
<223> OTHER INFORMATION: synthetic sequence

<400> SEQUENCE: 100

Gly Gly Ser Gly Gly Ser Gly Gly Ser Gly
1 5 10

<210> SEQ ID NO 101
<211> LENGTH: 34
<212> TYPE: PRT
<213> ORGANISM: Artificial sequence
<220> FEATURE:
<223> OTHER INFORMATION: synthetic sequence

<400> SEQUENCE: 101

Val Arg Leu Lys Lys Thr Ser Asp Gly Trp Ala Thr Thr Leu Asn Asn
1 5 10 15

Lys Glu Leu Lys Ala Glu Gly Gln Ile Thr Tyr Tyr Asn Arg Tyr Lys
20 25 30

Arg Gln

<210> SEQ ID NO 102
<211> LENGTH: 11
<212> TYPE: PRT
<213> ORGANISM: Artificial sequence
<220> FEATURE:
<223> OTHER INFORMATION: synthetic sequence

<400> SEQUENCE: 102

Gln Ile Thr Tyr Tyr Asn Arg Tyr Lys Arg Gln
1 5 10

<210> SEQ ID NO 103
<211> LENGTH: 123
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (103)..(123)
<223> OTHER INFORMATION: n is a, c, g, or t

<400> SEQUENCE: 103
ggcgcgttta ttccattact ttggagccag tcccagcgac tatgtcgtat ggacgaagcg 60
cttatttatc ggagagaaac cgataagtaa aacgcatcaa agnnnnnnnn nnnnnnnnnn 120 nnn 123

<210> SEQ ID NO 104
<211> LENGTH: 88
<212> TYPE: DNA
<213> ORGANISM: Artificial sequence
<220> FEATURE:
<223> OTHER INFORMATION: synthetic sequence

<400> SEQUENCE: 104
ggcgcgttta ttccattact ttggagccag tcccatggac gaagcgctta tttatcggag 60
agaaaccgat aagtaaaacg catcaaag 88

<210> SEQ ID NO 105
<211> LENGTH: 96
<212> TYPE: DNA
<213> ORGANISM: Artificial sequence
<220> FEATURE:
<223> OTHER INFORMATION: synthetic sequence

<400> SEQUENCE: 105
ggcgcgttta ttccattact ttggagccag tcccagctat gtatggacga agcgcttatt 60
tatcggagag aaaccgataa gtaaaacgca tcaaag 96

<210> SEQ ID NO 106
<211> LENGTH: 100
<212> TYPE: DNA
<213> ORGANISM: Artificial sequence
<220> FEATURE:
<223> OTHER INFORMATION: synthetic sequence

<400> SEQUENCE: 106
ggcgcgttta ttccattact ttggagccag tcccagcgat attcgtatgg acgaagcgct 60
tatttatcgg agagaaaccg ataagtaaaa cgcatcaaag 100

<210> SEQ ID NO 107
<211> LENGTH: 102
<212> TYPE: DNA
<213> ORGANISM: Artificial sequence
<220> FEATURE:
<223> OTHER INFORMATION: synthetic sequence

<400> SEQUENCE: 107
ggcgcgttta ttccattact ttggagccag tccaugcgac tatgtcgtat ggacgaagcg 60
cttatttatc ggagagaaac cgataagtaa aacgcatcaa ag 102

<210> SEQ ID NO 108
<211> LENGTH: 102
<212> TYPE: DNA
<213> ORGANISM: Artificial sequence
<220> FEATURE:
<223> OTHER INFORMATION: synthetic sequence

<400> SEQUENCE: 108
ggcgcgttta ttccattact ttggagccag tcccagcgac tatgtcgtat ggacgaagcg 60
cttatttatc ggagagaaac cgataagtaa aacgcatcgg gg 102

<210> SEQ ID NO 109
<211> LENGTH: 102
<212> TYPE: DNA
<213> ORGANISM: Artificial sequence
<220> FEATURE:

<223> OTHER INFORMATION: synthetic sequence

<400> SEQUENCE: 109
ggcgcgttta ttccattact ttggagccag tcccagcgac tatgtcgtat ggacgaagcg 60
cttatttatc ggagagaaac cgataagtaa aacgcatcuu ug 102

<210> SEQ ID NO 110
<211> LENGTH: 102
<212> TYPE: DNA
<213> ORGANISM: Artificial sequence
<220> FEATURE:
<223> OTHER INFORMATION: synthetic sequence

<400> SEQUENCE: 110
ggcgcgttta ttccattact ttggagccag tcccagcgac tatgtcgtat ggacgaagcg 60
cttatttatc ggagagaaac cgataagtaa aacgcatccc cg 102

<210> SEQ ID NO 111
<211> LENGTH: 102
<212> TYPE: DNA
<213> ORGANISM: Artificial sequence
<220> FEATURE:
<223> OTHER INFORMATION: synthetic sequence

<400> SEQUENCE: 111
ggcgcgccca ttccattacc ccggagccag tcccagcgac tatgtcgtat ggacgaagcg 60
cttatttatc ggagagaaac cgataagtaa aacgcatcgg gg 102

<210> SEQ ID NO 112
<211> LENGTH: 90
<212> TYPE: DNA
<213> ORGANISM: Artificial sequence
<220> FEATURE:
<223> OTHER INFORMATION: synthetic sequence

<400> SEQUENCE: 112
ggcgcgttta ttccattact ttggagccag tcccagcgac tatgtcgtat ggacgaagcg 60
cttatagaga aaaagtaaaa cgcatcaaag 90

<210> SEQ ID NO 113
<211> LENGTH: 92
<212> TYPE: DNA
<213> ORGANISM: Artificial sequence
<220> FEATURE:
<223> OTHER INFORMATION: synthetic sequence

<400> SEQUENCE: 113
ggcgcgttta ttccattact ttggagccag tcccagcgac tatgtcgtat ggacgaagcg 60
cttatttaga gaaaaagtaa aacgcatcaa ag 92

<210> SEQ ID NO 114
<211> LENGTH: 96
<212> TYPE: DNA
<213> ORGANISM: Artificial sequence
<220> FEATURE:
<223> OTHER INFORMATION: synthetic sequence

<400> SEQUENCE: 114
ggcgcgttta ttccattact ttggagccag tcccagcgac tatgtcgtat ggacgaagcg 60
cttatttata gagaaaataa gtaaaacgca tcaaag 96

VARIANT TYPE V CRISPR/CAS EFFECTOR POLYPEPTIDES AND METHODS OF USE THEREOF

CROSS-REFERENCE

This application is a national stage filing of PCT/US2019/047488, filed Aug. 21, 2019, which claims the benefit of U.S. Provisional Patent Application No. 62/721,528 filed Aug. 22, 2018, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-397_SEQ LISTING_ST25.txt" created on Jan. 13, 2024 and having a size of 74,933 bytes. The contents of the text file are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

SUMMARY

The present disclosure provides variant type V CRISPR/Cas effector polypeptides, fusion polypeptides comprising the variant type V CRISPR/Cas effector polypeptides, and nucleic acids comprising nucleotide sequences encoding the variant polypeptides and fusion polypeptides. The present disclosure provides methods of binding, or binding and nicking, a target nucleic acid, using a variant type V CRISPR/Cas effector polypeptide of the present disclosure. The present disclosure provides methods of detecting a single-stranded DNA, using a variant type V CRISPR/Cas effector polypeptide of the present disclosure.

BRIEF DESCRIPTION OF THE DRAWINGS

FIG. 12A-12G depict structural comparison of CRISPR effectors.

FIG. 16 provides an amino acid sequence of CasX1. The double underline indicates the NTSB, and the amino acids in bold are examples of amino acids that can be substituted to generate a nuclease-deficient variant. Single underline indicates zinc finger motifs (CSNC (SEQ ID NO:84); and CLDC (SEQ ID NO:85); and the Δ2.3 sequence (QITYYNRYKRQ; SEQ ID NO:6; see FIG. 7).

FIG. 17 provides an amino acid sequence of CasX2. The double underline indicates the NTSB, and the amino acids in bold are examples of amino acids that can be substituted to generate a nuclease-deficient variant. Single underline indicates zinc finger motifs (CSNC (SEQ ID NO:84); and CLDC (SEQ ID NO:85); and the Δ2.3 sequence (QITYYNRYKRQ; SEQ ID NO:6; see FIG. 7).

DEFINITIONS

Figure 1A:
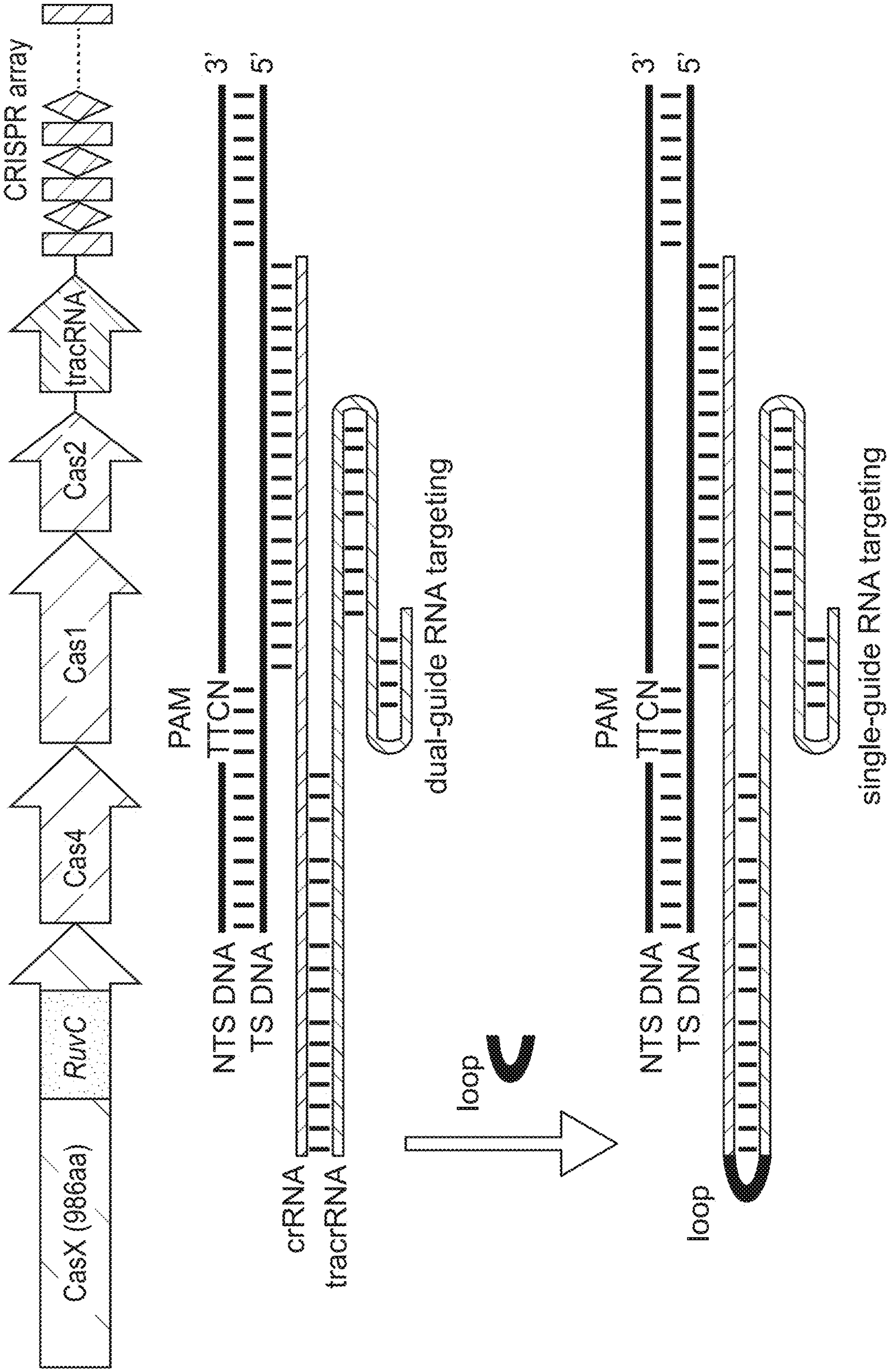
FIG. 1A-1E depict data showing that CasX cuts double stranded DNA with single guide RNA in vitro.

"Heterologous," as used herein, means a nucleotide or polypeptide sequence that is not found in the native nucleic acid or protein, respectively. For example, relative to a variant CasX polypeptide of the present disclosure, a heterologous polypeptide comprises an amino acid sequence from a protein other than the variant CasX polypeptide. As another example, a variant CasX polypeptide of the present disclosure can be fused to an active domain from a non-CasX protein (e.g., a histone deacetylase), and the sequence of the active domain could be considered a heterologous polypeptide (it is heterologous to the variant CasX protein).

The terms "polynucleotide" and "nucleic acid." used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide." "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences." "control elements," and "regulatory elements." used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term “conservative amino acid substitution” refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent “sequence identity” to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms “treatment,” “treating.” and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. “Treatment,” as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms “individual,” “subject.” “host.” and “patient.” used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a,” “an.” and “the” include plural referents unless the context clearly dictates otherwise. Thus, for example, reference to “a variant CasX polypeptide” includes a plurality of such polypeptides and reference to “the CasX guide RNA” includes reference to one or more CasX guide RNAs and equivalents thereof known to those skilled in the art, and so forth. It is further noted that the claims may be drafted to exclude any optional element. As such, this statement is intended to serve as antecedent basis for use of such exclusive terminology as “solely.” “only” and the like in connection with the recitation of claim elements, or use of a “negative” limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant type V CRISPR/Cas effector polypeptides, fusion polypeptides comprising the variant type V CRISPR/Cas effector polypeptides, and nucleic acids comprising nucleotide sequences encoding the variant polypeptides and fusion polypeptides. The present disclosure provides methods of binding, or binding and nicking, a target nucleic acid, using a variant type V CRISPR/Cas effector polypeptide of the present disclosure. The present disclosure provides methods of detecting a single-stranded DNA, using a variant type V CRISPR/Cas effector polypeptide of the present disclosure.

Variant CasX Polypeptides

The present disclosure provides variant CasX polypeptides, and fusion polypeptides comprising a variant CasX polypeptide of the present disclosure. A variant CasX polypeptide of the present disclosure can comprise one or more of: i) an insertion of one or more amino acids; ii) a substitution ("replacement") of one or more amino acids; and iii) a deletion of one or more amino acids, compared to the amino acid sequence of SEQ ID NO:1 (CasX1), SEQ ID NO:2 (CasX2), or another wild-type CasX polypeptide. CasX is also referred to in the art as Cas12e. (see Makarova et al. (2018) *CRISPR J* 1(5):325.)

TSLD Variant CasX—Deletion or Replacement of all or a Portion of a TSL Domain

The present disclosure provides a variant CasX polypeptide in which one or more amino acids of a target-strand loading domain (TSLD) are deleted or replaced (substituted).

A TSLD of a CasX polypeptide comprises amino acids 825-934 of a CasX1 amino acid sequence depicted in FIG. 16 and set forth in SEQ ID NO:1.

SEQ ID NO:1 (CasX1) amino acid sequence is set forth below:

```
                                        (SEQ ID NO: 1)
MEKRINKIRKKLSADNATKPVSRSGPMKTLLVRVMTDDLKKRLEKRRKK

PEVMPQVISNNAANNLRMLLDDYTKMKEAILQVYWQEFKDDHVGLMCKF

AQPASKKIDQNKLKPEMDEKGNLTTAGFACSQCGQPLFVYKLEQVSEKG

KAYTNYFGRCNVAEHEKLILLAQLKPEKDSDEAVTYSLGKFGQRALDFY

SIHVTKESTHPVKPLAQIAGNRYASGPVGKALSDACMGTIASFLSKYQD

IIIEHQKVVKGNQKRLESLRELAGKENLEYPSVTLPPQPHTKEGVDAYN

EVIARVRMWVNLNLWQKLKLSRDDAKPLLRLKGFPSFPVVERRENEVDW

WNTINEVKKLIDAKRDMGRVFWSGVTAEKRNTILEGYNYLPNENDHKKR

EGSLENPKKPAKRQFGDLLLYLEKKYAGDWGKVFDEAWERIDKKIAGLT

SHIEREEARNAEDAQSKAVLTDWLRAKASFVLERLKEMDEKEFYACEIQ

LQKWYGDLRGNPFAVEAENRVVDISGFSIGSDGHSIQYRNLLAWKYLEN

GKREFYLLMNYGKKGRIRFTDGTDIKKSGKWQGLLYGGGKAKVIDLTFD

PDDEQLIILPLAFGTRQGREFIWNDLLSLETGLIKLANGRVIEKTIYNK

KIGRDEPALFVALTFERREVVDPSNIKPVNLIGVDRGENIPAVIALTDP

EGCPLPEFKDSSGGPTDILRIGEGYKEKQRAIQAAKEVEQRRAGGYSRK

FASKSRNLADDMVRNSARDLFYHAVTHDAVLVFENLSRGFGRQGKRTFM

TERQYTKMEDWLTAKLAYEGLTSKTYLSKTLAQYTSKTCSNCGFTITTA

-continued
DYDGMLVRLKKTSDGWATTLNNKELKAEGQITYYNRYKRQTVEKELSAE

LDRLSEESGNNDISKWTKGRRDEALFLLKKRFSHRPVQEQFVCLDCGHE

VHADEQAALNIARSWLFLNSNSTEFKSYKSGKQPFVGAWQAFYKRRLKE

VWKPNA.
```

Amino acids in bold underline are examples of amino acids that, when substituted, can generate a nuclease-deficient CasX. CSNC (SEQ ID NO:84; underlined) and CLDC (SEQ ID NO:85; underlined) are zinc finger motifs. QITYYNRYKRQ (SEQ ID NO:6; underlined) is the "Δ2.3" peptide (see FIG. 7; and the Example).

A CasX TSLD comprises amino acids including and between the two CXXC zinc finger motifs (underlined in the CasX1 amino acid sequence, above) of the CasX1 amino acid sequence set forth in SEQ ID NO:1 or any corresponding region in another CasX sequence. For example, in some cases, a TSLD comprises at least 70%, at least 85%, at least 90%, at least 95%, at least 98%, or 100%, amino acid sequence identity to the following amino acid sequence:

```
                                        (SEQ ID NO: 3)
CSNCGFTITTADYDGMLVRLKKTSDGWATTLNNKELKAEGQITYYNRYK

RQTVEKELSAELDRLSEESGNNDISKWTKGRRDEALFLLKKRFSHRPVQ

EQFVCLDC,
```

and has a length of from about 80 amino acids to about 106 amino acids.

In some cases, a TSLD variant CasX polypeptide comprises an amino acid sequence having at least 70%, at least 85%, at least 90%, at least 95%, at least 98%, or 100%, amino acid sequence identity to the amino acid sequence depicted in FIG. 16 or FIG. 17; where the variant CasX polypeptide lacks all or a portion of the TSLD. In some cases, from 5 amino acids to 106 amino acids of the TSLD is deleted. In some cases, from 5 amino acids to 10 amino acids, from 10 amino acids to 25 amino acids, from 25 amino acids to 50 amino acids, from 50 amino acids to 75 amino acids, from 75 amino acids to 100 amino acids, or from 100 amino acids to 106 amino acids, are deleted.

In some cases, a TSLD variant CasX polypeptide comprises an amino acid sequence having at least 70%, at least 85%, at least 90%, at least 95%, at least 98%, or 100%, amino acid sequence identity to the amino acid sequence depicted in FIG. 16 or FIG. 17, wherein all or a portion of the TSLD is replaced with a heterologous polypeptide. In some cases, from 5 amino acids to 106 amino acids of the TSLD is replaced. In some cases, from 5 amino acids to 10 amino acids, from 10 amino acids to 25 amino acids, from 25 amino acids to 50 amino acids, from 50 amino acids to 75 amino acids, from 75 amino acids to 100 amino acids, or from 100 amino acids to 106 amino acids, are replaced.

In some cases, a variant CasX polypeptide comprises an amino acid sequence having at least 70%, at least 85%, at least 90%, at least 95%, at least 98%, or 100%, amino acid sequence identity to the following amino acid sequence:

```
                                        (SEQ ID NO: 4)
MEKRINKIRKKLSADNATKPVSRSGPMKTLLVRVMTDDLKKRLEKRRKK

PEVMPQVISNNAANNLRMLLDDYTKMKEAILQVYWQEFKDDHVGLMCKF

AQPASKKIDQNKLKPEMDEKGNLTTAGFACSQCGQPLFVYKLEQVSEKG
```

-continued

KAYTNYFGRCNVAEHEKLILLAQLKPEKDSDEAVTYSLGKFGQRALDFY
SIHVTKESTHPVKPLAQIAGNRYASGPVGKALSDACMGTIASFLSKYQD
IIIEHQKVVKGNQKRLESLRELAGKENLEYPSVTLPPQPHTKEGVDAYN
EVIARVRMWVNLNLWQKLKLSRDDAKPLLRLKGFPSFPVVERRENEVDW
WNTINEVKKLIDAKRDMGRVFWSGVTAEKRNTILEGYNYLPNENDHKKR
EGSLENPKKPAKRQFGDLLLYLEKKYAGDWGKVFDEAWERIDKKIAGLT
SHIEREEARNAEDAQSKAVLTDWLRAKASFVLERLKEMDEKEFYACEIQ
LQKWYGDLRGNPFAVEAENRVVDISGFSIGSDGHSIQYRNLLAWKYLEN
GKREFYLLMNYGKKGRIRFTDGTDIKKSGKWQGLLYGGGKAKVIDLTFD
PDDEQLIILPLAFGTRQGREFIWNDLLSLETGLIKLANGRVIEKTIYNK
KIGRDEPALFVALTFERREVVDPSNIKPVNLIGVDRGENIPAVIALTDP
EGCPLPEFKDSSGGPTDILRIGEGYKEKQRAIQAAKEVEQRRAGGYSRK
FASKSRNLADDMVRNSARDLFYHAVTHDAVLVFENLSRGFGRQGKRTFM
TERQYTKMEDWLTAKLAYEGLTSKTYLSKTLAQYTSKTGHEVHADEQAA
LNIARSWLFLNSNSTEFKSYKSGKQPFVGAWQAFYKRRLKEVWKPNA;

and has a length of from about 880 amino acids to about 1000 amino acids (e.g., from about 880 amino acids to about 900 amino acids, from about 900 amino acids to about 950 amino acids, from about 950 amino acids to about 980 amino acids, or from about 980 amino acids to about 1000 amino acids). Amino acids in bold underline are examples of amino acids that, when substituted, can generate a nuclease-deficient CasX.

In some cases, a TSLD variant CasX polypeptide comprises an amino acid sequence having at least 70%, at least 85%, at least 90%, at least 95%, at least 98%, or 100%, amino acid sequence identity to the following amino acid sequence:

(SEQ ID NO: 5)
MEKRINKIRKKLSADNATKPVSRSGPMKTLLVRVMTDDLKKRLEKRRKK
PEVMPQVISNNAANNLRMLLDDYTKMKEAILQVYWQEFKDDHVGLMCKF
AQPASKKIDQNKLKPEMDEKGNLTTAGFACSQCGQPLFVYKLEQVSEKG
KAYTNYFGRCNVAEHEKLILLAQLKPEKDSDEAVTYSLGKFGQRALDFY
SIHVTKESTHPVKPLAQIAGNRYASGPVGKALSDACMGTIASFLSKYQD
IIIEHQKVVKGNQKRLESLRELAGKENLEYPSVTLPPQPHTKEGVDAYN
EVIARVRMWVNLNLWQKLKLSRDDAKPLLRLKGFPSFPVVERRENEVDW
WNTINEVKKLIDAKRDMGRVFWSGVTAEKRNTILEGYNYLPNENDHKKR
EGSLENPKKPAKRQFGDLLLYLEKKYAGDWGKVFDEAWERIDKKIAGLT
SHIEREEARNAEDAQSKAVLTDWLRAKASFVLERLKEMDEKEFYACEIQ
LQKWYGDLRGNPFAVEAENRVVDISGFSIGSDGHSIQYRNLLAWKYLEN
GKREFYLLMNYGKKGRIRFTDGTDIKKSGKWQGLLYGGGKAKVIDLTFD
PDDEQLIILPLAFGTRQGREFIWNDLLSLETGLIKLANGRVIEKTIYNK
KIGRDEPALFVALTFERREVVDPSNIKPVNLIGVDRGENIPAVIALTDP
EGCPLPEFKDSSGGPTDILRIGEGYKEKQRAIQAAKEVEQRRAGGYSRK

-continued

FASKSRNLADDMVRNSARDLFYHAVTHDAVLVFENLSRGFGRQGKRTFM
TERQYTKMEDWLTAKLAYEGLTSKTYLSKTLAQYTSKTCSNCGFTITTA
DYDGMLVRLKKTSDGWATTLNNKELKAEGTVEKELSAELDRLSEESGNN
DISKWTKGRRDEALFLLKKRFSHRPVQEQFVCLDCGHEVHADEQAALNI
ARSWLFLNSNSTEFKSYKSGKQPFVGAWQAFYKRRLKEVWKPNA;

where the variant CasX polypeptide lacks the amino acid sequence QITYYNRYKRQ (SEQ ID NO:6). Amino acids in bold underline are examples of amino acids that, when substituted, generate a nuclease-deficient CasX. CSNC (SEQ ID NO:84; underlined) and CLDC (SEQ ID NO:85; underlined) are zinc finger motifs.

A TSLD variant CasX polypeptide of the present disclosure retains the ability, when complexed with a CasX guide RNA, to bind to a target nucleic acid comprising a nucleotide sequence having complementarity to a target-binding segment of the CasX guide RNA.

In some cases, a TSLD variant CasX polypeptide of the present disclosure retains the ability, when complexed with a CasX guide RNA, to bind to a target nucleic acid comprising a nucleotide sequence having complementarity to a target-binding segment of the CasX guide RNA; and the TSLD variant CasX polypeptide does not substantially cleave the target nucleic acid (e.g., does not carry out double-strand cleavage of the target nucleic acid and does not carry out single-strand cleavage ("nicking") of the target nucleic acid.

In some cases, a TSLD variant CasX polypeptide of the present disclosure retains the ability, when complexed with a CasX guide RNA, to bind to a target nucleic acid comprising a nucleotide sequence having complementarity to a target-binding segment of the CasX guide RNA; and the TSLD variant CasX polypeptide does not substantially carry out double-strand cleavage of the target nucleic acid, and does carry out single-strand cleavage ("nicking") of the target nucleic acid.

NTSBD Variant CasX Polypeptide—Deletion or Replacement of all or a Portion of a NTSB Domain The present disclosure provides a variant CasX polypeptide, where all or a portion of (one or more amino acids of) the non-target strand binding domain (NTSBD) is deleted, or in which one or more amino acids in the NTSBD have been replaced (substituted). Such a variant CasX polypeptide does not substantially exhibit double-stranded DNA unwinding and binding activity, but retains single-stranded DNA binding activity.

The NTSBD comprises amino acids 101-191 of the CasX amino acid sequence set forth in SEQ ID NO:1, or a corresponding region in another CasX polypeptide. For example, an NTSBD can comprise an amino acid sequence having at least 70%, at least 85%, at least 90%, at least 95%, at least 98%, or 100%, amino acid sequence identity to the following amino acid sequence:

(SEQ ID NO: 7)
PASKKIDQNKLKPEMDEKGNLTTAGFACSQCGQPLFVYKLEQVSEKGKA
YTNYFGRCNVAEHEKLILLAQLKPEKDSDEAVTYSLGKFGQR;

and can have a length of from 75 amino acids to 91 amino acids (e.g., from 75 amino acids to 80 amino acids, from 80 amino acids to 85 amino acids, or from 85 amino acids to 91 amino acids).

In some cases, an NTSBD variant CasX polypeptide of the present disclosure comprises an amino acid sequence having at least 70%, at least 85%, at least 90%, at least 95%, or at least 98%, amino acid sequence identity to the CasX1 amino acid sequence depicted FIG. 16, and lacks from about 1 amino acid to 91 amino acids (from 1 amino acid to 5 amino acids, from 5 amino acids to 10 amino acids, from 10 amino acids to 20 amino acids, from 20 amino acids to 25 amino acids, from 25 amino acids to 50 amino acids, from 50 amino acids to 75 amino acids, or from 75 amino acids to 91 amino acids) of the NTSBD.

In some cases, an NTSBD variant CasX polypeptide of the present disclosure comprises an amino acid sequence having at least 70%, at least 85%, at least 90%, at least 95%, or at least 98%, amino acid sequence identity to the following amino acid sequence:

(SEQ ID NO: 8)

MEKRINKIRKKLSADNATKPVSRSGPMKTLLVRVMTDDLKKRLEKRRKK

PEVMPQVISNNAANNLRMLLDDYTKMKEAILQVYWQEFKDDHVGLMCKF

AQALDFYSIHVTKESTHPVKPLAQIAGNRYASGPVGKALSDACMGTIAS

FLSKYQDIIIEHQKVVKGNQKRLESLRELAGKENLEYPSVTLPPQPHTK

EGVDAYNEVIARVRMWVNLNLWQKLKLSRDDAKPLLRLKGFPSFPVVER

RENEVDWWNTINEVKKLIDAKRDMGRVFWSGVTAEKRNTILEGYNYLPN

ENDHKKREGSLENPKKPAKRQFGDLLLYLEKKYAGDWGKVFDEAWERID

KKIAGLTSHIEREEARNAEDAQSKAVLTDWLRAKASFVLERLKEMDEKE

FYACEIQLQKWYGDLRGNPFAVEAENRVVDISGFSIGSDGHSIQYRNLL

AWKYLENGKREFYLLMNYGKKGRIRFTDGTDIKKSGKWQGLLYGGGKAK

VIDLTFDPDDEQLIILPLAFGTRQGREFIWNDLLSLETGLIKLANGRVI

EKTIYNKKIGRDEPALFVALTFERREVVDPSNIKPVNLIGVDRGENIPA

VIALTDPEGCPLPEFKDSSGGPTDILRIGEGYKEKQRAIQAAKEVEQRR

AGGYSRKFASKSRNLADDMVRNSARDLFYHAVTHDAVLVFENLSRGFGR

QGKRTFMTERQYTKMEDWLTAKLAYEGLTSKTYLSKTLAQYTSKTCSNC

GFTITTADYDGMLVRLKKTSDGWATTLNNKELKAEGQITYYNRYKRQTV

EKELSAELDRLSEESGNNDISKWTKGRRDEALFLLKKRFSHRPVQEQFV

CLDCGHEVHADEQAALNIARSWLFLNSNSTEFKSYKSGKQPFVGAWQAF

YKRRLKEVWKPNA;

and has a length of from about 895 amino acids to about 986 amino acids.

An NTSBD variant CasX polypeptide of the present disclosure does not substantially exhibit double-stranded DNA unwinding and binding activity, but retains single-stranded DNA binding activity. In some cases, an NTSBD variant CasX polypeptide of the present disclosure: i) binds a single-stranded target DNA when complexed with a CasX guide RNA; and ii) exhibits trans cleavage of a non-target single-stranded DNA (where a non-target single-stranded DNA is one that does not include a target nucleotide sequence that is complementary to a target-binding nucleotide sequence present in the CasX guide RNA).

In some cases, an NTSBD variant CasX polypeptide of the present disclosure: i) binds a single-stranded target DNA when complexed with a CasX guide RNA; and ii) exhibits increased trans cleavage of a non-target single-stranded DNA, compared to the trans cleavage activity of the non-target single-stranded DNA exhibited by a CasX polypeptide comprising the amino acid sequence set forth in SEQ ID NO:1.

For example, in some cases, an NTSBD variant CasX polypeptide of the present disclosure: i) binds a single-stranded target DNA when complexed with a CasX guide RNA; and ii) exhibits at least 10%, at least 20%, at least 25%, at least 50%, at least 2-fold, at least 5-fold, or at least 10-fold, greater trans cleavage of a non-target single-stranded DNA, compared to the trans cleavage activity of the non-target single-stranded DNA exhibited by a CasX polypeptide comprising the amino acid sequence set forth in SEQ ID NO:1.

Fusion Polypeptide

The present disclosure provides a CasX fusion polypeptide comprising: a) a variant CasX polypeptide of the present disclosure (e.g., a TSLD variant CasX polypeptide of the present disclosure; or an NTSBD variant CasX polypeptide of the present disclosure; and b) a heterologous fusion partner (i.e., one or more heterologous fusion partners).

In some cases, the heterologous fusion partner is a nuclear localization sequence (NLS). Suitable NLSs are described elsewhere herein. In some cases, a variant CasX polypeptide of the present disclosure comprises an NLS at the N-terminus of the variant CasX polypeptide. In some cases, a variant CasX polypeptide of the present disclosure comprises an NLS at the C-terminus of the variant CasX polypeptide. In some cases, a variant CasX polypeptide of the present disclosure comprises an NLS at the N-terminus of the variant CasX polypeptide and at the C-terminus of the variant CasX polypeptide.

In some cases, the heterologous fusion partner is a targeting polypeptide that provides for binding to a cell surface moiety on a target cell or target cell type. Suitable examples of such fusion partners are described elsewhere herein.

In some cases, the heterologous fusion partner polypeptide exhibits an enzymatic activity that modifies target DNA. Examples of such fusion partners are described elsewhere herein. For example, in some cases, the heterologous fusion partner exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity. In some cases, the heterologous fusion partner exhibits one or more enzymatic activities selected from: nuclease activity, methyltransferase activity, demethylase activity, deamination activity, depurination activity, integrase activity, transposase activity, and recombinase activity.

In some cases, the heterologous fusion partner exhibits an enzymatic activity that modifies a target polypeptide associated with a target nucleic acid. In some cases, the heterologous fusion partner is an endosomal escape polypeptide. In some cases, the heterologous fusion partner is a protein that increases or decreases transcription.

In some cases, a CasX fusion polypeptide of the present disclosure comprises combinations of heterologous fusion partners. In some cases, a CasX fusion polypeptide of the present disclosure comprises one or more NLS sequences and further comprises a heterologous fusion partner that exhibits enzymatic activity, for example DNA modification activity or any enzymatic activity described above, in any combination and order.

Modified Guide RNAs

The present disclosure provides a modified CasX single-molecule guide RNA (sgRNA). A modified CasX sgRNA of the present disclosure comprises a heterologous RNA inserted into, or replacing all or a part of, an extended stem portion of a native CasX guide RNA.

The extended stem portion of a CasX guide RNA comprises a nucleotide sequence having at least 90%, at least 95%, at least 98%, at least 99%, or 100%, nucleotide sequence identity to the following nucleotide sequence: 5'-GCGCUUAUUUAUCGGAGAGAAACCGAUA-AGUAAAACGC-3' (SEQ ID NO:9); and has a length of about 38 nucleotides (e.g., 35 nucleotides, 36 nucleotides, 37 nucleotides, or 38 nucleotides).

In some cases, from 1 nucleotide to 38 nucleotides (from 1 nucleotide to 5 nucleotides, from 5 nucleotides to 10 nucleotides, from 10 nucleotides to 15 nucleotides, from 15 nucleotides to 20 nucleotides, from 20 nucleotides to 25 nucleotides, from 25 nucleotides to 30 nucleotides, from 30 nucleotides to 35 nucleotides, or from 35 nucleotides to 38 nucleotides) of the extended stem portion of a CasX guide RNA is replaced with a heterologous RNA, to generate a modified CasX guide RNA of the present disclosure.

In some cases, a heterologous RNA is inserted into the extended stem portion of a CasX guide RNA, to generate a modified CasX guide RNA of the present disclosure.

The heterologous RNA can have a length of from 5 nucleotides to 1000 nucleotides, or more than 1000 nucleotides. The heterologous RNA can have a length of from 5 nucleotides to 500 nucleotides. The heterologous RNA can have a length of from 5 nucleotides to 100 nucleotides. The heterologous RNA can have a length of from 5 nucleotides to 50 nucleotides. The heterologous RNA can have a length of from 5 nucleotides to 25 nucleotides, from 25 nucleotides to 50 nucleotides, from 50 nucleotides to 100 nucleotides, from 100 nucleotides to 500 nucleotides, or from 500 nucleotides to 1000 nucleotides. The heterologous RNA can have a length of 5, 6, 7, 8, 9, 10, 11, 12, 13, 14, 15, 16, 17, 18, 19, 20, 21, 22, 23, 24, or 25 nucleotides.

Suitable heterologous RNAs include, but are not limited to, an aptamer, a noncoding RNA, a ribozyme, a functional RNA sequence, one of a pool of random RNA sequences, an RNA scaffold, an RNA-based sensor, an RNA-based signal processor, an RNA-based signaling device, a naturally occurring long non-coding RNA (lncRNA), a lncRNA subdomain, a synthetic lncRNA, and a synthetic lncRNA subdomain.

In some cases, the heterologous RNA is an aptamer. In some cases, the heterologous RNA is an aptamer that binds to a protein such as an adaptor protein. Non-limiting examples of adaptor proteins include MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, and PRR1.

In some cases, the heterologous RNA is an MS2 stem-loop, a PP7 stem-loop, or an L7Ae motif. An MS2 stem-loop RNA can have the following nucleotide sequence 5'-ACAUGAGGAUUACCCAUGU-3' (SEQ ID NO:65).

The present disclosure provides a system comprising: a) a modified CasX guide RNA of the present disclosure; and b) a CasX polypeptide, or a nucleic acid comprising a nucleotide sequence encoding the CasX polypeptide. The present disclosure provides a composition comprising: a) a modified CasX guide RNA of the present disclosure; and b) a CasX polypeptide, or a nucleic acid comprising a nucleotide sequence encoding the CasX polypeptide. Suitable CasX polypeptides include: a) a TSLD CasX variant polypeptide of the present disclosure; b) an NTSBD CasX variant polypeptide of the present disclosure; c) a fusion CasX polypeptide of the present disclosure (e.g., comprising a variant CasX polypeptide of the present disclosure); d) a CasX polypeptide; and e) a fusion CasX polypeptide. Suitable (d) CasX polypeptides and (d) fusion CasX polypeptides are described below.

CRISPR/CasX Proteins and Guide RNAs

A CRISPR/Cas endonuclease (e.g., a CasX protein) interacts with (binds to) a corresponding guide RNA (e.g., a CasX guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasX protein forms a complex with a CasX guide RNA and the guide RNA provides sequence specificity to the RNP complex via the guide sequence. The CasX protein of the complex provides the site-specific activity. In other words, the CasX protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasX polypeptide (and/or a nucleic acid encoding the CasX polypeptide) (e.g., where the CasX polypeptide can be a naturally existing protein, a nickase CasX protein, a dCasX protein (a CasX protein that does not exhibit nuclease activity), a chimeric CasX protein, etc.). The present disclosure provides compositions comprising a CasX guide RNA (and/or a nucleic acid encoding the CasX guide RNA) (e.g., where the CasX guide RNA can be in dual or single guide format). The present disclosure provides compositions comprising (a) a CasX polypeptide (and/or a nucleic acid encoding the CasX polypeptide) (e.g., where the CasX polypeptide can be a naturally existing protein, a nickase CasX protein, a dCasX protein, a chimeric CasX protein, etc.) and (b) a CasX guide RNA (and/or a nucleic acid encoding the CasX guide RNA) (e.g., where the CasX guide RNA can be in dual or single guide format). The present disclosure provides a nucleic acid/protein complex (RNP complex) comprising: (a) a CasX polypeptide of the present disclosure (e.g., where the CasX polypeptide can be a naturally existing protein, a nickase CasX protein, a dCasX protein, a chimeric CasX protein, etc.); and (b) a CasX guide RNA (e.g., where the CasX guide RNA can be in dual or single guide format).

CasX Protein

A CasX polypeptide (this term is used interchangeably with the term "CasX protein") can bind and/or modify (e.g., cleave, nick, methylate, demethylate, etc.) a target nucleic acid and/or a polypeptide associated with target nucleic acid (e.g., methylation or acetylation of a histone tail) (e.g., In some cases, the CasX protein includes a fusion partner with an activity, and In some cases, the CasX protein provides nuclease activity). In some cases, the CasX protein is a naturally-occurring protein (e.g., naturally occurs in prokaryotic cells). In other cases, the CasX protein is not a naturally-occurring polypeptide (e.g., the CasX protein is a variant CasX protein, a chimeric protein, and the like).

Assays to determine whether given protein interacts with a CasX guide RNA can be any convenient binding assay that tests for binding between a protein and a nucleic acid. Suitable binding assays (e.g., gel shift assays) will be known to one of ordinary skill in the art (e.g., assays that include adding a CasX guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CasX protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring guide RNA includes a tracrRNA hybridized to a crRNA, where the crRNA includes a guide sequence that hybridizes to a target sequence in the target DNA.

In some embodiments, the CasX protein of the subject methods and/or compositions is (or is derived from) a naturally occurring (wild type) protein. Examples of naturally occurring CasX proteins are depicted in FIG. 16 and FIG. 17.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX amino acid sequence depicted in FIG. 16. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX amino acid sequence depicted in FIG. 16. In some cases, a CasX protein includes an amino acid sequence having 80% or more sequence identity (e.g., 85% or more, 90% or more, 95% or more, 97% or more, 98% or more, 99% or more, or 100% sequence identity) with the CasX amino acid sequence depicted in FIG. 16. In some cases, a CasX protein includes an amino acid sequence having 90% or more sequence identity (e.g., 95% or more, 97% or more, 98% or more, 99% or more, or 100% sequence identity) with the CasX amino acid sequence depicted in FIG. 16. In some cases, a CasX protein includes an amino acid sequence having the CasX amino acid sequence depicted in FIG. 16. In some cases, a CasX protein includes an amino acid sequence having the CasX amino acid sequence depicted in FIG. 16, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX amino acid sequence depicted in FIG. 17. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX amino acid sequence depicted in FIG. 17. In some cases, a CasX protein includes an amino acid sequence having 80% or more sequence identity (e.g., 85% or more, 90% or more, 95% or more, 97% or more, 98% or more, 99% or more, or 100% sequence identity) with the CasX amino acid sequence depicted in FIG. 17. In some cases, a CasX protein includes an amino acid sequence having 90% or more sequence identity (e.g., 95% or more, 97% or more, 98% or more, 99% or more, or 100% sequence identity) with the CasX amino acid sequence depicted in FIG. 17. In some cases, a CasX protein includes an amino acid sequence having the CasX amino acid sequence depicted in FIG. 17. In some cases, a CasX protein includes an amino acid sequence having the CasX amino acid sequence depicted in FIG. 17, with the exception that the sequence includes an amino acid substitution (e.g., 1, 2, or 3 amino acid substitutions) that reduces the naturally occurring catalytic activity of the protein (e.g., such as at amino acid positions described below).

CasX Protein Domains

The domains of a CasX protein are generally as follows: a CasX protein includes an N-terminal domain roughly 650 amino acids in length (e.g., 663 for CasX1 and 650 for CasX2), and a C-terminal domain that includes 3 partial RuvC domains (RuvC-I, RuvC-II, and RuvC-III, also referred to herein as subdomains) that are not contiguous with respect to the primary amino acid sequence of the CasX protein, but form a RuvC domain once the protein is produced and folds. Thus, in some cases, a CasX protein (of the subject compositions and/or methods) includes an amino acid sequence with an N-terminal domain (e.g., not including any fused heterologous sequence such as an NLS and/or a domain with a catalytic activity) having a length in a range of from 500-750 amino acids (e.g., from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids). In some cases, a CasX protein (of the subject compositions and/or methods) includes an amino acid sequence having a length (e.g., not including any fused heterologous sequence such as an NLS and/or a domain with a catalytic activity) in a range of from 500-750 amino acids (e.g. from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids) that is N-terminal to a split Ruv C domain (e.g., 3 partial RuvC domains—RuvC-I, RuvC-II, and RuvC-III).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 16. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 16. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 16. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 16.

CasX Variants

A variant CasX protein has an amino acid sequence that is different by at least one amino acid (e.g., has a deletion, insertion, substitution, fusion) when compared to the amino acid sequence of the corresponding wild type CasX protein. A CasX protein that cleaves one strand but not the other of a double stranded target nucleic acid is referred to herein as a "nickase" (e.g., a "nickase CasX"). A CasX protein that has substantially no nuclease activity is referred to herein as a dead CasX protein ("dCasX") (with the caveat that nuclease activity can be provided by a heterologous polypeptide—a fusion partner—in the case of a chimeric CasX protein, which is described in more detail below). For any of the CasX variant proteins described herein (e.g., nickase CasX, dCasX, chimeric CasX), the CasX variant can include a CasX protein sequence with the same parameters described above (e.g., domains that are present, percent identity, and the like).

Variants—Catalytic Activity

In some cases, the CasX protein is a variant CasX protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasX protein is a catalytically 'dead' protein (has substantially no cleavage activity) and can be referred to as a 'dCasX.' In some cases, the variant CasX protein is a nickase (cleaves only one strand of a double stranded target nucleic acid, e.g., a double stranded target DNA). As described in more detail herein, in some cases, a CasX protein (in some case a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein).

Conserved catalytic residues of CasX include D672, E769, D935 when numbered according to CasX1 (SEQ ID NO:1) and 659D, 756E, and 922D when numbered according to CasX2 (SEQ ID NO:2) (these residues are underlined in FIG. 16).

Thus, in some cases, the CasX protein has reduced activity and one or more of the above described amino acids (or one or more corresponding amino acids of any CasX protein) are mutated (e.g., substituted with an alanine). In some cases, the variant CasX protein is a catalytically "dead" protein (is catalytically inactive) and is referred to as "dCasX." A dCasX protein can be fused to a fusion partner that provides an activity, and in some cases, the dCasX (e.g., one without a fusion partner that provides catalytic activity—but which can have an NLS when expressed in a eukaryotic cell) can bind to target DNA and can block RNA polymerase from translating from a target DNA. In some cases, the variant CasX protein is a nickase (cleaves only one strand of a double stranded target nucleic acid, e.g., a double stranded target DNA).

Variants—Chimeric CasX (i.e., Fusion Proteins)

As noted above, in some cases, a CasX protein (in some cases a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein). A heterologous polypeptide to which a CasX protein can be fused is referred to herein as a 'fusion partner.'

The fusion partners described below can also be fusion partners of a TSLD variant CasX polypeptide of the present disclosure, or an NTSBD variant CasX polypeptide of the present disclosure.

In some cases, the fusion partner can modulate transcription (e.g., inhibit transcription, increase transcription) of a target DNA. For example, in some cases, the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases, the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasX protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasX protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of suitable fusion partners are dihydrofolate reductase (DHFR) destabilization domain (e.g., to generate a chemically controllable chimeric CasX protein), and a chloroplast transit peptide. Suitable chloroplast transit peptides include, but are not limited to:

```
                                      (SEQ ID NO: 10)
MASMISSSAVTTVSRASRGQSAAMAPFGGLKSMTGFPVRKVNTDITSIT
SNGGRVKCMQVWPPIGKKKFETLSYLPPLTRDSRA;

                                      (SEQ ID NO: 11)
MASMISSSAVTTVSRASRGQSAAMAPFGGLKSMTGFPVRKVNTDITSIT
SNGGRVKS;

                                      (SEQ ID NO: 16)
MASSMLSSATMVASPAQATMVAPFNGLKSSAAFPATRKANNDITSITSN
GGRVNCMQVWPPIEKKKFETLSYLPDLTDSGGRVNC;

                                      (SEQ ID NO: 17)
MAQVSRICNGVQNPSLISNLSKSSQRKSPLSVSLKTQQHPRAYPISSSW
GLKKSGMTLIGSELRPLKVMSSVSTAC;

                                      (SEQ ID NO: 18)
MAQVSRICNGVWNPSLISNLSKSSQRKSPLSVSLKTQQHPRAYPISSSW
GLKKSGMTLIGSELRPLKVMSSVSTAC;

                                      (SEQ ID NO: 19)
MAQINNMAQGIQTLNPNSNFHKPQVPKSSSFLVFGSKKLKNSANSMLVL
KKDSIFMQLFCSFRISASVATAC;

                                      (SEQ ID NO: 20)
MAALVTSQLATSGTVLSVTDRFRRPGFQGLRPRNPADAALGMRTVGASA
APKQSRKPHRFDRRCLSMVV;

                                      (SEQ ID NO: 22)
MAALTTSQLATSATGFGIADRSAPSSLLRHGFQGLKPRSPAGGDATSLS
VTTSARATPKQQRSVQRGSRRFPSVVVC;

                                      (SEQ ID NO: 23)
MASSVLSSAAVATRSNVAQANMVAPFTGLKSAASFPVSRKQNLDITSIA
SNGGRVQC;

                                      (SEQ ID NO: 24)
MESLAATSVFAPSRVAVPAARALVRAGTVVPTRRTSSTSGTSGVKCSAA
VTPQASPVISRSAAAA; and

                                      (SEQ ID NO: 26)
MGAAATSMQSLKFSNRLVPPSRRLSPVPNNVTCNNLPKSAAPVRTVKCC
ASSWNSTINGAAATTNGASAASS.
```

In some case, a CasX fusion polypeptide of the present disclosure comprises: a) a CasX polypeptide of the present disclosure; and b) a chloroplast transit peptide. Thus, for example, a CRISPR-CasX complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasX fusion polypeptide of the present disclosure can comprise: a) a CasX polypeptide of the present disclosure; and b) an endosomal escape peptide. In some cases, an endosomal escape polypeptide comprises the amino acid sequence GLFXALLXLLXSLWXLLLXA (SEQ ID NO:27), wherein each X is independently selected from lysine, histidine, and arginine. In some cases, an endosomal escape polypeptide comprises the amino acid sequence GLFHALLHLLHSLWHLLLHA (SEQ ID NO:79).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et. al., Cell. 2013 Jul. 18; 154(2):442-51; Kearns et al., Nat Methods. 2015 May; 12(5):401-3; Mendenhall et. al., Nat Biotechnol. 2013 December; 31(12):1133-6; Hilton et. al., Nat Biotechnol. 2015 May; 33(5):510-7; Gordley et. al., Proc Natl Acad Sci USA. 2009 Mar. 31; 106(13):5053-8; Akopian et. al., Proc Natl Acad Sci USA. 2003 Jul. 22; 100(15):8688-91; Tan et., al., J Virol. 2006 February; 80(4): 1939-48; Tan et. al., Proc Natl Acad Sci USA. 2003 Oct. 14; 100(21):11997-2002; Papworth et. al., Proc Natl Acad Sci USA. 2003 Feb. 18; 100(4):1621-6; Sanjana et. al., Nat Protoc. 2012 Jan. 5; 7(1):171-92; Beerli et. al., Proc Natl Acad Sci USA. 1998 Dec. 8; 95(25):14628-33; Snowden et. al., Curr Biol. 2002 Dec. 23; 12(24):2159-66; Xu et. al., Xu et. al., Cell Discov. 2016 May 3; 2:16009; Komor et al., Nature. 2016 Apr. 20; 533(7603):420-4; Chaikind et. al., Nucleic Acids Res. 2016 Aug. 11; Choudhury at. al., Oncotarget. 2016 Jun. 23; Du et. al., Cold Spring Harb Protoc. 2016 Jan. 4; Pham et. al., Methods Mol Biol. 2016; 1358: 43-57; Balboa et al., Stem Cell Reports. 2015 Sep. 8; 5(3):448-59; Hara et. al., Sci Rep. 2015 Jun. 9; 5:11221; Piatek et. al., Plant Biotechnol J. 2015 May; 13(4):578-89; Hu et al., Nucleic Acids Res. 2014 April; 42(7):4375-90; Cheng et. al., Cell Res. 2013 October; 23(10):1163-71; cheng et. al., Cell Res. 2013 October; 23(10):1163-71; and Macder et. al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasX polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasX polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., cIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., cIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasX polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple co-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A. Lamin B, etc.), protein docking elements (e.g., FKBP/FRB, Pil1/Aby1, etc.).

Examples of various additional suitable heterologous polypeptide (or fragments thereof) for a subject chimeric CasX polypeptide include, but are not limited to those described in the following applications (which publications are related to other CRISPR endonucleases such as Cas9, but the described fusion partners can also be used with CasX instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasX fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for case of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases, a CasX protein (e.g., a wild type CasX protein, a variant CasX protein, a chimeric CasX protein, a dCasX protein, a chimeric CasX protein where the CasX portion has reduced nuclease activity-such as a dCasX protein fused to a fusion partner, and the like) includes (is fused to) a nuclear localization signal (NLS) (e.g. in some cases 2 or more, 3 or more, 4 or more, or 5 or more NLSs). Thus, in some cases, a CasX polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasX protein (e.g., a wild type CasX protein, a variant CasX protein, a chimeric CasX protein, a dCasX protein, a chimeric CasX protein where the CasX portion has reduced nuclease activity-such as a dCasX protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO:28); the NLS from nucleoplasmin (e.g., the nucleoplasmin bipartite NLS with the sequence KRPAATKKAGQAKKKK (SEQ ID NO:29)); the c-myc NLS having the amino acid sequence PAAKRVKLD (SEQ ID NO:30) or RQRRNELKRSP (SEQ ID NO:31); the hRNPA1 M9 NLS having the sequence NQSSNFGPMKGGNFGGRSSGPYGGGGQYFAKPRNQGGY (SEQ ID NO:32); the sequence RMRIZFKNKGKDTAELRRRRVEVSVELRKAKKDEQILKRRNV (SEQ ID NO:33) of the IBB domain from importin-alpha; the sequences VSRKRPRP (SEQ ID NO:34) and PPKKARED (SEQ ID NO:77) of the myoma T protein; the sequence PQPKKKPL (SEQ ID NO:35) of human p53; the sequence SALIKKKKKMAP (SEQ ID NO:36) of mouse c-abl IV; the sequences DRLRR (SEQ ID NO:37) and PKQKKRK (SEQ ID NO:38) of the influenza virus NS1; the sequence RKLKKKIKKL (SEQ ID NO:39) of the Hepatitis virus delta antigen; the sequence REKKKFLKRR (SEQ ID NO:66) of the mouse Mx1 protein; the sequence KRKGDEVDGVDEVAKKKSKK (SEQ ID NO:40) of the human poly(ADP-ribose) polymerase; and the sequence RKCLQAGMNLEARKTKK (SEQ ID NO:41) of the steroid hormone receptors (human) glucocorticoid. In general, NLS (or multiple NLSs) are of sufficient strength to drive accumulation of the CasX protein in a detectable amount in the nucleus of a eukaryotic cell. Detection of accumulation in the nucleus may be performed by any suitable technique. For example, a detectable marker may be fused to the CasX protein such that location within a cell may be visualized. Cell nuclei may also be isolated from cells, the contents of which may then be analyzed by any suitable process for detecting protein, such as immunohistochemistry. Western blot, or enzyme activity assay. Accumulation in the nucleus may also be determined indirectly.

In some cases, a CasX fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasX to generate a fusino protein, or linked to a variant CasX protein such as a dCasX, nickase CasX, or chimeric CasX protein to generate a fusion protein). In some embodiments, a PTD is covalently linked to the carboxyl terminus of a polypeptide (e.g., linked to a wild type CasX to generate a fusino protein, or linked to a variant CasX protein such as a dCasX, nickase CasX, or chimeric CasX protein to generate a fusion protein). In some cases, the PTD is inserted internally in the CasX fusion polypeptide (i.e., is not at the N- or C-terminus of the CasX fusion polypeptide) at a suitable insertion site. In some cases, a subject CasX fusion polypeptide includes (is conjugated to, is fused to) one or more PTDs (e.g., two or more, three or more, four or more PTDs). In some cases a PTD includes a nuclear localization signal (NLS) (e.g. in some cases 2 or more, 3 or more, 4 or more, or 5 or more NLSs). Thus, in some cases, a CasX fusion polypeptide includes one or more NLSs (e.g., 2 or more, 3 or more, 4 or more, or 5 or more NLSs). In some embodiments, a PTD is covalently linked to a nucleic acid (e.g., a CasX guide nucleic acid, a polynucleotide encoding a CasX guide nucleic acid, a polynucleotide encoding a CasX fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:44); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9 (6):489-96); an *Drosophila* Antennapedia protein transduction domain (Noguchi et al. (2003) *Diabetes* 52 (7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:45); Transportan GWTLNSAGYLLGKINLKALAALAKKIL (SEQ ID NO:46); KALAWEAKLAKALAKALAKHLAKALAKALKCEA (SEQ ID NO:47); and RQIKIWFQNRRMKWKK (SEQ ID NO:48). Exemplary PTDs include but are not limited to, YGRKKRRQRRR (SEQ ID NO:44), RKKRRQRRR (SEQ ID NO:49); an arginine homopolymer of from 3 arginine residues to 50 arginine residues; Exemplary PTD domain amino acid sequences include, but are not limited to, any of the following: YGRKKRRQRRR (SEQ ID NO:44); RKKRRQRR (SEQ ID NO:50); YARAAARQARA (SEQ ID NO:80); THRLPRRRRRR (SEQ ID NO:51); and GGRRARRRRRR (SEQ ID NO:52). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject CasX protein can be fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO:53), $GGSGGS_n$ (SEQ ID NO:54), and $GGGS_n$ (SEQ ID NO:55), where n is an integer of at least one), glycine-alanine polymers, alanine-serine polymers. Exemplary linkers can comprise amino acid sequences including, but not limited to, GGSG (SEQ ID NO:56), GGSGG (SEQ ID NO:57), GSGSG (SEQ ID NO:58), GSGGG (SEQ ID NO:59), GGGSG (SEQ ID NO:60), GGGS (SEQ ID NO:61), GSSSG (SEQ ID NO:62), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasX polypeptide of the present disclosure (including a TSLD variant CasX polypeptide of the present disclosure; an NTSBD variant CasX polypeptide of the present disclosure; a fusion CasX polypeptide of the present disclosure) comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycocrythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A CasX protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for a CasX protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some embodiments (e.g., when CasX1 as described herein is used), the PAM sequence of the non-complementary strand is 5'-TCN-3' (and in some cases TTCN), where N is any DNA nucleotide. As an example, the PAM (TCN) (on the non-complementary strand) can be TCA or TTCA, and the PAM is 5' of the target sequence.

In some cases, different CasX proteins (i.e., CasX proteins from various species) may be advantageous to use in the various provided methods in order to capitalize on various enzymatic characteristics of the different CasX proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasX proteins from different species may require different PAM sequences in the target DNA. Thus, for a particular CasX protein of choice, the PAM sequence requirement may be different than 5'-TCN-3' sequence described above. Various methods (including in silico and/or wet lab methods) for identification of the appropriate PAM sequence are known in the art and are routine, and any convenient method can be used.

CasX Guide RNA

A nucleic acid molecule that binds to a CasX protein, forming a ribonucleoprotein complex (RNP), and targets the complex to a specific location within a target nucleic acid (e.g., a target DNA) is referred to herein as a "CasX guide RNA" or simply as a "guide RNA." It is to be understood that in some cases, a hybrid DNA/RNA can be made such that a CasX guide RNA includes DNA bases in addition to RNA bases, but the term "CasX guide RNA" is still used to encompass such a molecule herein.

A CasX guide RNA can be said to include two segments, a targeting segment and a protein-binding segment. The targeting segment of a CasX guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasX polypeptide. The protein-binding segment of a subject CasX guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasX guide RNA (the guide sequence of the CasX guide RNA) and the target nucleic acid.

A CasX guide RNA and a CasX protein, e.g., a fusion CasX polypeptide, form a complex (e.g., bind via non-covalent interactions). The CasX guide RNA provides target specificity to the complex by including a targeting segment, which includes a guide sequence (a nucleotide sequence that is complementary to a sequence of a target nucleic acid). The CasX protein of the complex provides the site-specific activity (e.g., cleavage activity provided by the CasX protein and/or an activity provided by the fusion partner in the case of a chimeric CasX protein). In other words, the CasX protein is guided to a target nucleic acid sequence (e.g. a target sequence) by virtue of its association with the CasX guide RNA.

The "guide sequence" also referred to as the "targeting sequence" of a CasX guide RNA can be modified so that the CasX guide RNA can target a CasX protein (e.g., a naturally occurring CasX protein, a fusion CasX polypeptide (chimeric CasX), and the like) to any desired sequence of any desired target nucleic acid, with the exception (e.g., as described herein) that the PAM sequence can be taken into account. Thus, for example, a CasX guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

A subject CasX guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "CasX dual guide RNA"). In some embodiments, the activator and targeter are covalently linked to one another (e.g., via intervening nucleotides) and the guide RNA is referred to herein as a "single guide RNA", an "sgRNA." a "single-molecule guide RNA," or a "one-molecule guide RNA" (e.g., a "CasX single guide RNA"). Thus, a subject CasX single guide RNA comprises a targeter (e.g., targeter-RNA) and an activator (e.g., activator-RNA) that are linked to one another (e.g., by intervening nucleotides), and hybridize to one another to form the double stranded RNA duplex (dsRNA duplex) of the protein-binding segment of the guide RNA, thus resulting in a stem-loop structure. Thus, the targeter and the activator each have a duplex-forming segment, where the duplex forming segment of the targeter and the duplex-forming segment of the activator have complementarity with one another and hybridize to one another.

In some embodiments, the linker of a CasX single guide RNA is a stretch of nucleotides (e.g., GAAA). In some cases, the targeter and activator of a CasX single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a CasX single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a CasX single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

Guide Sequence of a CasX Guide RNA

The targeting segment of a subject CasX guide RNA includes a guide sequence (i.e., a targeting sequence), which is a nucleotide sequence that is complementary to a sequence (a target site) in a target nucleic acid. In other words, the targeting segment of a CasX guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasX guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 19-30 nucleotides (nt) (e.g., from 19-25, 19-22, 19-20, 20-30, 20-25, or 20-22 nt). In some cases, the guide sequence has a length in a range of from 19-25 nucleotides (nt) (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt.

Protein-Binding Segment of a CasX Guide RNA

The protein-binding segment of a subject CasX guide RNA interacts with a CasX protein. The CasX guide RNA guides the bound CasX protein to a specific nucleotide sequence within target nucleic acid via the above mentioned guide sequence. The protein-binding segment of a CasX guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some embodiments, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject CasX guide RNA (in dual guide or single guide RNA format) can include one or more (1, 2, 3, 4, 5, etc) mutations relative to a naturally occurring duplex region. For example, in some cases a base pair can be maintained while the nucleotides contributing to the base pair from each segment (targeter and activator) can be different. In some cases, the duplex region of a subject CasX guide RNA includes more paired bases, less paired bases, a smaller bulge, a larger bulge, fewer bulges, more bulges, or any convenient combination thereof, as compared to a naturally occurring duplex region (of a naturally occurring CasX guide RNA).

In some cases, the activator (e.g., activator-RNA) of a subject CasX guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex. In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of 5'-most hairpin stem. In some cases, the activator-RNA (e.g., in dual or single guide RNA format) comprises at least 4 nt 5' of 5'-most hairpin stem.

In some cases, the activator-RNA (e.g., in dual or single guide format) has a length of 65 nucleotides (nt) or more (e.g., 66 or more, 67 or more, 68 or more, 69 or more, 70 or more, or 75 or more nt). In some cases, the activator-RNA (e.g., in dual or single guide format) has a length of 66 nt or more (e.g., 67 or more, 68 or more, 69 or more, 70 or more, or 75 or more nt). In some cases, the activator-RNA (e.g., in dual or single guide format) has a length of 67 nt or more (e.g., 68 or more, 69 or more, 70 or more, or 75 or more nt).

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at 5' end relative to a naturally occurring CasX activator. In some cases, the activator is extended at the 5' end relative to a naturally occurring CasX activator.

The term "activator" or "activator RNA" is used herein to mean a tracrRNA-like molecule (tracrRNA: "trans-acting CRISPR RNA") of a CasX dual guide RNA (and therefore of a CasX single guide RNA when the "activator" and the "targeter" are linked together by, e.g., intervening nucleotides). Thus, for example, a CasX guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a CasX dual guide RNA. The term "activator" is used herein to encompass naturally existing tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which CasX protein binds). In some cases, the activator provides one or more stem loops that can interact with CasX protein. An activator can be referred to as having a tracr sequence (tracrRNA sequence) and in some cases is a tracrRNA, but the term "activator" is not limited to naturally existing tracrRNAs.

In some cases (e.g., in some cases where the guide RNA is in single guide format), the activator-RNA is truncated (shorter) relative to the corresponding wild type tracrRNA. In some cases (e.g., in some cases where the guide RNA is in single guide format) the activator-RNA is not truncated (shorter) relative to the corresponding wild type tracrRNA. In some cases (e.g., in some cases where the guide RNA is in single guide format) the activator-RNA has a length that is greater than 50 nt (e.g., greater than 55 nt, greater than 60 nt, greater than 65 nt, greater than 70 nt, greater than 75 nt, greater than 80 nt). In some cases (e.g., in some cases where the guide RNA is in single guide format) the activator-RNA has a length that is greater than 80 nt. In some cases (e.g., in some cases where the guide RNA is in single guide format) the activator-RNA has a length in a range of from 51 to 90 nt (e.g., from 51-85, 51-84, 55-90, 55-85, 55-84, 60-90, 60-85, 60-84, 65-90, 65-85, 65-84, 70-90, 70-85, 70-84, 75-90, 75-85, 75-84, 80-90, 80-85, or 80-84 nt). In some cases (e.g., in some cases where the guide RNA is in single guide format) the activator-RNA has a length in a range of from 80-90 nt.

The term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together, e.g., by intervening nucleotides). Thus, for example, a CasX guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail herein), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

As noted above, a targeter comprises both the guide sequence of the CasX guide RNA and a stretch (a "duplex-forming segment") of nucleotides that forms one half of the dsRNA duplex of the protein-binding segment of the CasX guide RNA. A corresponding tracrRNA-like molecule (activator) comprises a stretch of nucleotides (a duplex-forming segment) that forms the other half of the dsRNA duplex of the protein-binding segment of the CasX guide RNA. In other words, a stretch of nucleotides of the targeter is complementary to and hybridizes with a stretch of nucleotides of the activator to form the dsRNA duplex of the protein-binding segment of a CasX guide RNA. As such, each targeter can be said to have a corresponding activator (which has a region that hybridizes with the targeter). The targeter molecule additionally provides the guide sequence. Thus, a targeter and an activator (as a corresponding pair) hybridize to form a CasX guide RNA. The particular sequence of a given naturally existing crRNA or tracrRNA molecule can be characteristic of the species in which the RNA molecules are found. Examples of suitable activators and targeters are provided herein.

Example Guide RNA Sequences

The following are non-limiting examples of CasX1 tracrRNA sequences:

```
                                             (SEQ ID NO: 63)
UUAUUCCAUUACUUUGGAGCCAGUCCCAGCGACUAUGUCGUAUGGACGA
AGCGCUUAUUUAUCGGAGA and
                                             (SEQ ID NO: 64)
UUAUUCCAUUACUUUGGAGCCAGUCCCAGCGACUAUGUCGUAUGGACGA
AGCGCUUAUUUAUCGG.
```

The following are non-limiting examples of CasX2 tracrRNA sequences:

```
                                             (SEQ ID NO: 67)
UUAUCUCAUUACUUUGAGAGCCAUCACCAGCGACUAUGUCGUAUGGGUA
AAGCGCUUAUUUAUCGGAGA and

                                             (SEQ ID NO: 68)
UUAUCUCAUUACUUUGAGAGCCAUCACCAGCGACUAUGUCGUAUGGGUA
AAGCGCUUAUUUAUCGG.
```

The CasX1 crRNA sequence CCGAUAAGUAAAACG-CAUCAAAGNNNNNNNNNNNNNNNNNNNN (SEQ ID NO:69) can be compared to the CasX2 crRNA sequence UCUCCGAUAAAUAAGAAGCAU-CAAAGNNNNNNNNNNNNNNNNNNNN (SEQ ID NO:70).

Example Targeter-RNA (e.g., crRNA) Sequences

In some cases, the targeter-RNA (e.g., in dual or single guide RNA format) comprises (e.g., in addition to a guide sequence) the crRNA sequence CCGAUAAGUAAAACG-CAUCAAAG (SEQ ID NO:71). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence CCGAUAAGUAAAACGCAUCAAAG (SEQ ID NO:71).

In some cases, the targeter-RNA comprises (e.g., in addition to a guide sequence) the crRNA sequence AUUUGAAGGUAUCUCCGAUAAGUAAAACGCAU-CAAAG (SEQ ID NO:12). In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence AUUUGAAGGUAUCUCCGAUA-AGUAAAACGCAUCAAAG (SEQ ID NO:12).

In some cases, the targeter-RNA (e.g., in dual or single guide RNA format) comprises (e.g., in addition to a guide sequence) the crRNA sequence UCUCCGAUAAAUAAGAAGCAUCAAAG (SEQ ID NO:72). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence UCUCCGAUAAAUAAGAAGCAUCAAAG (SEQ ID NO:72).

In some cases, the targeter-RNA (e.g., in dual or single guide RNA format) comprises (e.g., in addition to a guide sequence) the crRNA sequence GUUUACACACUCCCU-CUCAUAGGGU (SEQ ID NO:14). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence GUUUACACACUCCCUCU-CAUAGGGU (SEQ ID NO:14).

In some cases, the targeter-RNA (e.g., in dual or single guide RNA format) comprises (e.g., in addition to a guide sequence) the crRNA sequence GUUUACACACUCCCU-CUCAUGAGGU (SEQ ID NO:13). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence GUUUACACACUCCCUCU-CAUGAGGU (SEQ ID NO:13).

In some cases, the targeter-RNA (e.g., in dual or single guide RNA format) comprises (e.g., in addition to a guide sequence) the crRNA sequence UUUUACAUACCCCCU-CUCAUGGGAU (SEQ ID NO:15). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence UUUUACAUACCCCCUCUCAUGG-GAU (SEQ ID NO:15).

In some cases, the targeter-RNA (e.g., in dual or single guide RNA format) comprises (e.g., in addition to a guide sequence) the crRNA sequence GUUUACACACUCCCU-CUCAUGGGGG (SEQ ID NO:73). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence GUUUACACACUCCCUCU-CAUGGGGG (SEQ ID NO:73).

Example Activator-RNAs (e.g., tracrRNA) Sequences

In some cases, the activator-RNA (e.g., in dual or single guide RNA format) comprises the tracrRNA sequence (SEQ ID NO: 21)
ACAUCUGGCGCGUUUAUUCCAUUACUUUGGAGCCAGUCCCAGCGACUAU
GUCGUAUGGACGAAGCGCUUAUUUAUCGGAGA.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 21)
ACAUCUGGCGCGUUUAUUCCAUUACUUUGGAGCCAGUCCCAGCGACUAU
GUCGUAUGGACGAAGCGCUUAUUUAUCGGAGA.

In some cases, the activator-RNA (e.g., in dual or single guide RNA format) comprises the tracrRNA sequence (SEQ ID NO: 64)
UUAUUCCAUUACUUUGGAGCCAGUCCCAGCGACUAUGUCGUAUGGACGA
AGCGCUUAUUUAUCGG.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 64)
UUAUUCCAUUACUUUGGAGCCAGUCCCAGCGACUAUGUCGUAUGGACGA
AGCGCUUAUUUAUCGG.

In some cases, the activator-RNA (e.g., in dual or single guide RNA format) comprises the tracrRNA sequence (SEQ ID NO: 74)
AAGUAGUAAAUUACAUCUGGCGCGUUUAUUCCAUUACUUUGGAGCCAGU
CCCAGCGACUAUGUCGUAUGGACGAAGCGCUUAUUUAUCGGAGA.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 74)
AAGUAGUAAAUUACAUCUGGCGCGUUUAUUCCAUUACUUUGGAGCCAGU
CCCAGCGACUAUGUCGUAUGGACGAAGCGCUUAUUUAUCGGAGA.

In some cases, the activator-RNA (e.g., in dual or single guide RNA format) comprises the tracrRNA sequence (SEQ ID NO: 63)
UUAUUCCAUUACUUUGGAGCCAGUCCCAGCGACUAUGUCGUAUGGACGA
AGCGCUUAUUUAUCGGAGA.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 63)
UUAUUCCAUUACUUUGGAGCCAGUCCCAGCGACUAUGUCGUAUGGACGA
AGCGCUUAUUUAUCGGAGA.

In some cases, the activator-RNA (e.g., in dual or single guide RNA format) comprises the tracrRNA sequence (SEQ ID NO: 67)
UUAUCUCAUUACUUUGAGAGCCAUCACCAGCGACUAUGUCGUAUGGGUA
AAGCGCUUAUUUAUCGGAGA.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 67)
UUAUCUCAUUACUUUGAGAGCCAUCACCAGCGACUAUGUCGUAUGGGUA
AAGCGCUUAUUUAUCGGAGA.

In some cases, the activator-RNA (e.g., in dual or single guide RNA format) comprises the tracrRNA sequence (SEQ ID NO: 68)
UUAUCUCAUUACUUUGAGAGCCAUCACCAGCGACUAUGUCGUAUGGGUA
AAGCGCUUAUUUAUCGG.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 68)
UUAUCUCAUUACUUUGAGAGCCAUCACCAGCGACUAUGUCGUAUGGGUA
AAGCGCUUAUUUAUCGG In some cases, the activator-RNA (e.g., in dual or single guide RNA format) comprises a tracrRNA sequence from within the following sequence:

(SEQ ID NO: 75)
UAAAUUUUUUGAGCCCUAUCUCCGCGAGGAAGACAGGGCUCUUUUCAUG
AGAGGAAGCUUUUAUACCCGACCGGUAAUCCGGUCGGGGGAUUGGCCGU
UGAAACGAUUUUAAAGCGGCCAAUGGGCCCCUCUAUAUGGAUACUACUU
AUAUAAGGAGCUUGGGGAAGAAGAUAGCUUAAUCCCGCUAUCUUGUCAA
GGGGUUGGGGGAGUAUCAGUAUCCGGCAGGCGCC.

In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the a tracrRNA sequence from within:

(SEQ ID NO: 75)
UAAAUUUUUUGAGCCCUAUCUCCGCGAGGAAGACAGGGCUCUUUUCAUG
AGAGGAAGCUUUUAUACCCGACCGGUAAUCCGGUCGGGGGAUUGGCCGU
UGAAACGAUUUUAAAGCGGCCAAUGGGCCCCUCUAUAUGGAUACUACUU
AUAUAAGGAGCUUGGGGAAGAAGAUAGCUUAAUCCCGCUAUCUUGUCAA
GGGGUUGGGGGAGUAUCAGUAUCCGGCAGGCGCC.

In some cases, a CasX single guide RNA comprises the sequence (SEQ ID NO: 76)
UUAUUCCAUUACUUUGGAGCCAGUCCCAGCGACUAUGUCGUAUGGACGA
AGCGCUUAUUUAUCGGgaaaCCGAUAAGUAAAACGCAUCAAAG.

In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 76)
UUAUUCCAUUACUUUGGAGCCAGUCCCAGCGACUAUGUCGUAUGGACGA
AGCGCUUAUUUAUCGGgaaaCCGAUAAGUAAAACGCAUCAAAG.

In some cases, a CasX single guide RNA comprises the sequence (SEQ ID NO: 42)
ACAUCUGGCGCGUUUAUUCCAUUACUUUGGAGCCAGUCCCAGCGACUAU
GUCGUAUGGACGAAGCGCUUAUUUAUCGGAGAgaaaCCGAUAAGUAAAA
CGCAUCAAAG.

In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 42)
ACAUCUGGCGCGUUUAUUCCAUUACUUUGGAGCCAGUCCCAGCGACUAU
GUCGUAUGGACGAAGCGCUUAUUUAUCGGAGAgaaaCCGAUAAGUAAAA
CGCAUCAAAG.

In some cases, a CasX single guide RNA comprises the sequence (SEQ ID NO: 43)
UUAUCUCAUUACUUUGAGAGCCAUCACCAGCGACUAUGUCGUAUGGGUA
AAGCGCUUAUUUAUCGGgaaaUCUCCGAUAAAUAAGAAGCAUCAAAG.

In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence (SEQ ID NO: 43)
UUAUCUCAUUACUUUGAGAGCCAUCACCAGCGACUAUGUCGUAUGGGUA
AAGCGCUUAUUUAUCGGgaaaUCUCCGAUAAAUAAGAAGCAUCAAAG.

CasX Systems

The present disclosure provides a CasX system. A CasX system of the present disclosure can comprise: a) a TSLD variant CasX polypeptide of the present disclosure and a CasX guide RNA; b) an NTSBD variant CasX polypeptide of the present disclosure and a CasX guide RNA; c) a TSLD CasX fusion polypeptide of the present disclosure and a CasX guide RNA; d) an NTSBD CasX fusion polypeptide of the present disclosure and a CasX guide RNA; e) an mRNA encoding a TSLD CasX variant polypeptide of the present disclosure; and a CasX guide RNA; f) an mRNA encoding an NTSBD variant CasX polypeptide of the present disclosure and a CasX guide RNA; g) an mRNA encoding a CasX fusion polypeptide of the present disclosure; and a CasX guide RNA; h) a modified CasX sgRNA of the present disclosure and a CasX polypeptide; j) a recombinant expression vector comprising a nucleotide sequence encoding a CasX polypeptide of the present disclosure, a nucleotide sequence encoding a modified CasX sgRNA of the present disclosure; or some variation of one of (a) through (j).

Nucleic Acids

The present disclosure provides one ore more nucleic acids comprising one or more of: a donor polynucleotide sequence, a nucleotide sequence encoding a CasX polypeptide (e.g., a wild type CasX protein, a nickase CasX protein, a dCasX protein, chimeric CasX protein, and the like), a CasX guide RNA, and a nucleotide sequence encoding a CasX guide RNA (which can include two separate nucleotide sequences in the case of dual guide RNA format or which can include a singe nucleotide sequence in the case of single guide RNA format), a nucleotide sequence encoding a TSLD variant CasX polypeptide of the present disclosure, a nucleotide sequence encoding an NTSBD variant CasX polypeptide of the present disclosure, a nucleotide sequence encoding a modified CasX sgRNA of the present disclosure. The present disclosure provides a nucleic acid comprising a nucleotide sequence encoding a CasX fusion polypeptide. The present disclosure provides a nucleic acid comprising a nucleotide sequence encoding a TSLD variant CasX fusion polypeptide. The present disclosure provides a nucleic acid comprising a nucleotide sequence encoding an NTSBD CasX fusion polypeptide. The present disclosure provides a recombinant expression vector that comprises a nucleotide sequence encoding a CasX polypeptide. The present disclosure provides a recombinant expression vector that comprises a nucleotide sequence encoding a CasX fusion polypeptide. The present disclosure provides a recombinant expression vector that comprises: a) a nucleotide sequence encoding a CasX polypeptide; and b) a nucleotide sequence encoding a CasX guide RNA(s). The present disclosure provides a recombinant expression vector that comprises: a) a nucleotide sequence encoding a CasX fusion polypeptide; and b) a nucleotide sequence encoding a CasX guide RNA (s). In some cases, the nucleotide sequence encoding the CasX protein and/or the nucleotide sequence encoding the CasX guide RNA is operably linked to a promoter that is operable in a cell type of choice (e.g., a prokarytoic cell, a eukaryotic cell, a plant cell, an animal cell, a mammalian cell, a primate cell, a rodent cell, a human cell, etc.).

For simplicity, the following discussion refers to nucleic acids comprising nucleotide sequences encoding a "CasX polypeptide." Such discussion is meant to apply equally to a TSLD variant CasX polypeptide of the present disclosure, a fusion polypeptide comprising a TSLD variant CasX polypeptide of the present disclosure, an NTSBD variant CasX polypeptide of the present disclosure, and a fusion polypeptide comprising an NTSBD variant CasX polypeptide of the present disclosure. Similarly, discussion of nucleic acids comprising nucleotide sequence encoding a CasX guide RNA apply equally to a nucleic acid comprising a nucleotide sequence encoding a modified CasX sgRNA of the present disclosure.

In some cases, a nucleotide sequence encoding a CasX polypeptide of the present disclosure is codon optimized. This type of optimization can entail a mutation of a CasX-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX-encoding nucleotide sequence could be generated. As another non-limiting example, if the intended host cell were an insect cell, then an insect codon-optimized CasX-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a CasX protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a CasX protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasX guide RNA is operably linked to a control element, e.g., a transcriptional control element, such as a promoter. In some embodiments, a nucleotide sequence encoding a CasX protein or a CasX fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasX protein, thus resulting in a chimeric CasX polypeptide.

In some embodiments, a nucleotide sequence encoding a CasX guide RNA and/or a CasX fusion polypeptide is operably linked to an inducible promoter. In some embodiments, a nucleotide sequence encoding a CasX guide RNA and/or a CasX fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasX guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a CasX protein (e.g., a wild type CasX protein, a nickase CasX protein, a dCasX protein, a chimeric CasX protein and the like) is operably linked to a promoter operable in a eukaryotic cell (e.g., a CMV promoter, an EF1α promoter, an estrogen receptor-regulated promoter, and the like).

Examples of inducible promoters include, but are not limited toT7 RNA polymerase promoter. T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasX protein and/or a CasX guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasX protein can be provided as RNA. The RNA can be provided by direct chemical synthesis or may be transcribed in vitro from a DNA (e.g., encoding the CasX protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLOS ONE 5(7): e11756, and the commercially available TRANSMESSENGER® reagents from Qiagen, STEMFECT™ RNA Transfection Kit from Stemgent, and TRANSIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasX guide RNA; recombinant expression vectors encoding the CasX protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasX guide RNA and/or a CasX polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasX guide RNA and/or a CasX protein to a cell may include nucleic acid sequences that encode for selectable markers in the target cells, so as to identify cells that have taken up the CasX guide RNA and/or CasX protein.

A nucleic acid comprising a nucleotide sequence encoding a CasX polypeptide, or a CasX fusion polypeptide, is in some cases an RNA. Thus, a CasX fusion protein can be introduced into cells as RNA. Methods of introducing RNA into cells are known in the art and may include, for example, direct injection, electroporation, transfection, or any other method used for the introduction of DNA. A CasX protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally, or alternatively, a CasX polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO:48). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasX polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasX guide RNA, encoding a CasX fusion protein, etc.) and proteins (e.g., a CasX fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasX polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasX polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasX polypeptide, or a CasX fusion polypeptide, of the present disclosure is at least 80% pure, at least 85% pure, at least 90% pure, at least 95% pure, at least 98% pure, or at least 99% pure (e.g., free of contaminants, non-CasX proteins or other macromolecules, etc.).

To induce cleavage or any desired modification to a target nucleic acid (e.g., genomic DNA), or any desired modification to a polypeptide associated with target nucleic acid, the CasX guide RNA and/or the CasX polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasX guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasX guide RNA that does not change when the guide sequence is changed to hybrized to a desired target sequence (e.g., sequences that contribute to the CasX binding aspect of the guide RNA, e.g. the sequences that contribute to the dsRNA duplex(es) of the CasX guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasX guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, In some cases, the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasX guide RNA; e.g., a modified CasX sgRNA of the present disclosure) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasX guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular $-CH_2-NH-O-CH_2-$, $-CH_2-N(CH_3)-O-CH_2-$ (known as a methylene (methylimino) or MMI backbone), $-CH_2-O-N(CH_3)-CH_2-$, $-CH_2-N(CH_3)-N(CH_3)-CH_2-$ and $-O-N(CH_3)-CH_2-CH_2-$ (wherein the native phosphodiester internucleotide linkage is represented as $-O-P(=O)(OH)-O-CH_2-$). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331;

and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry,* 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($—CH_2—$), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy ($2'-O—CH_2\ CH_2OCH_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., $2'-O—CH_2—O—CH_2—N(CH_3)_2$.

Other suitable sugar substituent groups include methoxy ($—O—CH_3$), aminopropoxy ($—OCH_2CH_2CH_2NH_2$), allyl ($—CH_2—CH=CH_2$), —O-allyl ($—O—CH_2—CH=CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly 3' position of the sugar on 3' terminal nucleoside or in 2'-5' linked oligonucleotides and 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C=C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido (4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., *Chapter* 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci.* USA, 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Bchmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP-cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO:44); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9 (6):489-96); an *Drosophila* Antennapedia protein transduction domain (Noguchi et al. (2003) *Diabetes* 52 (7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:45); Transportan GWTLNSAGYLLGKINLKALAALAKKIL (SEQ ID NO:46); KALAWEAKLAKALAKALAKHLAKALAKALKCEA (SEQ ID NO:47); and RQIKIWFQNRRMKWKK (SEQ ID NO:48). Exemplary PTDs include but are not limited to, YGRKKRRQRRR (SEQ ID NO:44), RKKRRQRRR SEQ ID NO:49); an arginine homopolymer of from 3 arginine residues to 50 arginine residues; Exemplary PTD domain amino acid sequences include, but are not limited to, any of the following: YGRKKRRQRRR (SEQ ID NO:44); RKKRRQRR SEQ ID NO:50); YARAAARQARA (SEQ ID NO:80); THRLPRRRRRR (SEQ ID NO:51); and GGRRARRRRRR (SEQ ID NO:52). In some cases, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasX guide RNA (or a nucleic acid comprising a nucleotide sequence encoding same) and/or a modified CasX sgRNA of the present disclosure and/or a CasX polypeptide of the present disclosure (or a nucleic acid comprising a nucleotide sequence encoding same) and/or a CasX fusion polypeptide of the present disclosure (or a nucleic acid that includes a nucleotide sequence encoding a CasX fusion polypeptide of the present disclosure) and/or a TSLD variant CasX polypeptide of the present disclosure and/or an NTSBD polypeptide of the present disclosure and/or a donor polynucleotide (donor template) can be introduced into a host cell by any of a variety of well-known methods.

Any of a variety of compounds and methods can be used to deliver to a target cell a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; c) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). As a non-limiting example, a CasX system of the present disclosure can be combined with a lipid. As another non-limiting example, a CasX system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a CasX polypeptide of the present disclosure is provided as a nucleic acid (e.g., an mRNA, a DNA, a plasmid, an expression vector, a viral vector, etc.) that encodes the CasX polypeptide. In some cases, the CasX polypeptide of the present disclosure is provided directly as a protein (e.g., without an associated guide RNA or with an associate guide RNA, i.e., as a ribonucleoprotein complex). A CasX polypeptide of the present disclosure can be introduced into a cell (provided to the cell) by any convenient method; such methods are known to those of ordinary skill in the art. As an illustrative example, a CasX polypeptide of the present disclosure can be injected directly into a cell (e.g., with or without a CasX guide RNA or nucleic acid encoding a CasX guide RNA, and with or without a donor polynucleotide). As another example, a preformed complex of a CasX polypeptide of the present disclosure and a CasX guide RNA (an RNP) can be introduced into a cell (e.g. eukaryotic cell) (e.g., via injection, via nucleofection; via a protein transduction domain (PTD) conjugated to one or more components, e.g., conjugated to the CasX protein, conjugated to a guide RNA, conjugated to a CasX polypeptide of the present disclosure and a guide RNA; etc.).

In some cases, a CasX fusion polypeptide (e.g., dCasX fused to a fusion partner, nickase CasX fused to a fusion partner, etc.) of the present disclosure is provided as a nucleic acid (e.g., an mRNA, a DNA, a plasmid, an expression vector, a viral vector, etc.) that encodes the CasX fusion polypeptide. In some cases, the CasX fusion polypeptide of the present disclosure is provided directly as a protein (e.g., without an associated guide RNA or with an associate guide RNA, i.e., as a ribonucleoprotein complex). A CasX fusion polypeptide of the present disclosure can be introduced into a cell (provided to the cell) by any convenient method; such methods are known to those of ordinary skill in the art. As an illustrative example, a CasX fusion polypeptide of the present disclosure can be injected directly into a cell (e.g., with or without nucleic acid encoding a CasX guide RNA and with or without a donor polynucleotide). As another example, a preformed complex of a CasX fusion polypeptide of the present disclosure and a CasX guide RNA (an RNP) can be introduced into a cell (e.g., via injection, via nucleofection; via a protein transduction domain (PTD) conjugated to one or more components, e.g., conjugated to the CasX fusion protein, conjugated to a guide RNA, conjugated to a CasX fusion polypeptide of the present disclosure and a guide RNA; etc.).

In some cases, a nucleic acid (e.g., a CasX guide RNA; a nucleic acid comprising a nucleotide sequence encoding a CasX polypeptide of the present disclosure; etc.) is delivered to a cell (e.g., a target host cell) and/or a polypeptide (e.g., a CasX polypeptide; a CasX fusion polypeptide) in a particle, or associated with a particle. In some cases, a CasX system of the present disclosure is delivered to a cell in a particle, or associated with a particle. The terms "particle" and nanoparticle" can be used interchangeable, as appropriate. A recombinant expression vector comprising a nucleotide sequence encoding a CasX polypeptide of the present disclosure and/or a CasX guide RNA, an mRNA comprising a nucleotide sequence encoding a CasX polypeptide of the present disclosure, and guide RNA may be delivered simultaneously using particles or lipid envelopes; for instance, a CasX polypeptide and a CasX guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-diolcoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasX polypeptide and a CasX guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasX polypeptide of the present disclosure (or an mRNA comprising a nucleotide sequence encoding a CasX polypeptide of the present disclosure; or a recombinant expression vector comprising a nucleotide sequence encoding a CasX polypeptide of the present disclosure) and/or CasX guide RNA (or a nucleic acid such as one or more expression vectors encoding the CasX guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in U.S. patent application No. 20110293703) are also useful in the administration of polynucleotides, and can be used to deliver a CasX polypeptide of the present disclosure, a CasX fusion polypeptide of the present disclosure, an RNP of the present disclosure, a nucleic acid of the present disclosure, or a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; c) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell.

In some cases, lipid nanoparticles (LNPs) are used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylamino-ethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasX guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 25 nm to 200 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 100 nm or less In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 35 nm to 60 nm.

Nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell. A prototype nanoparticle of semi-solid nature is the liposome.

In some cases, an exosome is used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Exosomes are endogenous nano-vesicles that transport RNAs and proteins, and which can deliver RNA to the brain and other target organs.

In some cases, a liposome is used to deliver a CasX polypeptide of the present disclosure, a CasX fusion polypeptide of the present disclosure, an RNP of the present disclosure, a nucleic acid of the present disclosure, or a CasX system of the present disclosure, to a target cell.

Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminocthyl-[1,3]-dioxolane (DLin-KC2-DMA) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+-.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasX system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CasX system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasX system of the present disclosure, or a component thereof, may be delivered encapsulated in PLGA microspheres such as that further described in US published applications 20130252281 and 20130245107 and 20130244279.

Supercharged proteins can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasX polypeptide of the present disclosure, a CasX fusion polypeptide of the present disclosure, an RNP of the present disclosure, a nucleic acid of the present disclosure (e.g., a CasX guide RNA, a nucleic acid encoding a CasX guide RNA, a nucleic acid encoding CasX polypeptide, a donor template, and the like), or a CasX system of the present disclosure, to a target cell (e.g., a target cell in vivo, where the target cell is a target cell in circulation, a target cell in a tissue, a target cell in an organ, etc.). An implantable device suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasX polypeptide, the CasX fusion polypeptide, the RNP, or the CasX system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intraocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasX polypeptide of the present disclosure and/or a nucleic acid comprising a nucleotide sequence encoding a CasX polypeptide of the present disclosure. The present disclosure provides a modified cell comprising a CasX polypeptide of the present disclosure, where the modified cell is a cell that does not normally comprise a CasX polypeptide of the present disclosure. The present disclosure provides a modified cell (e.g., a genetically modified cell) comprising nucleic acid comprising a nucleotide sequence encoding a CasX polypeptide of the present disclosure. The present disclosure provides a genetically modified cell that is genetically modified with an mRNA comprising a nucleotide sequence encoding a CasX polypeptide of the present disclosure. The present disclosure provides a genetically modified cell that is genetically modified with a recombinant expression vector comprising a nucleotide sequence encoding a CasX polypeptide of the present disclosure. The present disclosure provides a genetically modified cell that is genetically modified with a recombinant expression vector comprising: a) a nucleotide sequence encoding a CasX polypeptide of the present disclosure; and b) a nucleotide sequence encoding a CasX guide RNA of the present disclosure. The present disclosure provides a genetically modified cell that is genetically modified with a recombinant expression vector comprising: a) a nucleotide sequence encoding a CasX polypeptide of the present disclosure; b) a nucleotide sequence encoding a CasX guide RNA of the present disclosure; and c) a nucleotide sequence encoding a donor template.

A cell that serves as a recipient for a CasX polypeptide of the present disclosure and/or a nucleic acid comprising a nucleotide sequence encoding a CasX polypeptide of the present disclosure and/or a CasX guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasX polypeptide of the present disclosure and/or a nucleic acid comprising a nucleotide sequence encoding a CasX polypeptide of the present disclosure and/or a CasX guide RNA of the present disclosure is referred to as a "host cell" or a "target cell." A host cell or a target cell can be a recipient of a CasX system of the present disclosure. A host cell or a target cell can be a recipient of a CasX RNP of the present disclosure. A host cell or a target cell can be a recipient of a single component of a CasX system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf-green), lettuce (oak leaf-red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasX system of the present disclosure, or a component of a CasX system of the present disclosure.

A kit of the present disclosure can comprise: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r).

A kit of the present disclosure can comprise: a) a component, as described above, of a CasX system of the present disclosure, or can comprise a CasX system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasX guide RNA; and the like. A kit of the present disclosure can comprise: a) a component, as described above, of a CasX system of the present disclosure, or can comprise a CasX system of the present disclosure; and b) a therapeutic agent.

A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; and b) a nucleotide sequence encoding the CasX-binding portion of a CasX guide RNA. A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; b) a nucleotide sequence encoding the CasX-binding portion of a CasX guide RNA; and c) a nucleotide sequence encoding a CasX polypeptide of the present disclosure.

Target Nucleic Acids and Target Cells of Interest

A CasX polypeptide of the present disclosure, or a CasX fusion polypeptide of the present disclosure, when bound to a CasX guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasX guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where “primary cells”, “primary cell lines”, and “primary cultures” are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasX protein (and/or nucleic acid encoding the protein such as DNA and/or RNA), and/or CasX guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled “Modified cells.” Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf-green), lettuce (oak leaf-red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas9 guide RNA (or a nucleic acid comprising a nucleotide sequence encoding same), and/or a Cas9 fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. Any or all of the components can be introduced into a cell as a composition (e.g., including any convenient combination of: a CasX polypeptide (e.g., a variant CasX polypeptide, etc.), a CasX guide RNA, a donor polynucleotide, etc.) using known methods, e.g., such as nucleofection.

Donor Polynucleotide (Donor Template)

Guided by a CasX dual or single guide RNA, a CasX protein in some cases generates site-specific double strand breaks (DSBs) or single strand breaks (SSBs) (e.g., when the CasX protein is a nickase variant) within double-stranded DNA (dsDNA) target nucleic acids, which are repaired either by non-homologous end joining (NHEJ) or homology-directed recombination (HDR).

In some cases, contacting a target DNA (with a CasX protein and a CasX guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, CasX guide RNA (or DNA encoding same) and a CasX protein (or a nucleic acid encoding same, such as an RNA or a DNA, e.g. one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasX guide RNA and CasX protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasX protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair ot a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasX guide RNA and/or a CasX fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasX polypeptide of the present disclosure; a nucleic acid comprising a nucleotide sequence encoding a CasX fusion polypeptide of the present disclosure; etc.), is used as a transgene to generate a transgenic non-human organism that produces a CasX polypeptide, or a CasX fusion polypeptide, of the present disclosure. The present disclosure provides a transgenic-non-human organism comprising a nucleotide sequence encoding a CasX polypeptide, or a CasX fusion polypeptide, of the present disclosure.

Method of Detecting a Target ss DNA

The present disclosure provides a method of detecting a target single-stranded DNA (ssDNA) in a sample. The method comprises: a) contacting the sample with: i) an NTSBD variant CasX polypeptide of the present disclosure; ii) a guide RNA comprising: a region that binds to the NTSBD variant CasX polypeptide, and a guide sequence that hybridizes with the target ssDNA; and (iii) a labeled detector DNA that is single stranded and does not hybridize with the guide sequence of the guide RNA; and (b) measuring a detectable signal produced by cleavage of the labeled detector DNA by the NTSBD variant CasX polypeptide, thereby detecting the target ss DNA. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

In some cases (e.g., when contacting with a guide RNA and an NTSBD variant CasX polypeptide), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, In some cases, the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

A method of the present disclosure for detecting a target DNA (single-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

The target DNA is single-stranded DNA. Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

A subject sample includes nucleic acid (e.g., a plurality of nucleic acids). The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5\times10^3$ or more, $10^4$ or more, $5\times10^4$ or more, $10^5$ or more, $5\times10^5$ or more, $10^6$ or more $5\times10^6$ or more, or $10^7$ or more, DNAs. In some cases, the sample comprises from 10 to 20, from 20 to 50, from 50 to 100, from 100 to 500, from 500 to $10^3$, from $10^3$ to $5\times10^3$, from $5\times10^3$ to $10^4$, from $10^4$ to $5\times10^4$, from $5\times10^4$ to $10^5$, from $10^5$ to $5\times10^5$, from $5\times10^5$ to $10^6$, from $10^6$ to $5\times10^6$, or from $5\times10^6$ to $10^7$, or more than $10^7$, DNAs. In some cases, the sample comprises from 5 to $10^7$ DNAs (e.g., that differ from one another in sequence) (e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, In some cases, the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, a DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5\times10^3$ non-target DNAs, one copy per $10^4$ non-target DNAs, one copy per $5\times10^4$ non-target DNAs, one copy per $10^5$ non-target DNAs, one copy per $5\times10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5\times10^3$ non-target DNAs, from 1 copy per $5\times10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g. Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of *Agaricus, Amanita, Boletus*, Cantherellus, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chactognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from *Giardia* spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis*, and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNAviruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Histoplasma capsulatum, Hemophilus influenzae* B. *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata,*

*Echinococcus granulosus, Mesocestoides corti, Mycoplasma arthritidis, M. hyorhinis, M. orale, M. arginini, Acholeplasma laidlawii, M. salivarium* and *M. pneumoniae.*

Detection of cleavage of the labelled detector DNA can be carried out using any known method. For example, In some cases, the step of detecting can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24):10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356): 348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

In some cases, the sample is subjected to an amplification step to increase the target DNA. In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

The detector DNA can comprise a fluorescence resonance energy transfer (FRET) pair or a quencher/fluor pair, or both.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair." both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

TABLE 1

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

In some cases, a labelled ssDNA detector includes a fluorescent moiety and a quencher moiety.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an ALEXA FLUOR® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DYLIGHT® dye, a cyanine dye (e.g., Cy2, Cy3, Cy3.5. Cy3b, Cy5, Cy5.5, Cy7, Cy7.5), a FLUOPROBES® dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an ALEXA FLUOR® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DYLIGHT® dye, a cyanine dye (e.g., Cy2, Cy3, Cy3.5, Cy3b, Cy5, Cy5.5, Cy7, Cy7.5), a FLUOPROBES® dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an ALEXA FLUOR® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DYLIGHT® dye, a cyanine dye (e.g., Cy2, Cy3, Cy3.5, Cy3b, Cy5, Cy5.5, Cy7, Cy7.5), a FLUOPROBES® dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: ALEXA FLUOR® ALEXA FLUOR® 350, ALEXA FLUOR® ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 635, ALEXA FLUOR® 647, ALEXA FLUOR® 660, ALEXA FLUOR® 680, ALEXA FLUOR® 700, ALEXA FLUOR® 750, ALEXA FLUOR® 790, and the like.

Examples of quencher moieties include, but are not limited to: a dark quencher, a BLACK HOLE QUENCHER® (BHQ®) (e.g., BHQ-0, BHQ-1, BHQ-2, BHQ-3), a Qxl quencher, an ATTO quencher (e.g., ATTO 540Q. ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a BLACK HOLE QUENCHER® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ. IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a BLACK HOLE QUENCHER® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

EXAMPLES OF NON-LIMITING ASPECTS OF THE DISCLOSURE

Aspect Set A

Aspects, including embodiments, of the present subject matter described above may be beneficial alone or in combination, with one or more other aspects or embodiments. Without limiting the foregoing description, certain non-limiting aspects of the disclosure numbered 1-82 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant CasX polypeptide comprising an amino acid sequence having at least 70% amino acid sequence identity to SEQ ID NO:1 (CasX1) or SEQ ID NO:2 (CasX2), wherein the variant CasX polypeptide comprises a deletion or a replacement of one or more amino acids in a target-strand loading domain (TSLD), wherein the variant CasX polypeptide retains DNA binding activity, and wherein the variant CasX polypeptide does not substantially exhibit double-stranded DNA cleavage activity, where the TSLD comprises amino acids 825-934 of the CasX1 amino acid sequence depicted in FIG. 16, or a corresponding region in a different CasX polypeptide.

Aspect 2. The variant CasX polypeptide of aspect 1, wherein the TSLD comprises amino acids 825 to 934 of the CasX1 amino acid sequence set forth in SEQ ID NO:1.

Aspect 3. The variant CasX polypeptide of aspect 1, wherein the variant CasX polypeptide comprises a deletion or a replacement of one or more amino acids 863-873 relative to the amino acid sequence set forth in SEQ ID NO:1.

Aspect 4. The variant CasX polypeptide of aspect 1, wherein the variant CasX polypeptide comprises a deletion or a replacement of one or more amino acids within amino acids 850-860 relative to the amino acid sequence set forth in SEQ ID NO:2.

Aspect 5. The variant CasX polypeptide of any one of aspects 1-4, wherein the variant CasX polypeptide comprises an amino acid sequence having at least 80% amino acid sequence identity to SEQ ID NO:1 (CasX1) or SEQ ID NO:2 (CasX2).

Aspect 6. The variant CasX polypeptide of any one of aspects 1-4, wherein the variant CasX polypeptide comprises an amino acid sequence having at least 90% amino acid sequence identity to SEQ ID NO:1 (CasX1) or SEQ ID NO:2 (CasX2).

Aspect 7. A CasX fusion polypeptide comprising:

a) the variant CasX polypeptide of any one of aspects 1-6; and b) a heterologous fusion partner.

Aspect 8. The fusion polypeptide of aspect 7, wherein the heterologous fusion partner is a nuclear localization sequence (NLS).

Aspect 9. The fusion polypeptide of aspect 8, wherein the fusion polypeptide comprises a single NLS at the N-terminus of the variant CasX polypeptide or at the C-terminus of the variant CasX polypeptide.

Aspect 10. The fusion polypeptide of aspect 8, wherein the fusion polypeptide comprises two or more NLSs.

Aspect 11. The fusion polypeptide of aspect 10, wherein the fusion polypeptide comprises a first NLS at the N-terminus of the variant CasX polypeptide and a second NLS at the C-terminus of the variant CasX polypeptide.

Aspect 12. The fusion polypeptide of aspect 7, wherein the heterologous polypeptide is a targeting polypeptide that provides for binding to a cell surface moiety on a target cell or target cell type.

Aspect 13. The fusion polypeptide of aspect 7, wherein the heterologous polypeptide exhibits an enzymatic activity that modifies target DNA.

Aspect 14. The fusion polypeptide of aspect 13, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 15. The fusion polypeptide of aspect 13, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 16. The fusion polypeptide of aspect 7, wherein the heterologous polypeptide exhibits an enzymatic activity that modifies a target polypeptide associated with a target nucleic acid.

Aspect 17. The fusion polypeptide of aspect 7, wherein the heterologous polypeptide is an endosomal escape polypeptide.

Aspect 18. The fusion polypeptide of aspect 7, wherein the heterologous polypeptide is a protein that increases or decreases transcription.

Aspect 19. A nucleic acid comprising a nucleotide sequence encoding the variant CasX polypeptide of any one of aspects 1-6, or the fusion CasX polypeptide of any one of aspects 7-18.

Aspect 20. The nucleic acid of aspect 19, wherein the nucleotide sequence is operably linked to a promoter.

Aspect 21. The nucleic acid of aspect 18 or aspect 19, further comprising a nucleotide sequence encoding a CasX guide RNA.

Aspect 22. The nucleic acid of aspect 21, wherein the CasX guide RNA is a single-guide RNA.

Aspect 23. The nucleic acid of aspect 21 or aspect 22, wherein the CasX guide RNA-encoding nucleotide sequence is operably linked to a promoter.

Aspect 24. A recombinant expression vector comprising the nucleic acid of any one of aspects 19-23.

Aspect 25. A cell comprising the nucleic acid of any one of aspects 19-23, or the recombinant expression vector of aspect 24.

Aspect 26. The cell of aspect 25, wherein the cell is a eukaryotic cell.

Aspect 27. The cell of aspect 25 or aspect 26, wherein the cell is in vitro.

Aspect 28. The cell of aspect 25 or aspect 26, wherein the cell is in vivo.

Aspect 29. A composition comprising:

a) the variant CasX polypeptide of any one of aspects 1-6, or the fusion polypeptide of any one of aspects 7-18, or the nucleic acid of any one of aspects 19-23, or the recombinant expression vector of aspect 24; and b) a CasX guide RNA, or one or more DNA molecules comprising a nucleotide sequence encoding the CasX guide RNA.

Aspect 30. The composition of aspect 29, wherein the CasX guide RNA is a single-guide RNA.

Aspect 31. The composition of aspect 29, wherein the CasX guide RNA-encoding nucleotide is operably linked to a promoter.

Aspect 32. The composition of any one of aspects 29-31, wherein the composition comprises a lipid.

Aspect 33. The composition of any one of aspects 29-31, wherein a) and b) are within a liposome.

Aspect 34. The composition of any one of aspects 29-31, wherein a) and b) are within a particle.

Aspect 35. The composition of any one of aspects 29-34, comprising one or more of: a buffer, a nuclease inhibitor, and a protease inhibitor.

Aspect 36. A method of binding, or binding and nicking, a target nucleic acid, the method comprising contacting the target nucleic acid with:

a) the variant CasX polypeptide of any one of aspects 1-7, or the fusion polypeptide of any one of aspects 7-18; and b) a CasX guide RNA comprising a guide sequence that hybridizes to a target sequence of the target nucleic acid, Aspect 37. The method of aspect 36, wherein said contacting results in: i) binding of the target nucleic acid by the variant CasX polypeptide or the CasX fusion polypeptide; or ii) nicking of the target nucleic acid by the variant CasX polypeptide or the CasX fusion polypeptide.

Aspect 38. The method of aspect 36 or aspect 37, wherein the target nucleic acid is selected from: double stranded DNA, single stranded DNA, RNA, genomic DNA, and extrachromosomal DNA.

Aspect 39. The method of any one of aspects 36-38, wherein said contacting takes place in vitro outside of a cell.

Aspect 40. The method of any one of aspects 36-38, wherein said contacting takes place inside of a cell in vitro.

Aspect 41. The method of any one of aspects 36-38, wherein said contacting takes place inside of a cell in vivo.

Aspect 42. The method of aspect 40 or aspect 41, wherein the cell is a eukaryotic cell.

Aspect 43. The method of aspect 42, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 44. The method of any one of aspects 40-43, wherein said contacting comprises: introducing into a cell: (a) the variant CasX polypeptide, or a nucleic acid molecule encoding the variant CasX polypeptide, and (b) the CasX guide RNA, or a nucleic acid molecule encoding the CasX guide RNA.

Aspect 45. The method of any one of aspects 40-43, wherein said contacting comprises: introducing into a cell: (a) the fusion CasX polypeptide, or a nucleic acid molecule encoding the fusion CasX polypeptide, and (b) the CasX guide RNA, or a nucleic acid molecule encoding the CasX guide RNA.

Aspect 46. The method of any one of aspect 36-45, wherein the CasX guide RNA is a single guide RNA.

Aspect 47. The method of any one of aspect 36-45, wherein the CasX guide RNA is a dual guide RNA.

Aspect 48. A method of modulating transcription from a target DNA, modifying a target nucleic acid, or modifying a protein associated with a target nucleic acid, the method comprising contacting the target nucleic acid with:

a1) a CasX fusion polypeptide comprising the variant CasX polypeptide of any one of aspects 1-6 fused to a heterologous polypeptide; and a2) a CasX guide RNA comprising a guide sequence that hybridizes to a target sequence of the target nucleic acid; or b1) a CasX polypeptide comprising amino acid substitutions of D672, E769, and E935 of the CasX1 polypeptide depicted in FIG. 16, or corresponding amino acid positions of another CasX polypeptide; and b2) a CasX guide RNA that comprise a guide sequence that hybridizes to a target sequence in a non-coding strand of a target nucleic acid.

Aspect 49. The method of aspect 48, wherein the CasX guide RNA is a single guide RNA.

Aspect 50. The method of aspect 48, wherein the CasX guide RNA is a dual guide RNA.

Aspect 51. The method of any one of aspects 48-50, wherein said modification is not cleavage of the target nucleic acid.

Aspect 52. The method of any one of aspects 48-51, wherein the target nucleic acid is selected from: double stranded DNA, single stranded DNA, RNA, genomic DNA, and extrachromosomal DNA.

Aspect 53. The method of any one of aspects 48-52, wherein said contacting takes place in vitro outside of a cell.

Aspect 54. The method of any one of aspects 48-52, wherein said contacting takes place inside of a cell in vitro.

Aspect 55. The method of any one of aspects 48-52, wherein said contacting takes place inside of a cell in vivo.

Aspect 56. The method of aspect 55, wherein the cell is a eukaryotic cell.

Aspect 57. The method of aspect 56, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 58. The method of any one of aspects 48-57, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 59. The method of any one of aspects 48-57, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 60. The method of any one of aspects 48-57, wherein the heterologous polypeptide is protein that increases or decreases transcription.

Aspect 61. The method of aspect 60, wherein the heterologous polypeptide is a transcriptional repressor domain.

Aspect 62. The method of aspect 60, wherein the heterologous polypeptide is a transcriptional activation domain.

Aspect 63. The method of any one of aspects 48-57, wherein the heterologous polypeptide is a protein binding domain.

Aspect 64. A modified CasX single-molecule guide RNA (sgRNA), wherein the modified CasX sgRNA comprises a heterologous RNA inserted into, or replacing all or part of, an extended stem portion of a native CasX guide RNA.

Aspect 65. The modified CasX sgRNA of aspect 64, wherein the extended stem portion comprises a nucleotide sequence having at least 90% nucleotide sequence identity to the following nucleotide sequence: 5'-GCGC-UUAUUUAUCGGAGAGAAACCGAUA-AGUAAAACGC-3' (SEQ ID NO:9).

Aspect 66. The modified CasX sgRNA of aspect 64 or aspect 65, wherein the heterologous RNA replaces from 1 nucleotide to 38 nucleotides of the extended stem.

Aspect 67. The modified CasX sgRNA of aspect 64 or aspect 65, wherein the heterologous RNA replaces from 5 nucleotides to 38 nucleotides of the extended stem.

Aspect 68. The modified CasX sgRNA of any one of aspects 64-67, wherein the heterologous RNA is an aptamer, a noncoding RNA, a ribozyme, a functional RNA sequence, one of a pool of random RNA sequences, an RNA scaffold, an RNA-based sensor, an RNA-based signal processor, an RNA-based signaling device, a naturally occurring long non-coding RNA (lncRNA), a lncRNA subdomain, a synthetic lncRNA, or a synthetic lncRNA subdomain.

Aspect 69. The modified CasX sgRNA of any one of aspects 64-67, wherein the heterologous RNA is an aptamer that binds to an adaptor protein, wherein the adaptor protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, and PRR1.

Aspect 70. The modified CasX sgRNA of any one of aspects 64-67, wherein the heterologous RNA is an MS2 stem-loop, a PP7 stem-loop, or an L7Ae motif.

Aspect 71. The modified CasX sgRNA of aspect 70, wherein the MS2 stem-loop comprises the nucleotide sequence 5'-ACAUGAGGAUUACCCAUGU-3' (SEQ ID NO:65).

Aspect 72. The modified CasX sgRNA of any one of aspects 64-71, wherein the heterologous RNA has a length of from 5 nucleotides to 500 nucleotides.

Aspect 73. The modified CasX sgRNA of any one of aspects 64-71, wherein the heterologous RNA has a length of from 5 nucleotides to 100 nucleotides.

Aspect 74. The modified CasX sgRNA of any one of aspects 64-71, wherein the heterologous RNA has a length of from 5 nucleotides to 50 nucleotides.

Aspect 75. A variant CasX polypeptide comprising an amino acid sequence having at least 70% amino acid sequence identity to SEQ ID NO:1 (CasX1) or SEQ ID NO:2 (CasX2), wherein the variant CasX polypeptide comprises a deletion or a replacement of one or more amino acids in a non-target strand binding domain (NTSBD), wherein the variant CasX polypeptide does not substantially exhibit double-stranded DNA unwinding and binding activity, and wherein the variant CasX polypeptide retains single-stranded DNA binding activity.

Aspect 76. The variant CasX polypeptide of aspect 75, wherein the NTSBD comprises amino acids 101-191 of the CasX amino acid sequence set forth in SEQ ID NO:1.

Aspect 77. The variant CasX polypeptide of aspect 75 or aspect 76, wherein the variant CasX polypeptide exhibits increased trans cleavage activity of a non-target single-stranded DNA, compared to the trans cleavage activity of the non-target single-stranded DNA exhibited by a CasX polypeptide comprising the amino acid sequence set forth in SEQ ID NO:1.

Aspect 78. A nucleic acid comprising a nucleotide sequence encoding the variant CasX polypeptide of any one of aspects 75-77.

Aspect 79. A method of detecting a target single-stranded DNA in a sample, the method comprising:

(a) contacting the sample with:

(i) the variant CasX polypeptide of any one of aspects 75-77;

(ii) a guide RNA comprising: a region that binds to the variant CasX polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the variant CasX polypeptide, thereby detecting the target DNA.

Aspect 80. The method of aspect 79, wherein the target DNA is viral DNA.

Aspect 81. The method of aspect 79 or aspect 80, wherein the single stranded detector DNA comprises a modified nucleobase, a modified sugar moiety, and/or a modified nucleic acid linkage.

Aspect 82. The method of any one of aspects 79-81, wherein the single stranded detector DNA comprises a fluorescence-emitting dye pair.

Aspect Set B

Aspects, including embodiments, of the present subject matter described above may be beneficial alone or in combination, with one or more other aspects or embodiments. Without limiting the foregoing description, certain non-limiting aspects of the disclosure numbered 1-126 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant CasX polypeptide, wherein the variant CasX polypeptide comprises a deletion or a replacement of one or more amino acids in a target-strand loading domain (TSLD) of a CasX polypeptide, wherein the variant CasX polypeptide retains DNA binding activity and wherein the variant CasX polypeptide does not exhibit double-stranded DNA cleavage activity.

Aspect 2. The variant CasX polypeptide of aspect 1, comprising a deletion or a replacement of one or more of amino acids 825-934 of SEQ ID NO:1 or SEQ ID NO:2, or a corresponding region in a different CasX polypeptide.

Aspect 3. The variant CasX polypeptide of aspect 1, wherein the variant CasX polypeptide lacks the TSLD.84

Aspect 4. The variant CasX polypeptide of aspect 1, wherein the variant CasX polypeptide lacks amino acids 825-934 of SEQ ID NO:1 or SEQ ID NO:2, or a corresponding region in a different CasX polypeptide.

Aspect 5. The variant CasX polypeptide of aspect 1, wherein at least 5 to 106 amino acids of the TSLD are deleted.

Aspect 6. The variant CasX polypeptide of aspect 1, wherein the variant CasX polypeptide lacks the sequence

```
                                        (SEQ ID NO: 86)
CSNCGFTITTADYDGMLVRLKKTSDGWATTLNNKELKAEGQITYYNRYK

RQTVEKELSAELDRLSEES GNNDISKWTKGRRDEALFLLKKRFSHRPV

QEQFVCLD.
```

Aspect 7. The variant CasX polypeptide of aspect 1, wherein the variant CasX polypeptide lacks amino acids 863-873 of SEQ ID NO:1.

Aspect 8. The variant CasX polypeptide of aspect 1, wherein the variant CasX polypeptide lacks amino acids 850-860 of SEQ ID NO:2.

Aspect 9. The variant CasX polypeptide of aspect 1, wherein the TSLD sequence lacks the sequence QITYYNRYKRQ (SEQ ID NO:6).

Aspect 10. A variant CasX polypeptide, wherein the variant CasX polypeptide comprises a deletion or a replacement of one or more amino acids in a non-target strand binding domain (NTSBD) of a CasX polypeptide, wherein the variant CasX polypeptide does not substantially exhibit double-stranded DNA unwinding and binding activity, and wherein the variant CasX polypeptide retains single-stranded DNA binding activity.

Aspect 11. The variant CasX polypeptide of aspect 10, comprising a deletion or a replacement of one or more amino acids 101-191 of SEQ ID NO:1, or a corresponding region in a different CasX polypeptide.

Aspect 12. The variant CasX polypeptide of aspect 10, wherein the variant CasX polypeptide lacks the NTSBD sequence of a CasX polypeptide.

Aspect 13. The variant CasX polypeptide of aspect 10, wherein the variant CasX polypeptide lacks amino acids 101-191 of SEQ ID NO:1, or a corresponding region in a different CasX polypeptide.

Aspect 14. The variant CasX polypeptide of aspect 10, wherein at least 1 amino acid to 91 amino acids of the NTSBD sequence are deleted.

Aspect 15. The variant CasX polypeptide of aspect 10, wherein the variant CasX polypeptide lacks the sequence

```
                                         (SEQ ID NO: 7)
PASKKIDQNKLKPEMDEKGNLTTAGFACSQCGQPLFVYKLEQVSEKGKA
YTNYFGRCNVAEHEKLILLAQLKPEKDSDEAVTYSLGKFGQR.
```

Aspect 16. The variant CasX polypeptide of any one of aspects 10-15, wherein the variant CasX polypeptide: i) binds a single-stranded target DNA when complexed with a CasX guide RNA; and ii) exhibits increased trans cleavage of a non-target single-stranded DNA compared to the trans cleavage activity of the non-target single-stranded DNA exhibited by a CasX polypeptide comprising the amino acid sequence set forth in SEQ ID NO:1.

Aspect 17. A CasX fusion polypeptide comprising: a) the variant CasX polypeptide of any one of aspects 1-9 or any one of aspects 10-16; and b) a heterologous fusion partner.

Aspect 18. The fusion polypeptide of aspect 17, wherein the heterologous fusion partner is a nuclear localization sequence (NLS).

Aspect 19. The fusion polypeptide of aspect 18, wherein the fusion polypeptide comprises a single NLS at the N-terminus of the variant CasX polypeptide or at the C-terminus of the variant CasX polypeptide.

Aspect 20. The fusion polypeptide of aspect 17, wherein the fusion polypeptide comprises two or more NLSs.

Aspect 21. The fusion polypeptide of aspect 20, wherein the fusion polypeptide comprises a first NLS at the N-terminus of the variant CasX polypeptide and a second NLS at the C-terminus of the variant CasX polypeptide.

Aspect 22. The fusion polypeptide of aspect 17, wherein the heterologous polypeptide is a targeting polypeptide that provides for binding to a cell surface moiety on a target cell or target cell type.

Aspect 23. The fusion polypeptide of aspect 17, wherein the heterologous polypeptide exhibits an enzymatic activity that modifies target DNA.

Aspect 24. The fusion polypeptide of aspect 17, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 25. The fusion polypeptide of aspect 17, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 26. The fusion polypeptide of aspect 17, wherein the heterologous polypeptide exhibits an enzymatic activity that modifies a target polypeptide associated with a target nucleic acid.

Aspect 27. The fusion polypeptide of aspect 17, wherein the heterologous polypeptide is an endosomal escape polypeptide.

Aspect 28. The fusion polypeptide of aspect 17, wherein the heterologous polypeptide is a protein that increases or decreases transcription.

Aspect 29. A nucleic acid comprising a nucleotide sequence encoding the variant CasX polypeptide of any one of aspects 1-9.

Aspect 30. The nucleic acid of aspect 29, wherein the nucleotide sequence is operably linked to a promoter.

Aspect 31. The nucleic acid of aspect 29 or aspect 30, further comprising a nucleotide sequence encoding a CasX guide RNA.

Aspect 32. The nucleic acid of aspect 31, wherein the CasX guide RNA is a single-guide RNA.

Aspect 33. The nucleic acid of aspect 31 or aspect 32, wherein the CasX guide RNA-encoding nucleotide sequence is operably linked to a promoter.

Aspect 34. A recombinant expression vector comprising the nucleic acid of any one of aspects 29-33.

Aspect 35. A nucleic acid comprising a nucleotide sequence encoding the variant CasX polypeptide of any one of aspects 10-16.

Aspect 36. The nucleic acid of aspect 35, wherein the nucleotide sequence is operably linked to a promoter.

Aspect 37. The nucleic acid of aspect 35 or 36, further comprising a nucleotide sequence encoding a CasX guide RNA.

Aspect 38. The nucleic acid of aspect 37, wherein the CasX guide RNA is a single-guide RNA.

Aspect 39. The nucleic acid of aspect 37 or aspect 38, wherein the CasX guide RNA-encoding nucleotide sequence is operably linked to a promoter.

Aspect 40. A recombinant expression vector comprising the nucleic acid of any one of aspects 35-39.

Aspect 41. A nucleic acid comprising a nucleotide sequence encoding the CasX fusion polypeptide of any one of aspects 17-28.

Aspect 42. The nucleic acid of aspect 41, wherein the nucleotide sequence is operably linked to a promoter.

Aspect 43. The nucleic acid of aspect 41, further comprising a nucleotide sequence encoding a CasX guide RNA.

Aspect 44. The nucleic acid of aspect 43 or 44, wherein the CasX guide RNA is a single-guide RNA.

Aspect 45. The nucleic acid of aspect 43 or 44, wherein the CasX guide RNA-encoding nucleotide sequence is operably linked to a promoter.

Aspect 46. A recombinant expression vector comprising the nucleic acid of any one of aspects 41-45.

Aspect 47. A cell comprising the nucleic acid of any one of aspects 29-33 and 35-39, or the recombinant expression vector of aspect 34 or aspect 40.

Aspect 48. The cell of aspect 47, wherein the cell is a eukaryotic cell.

Aspect 49. The cell of aspect 4 or aspect 48, wherein the cell is in vitro.

Aspect 50. The cell of aspect 47 or aspect 48, wherein the cell is in vivo.

Aspect 51. A cell comprising the nucleic acid of any one of aspects 41-45 or the recombinant expression vector of aspect 46.

Aspect 52. The cell of aspect 51, wherein the cell is a eukaryotic cell.

Aspect 53. The cell of aspect 51 or aspect 52, wherein the cell is in vitro.

Aspect 54. The cell of aspect 51 or aspect 52, wherein the cell is in vivo.

Aspect 55. A composition comprising: a) the variant CasX polypeptide of any one of aspects 1-9 or any one of aspects 10-16, or a nucleic acid comprising a nucleotide sequence encoding the variant CasX polypeptide; and b) a CasX guide RNA, or one or more DNA molecules comprising a nucleotide sequence encoding the CasX guide RNA.

Aspect 56. The composition of aspect 55, wherein the CasX guide RNA is a single-guide RNA.

Aspect 57. The composition of aspect 55 or aspect 56, wherein the encoding nucleotide sequence(s) is/are operably linked to a promoter.

Aspect 58. The composition of any one of aspects 55-57, wherein the composition comprises a lipid.

Aspect 59. The composition of any one of aspects 55-57, wherein a) and b) are within a liposome.

Aspect 60. The composition of any one of aspects 55-57, wherein a) and b) are within a particle.

Aspect 61. The composition of any one of aspects 55-60, comprising one or more of: a buffer, a nuclease inhibitor, and a protease inhibitor.

Aspect 62. A composition comprising: a) the fusion polypeptide of any one of aspects 17-28, or a nucleic acid comprising a nucleotide sequence encoding the fusion polypeptide; and b) a CasX guide RNA, or one or more DNA molecules comprising a nucleotide sequence encoding the CasX guide RNA.

Aspect 63. The composition of aspect 62, wherein the CasX guide RNA is a single-guide RNA.

Aspect 64. The composition of aspect 62 or aspect 63, wherein the CasX guide RNA-encoding nucleotide is operably linked to a promoter.

Aspect 65. The composition of any one of aspects 62-64, wherein the composition comprises a lipid.

Aspect 66. The composition of any one of aspects 62-64, wherein a) and b) are within a liposome.

Aspect 67. The composition of any one of aspects 62-64, wherein a) and b) are within a particle.

Aspect 68. The composition of any one of aspects 62-67, comprising one or more of: a buffer, a nuclease inhibitor, and a protease inhibitor.

Aspect 69. A method of binding, or binding and nicking, a target nucleic acid, the method comprising contacting the target nucleic acid with: a) the variant CasX polypeptide of any one of aspects 1-9 or any one of aspects 10-16; and b) a CasX guide RNA comprising a guide sequence that hybridizes to a target sequence of the target nucleic acid.

Aspect 70. The method of aspect 69, wherein the target nucleic acid is selected from: double stranded DNA, single stranded DNA, RNA, genomic DNA, and extrachromosomal DNA.

Aspect 71. The method of aspect 69 or aspect 70, wherein said contacting takes place in vitro outside of a cell.

Aspect 72. The method of aspect 69 or aspect 70, wherein said contacting takes place inside of a cell in vitro.

Aspect 73. The method of aspect 72, wherein the cell is a eukaryotic cell.

Aspect 74. The method of aspect 73, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 75. The method of aspect 69 of aspect 70, wherein said contacting takes place inside of a cell in vivo.

Aspect 76. The method of aspect 75, wherein the cell is a eukaryotic cell.

Aspect 77. The method of aspect 76, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 78. The method of any one of aspects 69, 70, and 72-77, wherein said contacting comprises: introducing into a cell: (a) the variant CasX polypeptide, or a nucleic acid comprising a nucleotide sequence encoding the variant CasX polypeptide, and (b) the CasX guide RNA, or a nucleic acid comprising a nucleotide sequence encoding the CasX guide RNA.

Aspect 79. The method of aspect 78, wherein the CasX guide RNA is a single-guide RNA.

Aspect 80. The method of aspect 78, wherein the CasX guide RNA is a dual-guide RNA.

Aspect 81. A method of binding, or binding and nicking, a target nucleic acid, the method comprising contacting the target nucleic acid with: a) the fusion polypeptide of any one of aspects 17-28; and b) a CasX guide RNA comprising a guide sequence that hybridizes to a target sequence of the target nucleic acid.

Aspect 82. The method of aspect 81, wherein said contacting results in: i) binding of the target nucleic acid by the variant CasX polypeptide or the CasX fusion polypeptide; or ii) nicking of the target nucleic acid by the variant CasX polypeptide or the CasX fusion polypeptide.

Aspect 83. The method of aspect 81 or aspect 82, wherein the target nucleic acid is selected from: double stranded DNA, single stranded DNA, RNA, genomic DNA, and extrachromosomal DNA.

Aspect 84. The method of any one of aspects 81-83, wherein said contacting takes place in vitro outside of a cell.

Aspect 85. The method of any one of aspects 81-83, wherein said contacting takes place inside of a cell in vitro.

Aspect 86. The method of aspect 85, wherein the cell is a eukaryotic cell.

Aspect 87. The method of aspect 86, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 88. The method of any one of aspects 81-83, wherein said contacting takes place inside of a cell in vivo.

Aspect 89. The method of aspect 88, wherein the cell is a eukaryotic cell.

Aspect 90. The method of aspect 89, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 91. The method of any one of aspects 81-83 and 85-90, wherein said contacting comprises introducing into a cell: (a) the fusion CasX polypeptide, or a nucleic acid comprising a nucleotide sequence encoding the fusion CasX polypeptide, and (b) the CasX guide RNA, or a nucleic acid comprising a nucleotide sequence encoding the CasX guide RNA.

Aspect 92. The method of aspect 91, wherein the CasX guide RNA is a single-guide RNA.

Aspect 93. The method of aspect 91, wherein the CasX guide RNA is a dual-guide RNA.

Aspect 94. A method of modulating transcription from a target DNA, modifying a target nucleic acid, or modifying a protein associated with a target nucleic acid, the method comprising contacting the target nucleic acid with:

- a1) the CasX fusion polypeptide of any one of aspects 17-28; and
- a2) a CasX guide RNA comprising a guide sequence that hybridizes to a target sequence of the target nucleic acid; or
- b1) a CasX polypeptide comprising amino acid substitutions of D672, E769, and E935 of the CasX1 polypeptide of SEQ ID NO:1, or corresponding amino acid positions of another CasX polypeptide; and
- b2) a CasX guide RNA that comprise a guide sequence that hybridizes to a target sequence in a non-coding strand of a target nucleic acid.

Aspect 95. The method of aspect 94, wherein the CasX guide RNA is a single-guide RNA.

Aspect 96. The method of aspect 94, wherein the CasX guide RNA is a dual-guide RNA.

Aspect 97. The method of any one of aspects 94-96, wherein said modification is not cleavage of the target nucleic acid.

Aspect 98. The method of any one of aspects 94-96, wherein the target nucleic acid is selected from: double stranded DNA, single stranded DNA, RNA, genomic DNA, and extrachromosomal DNA.

Aspect 99. The method of any one of aspects 94-98, wherein said contacting takes place in vitro outside of a cell.

Aspect 100. The method of any one of aspects 94-98, wherein said contacting takes place inside of a cell in vitro.

Aspect 101. The method of aspect 100, wherein the cell is a eukaryotic cell.

Aspect 102. The method of aspect 101, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 103. The method of any one of aspects 94-98, wherein said contacting takes place inside of a cell in vivo.

Aspect 104. The method of aspect 103, wherein the cell is a eukaryotic cell.

Aspect 105. The method of aspect 104, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 106. The method of any one of aspects 94-105, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 107. The method of any one of aspects 94-105, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 108. The method of any one of aspects 94-105, wherein the heterologous polypeptide is protein that increases or decreases transcription.

Aspect 109. The method of aspect 94, wherein the heterologous polypeptide is a transcriptional repressor domain.

Aspect 110. The method of aspect 94, wherein the heterologous polypeptide is a transcriptional activation domain.

Aspect 111. The method of any one of aspects 94-105, wherein the heterologous polypeptide is a protein binding domain.

Aspect 112. A modified CasX single-molecule guide RNA (sgRNA), wherein the modified CasX sgRNA comprises a heterologous RNA inserted into, or replacing all or part of, an extended stem portion of a native CasX guide RNA.

Aspect 113. The modified CasX sgRNA of aspect 112, wherein the extended stem portion comprises a nucleotide sequence having at least 90% nucleotide sequence identity to the following nucleotide sequence: 5'-GCGC-

UUAUUUAUCGGAGAGAAACCGAUA-AGUAAAACGC-3' (SEQ ID NO:9).

Aspect 114. The modified CasX sgRNA of aspect 112 or aspect 113, wherein the heterologous RNA replaces from 1 nucleotide to 38 nucleotides of the extended stem.

Aspect 115. The modified CasX sgRNA of aspect 112 or aspect 113, wherein the heterologous RNA replaces from 5 nucleotides to 38 nucleotides of the extended stem.

Aspect 116. The modified CasX sgRNA of any one of aspects 112-115, wherein the heterologous RNA is an aptamer, a noncoding RNA, a ribozyme, a functional RNA sequence, one of a pool of random RNA sequences, an RNA scaffold, an RNA-based sensor, an RNA-based signal processor, an RNA-based signaling device, a naturally occurring long non-coding RNA (lncRNA), a lncRNA subdomain, a synthetic lncRNA, or a synthetic lncRNA subdomain.

Aspect 117. The modified CasX sgRNA of any one of aspects 112-115, wherein the heterologous RNA is an aptamer that binds to an adaptor protein, wherein the adaptor protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, and PRR1.

Aspect 118. The modified CasX sgRNA of any one of aspects 112-115, wherein the heterologous RNA is an MS2 stem-loop, a PP7 stem-loop, or an L7Ae motif.

Aspect 119. The modified CasX sgRNA of aspect 118, wherein the MS2 stem-loop comprises the nucleotide sequence 5'-ACAUGAGGAUUACCCAUGU-3' (SEQ ID NO:65).

Aspect 120. The modified CasX sgRNA of any one of aspects 112-119, wherein the heterologous RNA has a length of from 5 nucleotides to 500 nucleotides.

Aspect 121. The modified CasX sgRNA of any one of aspects 112-119, wherein the heterologous RNA has a length of from 5 nucleotides to 100 nucleotides.

Aspect 122. The modified CasX sgRNA of any one of aspects 112-119, wherein the heterologous RNA has a length of from 5 nucleotides to 50 nucleotides.

Aspect 123. A method of detecting a target single-stranded DNA in a sample, the method comprising:

(a) contacting the sample with:

(i) the variant CasX polypeptide of any one of aspects 1-9 or any one of aspects 10-16;

(ii) a guide RNA comprising: a region that binds to the variant CasX polypeptide, and a guide sequence that hybridizes with the target DNA; and (iii) a detector DNA that is single stranded and does not hybridize with the guide sequence of the guide RNA; and (b) measuring a detectable signal produced by cleavage of the single-stranded detector DNA by the variant CasX polypeptide, thereby detecting the target DNA.

Aspect 124. The method of aspect 123, wherein the target DNA is viral DNA.

Aspect 125. The method of aspect 123 or aspect 124, wherein the single-stranded detector DNA comprises a modified nucleobase, a modified sugar moiety, and/or a modified nucleic acid linkage.

Aspect 126. The method of any one of aspects 123-125, wherein the single stranded detector DNA comprises a fluorescence-emitting dye pair.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular (ly); i.p., intraperitoneal (ly); s.c., subcutaneous (ly); and the like.

Example 1

Materials and Methods

Strains and Media

The in vivo CRISPRi (Larson et al. (2013) *Nat Protocol* 8:2180) and cleavage assays described below utilize *E. coli* MG1655 containing genomically-integrated and constitutively expressed Green fluorescent protein (GFP) and Red fluorescent protein (RFP). Standard cloning techniques were used to create all plasmids. Plasmid construction and retention was ensured with AmpR and CmR as selectable markers (Oakes et al. (2016) *Nat Biotechnol* 34:646). EZ-rich defined growth media (EZ-RDM, Teknova) was used in all CRISPRi assay fluorescent measurements. 2xYT (LB) with the addition of 1.5% Bacto Agar (BD) was used for all plating assays.

*E. coli* Assays

CRISPRi assays were performed in a similar manner to previous work. Oakes et al. (2016) supra. In brief to test CasX's ability to bind genomic DNA and repress transcription, electrocompetent *E. coli* were co-transformed with a plasmid encoding the guide RNA and a plasmid encoding the CasX protein as described. The transformed cells were grown on media containing two antibiotics to ensure selection for both plasmids. Colonies were picked in triplicate from these plates into EZ-RDM liquid media and grown for 12 hours. These saturated cultures were diluted 1:1000 into EZ-RDM media containing 2 nM anhydrotetracycline inducer and 150 μL of this mixture was followed for OD600 and GFP (a.u.) via a 96-well microplate reader (Tecan m1000) every 10 minutes over the course of 12 hours at 37° C. unless otherwise noted.

To perform the bacterial genome targeting assay, 100 ng of the CRISPR-Cas protein-encoding plasmid was electroporated into electrocompetent MG1655 *E. coli* expressing the GFP-targeting sgRNA plasmid using a BTX Harvard apparatus ECM 630 High Throughput Electroporation System in biological triplicate. The guide sequence was moved onto the protein-encoding plasmid and 200 ng of this was used in the transformation. The cells were recovered for one hour in 300 μL SOC medium at 37° C. unless otherwise noted. Two technical replicates of tenfold serial dilutions were spotted onto plates containing antibiotics for plasmid(s) used in the transformation. These grew at either 37° C. for 12 hours or 30° C. for 16 hours and were used to calculate CFU/mL.

Human Cell GFP Disruption

HEK 293T destabilized GFP experiments were conducted as previously described. Oakes et al. (2016) supra. Briefly the d2EGFP HEK293T reporter cells from our previous work were cultured and seeded into 96 well plates and transfected according to the manufacturer's protocol with Lipofectamine 2000 (Life Technologies) and the described to amount of plasmid DNA encoding the CasX sgRNA (Burstein et al. (2017) Nature 542:237) and CasX, P2A-puromycin fusion. 24 h post transfection cells were selected for the CasX plasmid with 1.5 μg/ml puromycin for 48 hours. Cells were allowed to regrow to confluence for ~5 days and analyzed for EGFP expression using an Attune NxT Flow Cytometer and high-throughput autosampler. For extended assays cells were passaged 1:10 and reanalyzed on the date notes.

T7EI Assay

T7EI assays were performed as previously described with slight modification. Oakes et al. (2016) supra. Briefly, cells were suspended 1:1 in QuickExtract (lucigen) buffer and DNA was extracted using the manufacturer's protocol. This mixture was used directly in a PCR reaction designed to amplify the GFP locus and ~200 ng of PCR product was utilized for denaturing, annealing & digestion with T7E1 (NEB) according to the manufacturer's protocol. Samples were analyzed on a 2% agarose gel with SYBRsafe (Thermo Fisher).

Protein Expression, Purification and Complex Reconstitution

The gene encoding CasX (Deltaproteobacteria (Dpb-CasX; SEQ ID NO:1; FIG. 16)) was sub-cloned into the 2CT-10 expression vector. CasX-D672A-E769A-D935A and CasXΔ101-191 were obtained by amplifying the CasX plasmid using mutagenetic PCR primers. All the proteins were expressed using ROSETTA™ *E. coli* cells (Millipore Sigma). Main culture (Terrific broth, containing 100 mg/L ampicillin) was inoculated with 3% of overnight culture grown in Luria broth. The main culture was grown to an OD of 0.5-0.6, cooled down and protein expression was induced by addition of IPTG to a final concentration of 0.5 mM, and expression was allowed to proceed overnight at 16° C. Cells were harvested, re-suspended in Ni buffer A (500 mM sodium chloride, 50 mM HEPES, pH 7.5, 10% glycerol, 0.5 mM TCEP) and frozen at −80° C. For wild type CasX protein preparation, cells were thawed, diluted twice with Ni buffer A, followed by addition of PMSF (final concentration 0.5 mM), and 3 tablets of Roche protease inhibitor cocktail per 100 ml of cell suspension. Cells were lysed by sonication, and pelleted at 35000 g for 30 min. Clarified lysate was purified using Ni-NTA agarose beads, using step gradient elution with imidazole-containing buffer (Ni buffer B (highest imidazole concentration): 500 mM sodium chloride, 500 mM imidazole, 50 mM HEPES, pH 7.5, 10% glycerol, 0.5 mM TCEP). The pure fractions were pooled and TEV protease was added (1 mg protease/20 mg purified protein in final concentration). The protein with TEV protease was dialyzed overnight against the following buffer: 500 mM sodium chloride, 50 mM HEPES, pH 7.5, 10% glycerol, 0.5 mM TCEP. Then protein was applied to a Maltose Binding Protein (MBP) column and the MBP flow-through was applied to a heparin column. Protein was eluted from the heparin column using a sodium chloride gradient up to 1M sodium chloride. For the wild type protein, there were two peaks containing CasX. The peak that eluted at lower salt concentration was found to contain inactive and aggregated protein and was not pooled; only the second peak contained active protein and only that protein was used for the assays. The active protein from the heparin column was concentrated and applied to a Superdex200 10/300 column in the following buffer: 500 mM potassium chloride, 50 mM HEPES, pH 7.5, 10% glycerol, 0.5 mM TCEP. Pure protein was concentrated and flash-frozen. CasXΔ101-191 purification was purified as the same way as wild type CasX. The overall expression yield was similar, but the amount of the well-folded protein (second peak) was lower than in case of wild type protein. For CasX-D672A-E769A-D935A, the purification was similar, except that dialysis buffer was: 300 mM sodium chloride, 50 mM HEPES, pH 7.5, 10% glycerol, 0.5 mM TCEP and size-exclusion buffer was 300 mM potassium chloride, 50 mM HEPES, pH 7.5, 10% glycerol, 0.5 mM TCEP, and all the protein eluted as a single well-folded protein peak on heparin column.

Single guide RNA was in vitro transcribed using T7 RNA polymerase and purified using 10% UREA-PAGE. The in vitro transcription template was as follows:

(SEQ ID NO: 78)

GAAATTAATACGACTCACTATAggCGCGTTTATTCCATTACTTTGGAGC

CAGTCCCAGCGACTATGTCGTATGGACGAAGCGCTTATTTATCGGAGAG

AAACCGATAAGTAAAACGCATCAAAGTCCTGCAGCAGAAAATCAAA

The CasX-sgRNA complex was assembled by incubating protein with 1.6×-fold stoichiometric excess of sgRNA for 30 min at room temperature. The ternary complexes were assembled by incubating CasX-sgRNA with 1.8×-fold stoichiometric excess of annealed DNA target for 30 min at room temperature. After the complexes were assembled, the assembled complexes were purified by size-exclusion chromatography using Superdex200 10/300 column.

DNA Cleavage Assays

DNA substrates were 5'-end-labeled with T4 PNK (NEB) in the presence of gamma $^{32}$P-ATP. Unless otherwise noted the following conditions were used: proteins were diluted to 4 μM with dilution buffer: 500 mM NaCl, 10% glycerol, 20 mM Tris-HCl, pH 7.5, 1 mM magnesium chloride, 0.5 mM TCEP. Single-guide RNA was diluted to 6 μM with reaction buffer: 20 mM HEPES, pH 7.5, 10 mM magnesium chloride, 150 mM potassium chloride, 1% glycerol, 0.5 mM TCEP. Resulting stocks of protein and sgRNA were mixed in 1:1 molar ratio and incubated for 10 min at room temperature to produce active complex. Cleavage reactions were conducted in 1× reaction buffer; the radiolabeled probe concentration was 2 nM. Reactions were initiated by addition of CasX-sgRNA to a final concentration of 200 nM. The reactions were conducted at 37° C., and aliquots were taken at the following time points: 0, 2, 5, 30, 60, 120 minutes. The aliquots were immediately mixed with formamide loading buffer (final concentration 45% formamide and 50 mM EDTA, with trace amount of bromophenol blue) and heated for 10 min at 90° C. for quenching. Samples were separated by 10% UREA-PAGE, gels were dried and the results were visualized using a phosphoimager (Amersham Typhoon (GE Healthcare)).

In the cleavage assays used to determine the DNA cut sites (FIG. 1*b, c*), the following concentrations were used: 100 nM Cas protein, 120 nM guide RNA. In the experiment where trans-cleavage activity was compared between different CRISPR-Cas proteins (FIG. 1*e*) the following concentrations were used: 100 nM Cas proteins, 120 nM guide RNA. 150 nM activator, and M13mp18 SSDNA (New England Biolabs). In the experiments where trans-cleavage activity was compared between CasX and CasXΔ101-191, a random 50 nt oligonucleotide substrate was used.

EM Sample Preparation and Data Collection

CasX complexes in a buffer containing 20 mM HEPES, pH 7.5, 150 mM KCl, 1 mM DTT, and 0.25% glycerol were used for cryo-EM sample preparation. Immediately after glow-discharging the grid for 14 seconds using a Solaris plasma cleaner. 3.6 μL droplets of the sample (~3 μM) were placed onto C-flat grids with 2 μm holes and 2 μm spacing between holes (Protochips Inc.). The grids were rapidly plunged into liquid ethane using an FEI Vitrobot MarkIV maintained at 8° C. and 100% humidity, after being blotted for 4 seconds with a blot force of 8. Data were acquired using an FEI Titan Krios transmission electron microscope operated at 300 keV with a GIF energy filter, at a nominal magnification of ×135,000 (0.9 Å pixel size) for ternary complexes and ×105,000 (1.15 Å pixel size) for binary complex, with defocus ranging from −0.5 to −2 μm. Micrographs were recorded using SerialEM on a Gatan K2 Summit direct electron detector operated in super-resolution mode. (Mastronarde (2003) *Micro Microanal* 9:1182-1183). A 4.8s exposure was collected and fractionated into 32, 150 ms frames with a dose of 9.58 e-Å-2$s^{-1}$.

Apo-CasX in a buffer containing 20 mM HEPES, pH 7.5, 500 mM NaCl, 1 mM DTT, and 5% glycerol was used for cryo-EM sample preparation by following the sample protocol as for CasX complexes. Data were acquired using an FEI Titan Krios transmission electron microscope operated at 300 keV with energy filter and Volta Phase plate, at a nominal magnification ×105,000 (1.15 Å pixel size) with the defocus of about −0.5 μm.

EM Data Analysis

For CasX binary and ternary complexes, the 28 frames (the first 2 and last 2 frames were skipped) of each image stack in super-resolution model were aligned, decimated, and summed and dose-weighted using Motioncor2 (Zheng et al. (2017) *Nat Methods* 14:331). CTF values of the summed micrographs were determined using Getf (Zhang (2016) *J Struct Biol* 193: 1-12). Initial particle picking to generate template images was performed using EMAN2 (Tang et al. (2007) *J Struct Biol* 157:38-46). About 10,000 particles were selected and then imported into Relion2.0 for reference-free 2D classification (Kimanius (2016) *eLife* 5:e18722). Particle picking for the complete dataset was carried out using Gautomatch with templates generated in the previous 2D classification. Local CTF was re-calculated by Gctf with the determined box files. Particles were extracted from the dose-weighted, summed micrographs in Relion2.0 and then imported into CryoSparc34 for 2D classification, ab initio modeling, heterogeneous refinement, homogenous refinement and local resolution calculation.

For images obtained with a Volta Phase Plate, following preprocessing the CTF and phase-shift values of the summed-micrographs were determined using Getf and then applied to dose-weighted, summed micrographs for further processing.

Cross-Linking and Mass Spectrometry

CasX samples in HEPES buffer were crossed-linked using 1 mM bis-sulfosuccinimidyl-suberate (BS3) at 30° C. for 30 mins. The reactions were stopped by adding 50 mM Tris (final concentration). Cross-linked samples were then digested by trypsin and purified for mass spectrometry analysis. Cross-linked peptides were identified using an upgraded version of pLink (Yang et al. (2012) *Nat Meth* 9:904). In pLink, parameter of cross-linker was set to BS3. Parameter of enzyme was set to trypsin with up to three missed cleavages. Precursor mass tolerance and fragment mass tolerance were both set to 20 ppm. At least 6 amino acids were required for each peptide chain. Carbamidomethylation on cysteine was searched as a fixed modification. Oxidation on methionine was searched as a variable modification. Search results were filtered by requiring False Discovery Rate (FDR)<5% at the spectral level. Further inspection of MS/MS spectra were performed using pLabel (Asara et al. (2008) *Proteomics* 8:994-999).

Atomic Model Building

For the CasX ternary complex containing a 30 bp target DNA, the cryo-EM density of State I at 3.7 Å resolution was used for secondary structure search in PHENIX with the "Find Helices and Strands" program (Adams et al. (2010) *Acta Crystallogr D Biol Crystallogr* 66:213-221). The protein main chain was manually traced in Coot (Emsley et al. (2010) *Acta Crystallogr D Biol Crystallogr* 66: 486-501). After main chain building, side chains were assigned manually based on the EM map in Coot and then were further improved using the cryo-EM map of State I with the full R-loop at a resolution of 3.2 Å. The DNA substrates and gRNA were manually built ab initio in Coot based on the cryo-EM density. To improve backbone geometry, the atomic model was subjected to PHENIX real space refinement (global minimization and ADP refinement) with secondary structure, Ramachandran, rotamer, and nucleic-acid restraints. The final model was validated using Molprobity (Chen et al. (2010) *Acta Crystallogr D Biol Crystallogr* 66: 12-21) and cross-linking MS data. The atomic models of State II were obtained by running flexible fitting on the State I atomic model against the State II cryo-EM map (4.2 Å resolution) with secondary structure restrains in MDFF (Trabuco et al. (2009) *Methods* 49:174-180). PHENIX real space refinement was further used to improve backbone geometry. This State II atomic model was directly adopted for structural interpretation of the CasX ternary complex State II with full R-loop DNA and shortened non-target strand DNA.

For the CasX-ternary complex containing a full R-loop DNA, the atomic model of CasX-ternary complex State I with 30 bp target DNA was fitted into the State I cryo-EM map of CasX-ternary complex containing full R-loop DNA (resolution of 3.2 Å) using UCSF-Chimera (Pettersen et al. (2004) *J Comp Chem* 25:1605-1612). Additional DNA nucleotides were manually built in Coot. The atomic model was subjected to PHENIX real space refinement against the cryo-EM map and validated using Molprobity.

For the CasX-ternary complex containing a shortened non-target strand DNA, the atomic model of CasX-ternary complex State I with 30 bp target DNA was fitted into the State I EM map of CasX-ternary complex containing the shortened non-target strand DNA (resolution 4.5 Å) using Chimera. DNA nucleotides were manually modified in Coot. The atomic model was subjected to PHENIX real space refinement against the cryo-EM map and validated using Molprobity.

Results

Reconstitution of crRNA-Guided CasX Cutting of Double-Stranded DNA

Figure 1B:
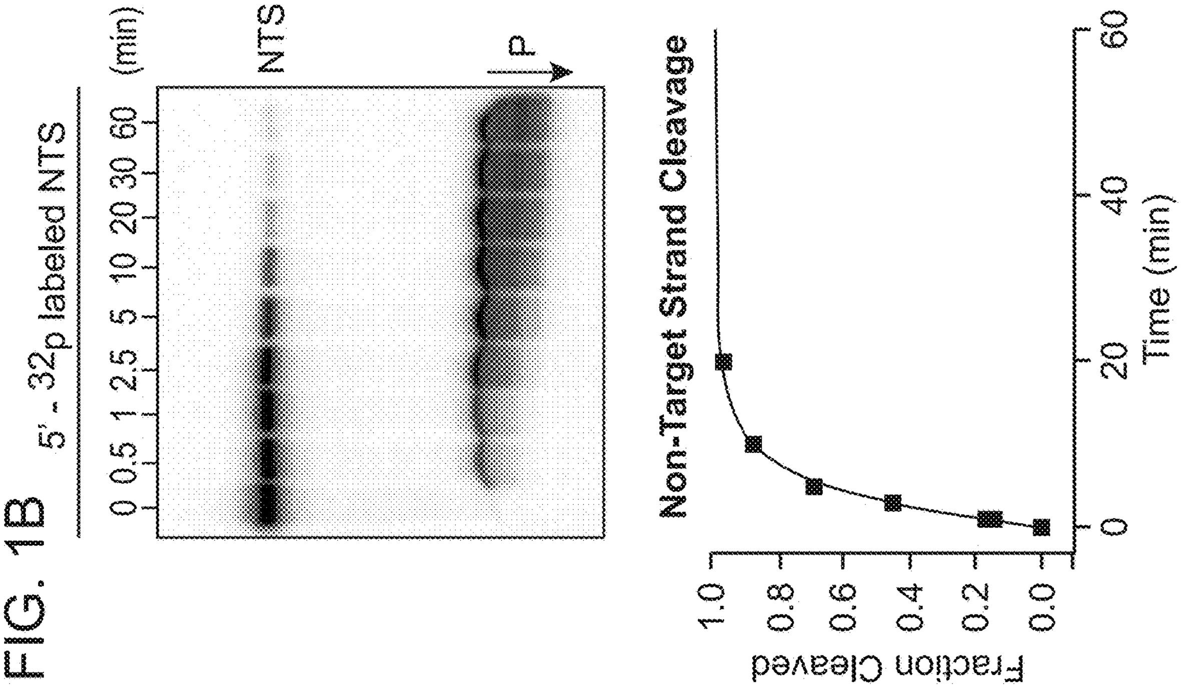
Figure 1C:
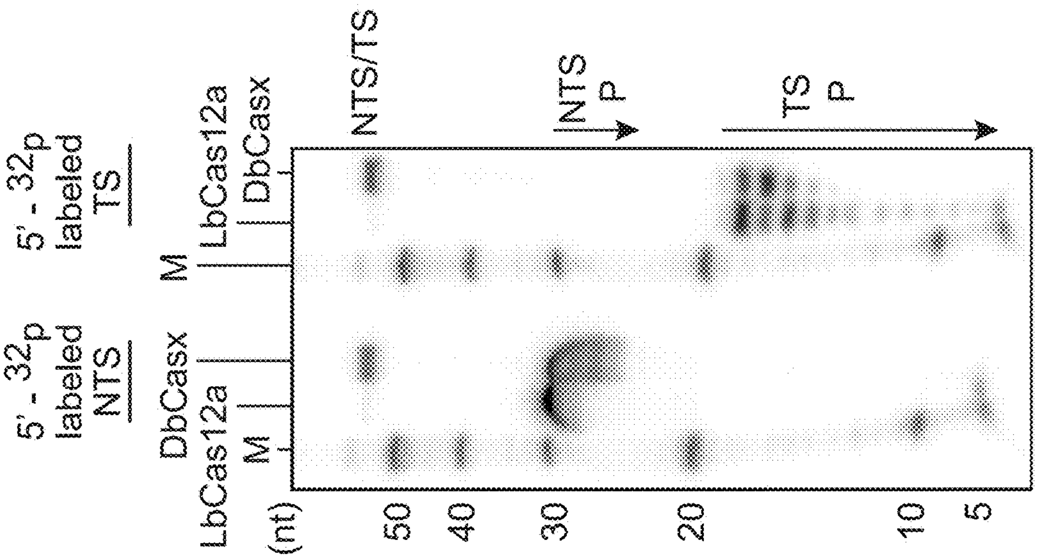
Figure 1D:
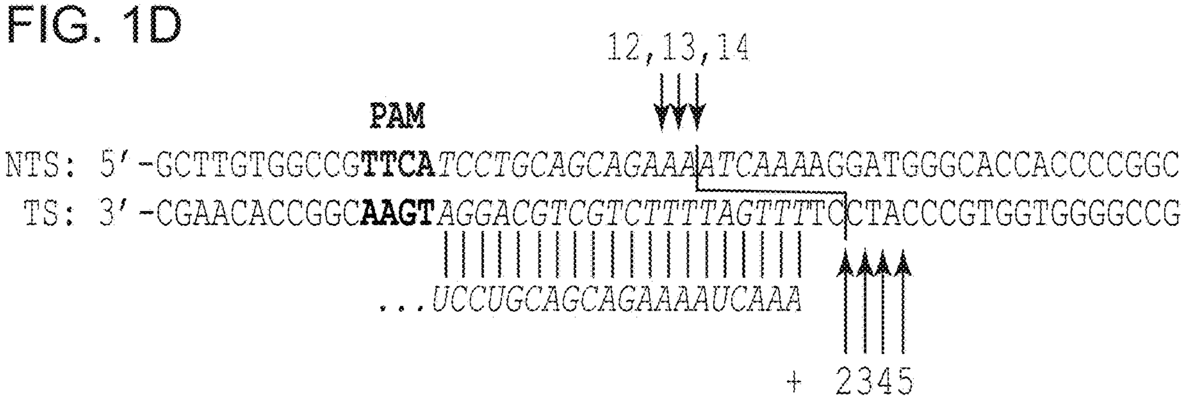

It was previously demonstrated that CasX proteins can perform RNA-dependent plasmid interference in bacteria and that the two natural RNAs necessary for this activity (crRNA and trans-activating CRISPR RNA (tracrRNA)) can be combined into a single-guide RNA format (Burstein et al. (2017) *Nature* 542:237) (FIG. 1*a*). To determine the molecular function of CasX, biochemical studies of both the wild-type and catalytically inactive triple mutant CasX from Deltaproteobacteria (DpbCasX) were undertaken. It was found that purified DpbCasX with single-guide RNA is capable of cleaving double-stranded DNA bearing a sequence complementary to the 20-nucleotide guide RNA segment and adjacent to a TTCN PAM motif (FIG. 1*b*). Mapping the cut sites for the target and non-target strands of the DNA showed that DpbCasX generates products with ~10-nucleotide staggered ends due to cleavage 12-14 nucleotides after the PAM on the non-target strand and 22-25 nucleotides after the PAM on the target strand (FIG. 1*c, d*). This mode of double-stranded DNA cleavage is consistent with the staggered cuts to DNA observed for Cas12a and Cas12b (C2c1), other CRISPR-Cas enzymes that use a single RuvC active site for DNA cleavage. (Koonin et al. (2017) *Curr Opin Microbiol* 37:67-78; Yang et al. (2016) *Cell* 167:1814-1828; Zetsche et al. (2015) *Cell* 163:759-771.

Figure 1E:
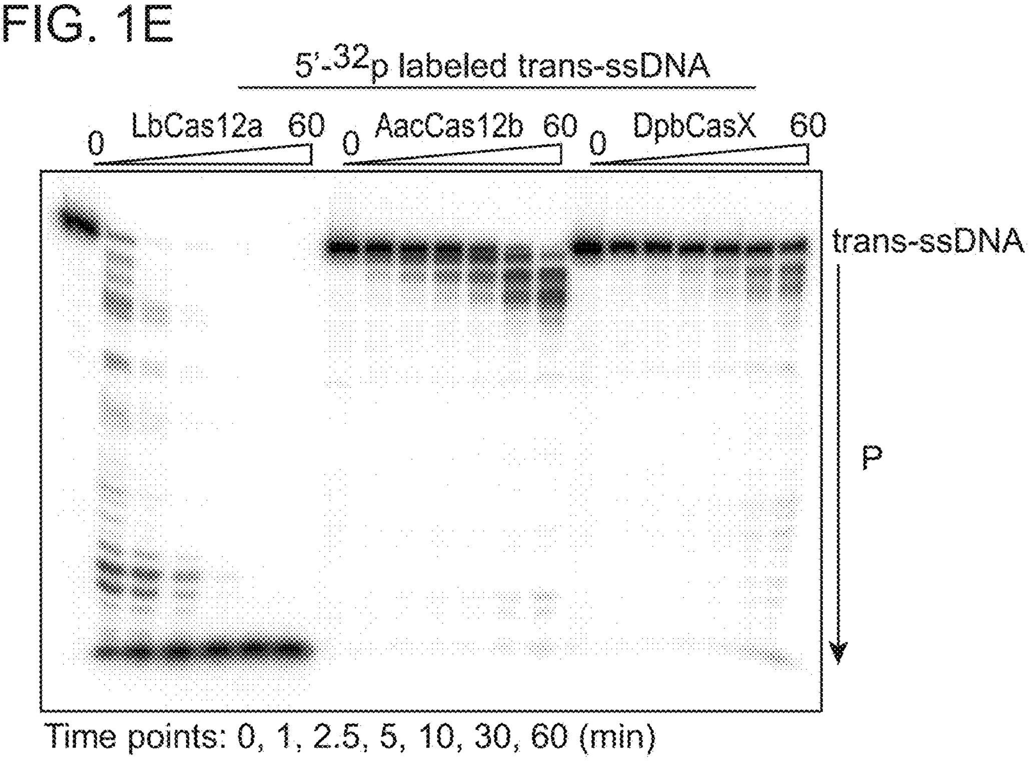

Unlike Cas9, Cas12a becomes a highly active single stranded DNA nuclease after target DNA binding, triggering non-specific single-stranded DNA degradation (Chen et al. (2018) *Science* 360:436-439; Swarts and Jinck (2018) *Mol. Cell* 73:589). To test whether CasX displays similar target-triggered activity, single-stranded phage DNA was incubated with DpbCasX-guide RNA complexes that target a separate unrelated double-stranded DNA substrate. It was found that trans-ssDNA cutting activity was minimal compared to that observed for LbCas12a or for the related enzyme Cas12b (FIG. 1*e*). These results indicate that the presence of a single active site for double-stranded DNA cleavage does not necessarily correspond to target-dependent trans-cleavage activity, raising the possibility of structural or mechanistic differences between these enzyme families.

FIG. 1A-1E. CasX cuts double stranded DNA with single guide RNA in vitro. a, A schematic of CRISPR-CasX locus. CasX is colored in light orange with RuvC domain highlighted. Cas4, Cas1 and Cas2 are colored in light blue, tracrRNA gene is colored in gray. CRISPR array is colored in teal. Cartoons of Cas protein genes are scaled according to the gene size. Schematic of the CasX dual-guide RNA and single guide is shown in the bottom panel—tracrRNA in gray, crRNA is teal and the target DNA is black. NTS indicates the non-target strand, and TS indicates the target strand. PAM sequence is shown on the NTS DNA. The RNA loop fusing tracrRNA and crRNA into single guide RNA is colored in red. b, DNA cleavage efficiency by DpbCasX. The non-target strand (NT) of a dsDNA substrate was labeled. The reaction time for each lane is marked. P indicates the cleavage product. The cleavage fraction is calculated based on the NTS band density compared to input NTS band density at reaction time of 0 min. c, Conservation of cleavage specificity of DpbCasx (labeled as "DdCasX" in the figure) with Lachnospiraceae bacterium Cas12a LbCas12a (Chen et al. (2018) *Science* 360(6387):436-439). Left panel shows that non-target strand (NT) of a dsDNA substrate was labeled, while in the right panel, the target strand (T) was labeled. Cleavage products were resolved in 12% urea-PAGE. Lane M shows labeled size ladders. d, The cleavage sites for non-target strand (NTS) and target strand (TS). Cleavage for NTS happens between the nucleotide 12 to 14 after the PAM marked with black arrows. Cleavage for TS happens between the nucleotide 2 to 5 after the spacer region. e, Weak cleavage activity of DpbCasX on labeled trans ssDNA as compared to LbCas12a and AacCas12b (*Alicyclobacillus acidoterrestritis* Cas12b, Yang et al. (2016) *Cell* 167:1814-1828). For a trans ssDNA cleavage assay, radiolabeled non-specific ssDNA was incubated with a specific Cas-crRNA RNP complex (shown in the figure) in the presence of its target ssDNA (activator) for different lengths of time at 37° C. Substrates (shown in lane 0) and cleavage products were resolved by denaturing 12% urea-PAGE.

CasX Triggers Genome Silencing and Editing in Bacterial and Human Cells

Figure 2A:
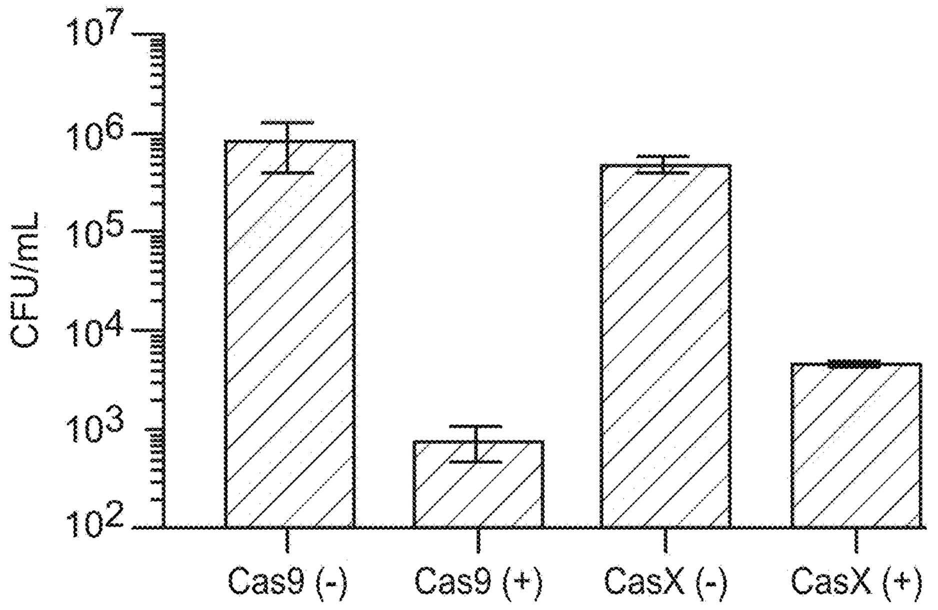
FIG. 2A-2J depict data showing that CasX effectively manipulates genomes in vivo.
Figure 2B:
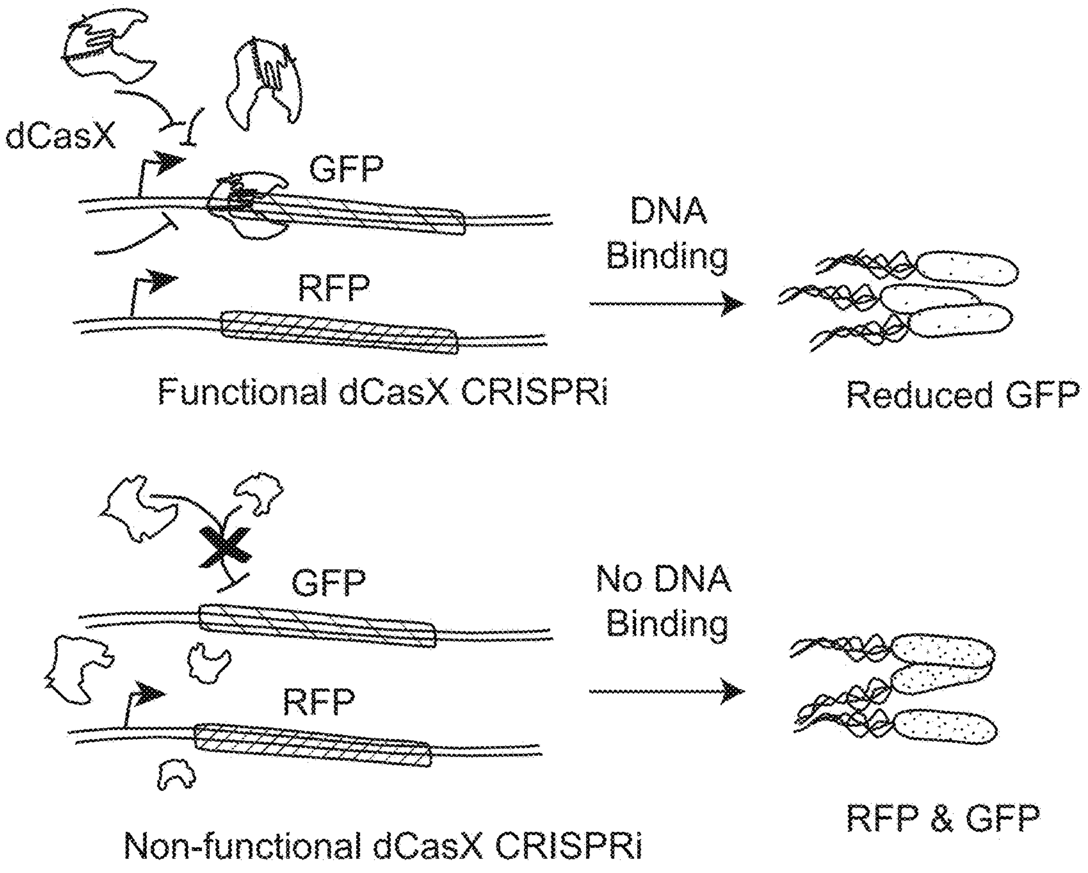
Figure 2C:
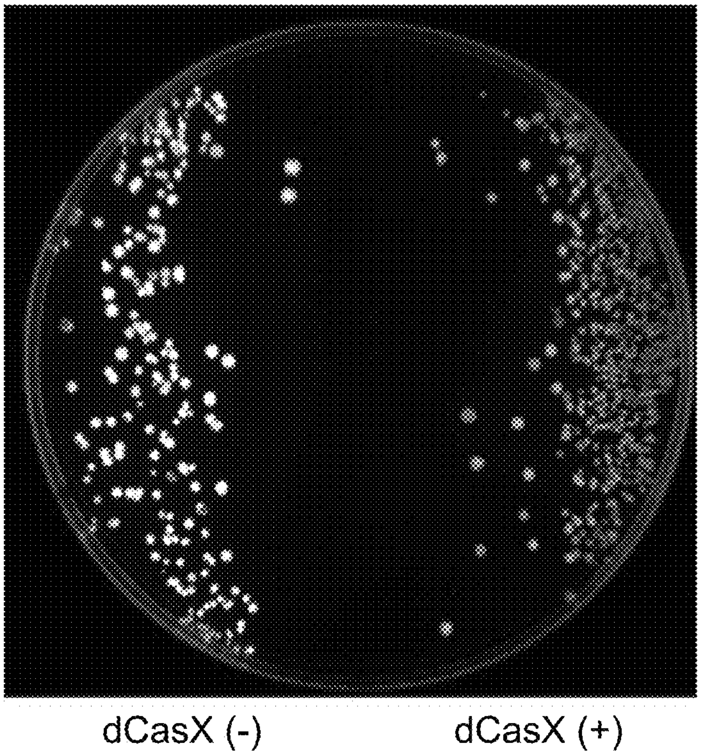
Figure 2D:
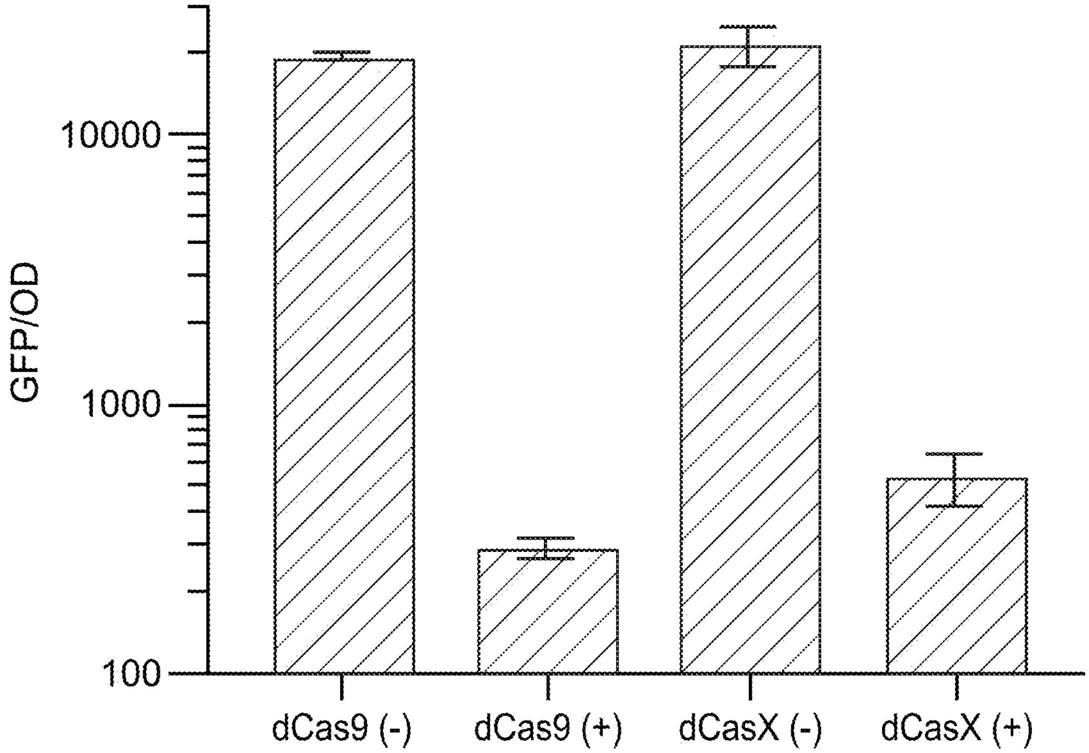

To determine whether the RNA-guided DNA cutting activity of CasX can be harnessed for programmed genome targeting, DpbCasX and its single-guide RNA (sgRNA) were expressed in *E. coli* using a guide sequence complementary to an integrated reporter in the genome of bacterial strain MG1655 (Oakes et al. (2014) *Meth Enzymol* 546: 491-511; Oakes (2016) *Nat Biotechnol* 34:646). It was found that DpbCasX reduced cell viability, at near but slightly less than CRISPR-Cas9 activity levels (FIG. 2*a*). It was then tested whether CasX can function as a CRISPRi effector in *E. coli* by mutating RuvC active site residues (D672A-E769A-D935A) to create a deactivated DpbCasX (dDpbCasX) competent for RNA-guided DNA binding and gene repression rather than cutting (FIG. 2*b*). Silencing of green fluorescent protein (GFP) expression was observed with this dDpbCasX construct using different guide RNAs targeting multiple sites within the GFP-encoding gene (FIG. 8). It was found that mutation of all three DpbCasX residues was required for maximal gene repression activity (depicted graphically in FIG. 8). CasX-based bacterial CRISPRi thus provides an ideal system for rapid, visual and quantitative in vivo characterization of CasX constructs (FIG. 8).

Figure 2E:
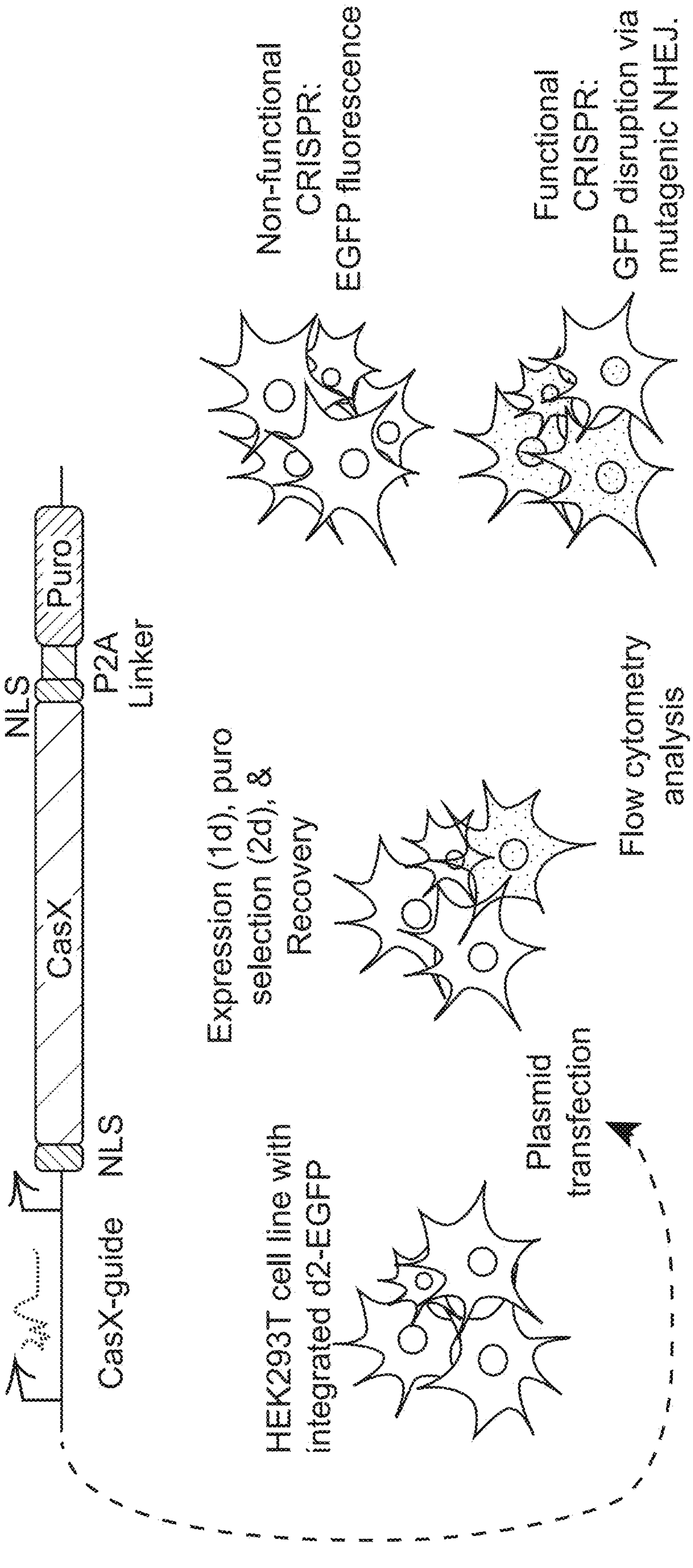
Figure 2F:
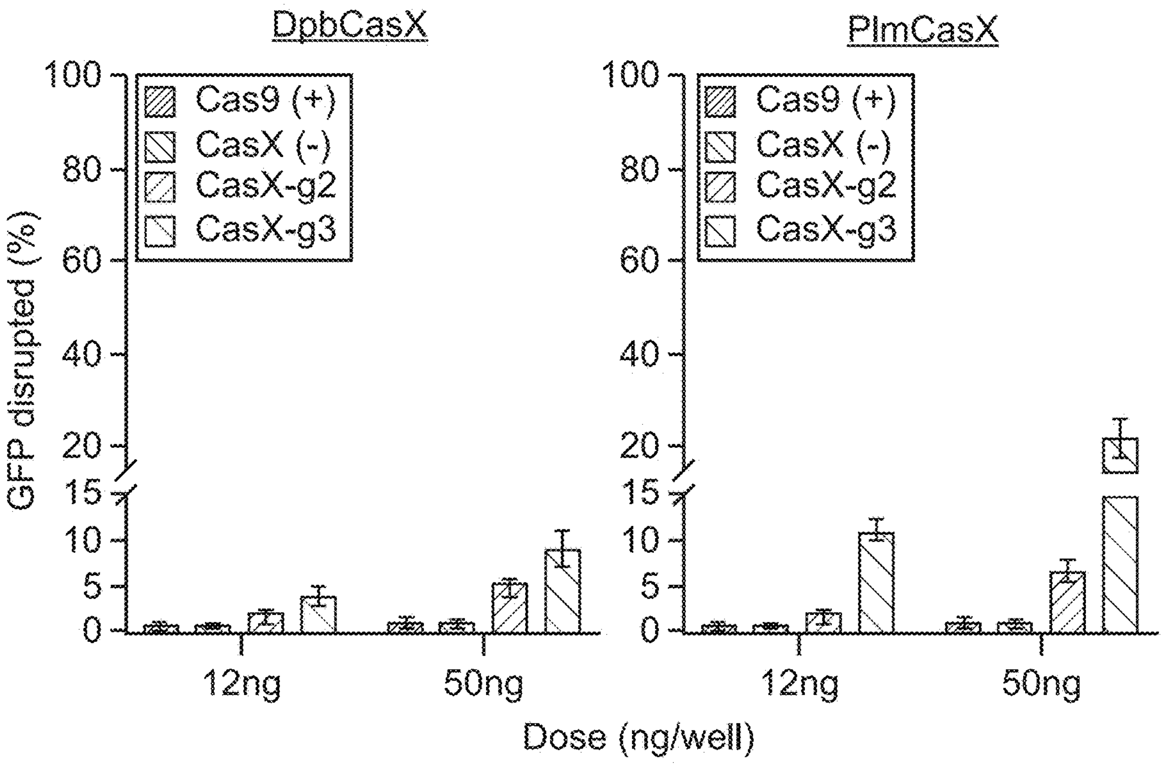
Figure 2G:
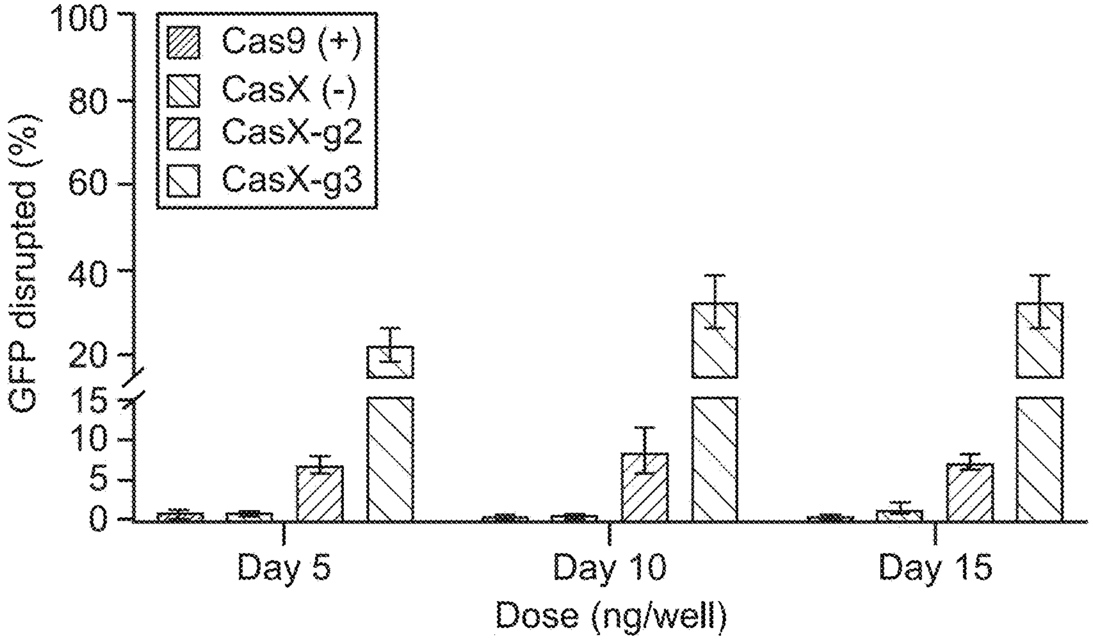
Figure 2H:
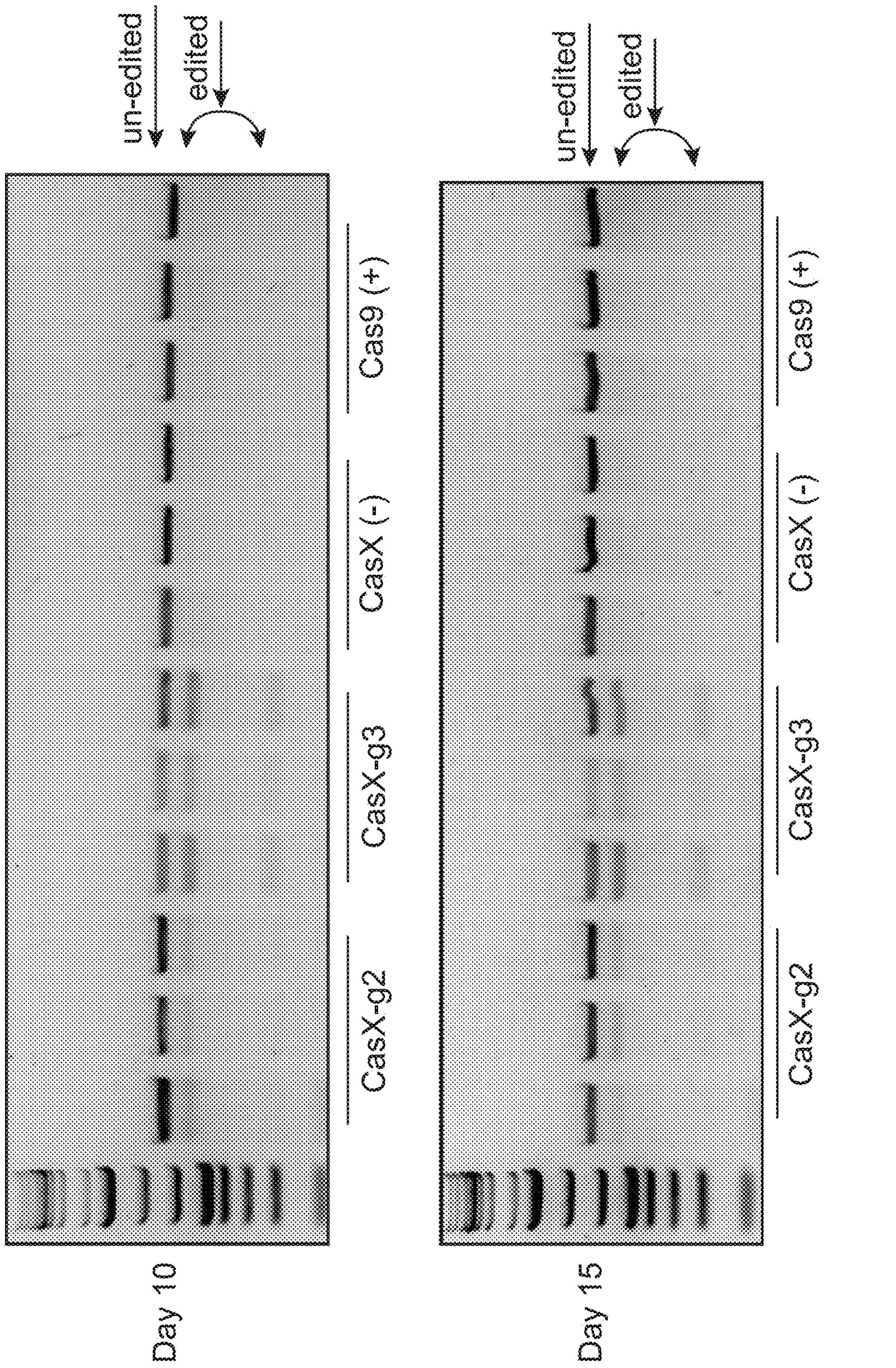
Figure 2I:
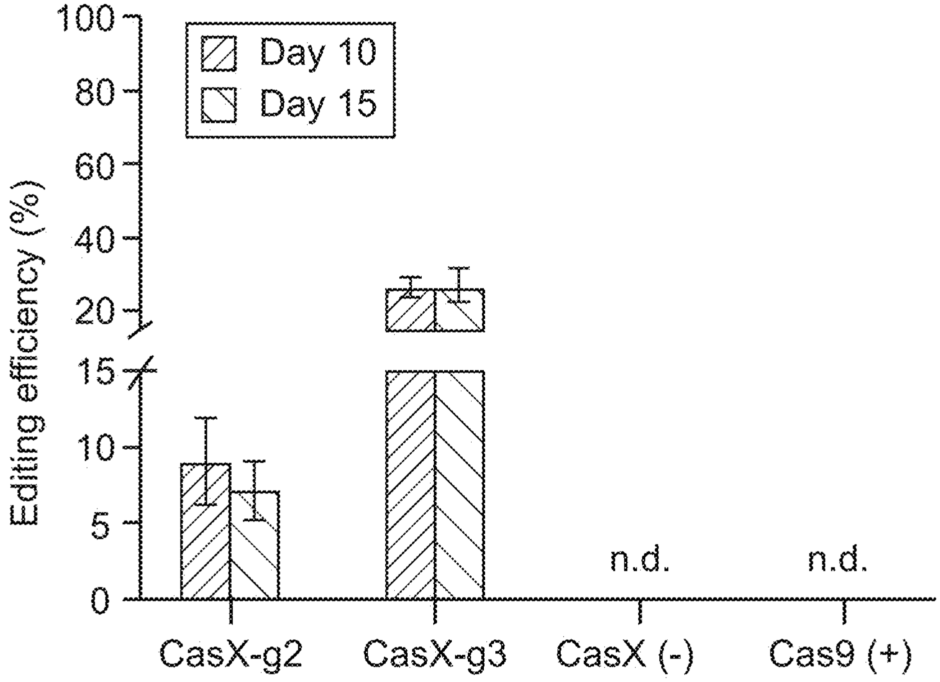
Figure 2J:
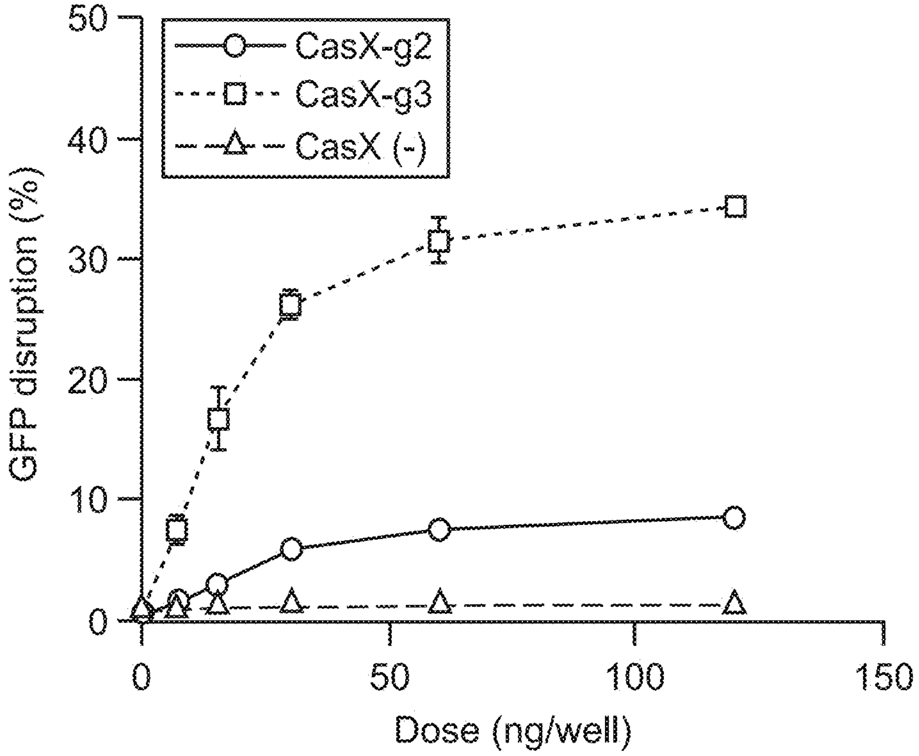

It was then tested whether CasX is capable of inducing cleavage and gene editing of mammalian genomes. Using a previously reported destabilized-GFP disruption assay (Oakes et al. (2016) supra) (FIG. 2*e*), it was found that DpbCasX can induce targeted GFP gene disruption in HEK293T cells with limited efficiency using guide RNAs complementary to either the template or coding strand (g2 or g3, respectively) (FIG. 2*f*). The effectiveness of the CasX molecule from Planctomycetes (PlmCasX; CasX2; FIG. 17) that bears ~70% sequence identity to DpbCasX and can utilize the same single guide RNA (Burstein (2017) *Nature* 542:237) was explored. It was found that PlmCasX enacts GFP gene editing with higher efficiency relative to DpbCasX (up to ~30% in this assay). Since the guide RNA recognizing the coding strand functioned more robustly in each case, it was asked if the additional GFP gene disruption observed for guide 3 could be explained by RNA targeting (Strutt et al. (2018) *eLife* 7, e32724; O'Connell et al. (2014) *Nature* 516: 263). However, there was no recovery of GFP expression in these cells over time (FIG. 2*g*), consistent with genome editing rather than transcript targeting. Furthermore, analysis of DNA derived from the PlmCasX-targeted GFP locus using a T7E1-based assay (Zhu et al. (2014) *Sci Rep* 4:6420) revealed levels of genome editing consistent with the observed GFP disruption (FIG. 2*h, i*). Finally, the effect of CasX-sgRNA-encoding plasmid concentration on the extent of genome editing was explored. The highest amounts of transfected PlmCasX plasmid produced GFP locus editing at levels comparable to genome editing levels observed in initial reports for CRISPR-Cas9 and CRISPR-Cas12a (Cpf1) (~34%) (Cong et al. (2013) *Science* 1231143; Jinck et al. (2013) *eLife* 2, e00471; Zetsche et al. (2015) *Cell* 163: 759-771; Mali et al. (2013) *Science* 339:823-826). These results demonstrate that CasX is capable of inducing targeted genomic regulation and editing, and motivated experiments aimed at determining the structural and mechanistic basis for these activities.

FIG. 2A-2J. CasX effectively manipulates genomes in vivo. a, Genomic cleavage assay in *E. coli*; (−) indicates no guide RNA, (+) indicates the presence of guide RNA. b, Schematic of *E. coli* CRISPRi and the mechanism of repression of fluorescent reporter expression by dCasX with functional DNA binding activity. c, *E. coli* GFP repression as visualized on plates on a dark reader demonstrating reduction of GFP expression in the presence of guide RNA. d, Quantitative analysis of *E. coli* CRISPRi based GFP repression at 12 hrs comparing CRISPRi activity using dCas9 or dCasX. e, Schematic of CasX human cell assay and readout where the assay detects targeted DNA cleavage activity at an integrated GFP gene. f, DpbCasX (Deltaproteobacteria CasX) and PlmCasX (Planctomycetes CasX) GFP disruption in a mammalian cell (HEK293T) assays at two doses of plasmids (12 ng or 50 ng). g, Sustained GFP disruption of the high dosage (50 ng) mammalian cell GFP disruption assay from f. h, PlmCasX T7E1 gene editing validation of the mammalian cell GFP disruption assay from g. Shown is an agarose gel containing samples from days 10 and 15 post treatment. Indicated in the figure are the unedited and edited DNA, indicating cleavage of the target. Two guide RNAs were tested with CasX, cither g2 or g3. Also shown is a lack of cleavage in the absence of guide RNA and cleavage by Cas9. i, PlmCasX T7EI quantification of h. j, PlmCasX GFP disruption dose response. All quantitate measurements were done in biological triplicate, error bars represent standard deviation. In the bacterial assays (−) indicates the Non-target guide, (+) indicates the targeting guide, *Streptococcus pyogenes* Cas9 or dead Cas9 (Cas9, dCas9) with was used as a positive control. In the human assays g2 & g3 are GFP targeting guides to the template and non-template strand respectively.

FIG. 8A-8D. CasX purification and substrate cleavage a, Schematic cartoon of GFP gene. Target regions for guides 1 to 9 are marked along the gene. b, CasX guide screening by GFP disruption c, CRISPRi efficiency for CasX active site mutations. "dX" indicates the D672A mutant, "dXX" indicates the D672A-E769A double mutant, and "dXXX" indicates the D672A-E769A-D935A triple mutant. For a-c, (+) indicates a targeting guide (−) indicates a non-targeting guide for negative control. GFP Disruption efficiency of targeting guide is shown by GFP signal/OD compared to the non-targeting guide control. All assays are done in biological triplicates, error bars represent S.D. d, Purification of ApoCasX, CasX-gRNA binary complex and CasX-gRNA-DNA ternary complex with three DNA designs by size exclusion chromatography. The representative S200 size exclusion traces by UV280 absorbance are shown. Samples were taken from the labeled peaks and analyzed with urea-PAGE with sybrGold. sgRNA indicates the single-guide RNA. NTS indicates the non-target strand from target DNA. TS indicates the target strand from target DNA.

CasX has a Unique Domain Composition

To understand how DpbCasX (hereafter CasX) binds to helical DNA, a ternary complex containing deactivated CasX (D672A-E769A-D935A), sgRNA (122 nt) and a complementary DNA substrate (30 base pairs (bp)) was analyzed by single particle cryo-electron microscopy (cryo-EM). Three-dimensional particle classification and refinement revealed two conformational populations of the ternary complex at resolutions of 3.7 Å and 4.2 Å (State I and State II, respectively) (FIG. 9). These two conformational states were also observed by cryo-EM analysis of a CasX complex containing a full R-loop (45 bp DNA substrate) and refined at resolutions of 3.2 Å (State I) and 5.2 Å (State II) (FIG. 10). With the cryo-EM maps, atomic models of CasX ternary complexes in State I and State II were built ab initio (FIG. 11). While structural alignment of the entire modeled polypeptide chain revealed some similarity between CasX and Cas12a (LbCpf1, PDB 5xuu, z-score 15.1) (Yamano et al. (2017) *Mol Cell* 67: 6330645 e633), a more detailed analysis of the domains showed that this similarity results exclusively from the RuvC and OBD domains (alignment of RuvC with LbCpf1 PDB 5xut has a z-score 13.8, alignment of OBD with LbCpf1 PDB 5xh6 has a z-score 9.6) (Holm et al. (2016) *Nucl Acid Res* 44: W351-355). Nonetheless, CasX possesses additional structural components that appear analogous to those identified in other Cas proteins including the Helical-I and -II and the REC1 and REC2 domains (FIG. 12).

Figure 3A:
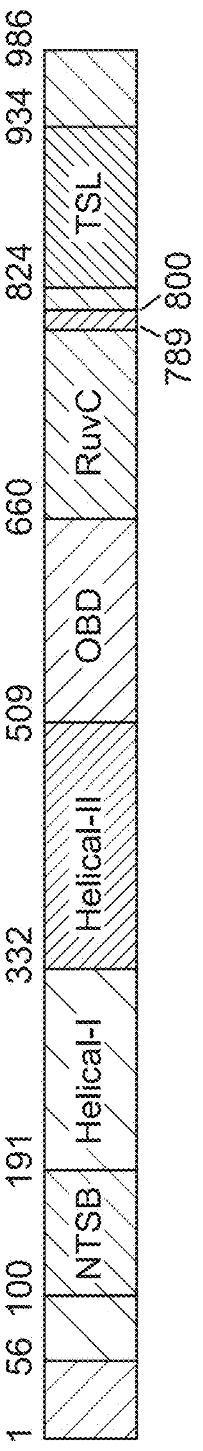
FIG. 3A-3G depict overall structure of the CasX ternary complex.
Figure 3B:
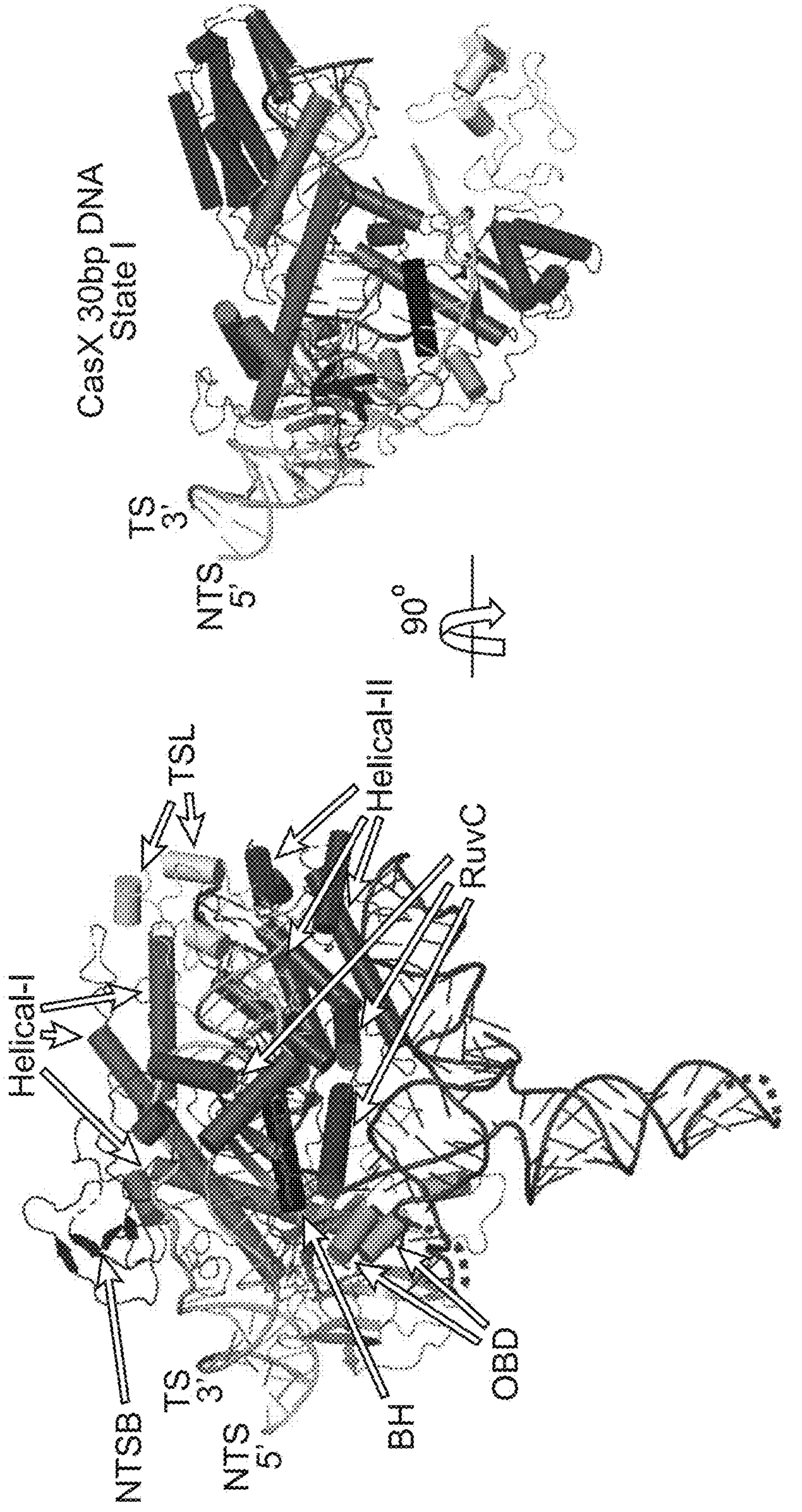

Two unique domains were identified adjacent to the separated DNA strands in the CasX complex and are referred to here as the non-target strand binding (NTSB) and the target-strand loading (TSL) domains (residues 101-191 (red) and 825-934 (pink) in FIGS. 3*a* and *b*). The first unique domain. NTSB, contains a four-stranded beta-sheet and sits next to the non-target strand of the DNA (FIG. 3*b*). Its function is discussed in the section below. The second unique domain, TSL is located in a position analogous to that of the so-called "Nuc" domain of other type V CRISPR-Cas enzymes. The domain TSL should be renamed since "Nuc" was hypothesized incorrectly to be a second nuclease domain responsible for DNA cleavage (Swarts and Jinck, 2018, ibid; Yamano 2016, ibid). The TSL is instead responsible for target strand placement in the RuvC active site (Yang et al. (2016) *Cell* 165:949-962). In the AsCas12a "Nuc" domain, amino acids Arg1226 and Asp1235 aid target strand cleavage and an Arg1226Ala mutation produced an AsCas12a nickase by abolishing Cas12a's ability to cut the target strand (Yamano 2016, ibid). In the CasX "Nuc"-analogous TSL domain, residues Arg917 and Gln920 interact with DNA (NTS in State I and TS in State II) that is adjacent to the active site (FIG. 3*b, c*). Intriguingly, within the CasX full R-loop structure in State I, a TSL loop containing three tyrosines (Tyr867, Tyr868, Tyr870) and three positively charged residues (Arg869, Lys871, Arg872) interacts with the migration point where the RNA-DNA duplex ends and the DNA-DNA duplex reforms (FIG. 3*d*; (FIG. 12). In other enzymes, similar loops or hairpin elements containing a large hydrophobic amino acid (tyrosine or phenylalanine) are thought to be involved in DNA strand separation (Moolenaar et al. (2001) *EMBO J* 20: 6140-6149; Shen et al. (2005) *Proc Natl Acad Sci USA* 102: 11248-11253; Castella et al. (2006) *Nucl Acids Res* 34: 3997-3019). Moreover, the TSL, domain also contains two CXXC motifs (residues 824-827 and 926-929) that form a Zinc finger/ribbon motif (FIG. 12) akin to those found in phage primases, transcription factors and the purported transposase ancestor for Class II CRISPR proteins, TnpB5 (Koonin (2017), ibid; Hahn and Roberts (2000) *Genes Dev* 14:719-730; Okuda et al. (2004) *J Biol Chem* 279: 51395-51403; Pan and Wigley (2000) *Structure* 8:231-239).

FIG. 3A-3G. Overall structure of the CasX ternary complex. a, Domain composition of CasX. CasX contains: Helical-I (yellow), NTSB (Non-target strand binding, red), Helical-II (orange), OBD (oligo binding domain, aquamarine), RuvC (green) and TSL (target-strand loading, pink) domains, and a BH (bridge helix, blue). b, Model of CasX ternary complex with 30 bp target DNA in State I is shown on side and top views. The different protein domains are colored as in a. sgRNA is colored in teal. For target DNA, the non-target strand (NTS) DNA is colored in magenta and target-strand (TS) DNA is colored in purple. c, Model of the CasX ternary complex with 30 bp target DNA in State II is shown on top view. Residues Arg917 and Gln920, shown as red sticks, are involved in positioning the target DNA strand.

The TSL-loop is shown as a red ribbon. The right panel shows the zoomed in view of the TSL domain in State II. d, Model of CasX ternary complex with a full R-loop structure in State I is shown on top view. Residues Arg917 and Gln920 are shown as red sticks. The RuvC active site residues positions are shown as red sticks as well to demonstrate the distance to the active site from the TSL domain elements. The TSL-loop is shown as a red ribbon. The right panel shows the zoomed in view of the TSL domain in State I. e, Schematic of the single guide RNA fold with tracrRNA sequence shown in gray, crRNA sequence in teal, and the joint loop in red. The triplex region, extended stem, and scaffold stem with RNA bubble are marked. f, Molecular interactions between CasX and gRNA. RNA recognition and interactions are mainly mediated by Helical-II (orange) and the OBD domains (aquamarine). Residues involved in RNA recognition are shown as magenta sticks. The structural regions are marked as in e. g, Models of CasX ternary complex with 30 bp target DNA in State I and II are aligned and superimposed. CasX is shown as a transparent grey cartoon, and the residues responsible for cleavage activity are shown in red. The nucleic acids are shown as ribbon to emphasize the rotation of the RNA-DNA duplex required for the transition between the two states.

FIG. 9A-9E. EM analysis of CasX-gRNA-DNA ternary complex with a 30 bp target DNA. a, Target DNA sequence in this complex. b, EM analysis pipeline. 1,698,815 particles were picked from 7.500 drift-corrected micrographs and then used for 2D classification. By 2D based manual screening, 713,219 good particles were selected for 3D classification into 4 classes. 363,431 particles from the class that shows the most intact architecture were further used for heterogeneous refinement, which generated two reconstructions. State I and State II, with 71% and 29% of the particles, respectively. State I and State II were then independently refined to 3.8 Å and 4.2 Å. c, Euler angle distribution of the refined particles belonging to State I and State II. d, Fourier shell correlation (FSC) curve calculated using two independent half maps. e, The density maps for both states, colored by local resolution as calculated in Cryopsarc. Resolution ranges from 3 Å to 7 Å. Panels c and d are directly taken from the standard output of Cryosparc.

FIG. 10A-10E. EM analysis of CasX-gRNA-DNA ternary complex with full R-loop (45 bp target DNA). a, Target DNA sequence in this complex. b, Cryo-EM analysis pipeline. 1,135,443 particles were picked from 5.000 drift-corrected micrographs and then used for 2D classification. By 2D based manual screening, 485,163 good particles were selected for 3D classification into 4 classes. 222,927 particles from the class showing better structure preservation were further used for heterogeneous refinement, which generated two models. State I and State II, with 67% and 33% of the particles, respectively. State I and State II were then independently refined to 3.2 Å and 5.2 Å. c, The Euler angle distribution for State I and State II. d, FSC curve calculated using two independent half maps. e, Cryo-EM structures of State I and State II colored by local resolution as calculated in Cryopsarc. Resolution ranges from 3 to 7 Å. Panels c and d are standard outputs of Cryosparc.

FIG. 11A-11D. Atomic model building of CasX ternary complexes for State I and State II. Atomic models and cryo-EM maps (shown with a threshold of 8σ or 9σ) for the CasX ternary complex with 30 bp DNA in State I (a) and State II (b), and for State I of the CasX ternary complex with full R-loop (45 bp DNA) (c). Representative regions of the cryo-EM density for different secondary structure regions are shown. d, Map against model FSCs.

Figure 3C:
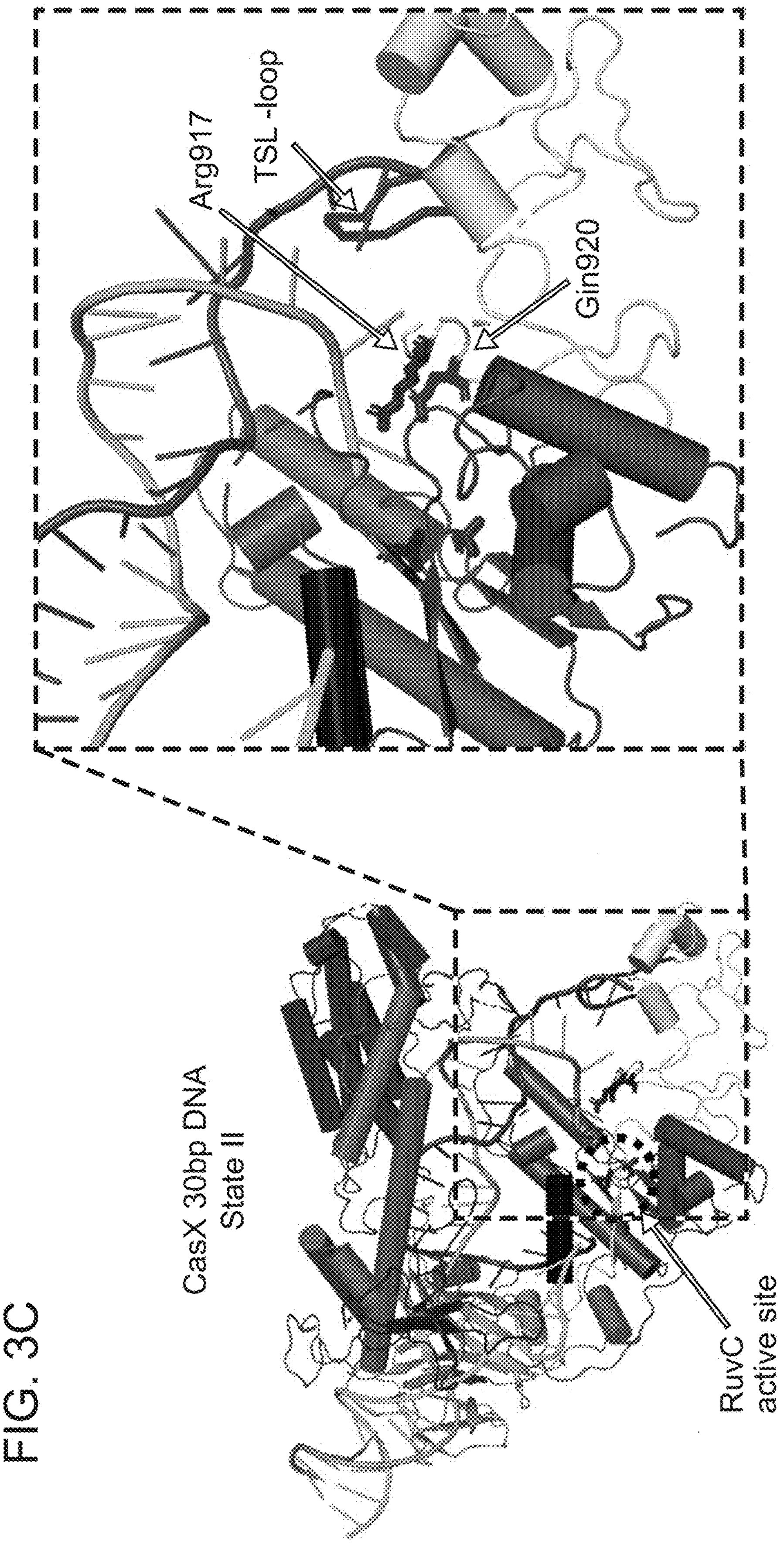
Figure 3D:
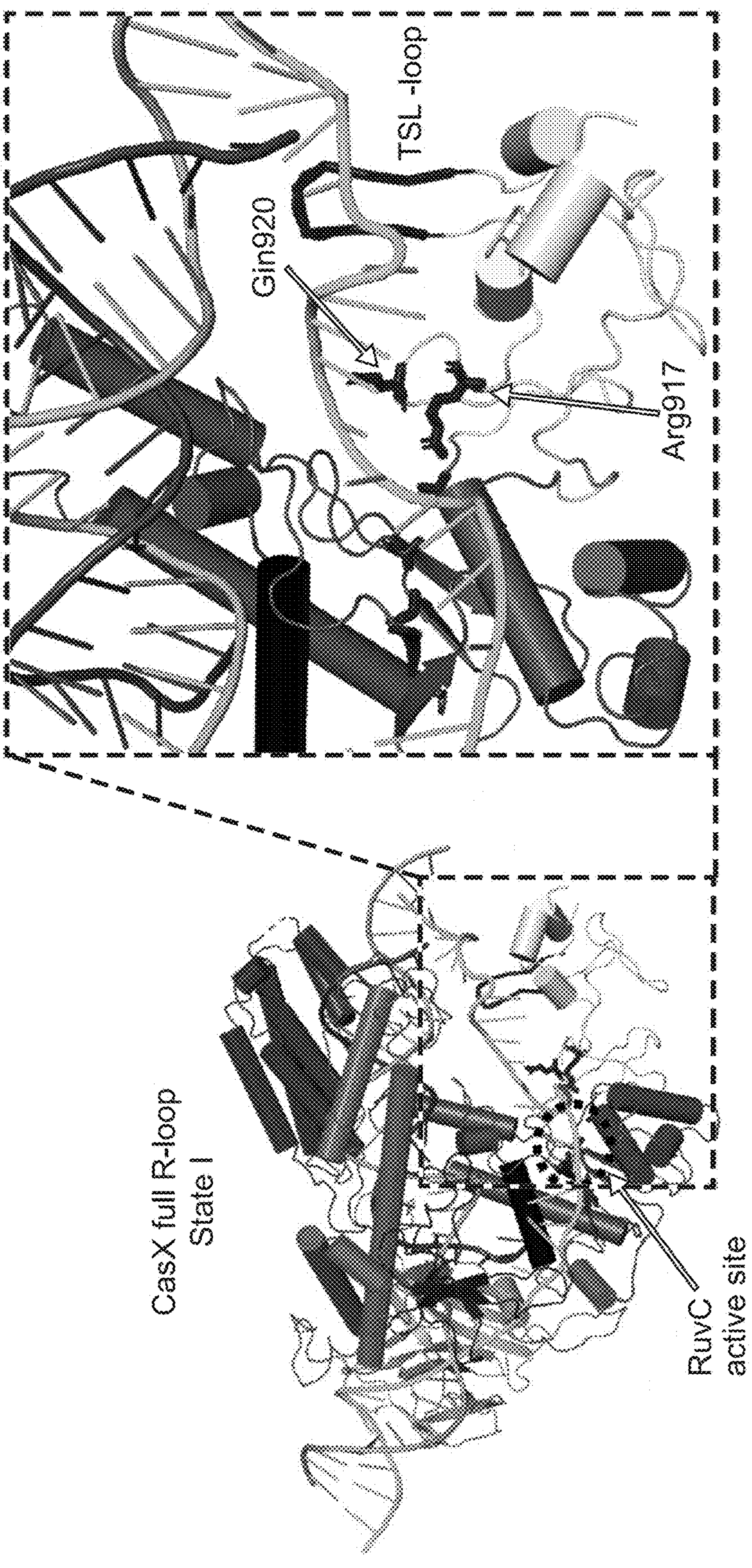
Figure 3E:
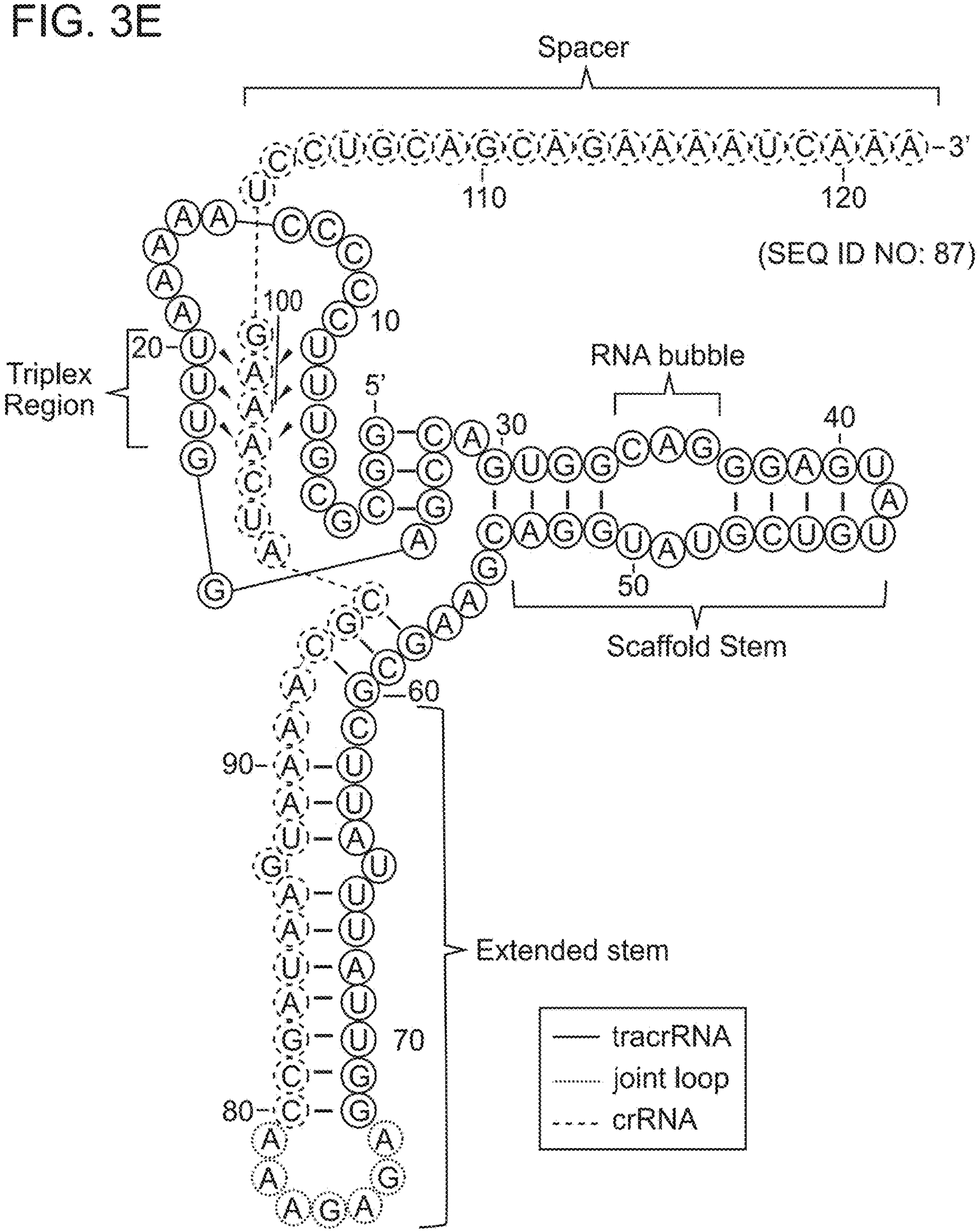
Figure 3F:
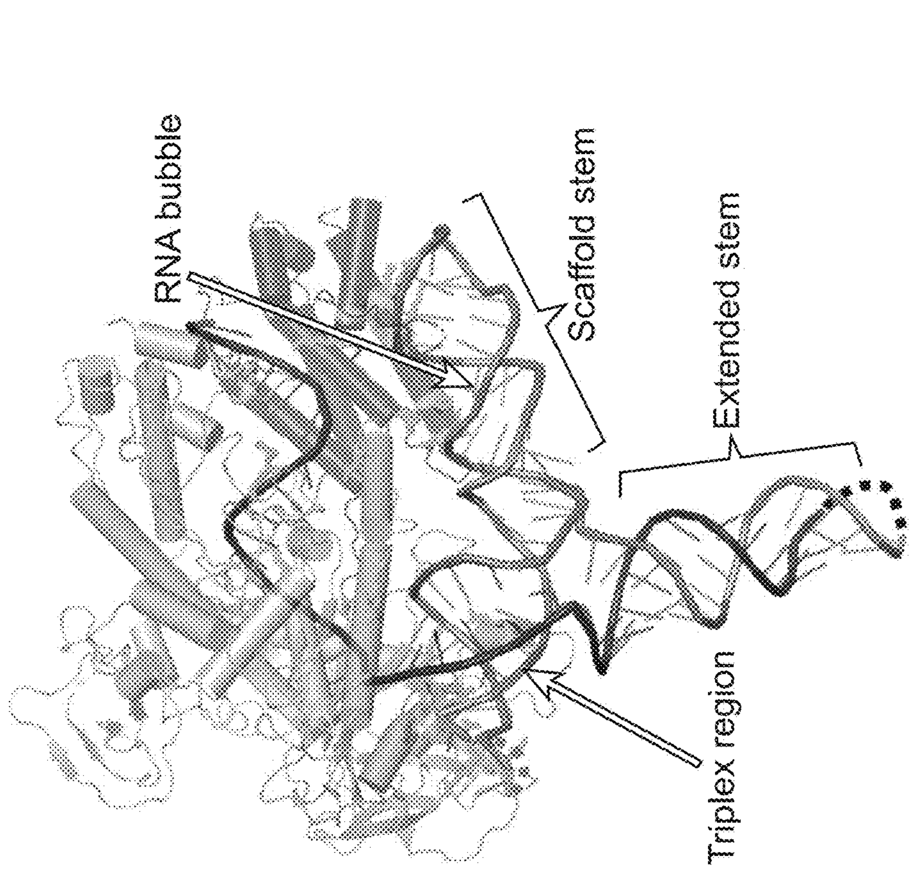
Figure 3G:
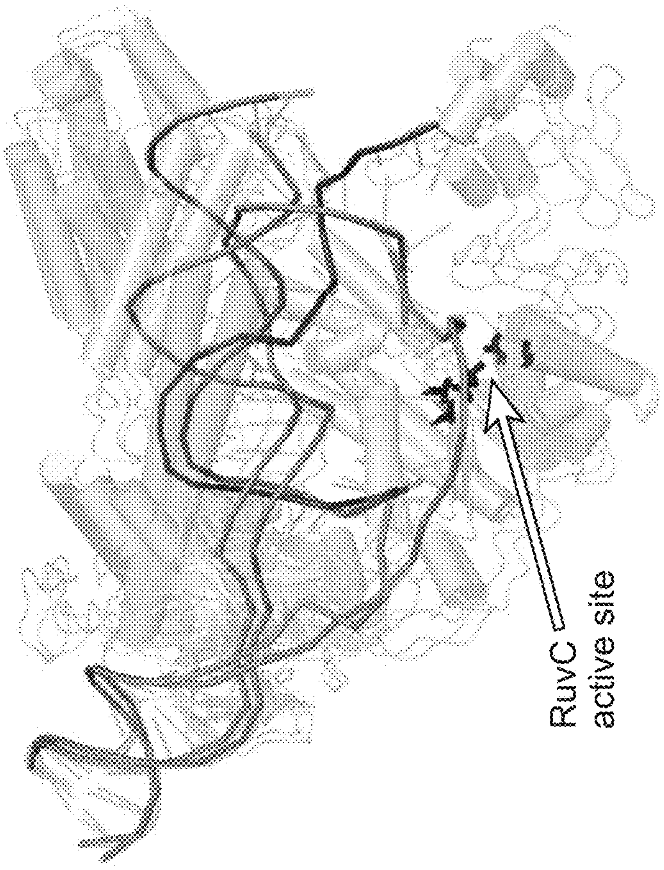

FIG. 12A-12G. Structural comparison of CRISPR effectors a, OBD (WED) domains are shown in aquamarine. Helical-I (REC1) domains are shown in yellow, Helical-II (REC2) domains are shown in orange. RuvC domains are shown in green. Nuc (TSL) domains are shown in pink. Bridge Helixes are shown in blue. NTSB domain in CasX is shown in red. PI domain of LbCas12a is shown in purple. Guide RNA and target DNA are shown in gray. Two orientations are presented for each model. b, Overall structure and individual domains of CasX were analyzed using Dali server against the full PDB. The protein hit with highest Z-score for each target is shown in left panel. The hits are marked with protein name and PDB code. The similarity scores between CasX overall structure/domains and AscCas12b are pulled out from Dali full PDB analysis and shown in middle panel. The similarity scores between CasX overall structure/domains and AscCas12a are pulled out from Dali full PDB analysis and shown in left panel. Z-score above 8 indicates a high degree of similarity. Z-score below 8 but above 2 indicates moderate similarity (usually irrelevant random match). Z-score below 2 indicates noise. c, TSL domain and full R-loop structures are subtracted from the ternary complex. Zinc ribbon residues are colored in blue. d, Primary sequence across TSL-loop. Tyrosines are marked with teal circles. Positive charged residues are marked with red circles. e, Atomic models of DpbcasX, AacCas12b, LbCas12a and SpyCas9 binary complexes are shown by surface representation. Protein parts are colored in cyan, and nucleic acid in dark gray. CasX. AacCas12b and SpyCas9 require both crRNA and tracrRNA (or a fused single guide RNA), while LbCas12a uses only crRNA. Guide RNAs are subtracted out from the complexes and shown as ribbons in bottom panels, independently. f, Mass ratio of protein and guide RNA. Values of relative mass occupancy for protein and guide RNA within the three binary complexes (protein+guide RNA) are shown. Protein mass occupancies are colored in cyan, and guide RNA in dark gray. g, CRISPRi efficiency by guide RNA mutation. Sequence for the fused single guide RNA is shown. tracrRNA, the joint loop, crRNA and spacer region are marked respectively. The sequences for mutated guide RNA are aligned with the original guide RNA sequence and shown. Cas9 is used for positive control. (+) indicates a targeting guide (−) indicates a non-targeting guide for negative control. NC indicates the non-complementary CasX guide. WT indicates the complementary wild type guide for CasX. GFP Disruption efficiency of targeting guide is shown by GFP signal/OD compared to the non-targeting guide control. All assays are done in biological triplicates, error bars represent S.D A Prominent Guide RNA Scaffold for CasX Notably, the guide RNA accounts for ~26% of the mass in the CasX-sgRNA binary complex, significantly higher than that observed for other type II or V CRISPR effector complexes (~8% in LbCas12a, ~20% in AacCas12b, and ~16% in SpyCas9; (FIG. 12). Dominating the CasX protein complex, the single-guide RNA includes three elements: a triplex stem loop that contacts the OBD, a 'scaffold' stem that interacts with the Helical-II domain, and a perpendicular stem loop that projects away from the center of mass of the particle (FIG. 3*e, f*). Mutation of the triplex or the scaffold stem diminished CasX activity in vivo, whereas truncated versions of the perpendicular stem loop retained activity (FIG. 12).

In the absence of guide RNA, the CasX protein is poorly resolved by cryo-EM (FIG. 13). Consistent with the importance of RNA in CasX protein architecture, CasX crosslinking before and after addition of the sgRNA followed by analytical mass spectrometry (MS) revealed significant RNA-induced CasX domain rearrangements (FIG. 13). In line with this analysis, a cryo-EM-derived model of the CasX-sgRNA complex (~7.5 Å resolution map) shows the OBD. RuvC and Helical-II domains assembled along the RNA scaffold while the NTSB domain associates with the RuvC. Helical-I and Helical-II domains near the nuclease active site (FIG. 13). Comparison to the DNA-bound structural model shows that upon DNA binding, the NTSB domain moves away from the center of protein mass (FIG. 13).

FIG. 13A-13K. Structural comparison of apo, binary and ternary CasX samples. a, Drift-corrected image of apoCasX obtained with a 70° phase shift and defocus of 0.5 μm. The scale bar is 50 nm. b, Drift-corrected image of CasX-gRNA complex with a defocus of −1.5 μm. c, Drift-corrected image of CasX-gRNA-DNA complex with a defocus of −1.5 μm. Representative reference-free 2D class-averages are shown on the bottom panels for the three samples. The scale bar is 20 nm. d, Cryo-EM reconstruction of apoCasX. 3 representative orientations are shown with colored domains. OBD colored by aquamarine. NTSB by red. Helical-I by yellow, Helical-II by orange, RuvC by dark green. TSL by light pink and the bridge helix by blue. e, BS3 cross-linking signals revealed by mass spectrometry for the apoCasX sample. The two lysine within a cross-linked pair are connected with purple curve. f, g, As d and e for CasX-gRNA binary complex. h, i, As d and e for CasX-gRNA-DNA ternary complex. j, k, Accessibility of target strand DNA by the RuvC domain in State I and State II. Distance between the TS DNA cleavage region and RuvC active site as calculated using Pymol is 43.8 Å for State I (j) and 10.9 Å for State II (k).

CasX Conformational States Suggest a Mechanism of Sequential DNA Cutting

Comparison of the two conformational states (I and II) of the CasX ternary complex revealed a large structural change that alters target DNA strand accessibility to the RuvC domain (FIG. 3*b, c*). In State I, non-target strand DNA sits in the RuvC active site while the target-strand DNA/gRNA duplex engages with the Helical-I and Helical-II domains (FIG. 3*b, d*). In State II, the target-strand DNA/guide RNA duplex is sharply bent, enabling RuvC access to the target-strand DNA (FIG. 3*c*). State I is compatible with non-target strand DNA cleavage, while State II is compatible with cleavage of the target strand DNA (FIG. 3*g*; (FIG. 13).

Figure 4A:
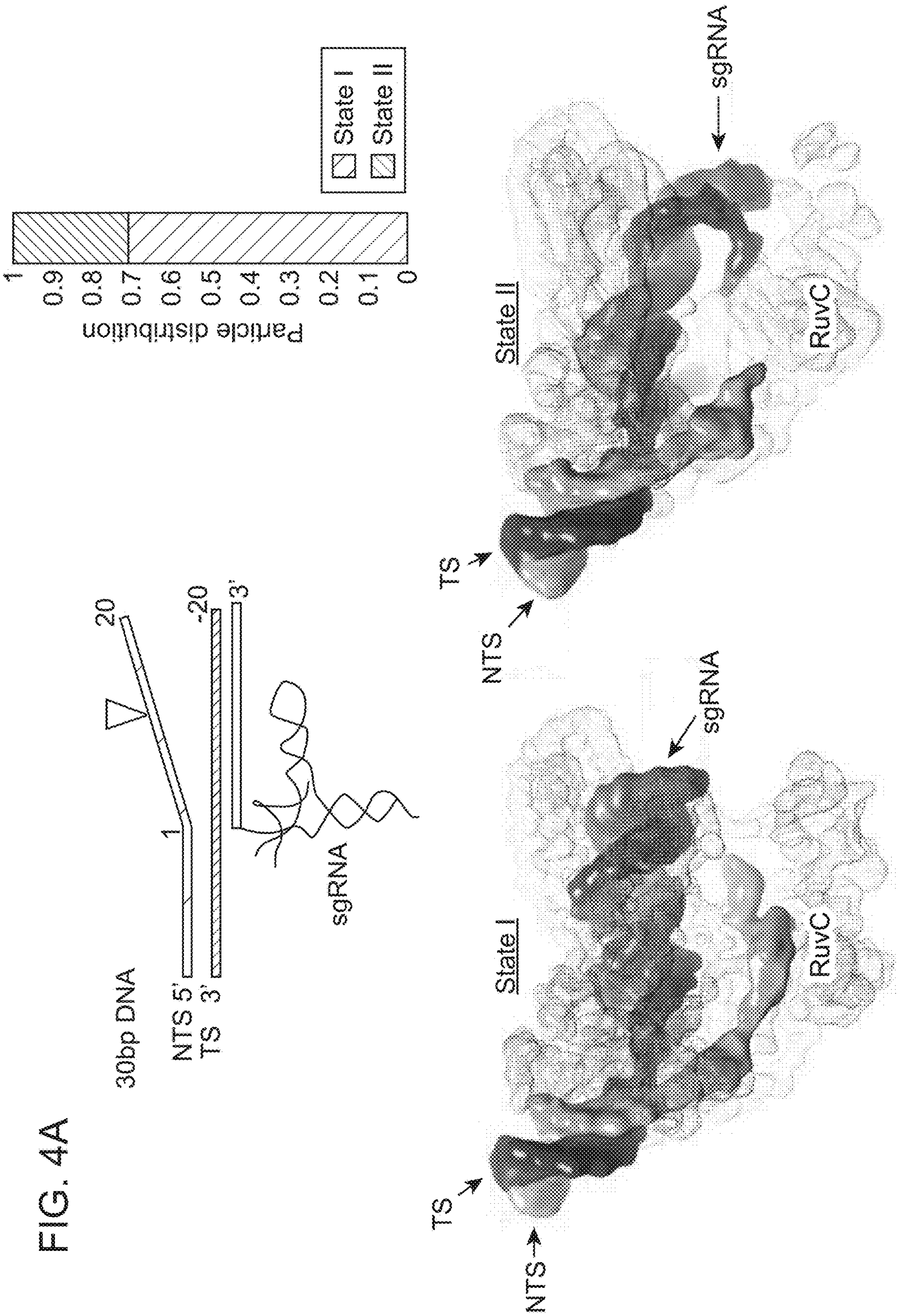
FIG. 4A-4C depict distinct CasX conformational states.
Figure 4B:
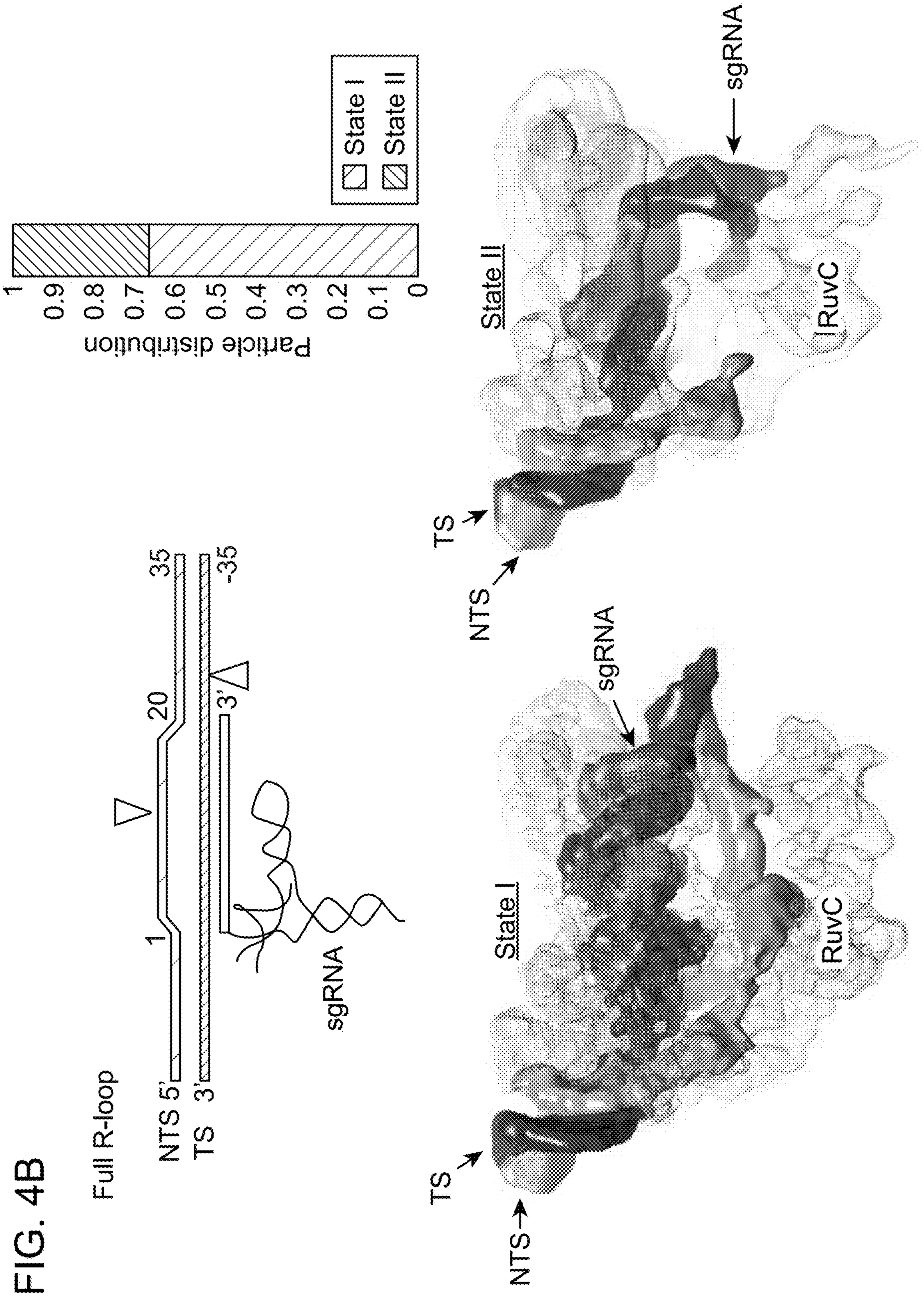

Statistical analysis by single particle sorting showed that the majority of particles (~71%) in the 30 bp target DNA ternary complex adopted the State I conformation with the remaining 29% of particles in State II ((FIG. 9; FIG. 4*a*). This preference suggests that non-target strand DNA is cleaved by the RuvC domain first, followed by displacement and target strand cleavage. Similar to the 30 bp DNA containing sample, 67% of full R-loop (45 bp) DNA particles adopted State I (FIG. 10; FIG. 4*b*).

Figure 4C:
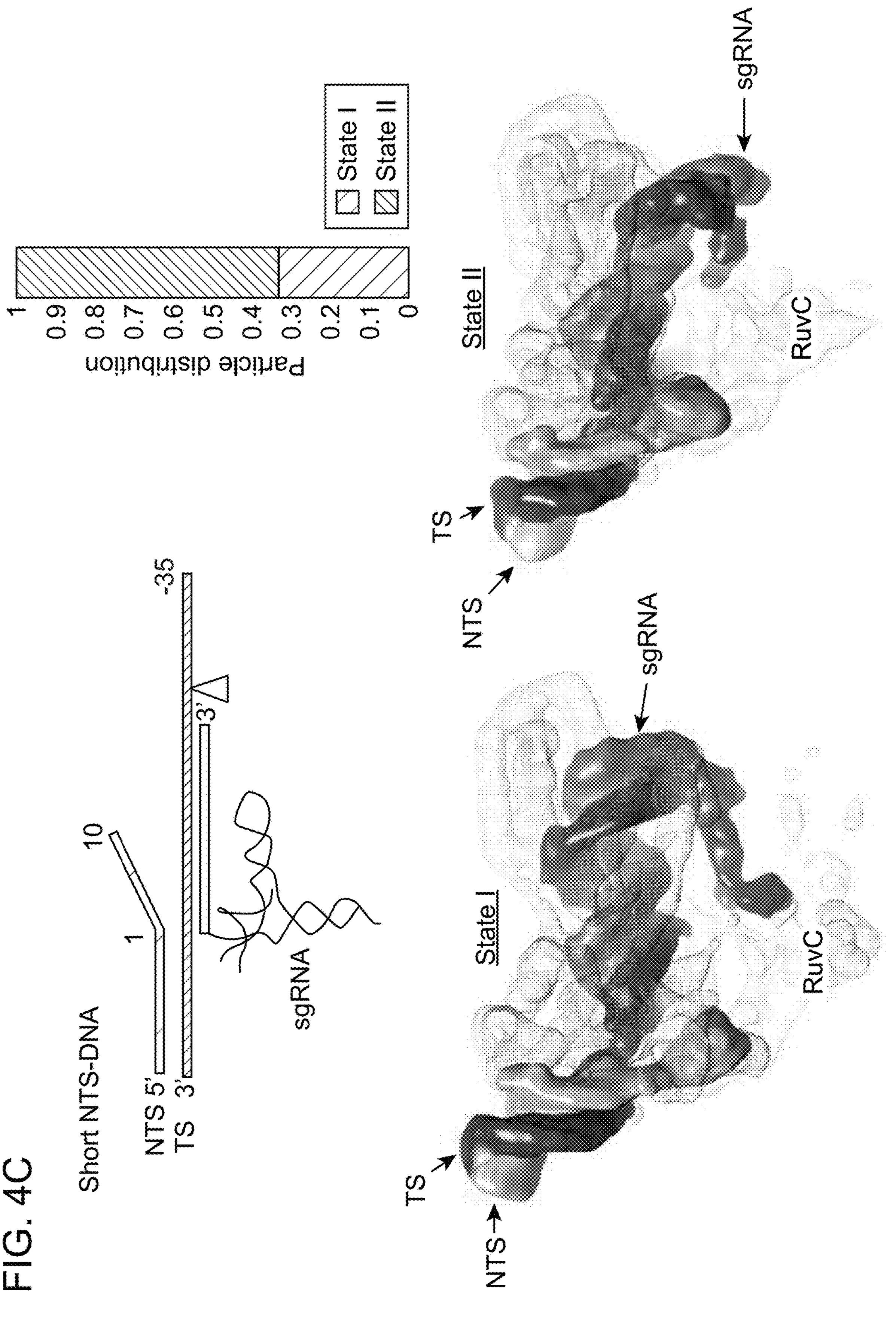

In the sequential model of CasX-mediated DNA cleavage, a substrate-bound complex mimicking the intermediate state that occurs after non-target strand cleavage should preferentially adopt State II. To test this idea, cryo-EM analysis was performed on a CasX ternary complex containing sgRNA and a DNA substrate comprising a 45-nt target strand and a post-cleavage-like 10-nt non-target strand (FIG. 14). In this intermediate-state sample, the majority of particles (~66.4%) adopted the State II conformation, with the target strand located near the RuvC active site (FIG. 4*c*). Interestingly, reconstruction of State I showed 5' end overhang of the target strand DNA folded back into the RuvC domain. This conformation is incompatible with double-stranded DNA cleavage at position 22 and is unlikely to occur natively (FIG. 1*d*; FIG. 4*c*).

FIG. 4A-4C. Distinct CasX conformational states. a, Conformational states and their sample distribution for the cryo-EM dataset with 30 bp target DNA; b, the cryoEM dataset with a DNA target forming the full R-loop; and c, the cryoEM dataset containing the short non-target strand DNA (20 nt) strand and the 45 nt target strand DNA. The schematic of the DNA probe used for each data collection is shown on the left, with cleavage sites shown with pink arrows. The top views of the cryo-EM maps for CasX ternary complex in States I and II are shown on the center panels. The target strand (TS) DNA density is colored purple, the non-target strand (NTS) DNA is colored magenta, the sgRNA density is colored teal. The RuvC domain is indicated in each map. All the EM maps are low-pass filtered to 4.5 Å for better comparison. The relative percentage of particles belonging to each state is shown in the right panel.

The CasX NTSB Domain is Required for DNA Unwinding

The distinct and smaller architecture of CasX relative to other double-stranded DNA targeting enzymes (Cas9, Cas12a, C2c1) implies a unique mechanism of substrate recognition, which requires guide RNA strand invasion into duplex DNA. Observation that the NTSB domain (residues 101-191, red in FIG. 3*b*) interacts directly with non-target DNA strand both in State I and State II (FIG. 5*a*) raised the possibility that this unique structure contributes fundamentally to the mechanism of DNA unwinding. To test this hypothesis, the behavior and activity of a protein construct lacking the NTSB domain (CasXΔ101-191) was analyzed. Although it showed similar physical behavior to that observed for the wild-type CasX on a size exclusion column (FIG. 15), CasXΔ101-191 was incapable of cleaving a double-stranded DNA substrate (FIG. 5*b*). Importantly, however, CasXΔ101-191 retains robust single-stranded DNA cleavage activity, including with mismatched duplex DNA substrates (FIG. 5*b*; (FIG. 15)). Together, these results suggest that the NTSB domain is responsible for initiating or stabilizing DNA duplex unwinding by CasX. This finding also hints at the interesting possibility that the self-contained NTSB domain could be introduced into or acquired by other enzymes to assist with or stabilize double-stranded DNA binding.

Figure 5A:
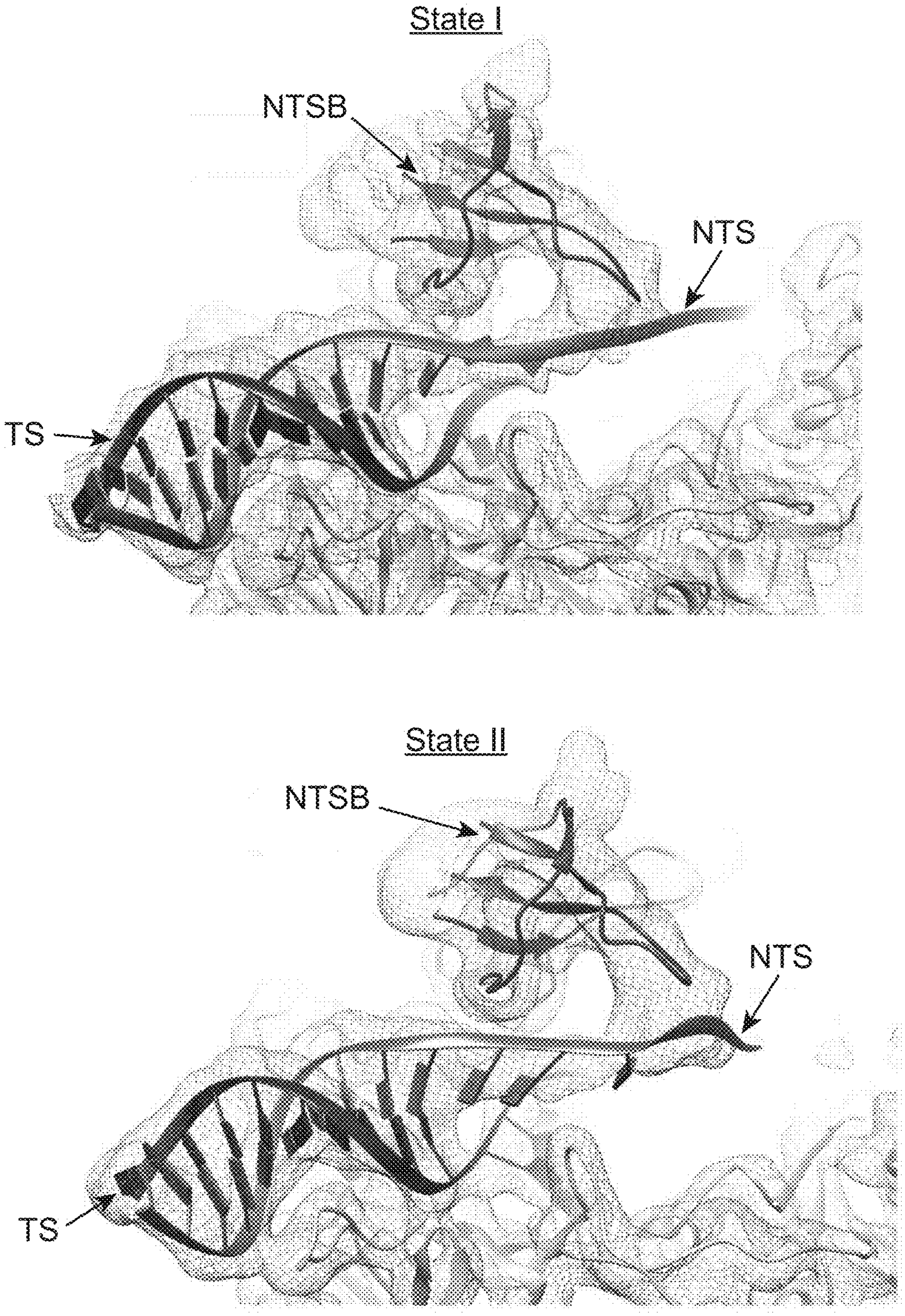
FIG. 5A-5B depict CasX domains for target DNA unwinding and loading.
Figure 5B:
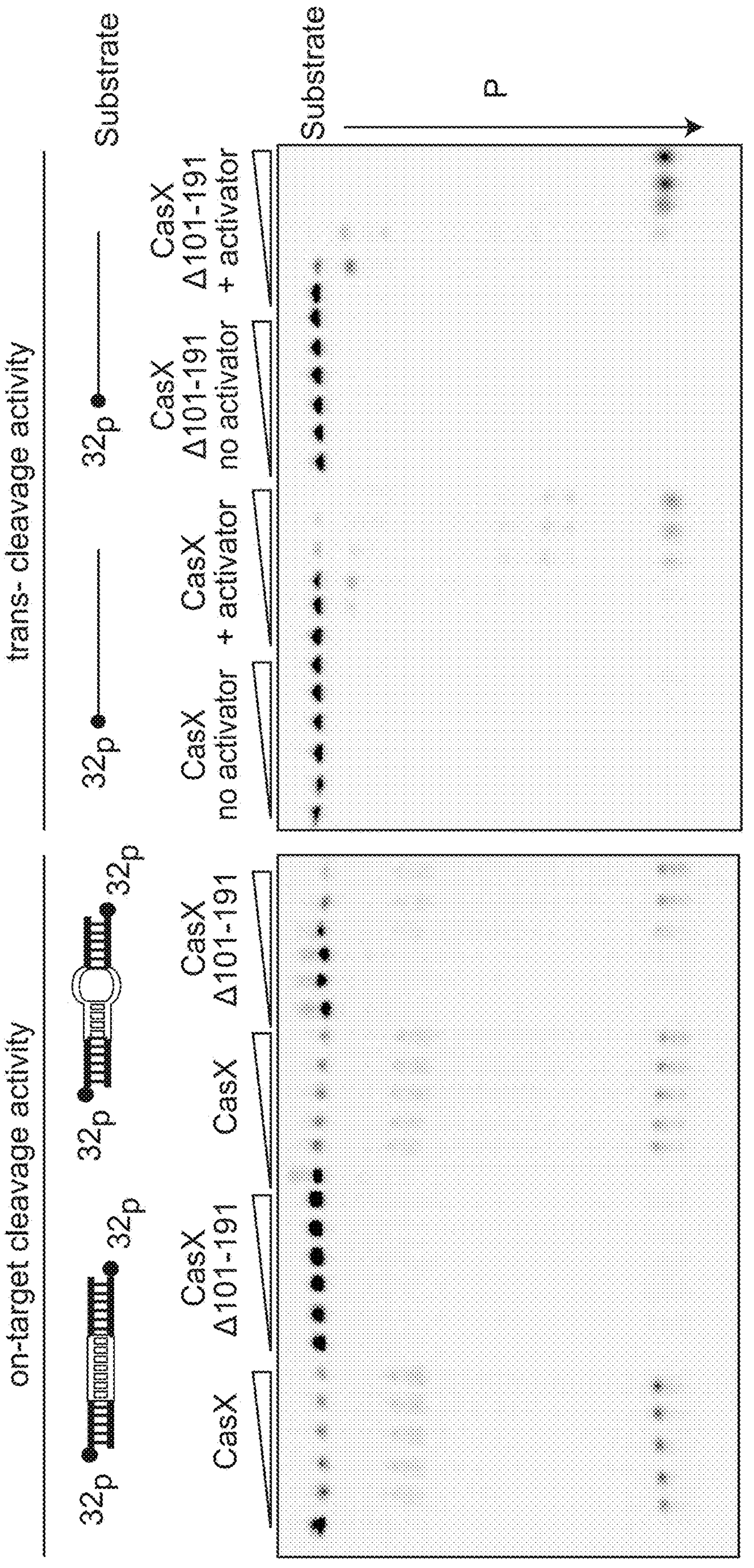
Figures 6A, 6B, 6C, 6D, 6E:
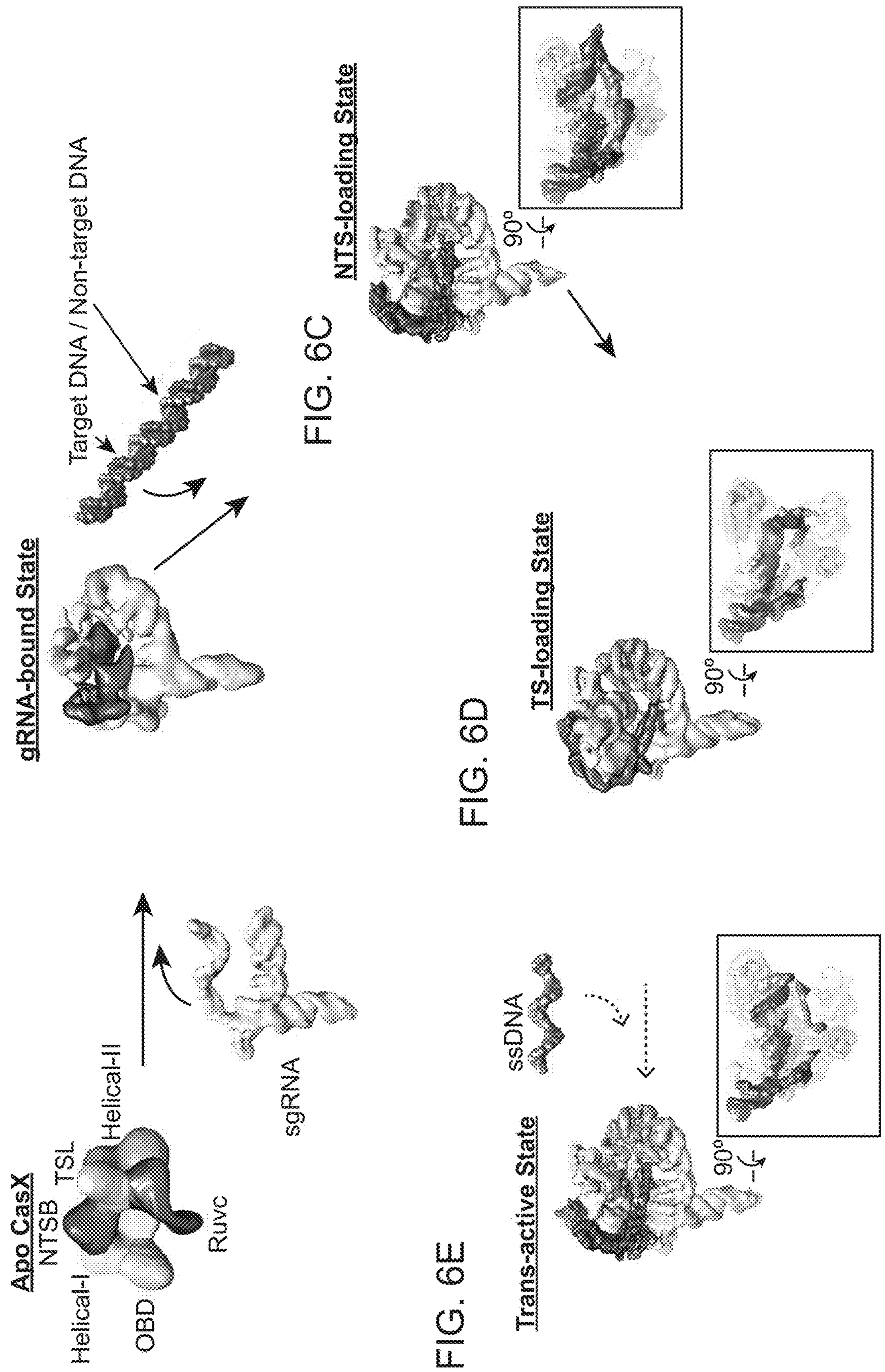
FIG. 6A-6E depict a proposed model for sequential CasX activation of DNA cleavage.
Figure 7A:
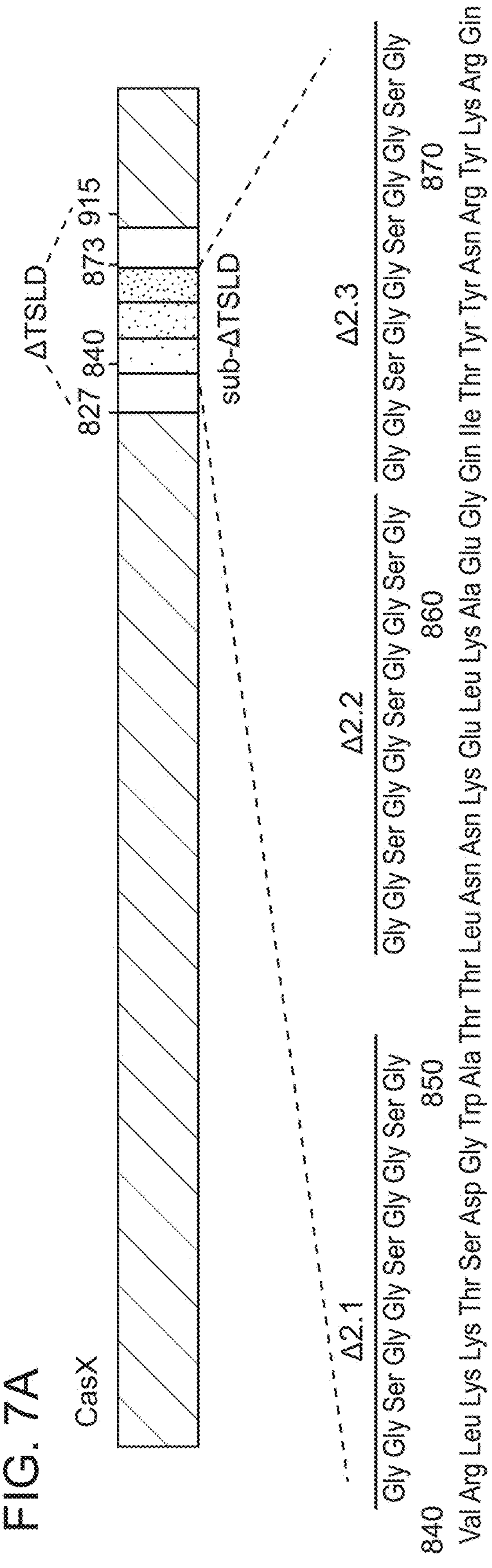
FIG. 7A-7D depict data on CasX with TSLD deletions.
Figure 7B:
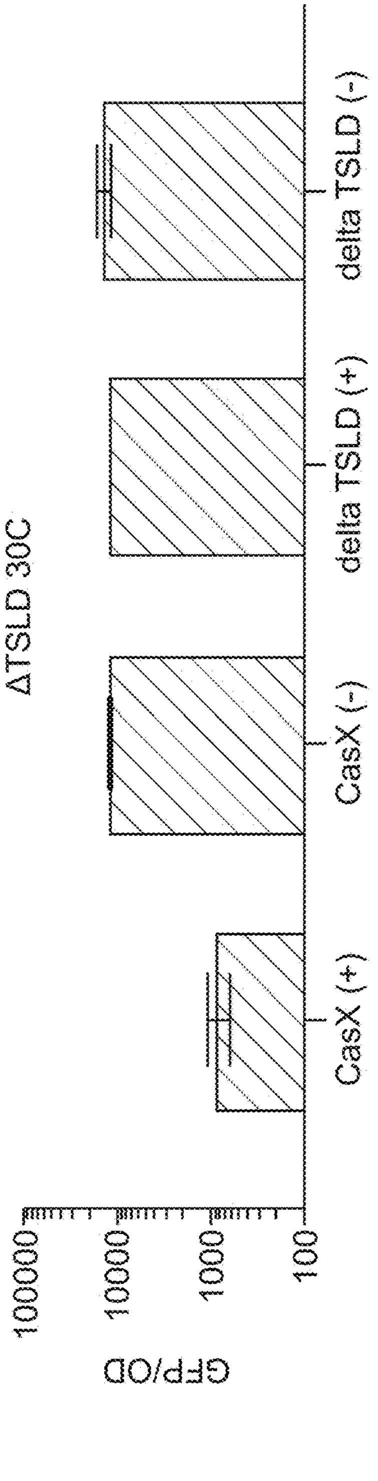
Figure 7C:
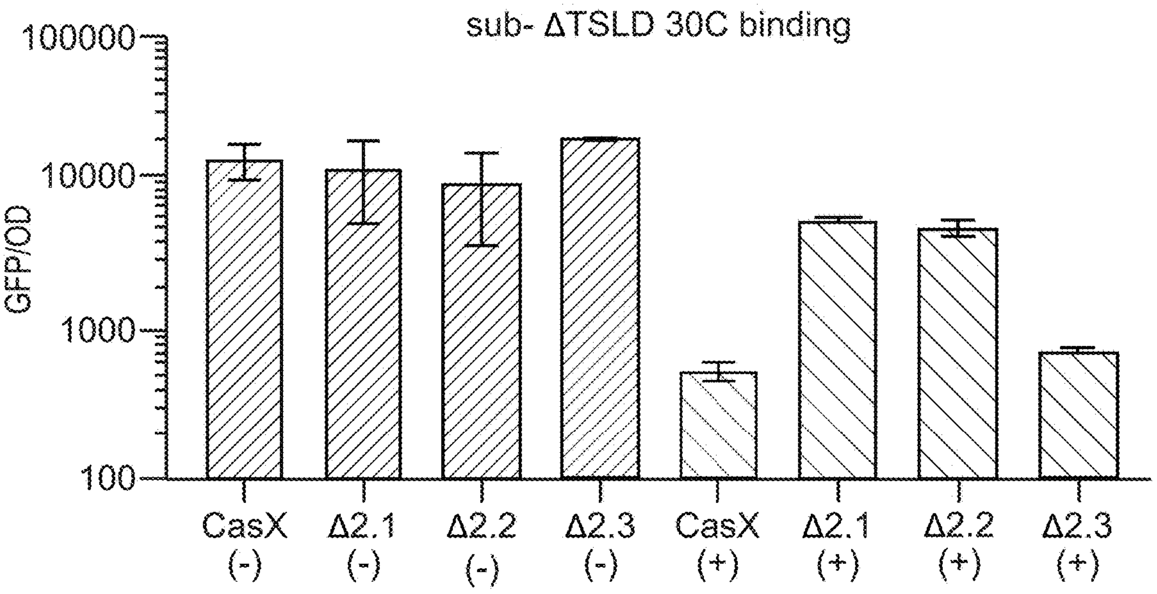
Figure 7D:
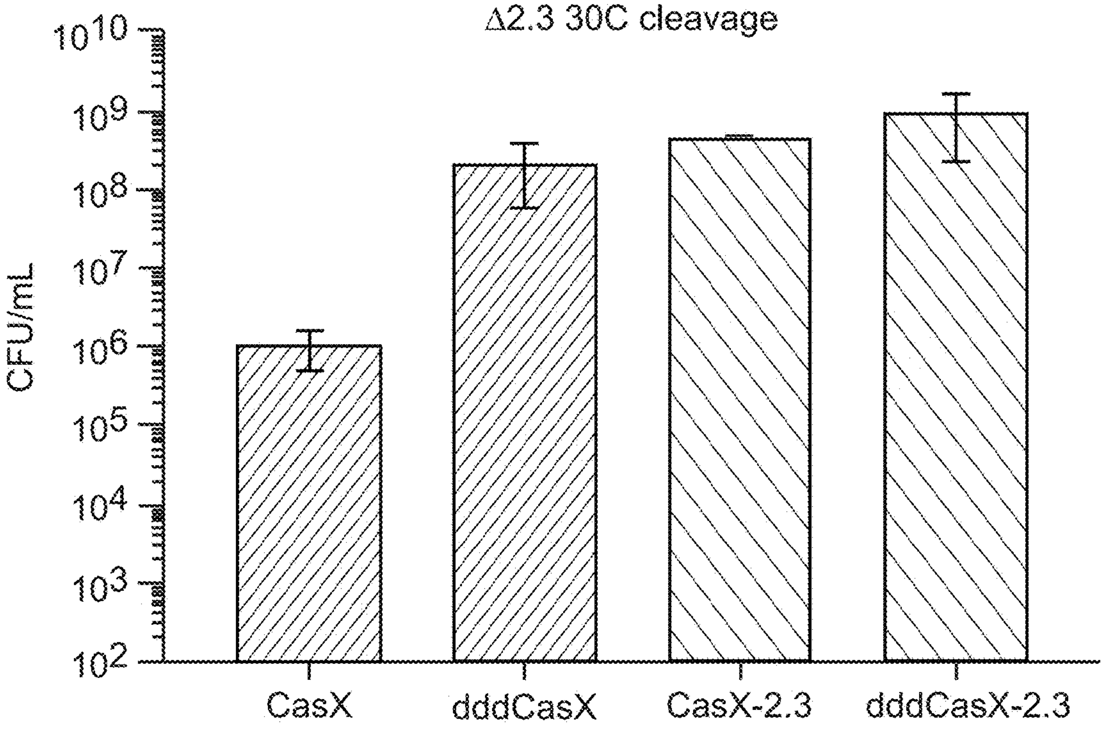
Figure 8A:
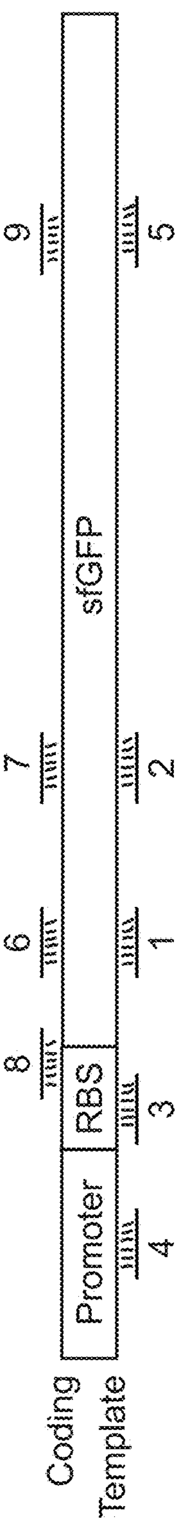
FIG. 8A-8D depict CasX purification and substrate cleavage.
Figure 8B:
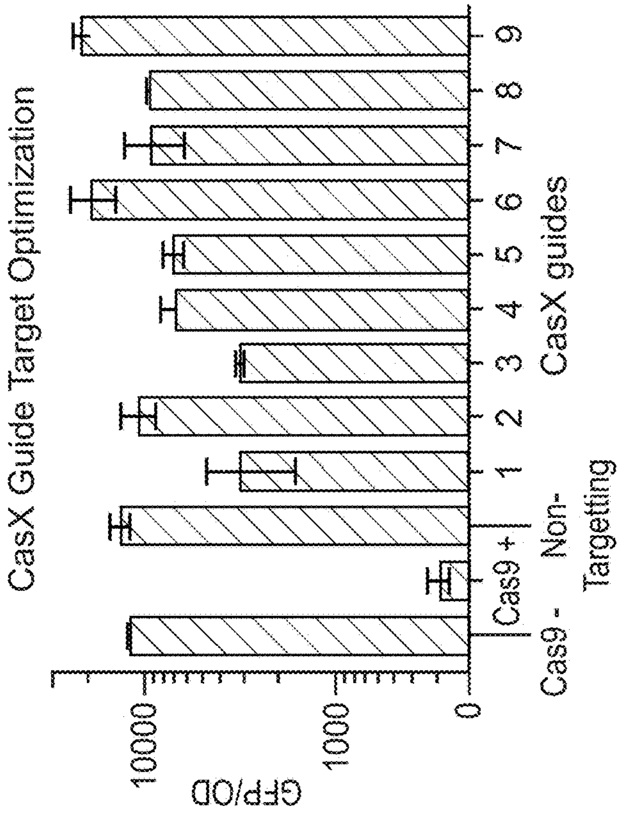
Figure 8C:
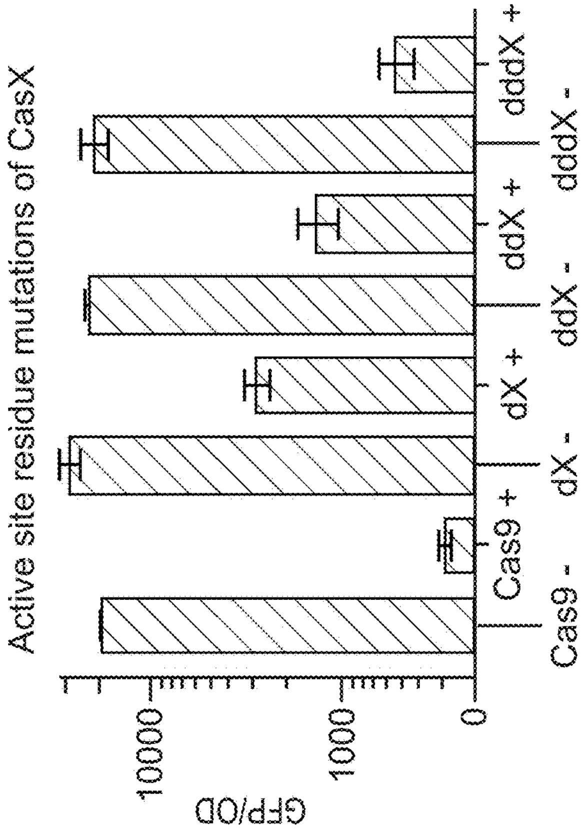
Figure 8D:
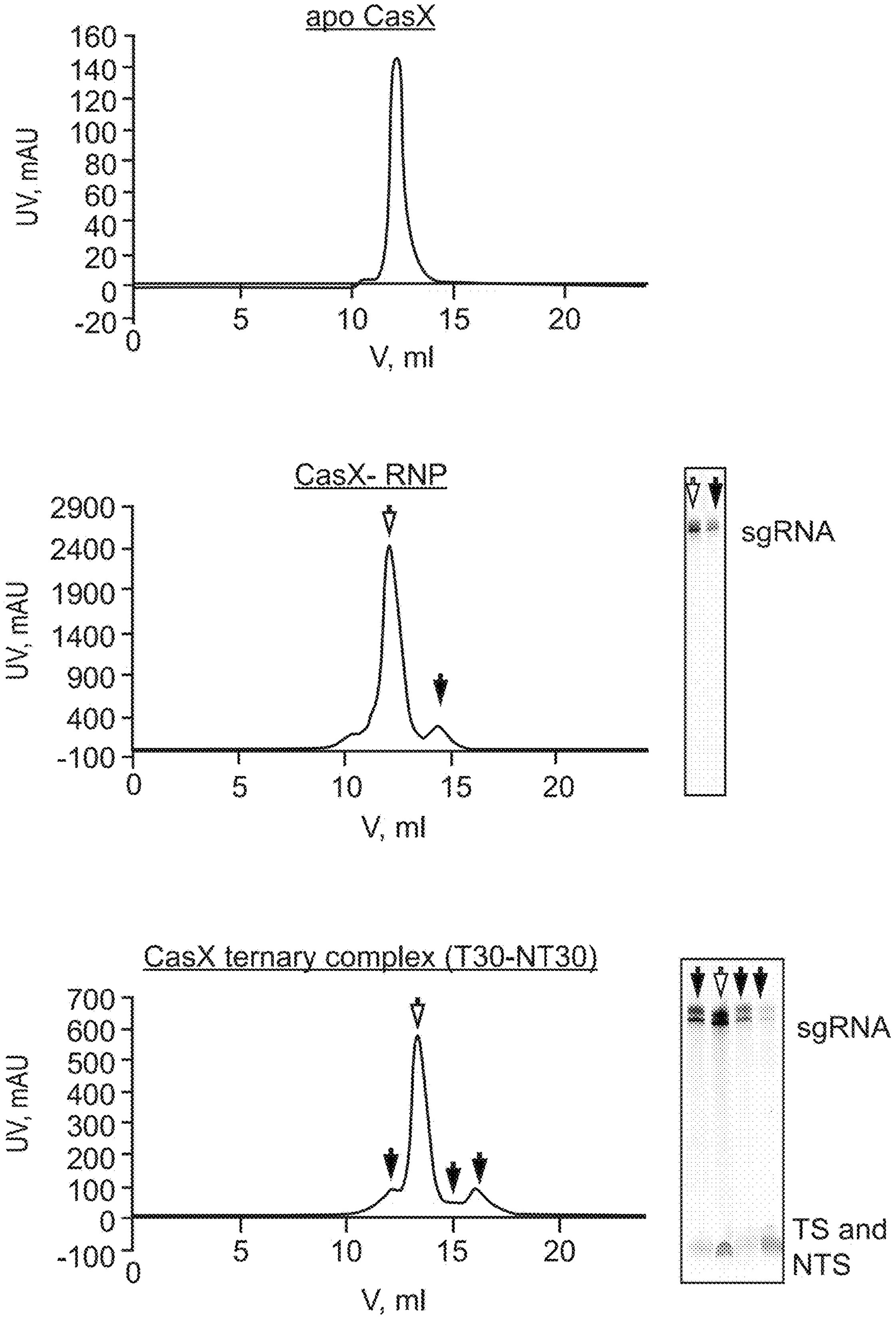
Figure 8D:
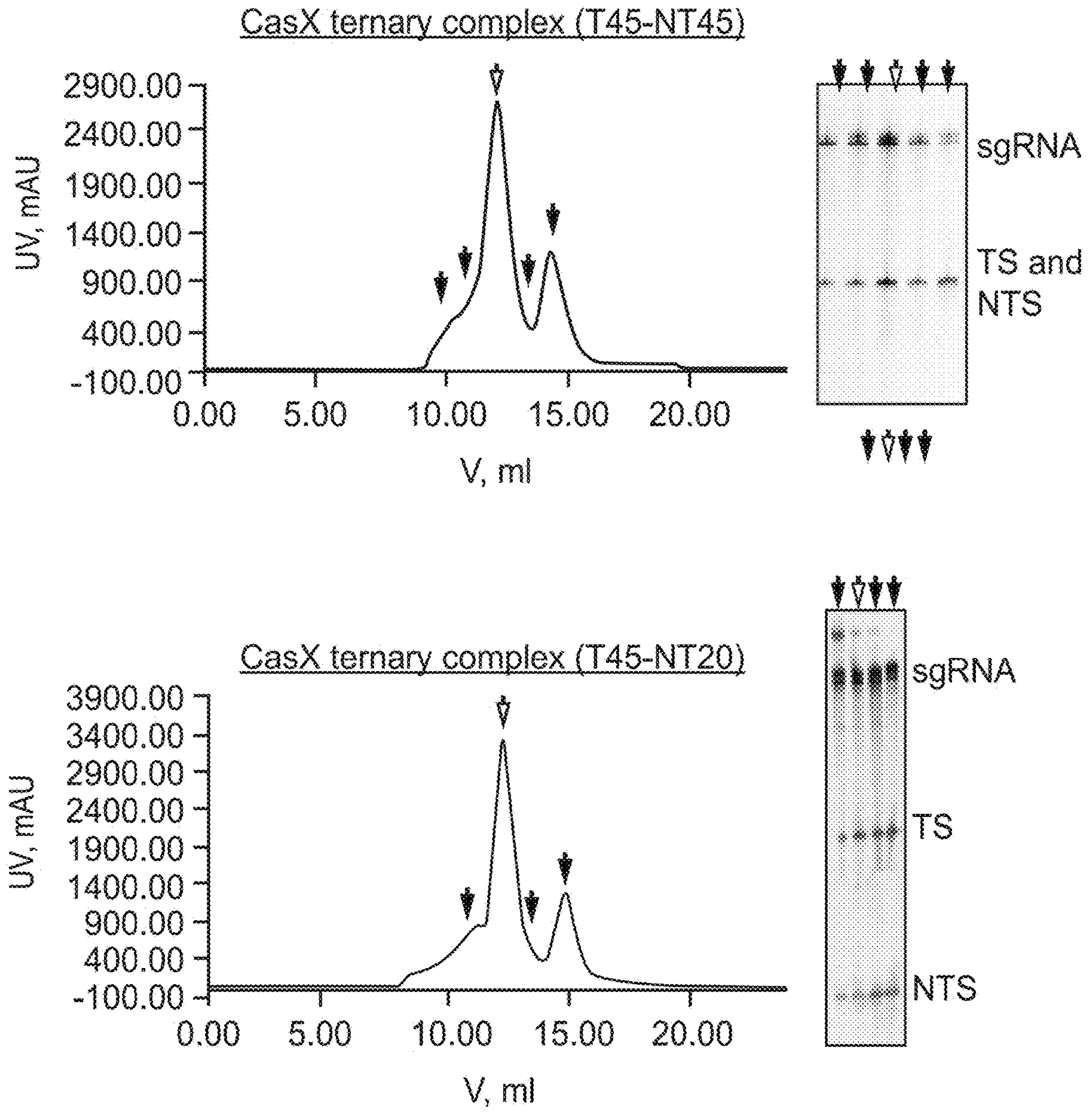
Figure 9A:
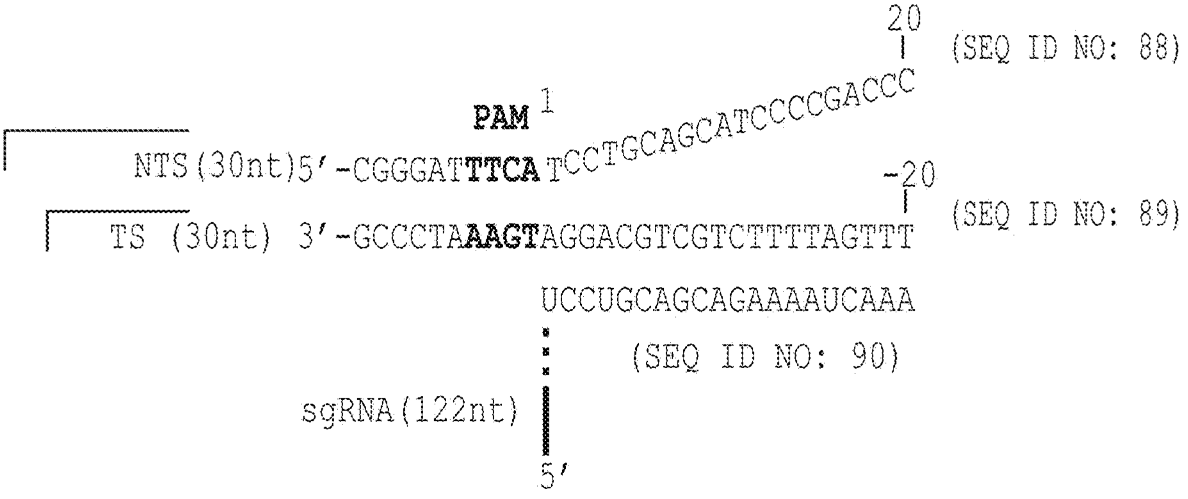
FIG. 9A-9E depict EM analysis of CasX-gRNA-DNA ternary complex with a 30 bp target DNA.
Figure 9B:
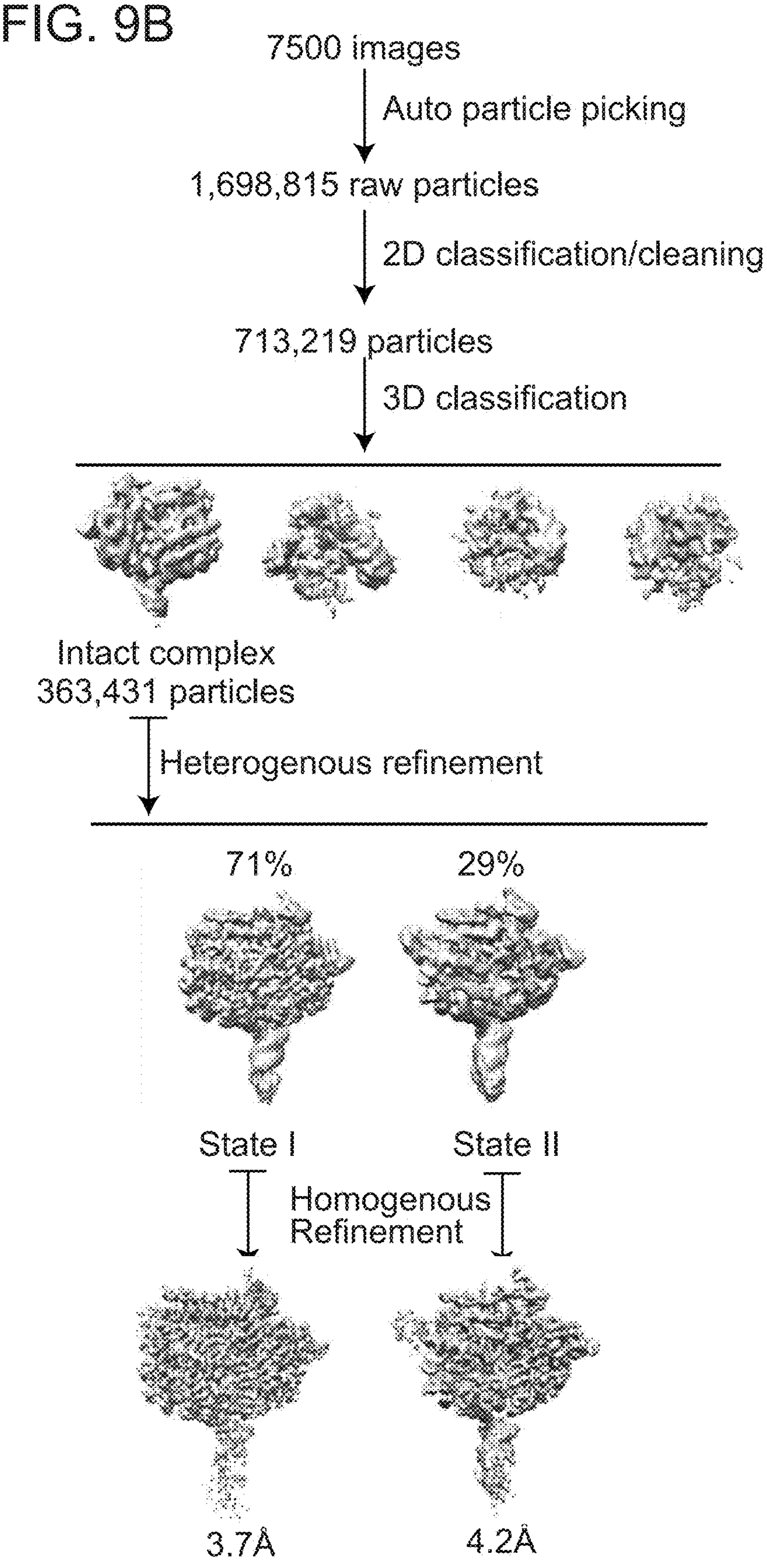
Figure 9C:
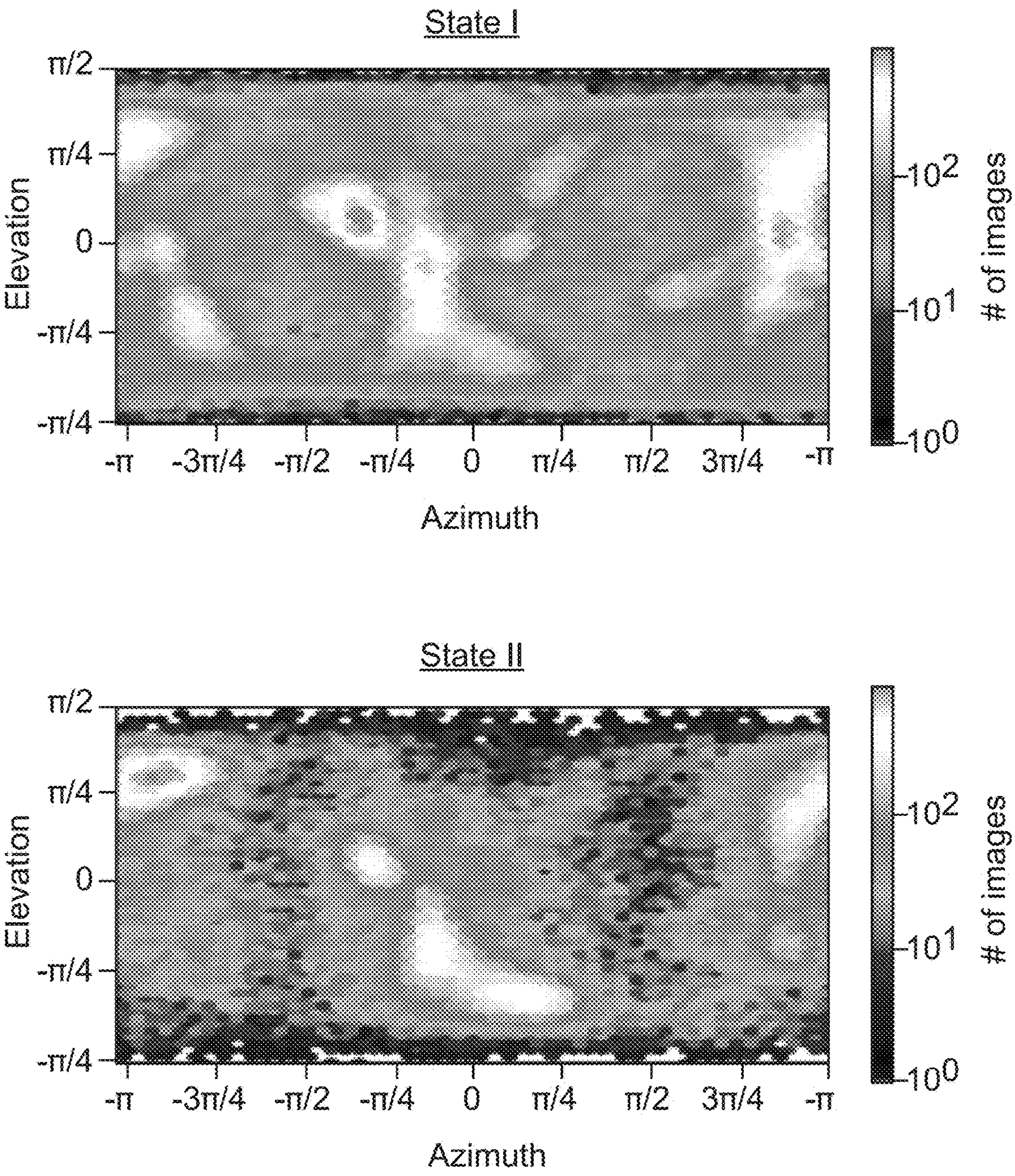
Figure 9D:
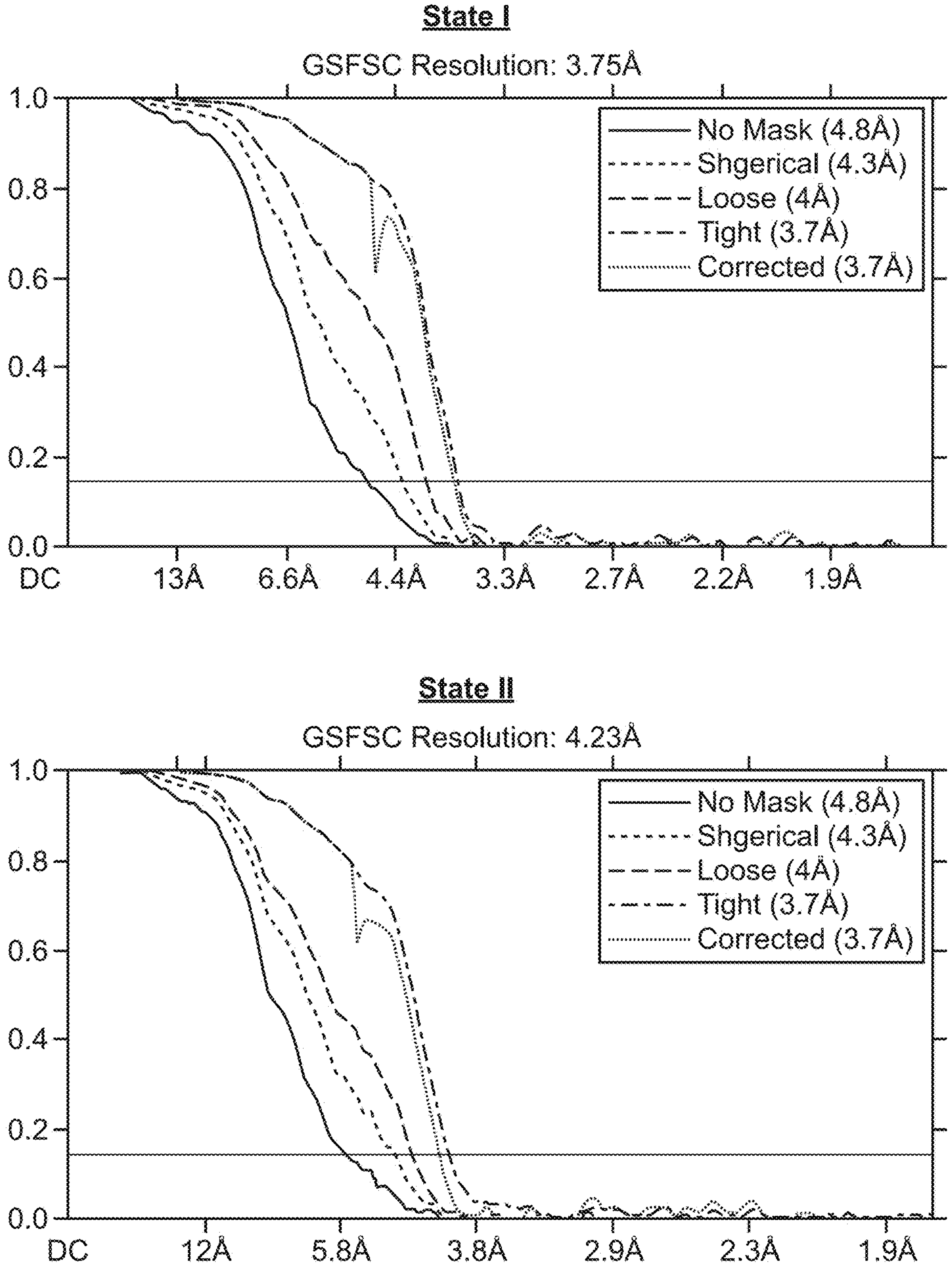
Figure 9E:
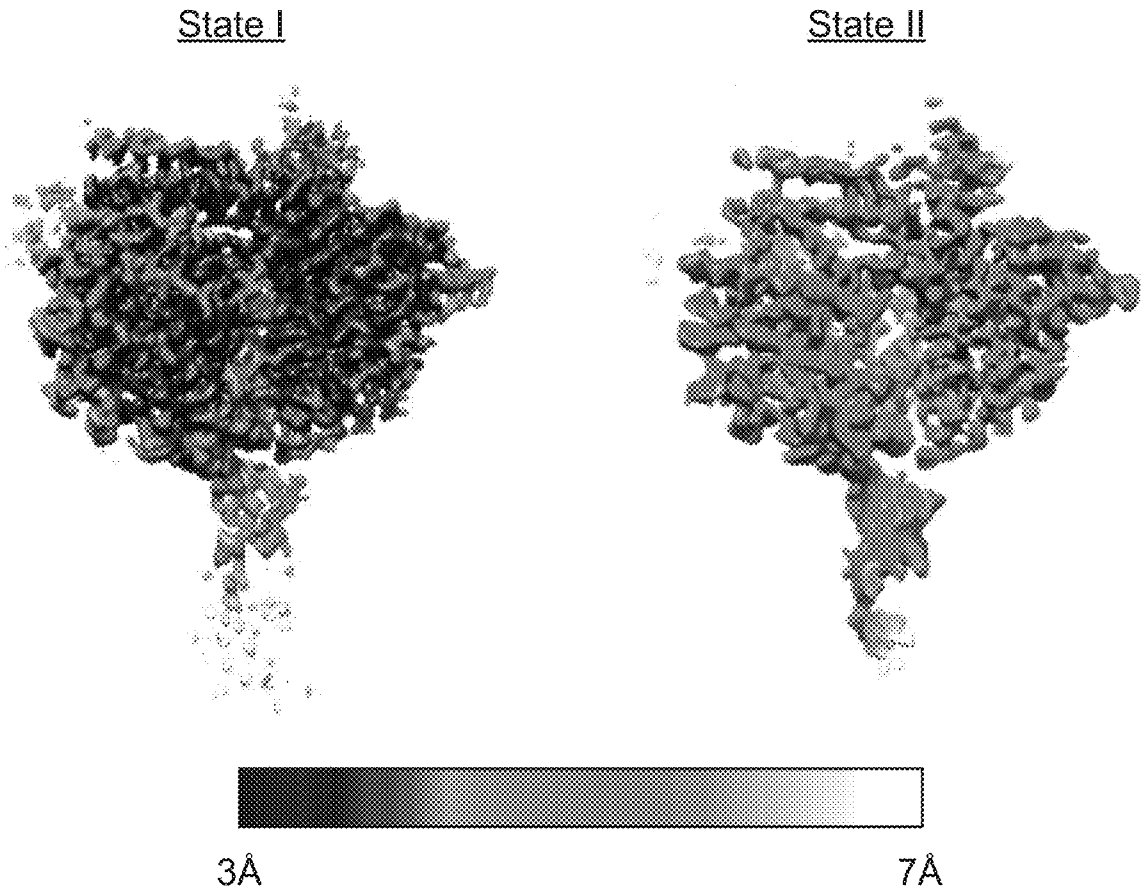
Figure 10A:
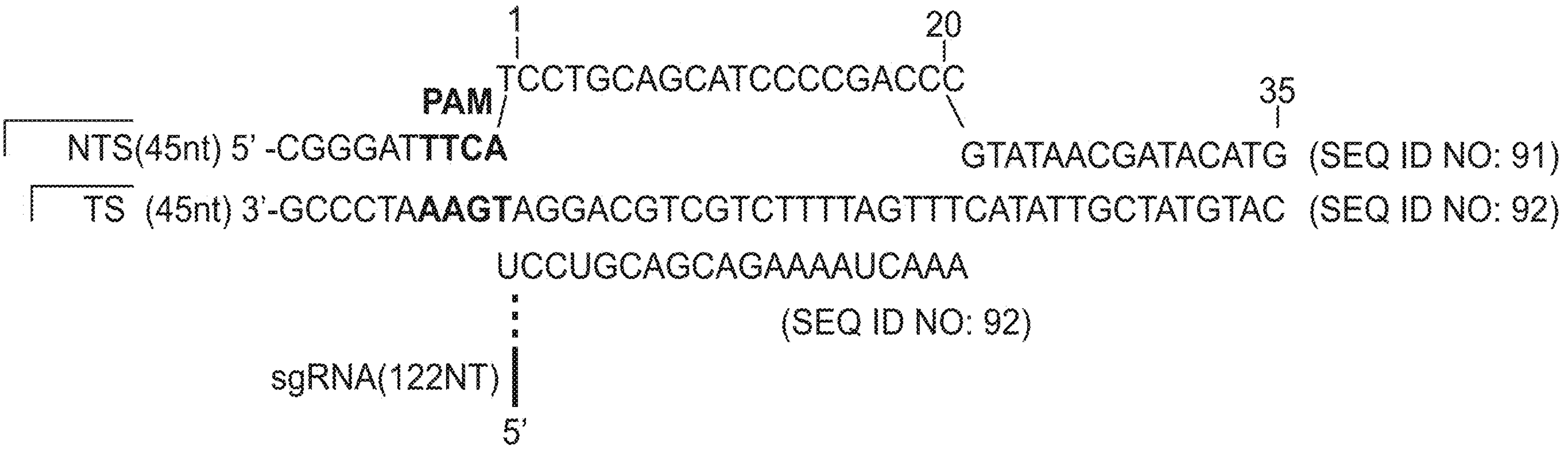
FIG. 10A-10E depict EM analysis of CasX-gRNA-DNA ternary complex with full R-loop (45 bp target DNA).
Figure 10B:
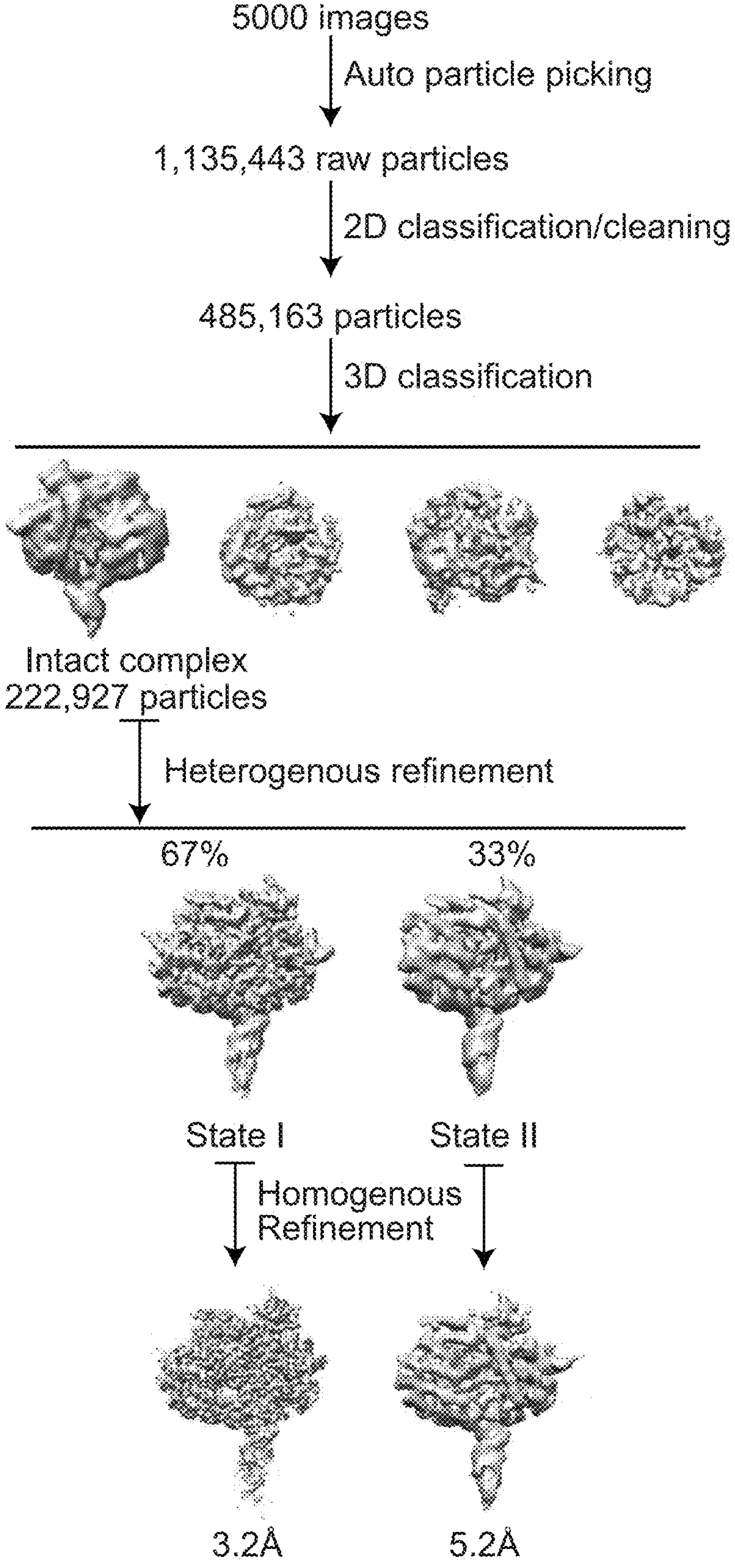
Figure 10C:
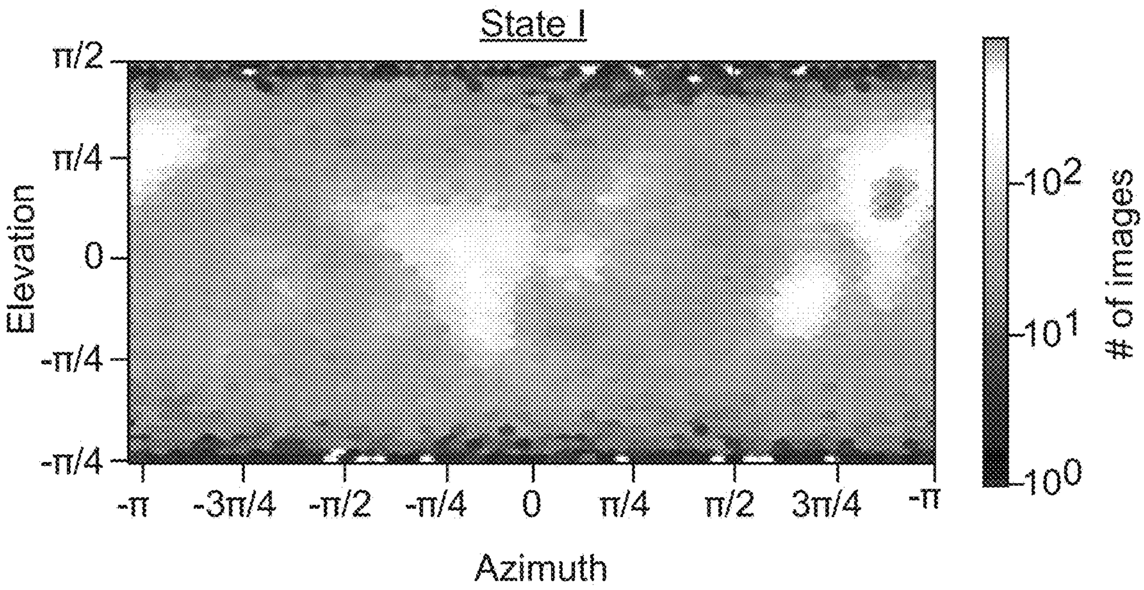
Figure 10C:
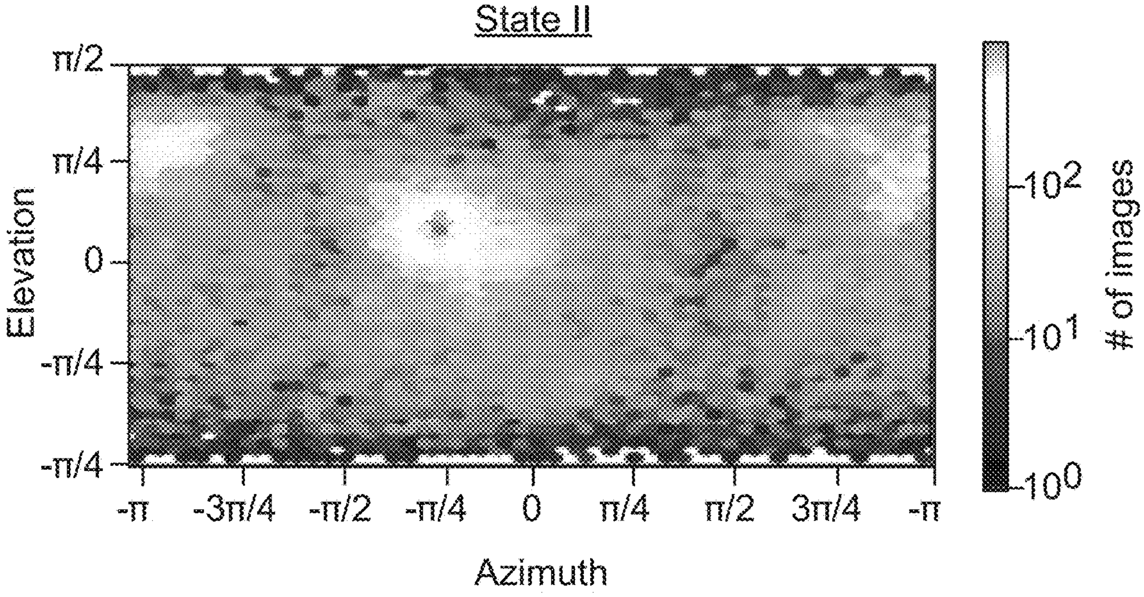
Figure 10D:
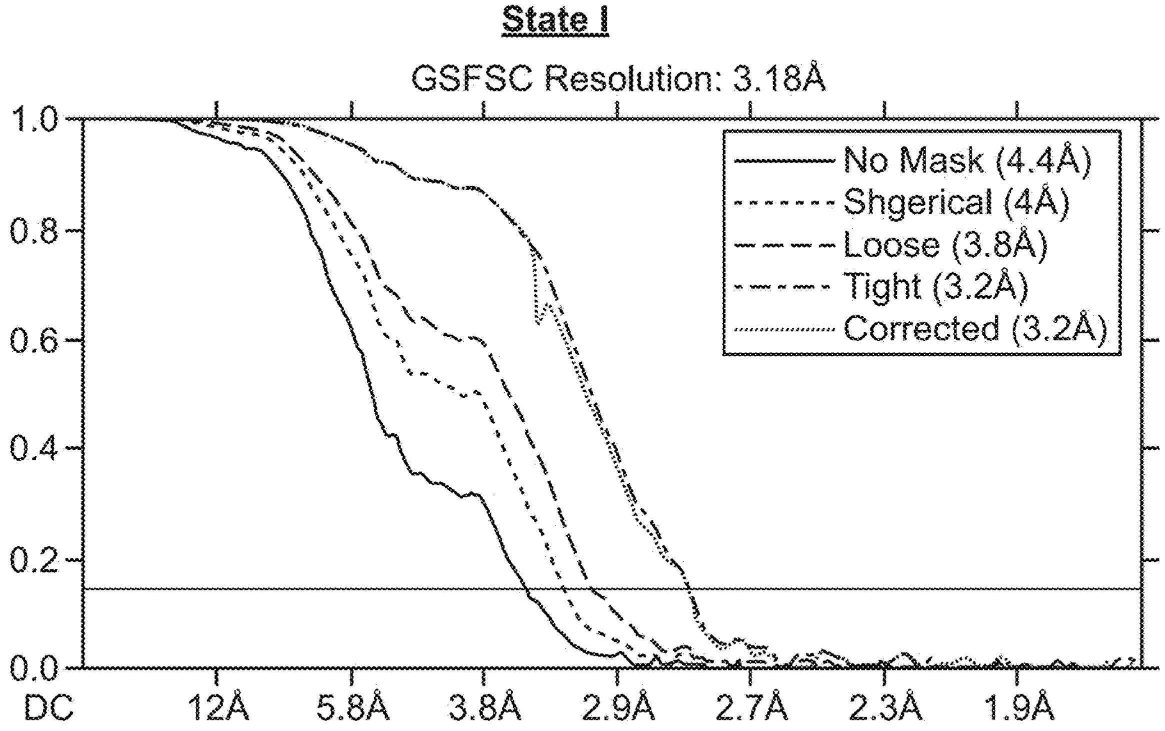
Figure 10D:
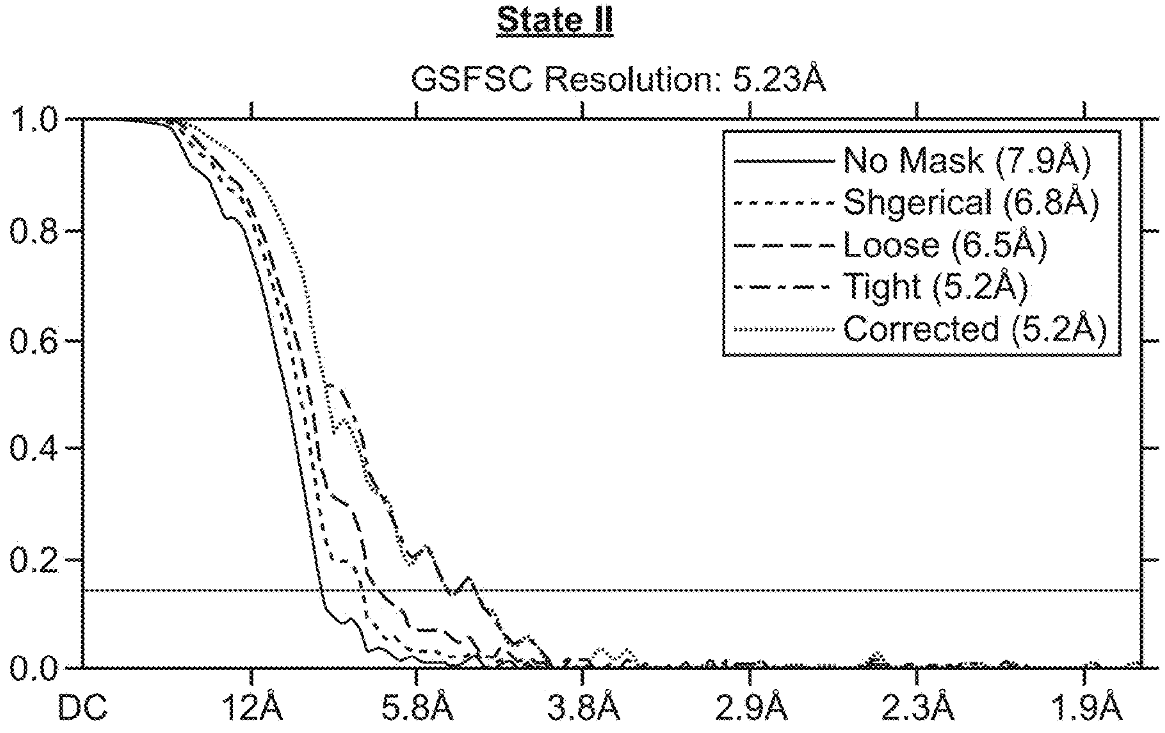
Figure 10E:
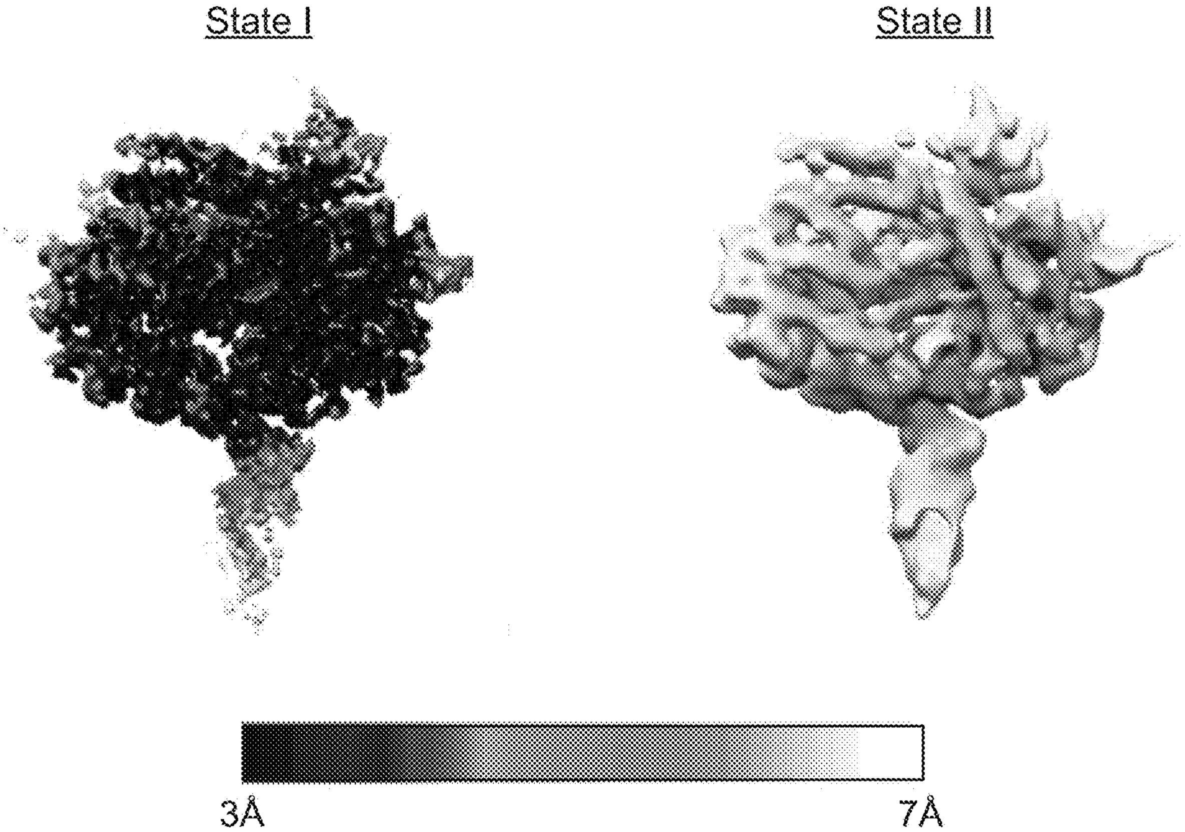
Figure 11A:
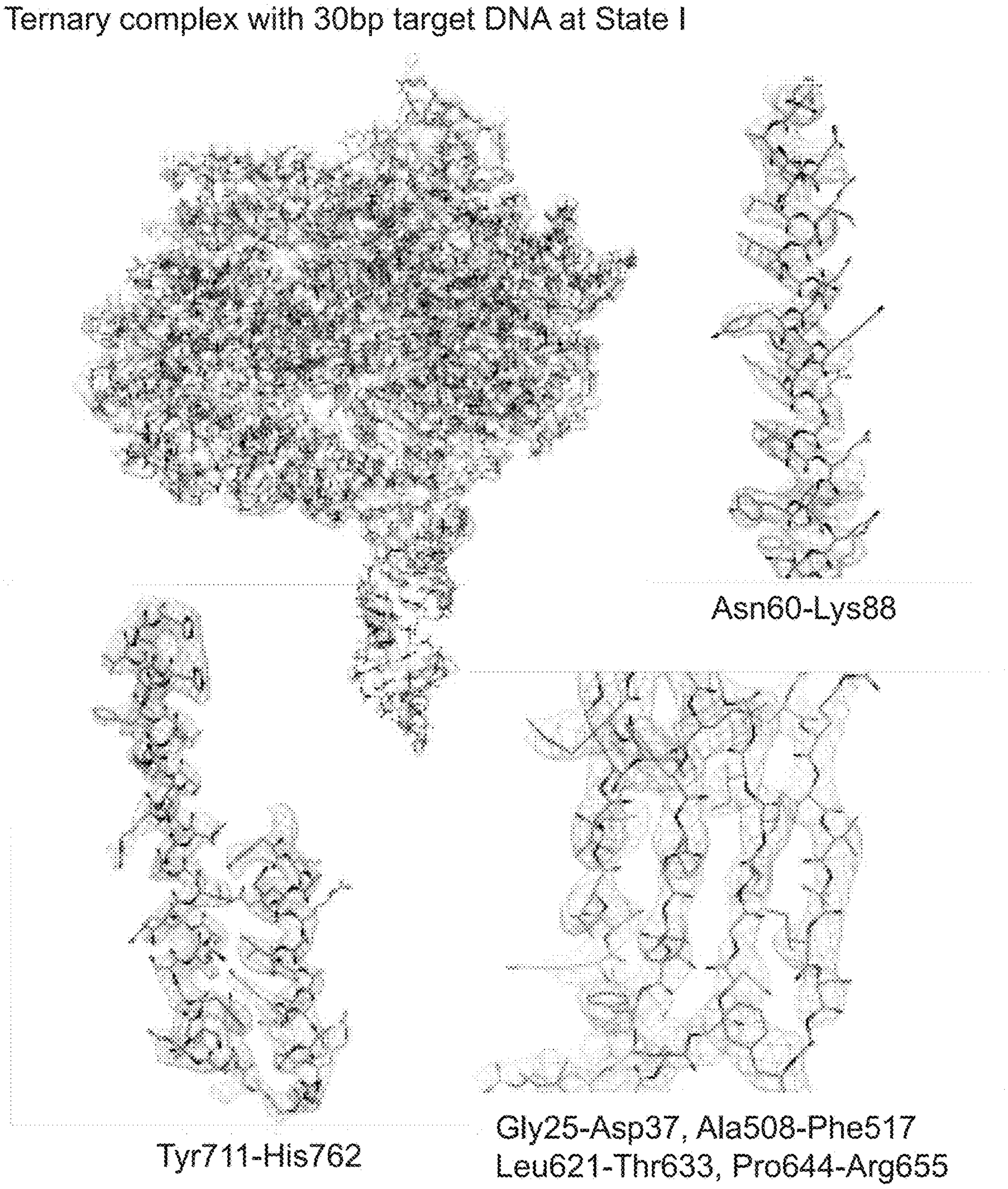
FIG. 11A-11D depict atomic model building of CasX ternary complexes for State I and State II.
Figure 11B:
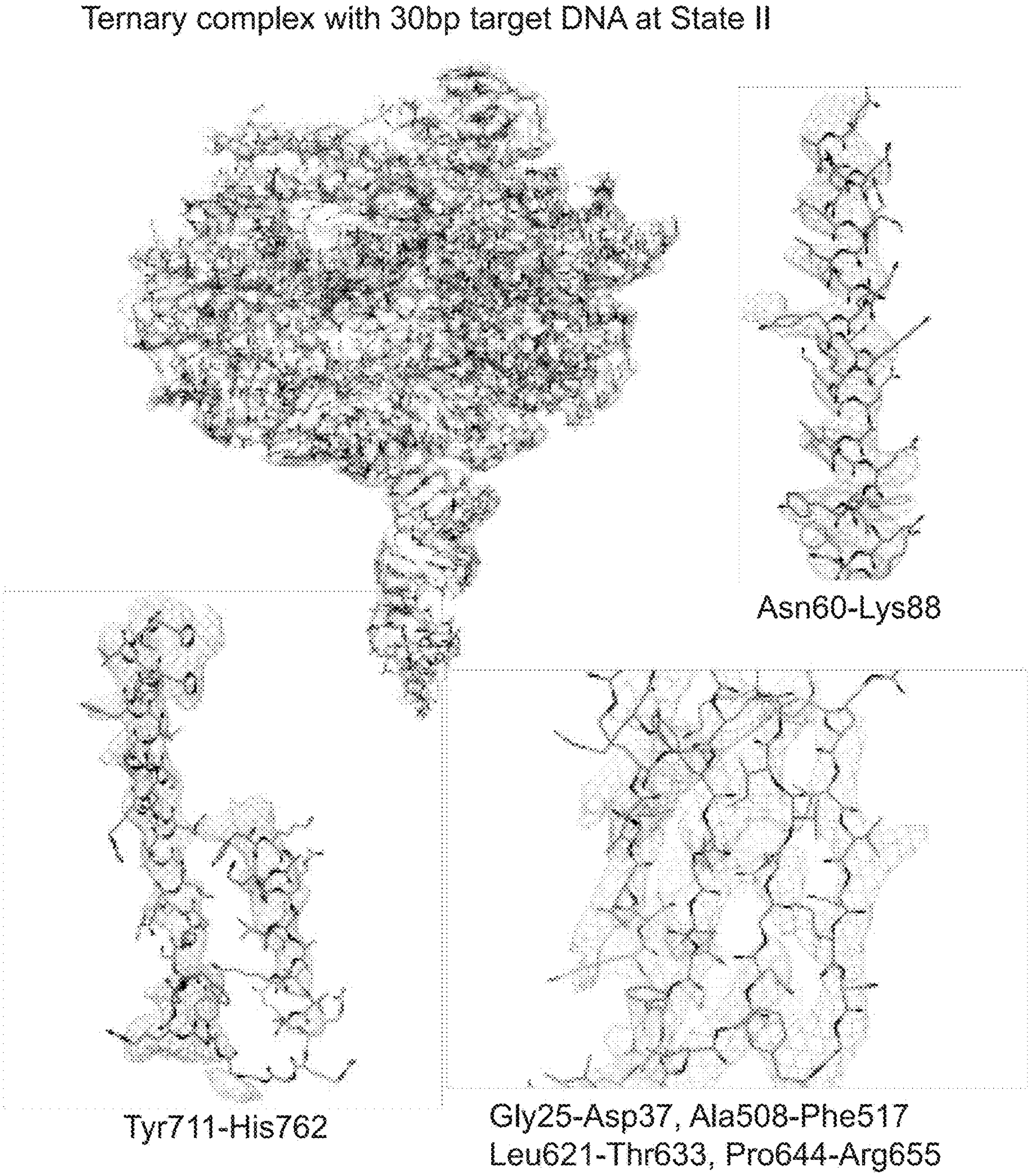
Figure 11C:
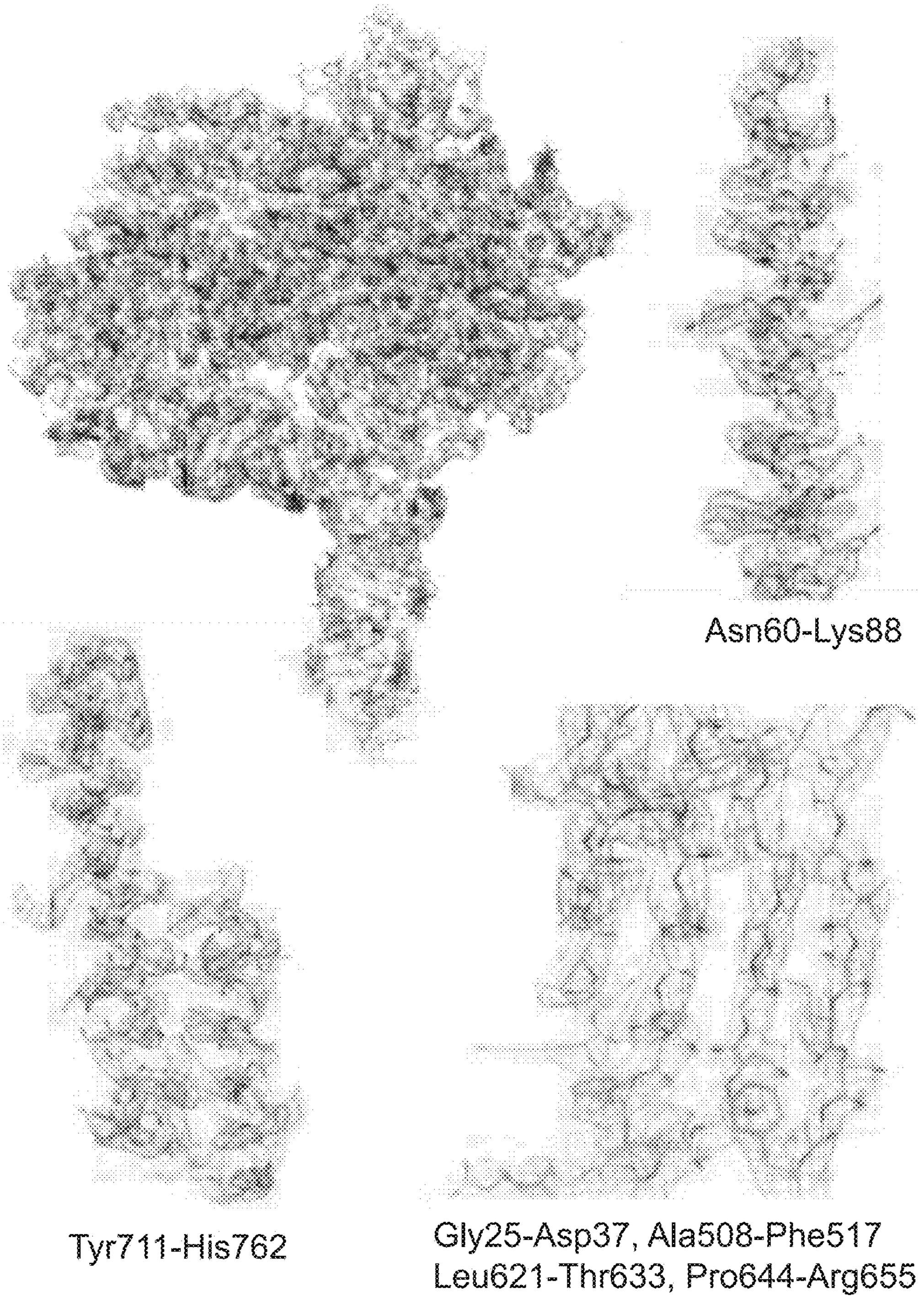
Figure 11D:
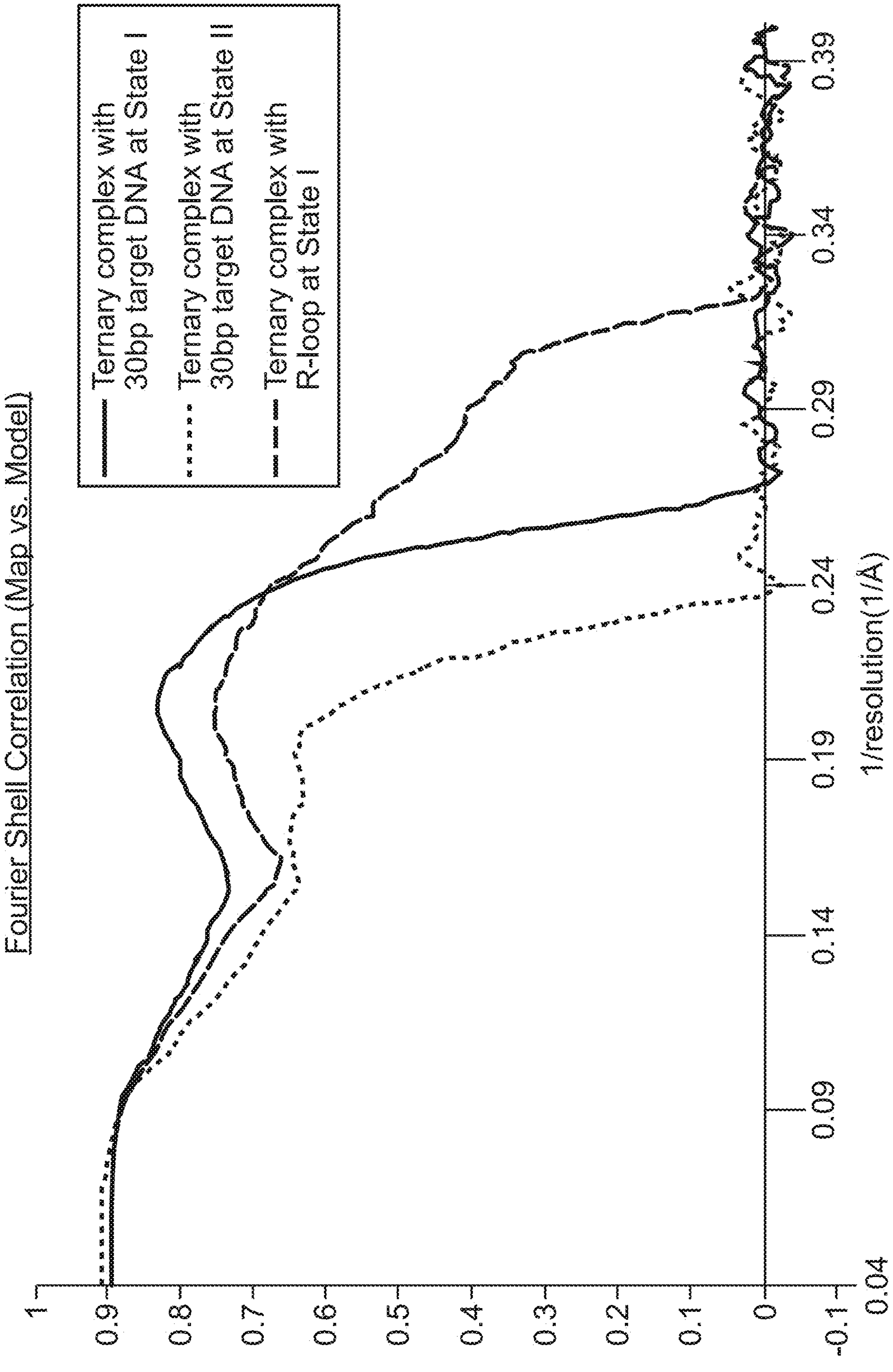
Figure 12A:
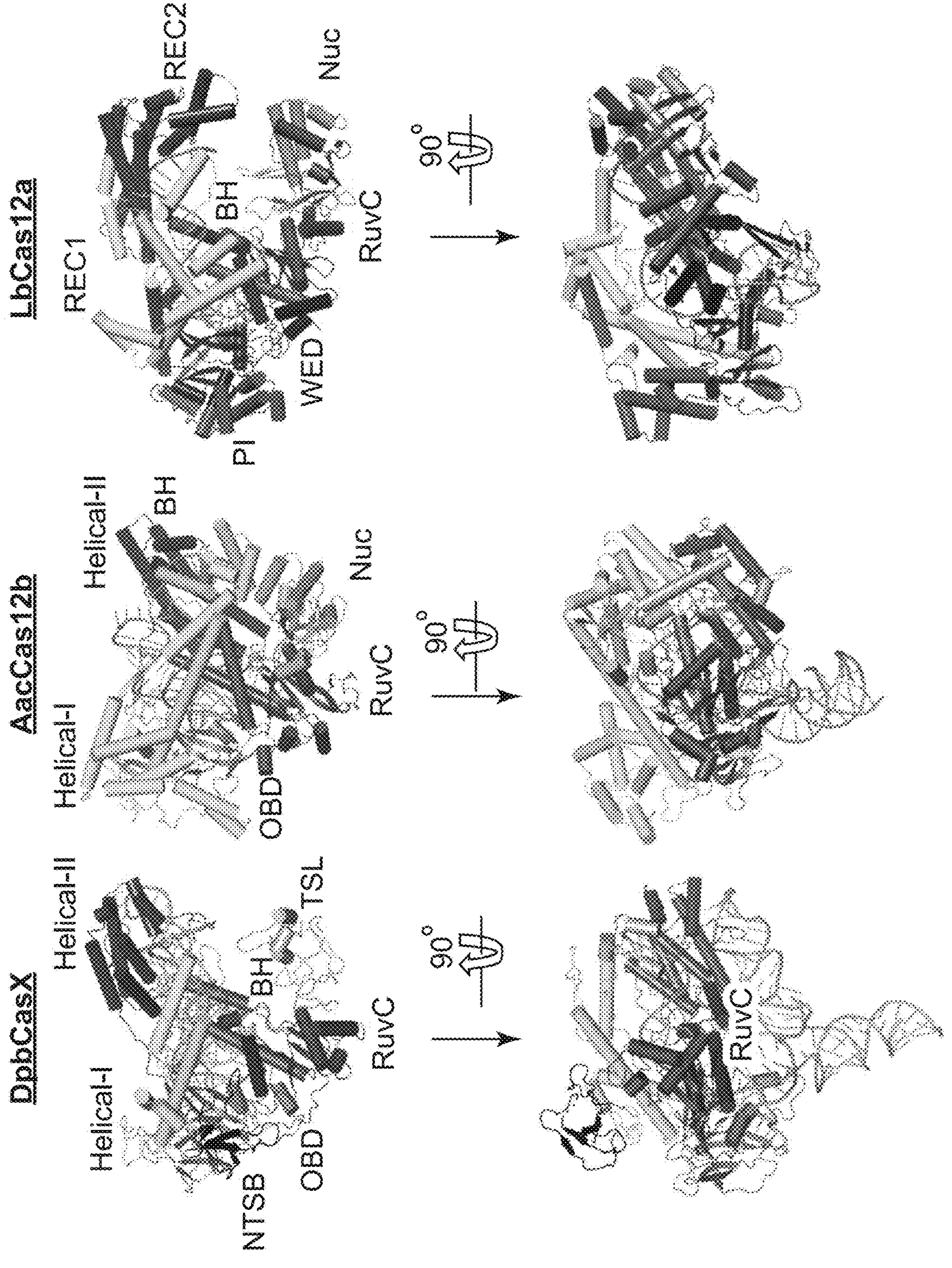
Figure 12B:
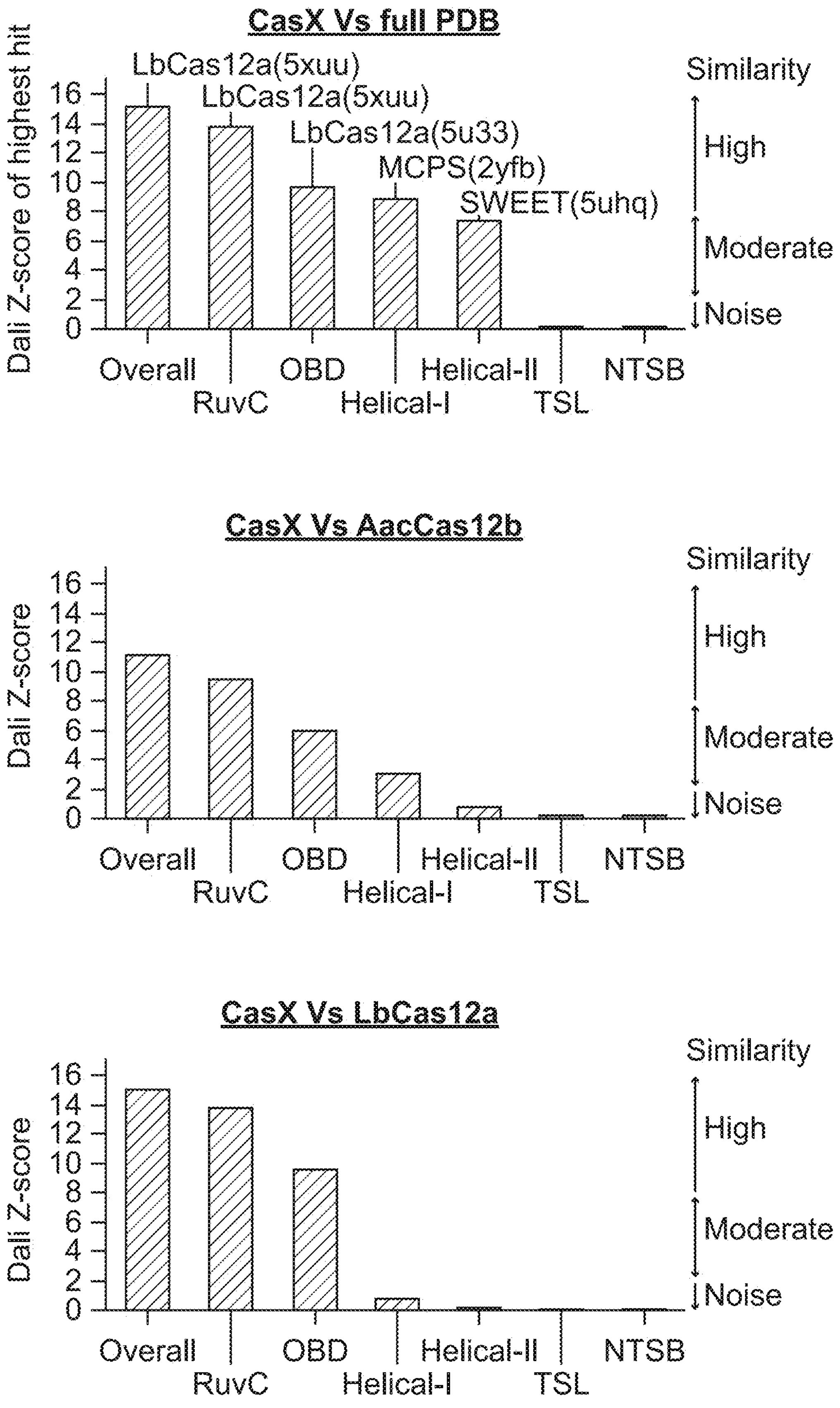
Figures 12C, 12D:
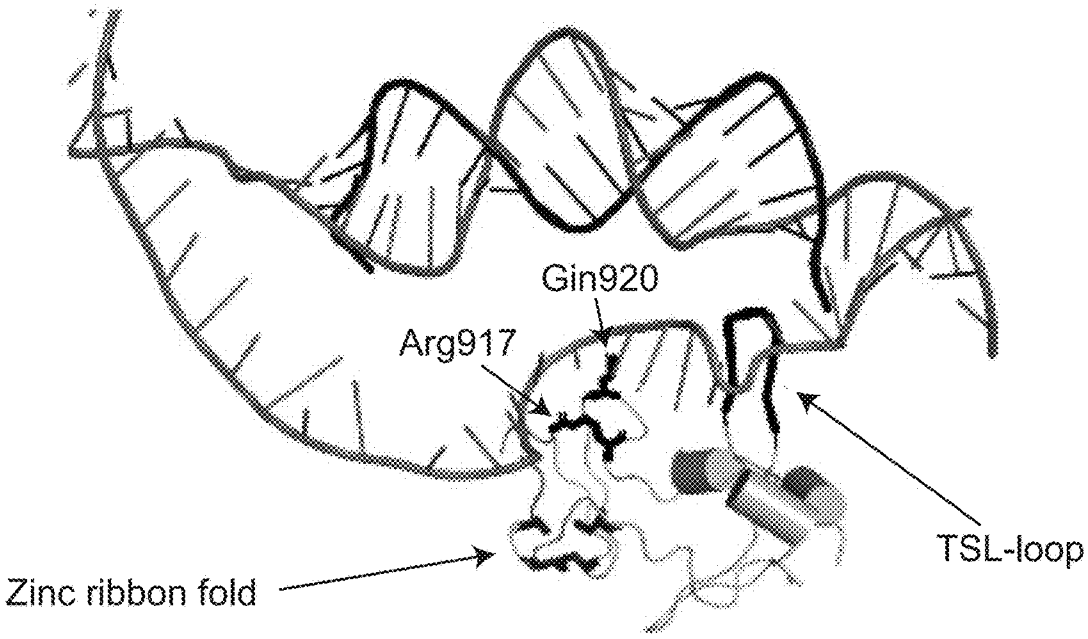
Figure 12E:
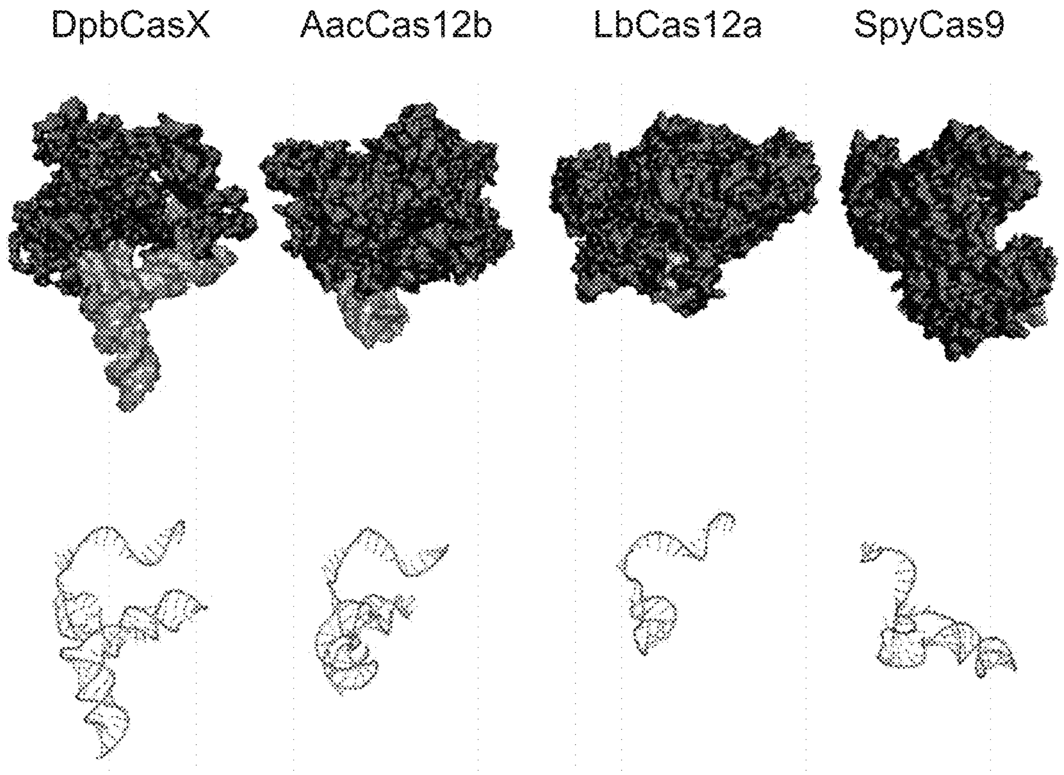
Figure 12F:
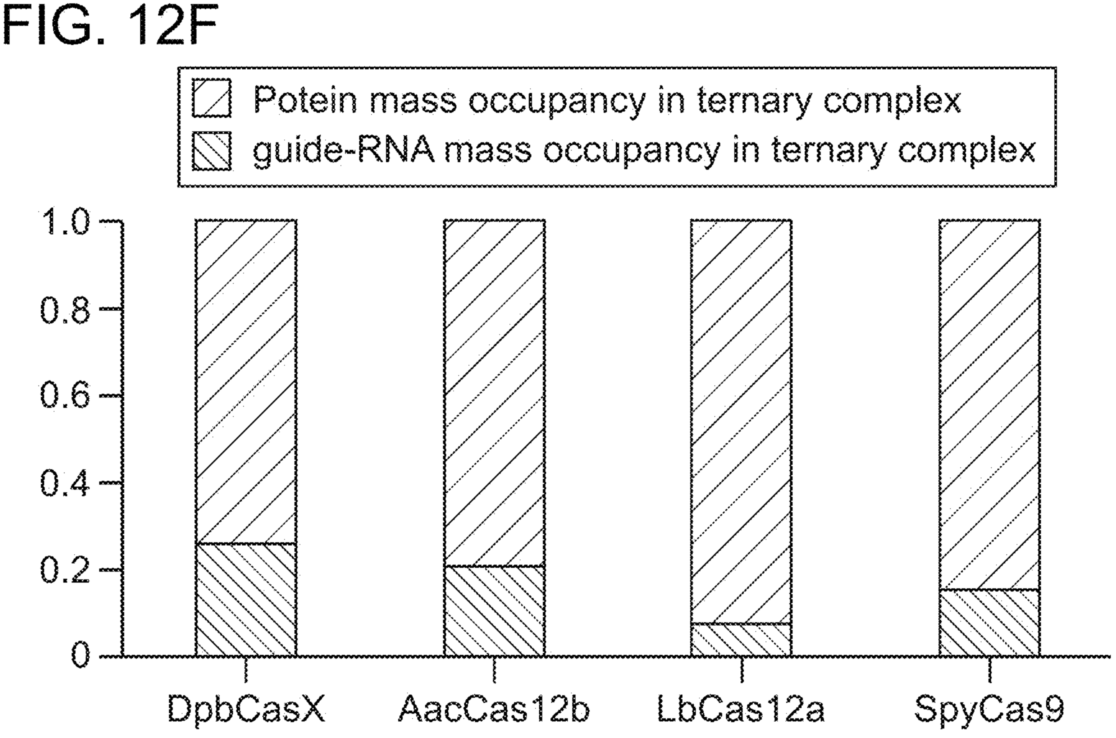
Figure 13C:
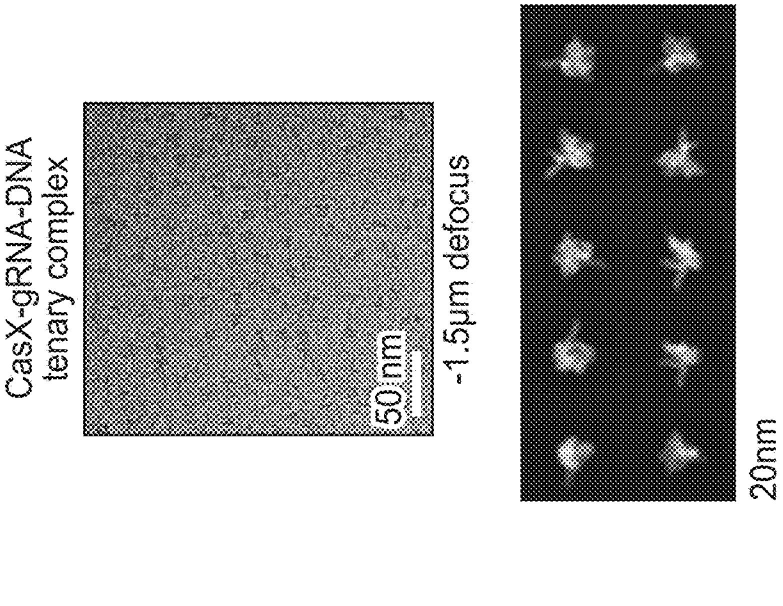
FIG. 13A-13K depict structural comparison of apo, binary and ternary CasX samples.
Figure 13B:
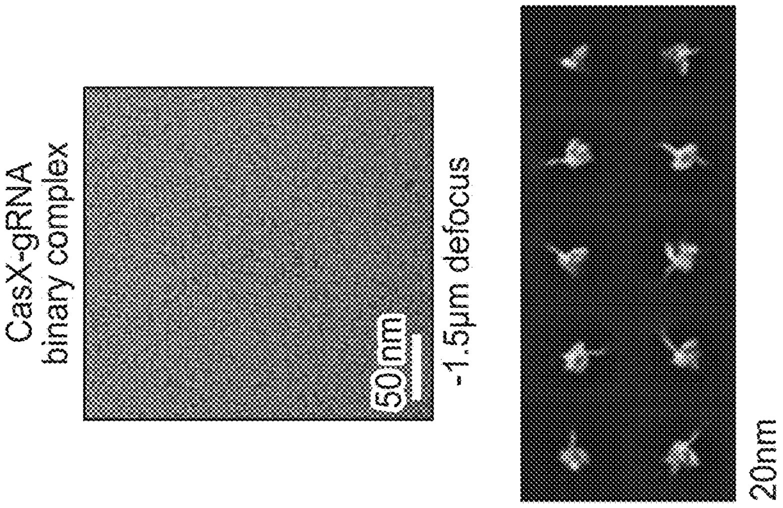
Figure 13A:
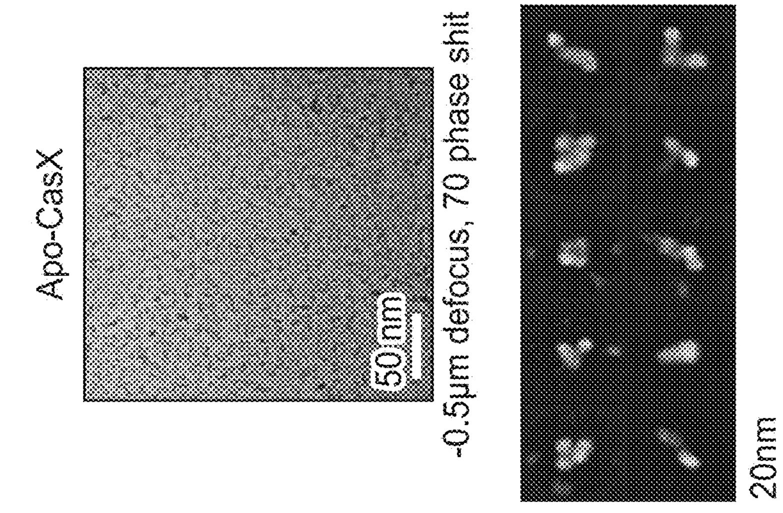
Figure 13D:
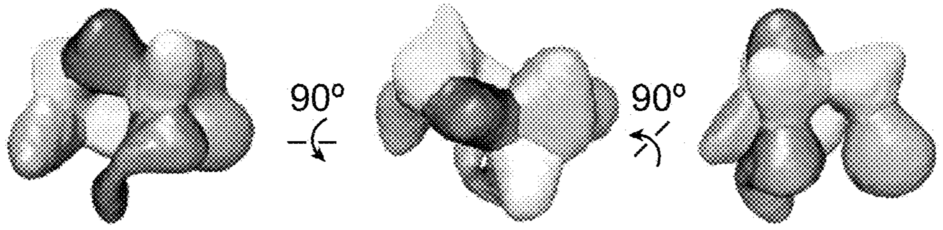
Figure 13E:
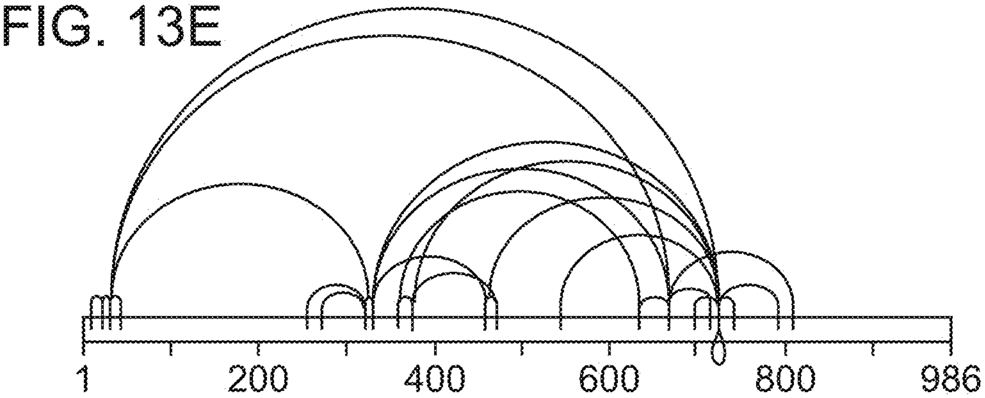
Figure 13F:
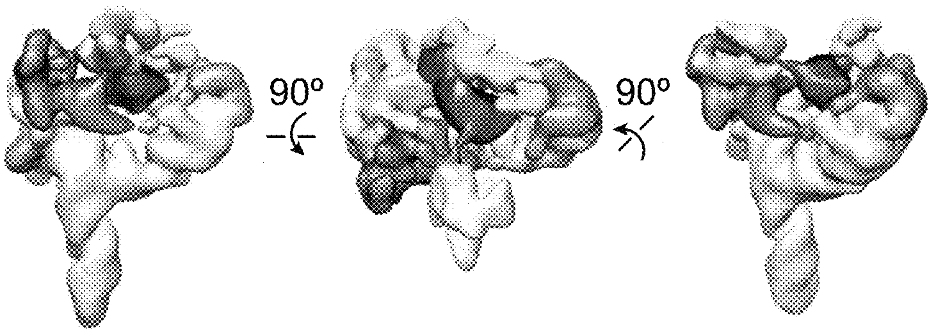
Figure 13G:
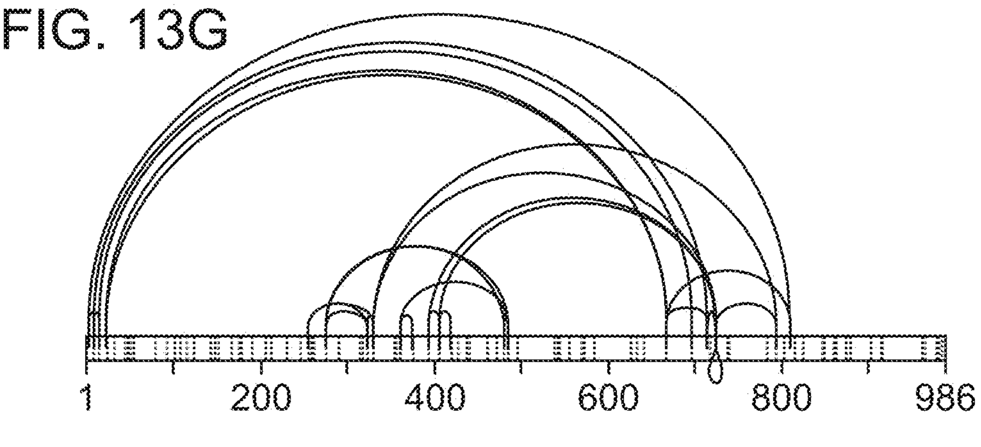
Figure 13H:
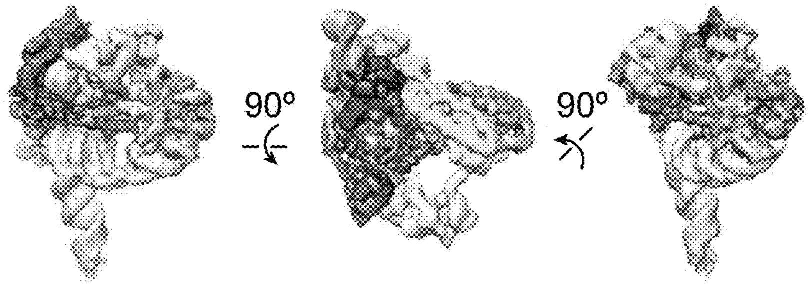
Figure 13I:
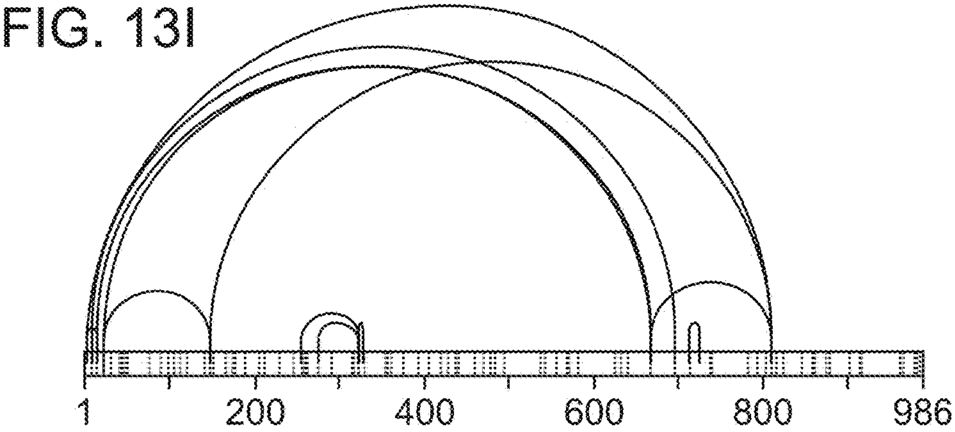
Figure 13J:
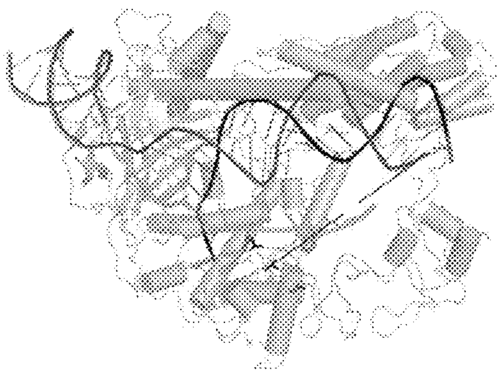
Figure 13K:
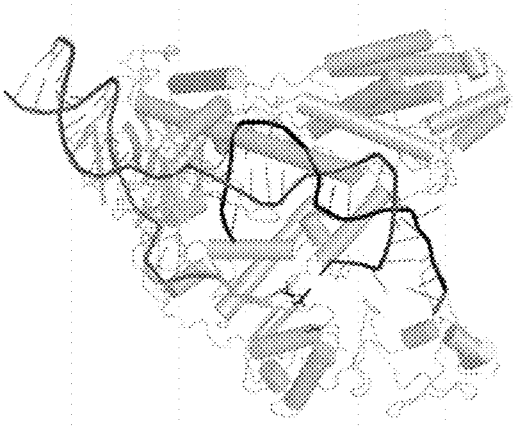
Figure 14A:
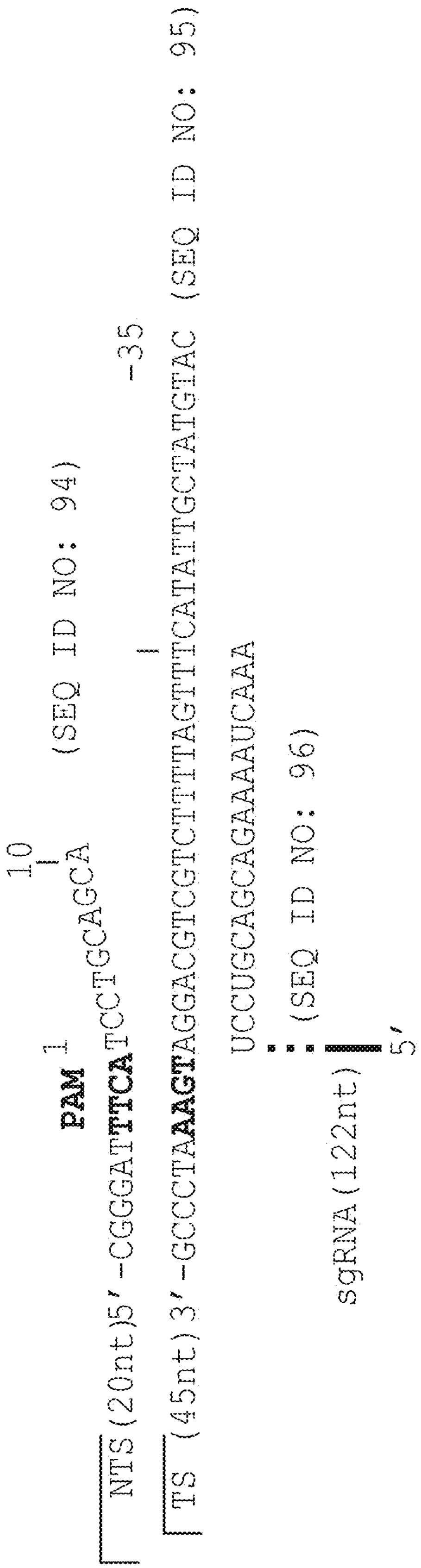
FIG. 14A-14E depict EM analysis of CasX-gRNA-DNA ternary complex with shortened NTS (20 nt NTS and 45 nt TS). Sequences from top to bottom: SEQ ID NOs:81-83.
Figure 14B:
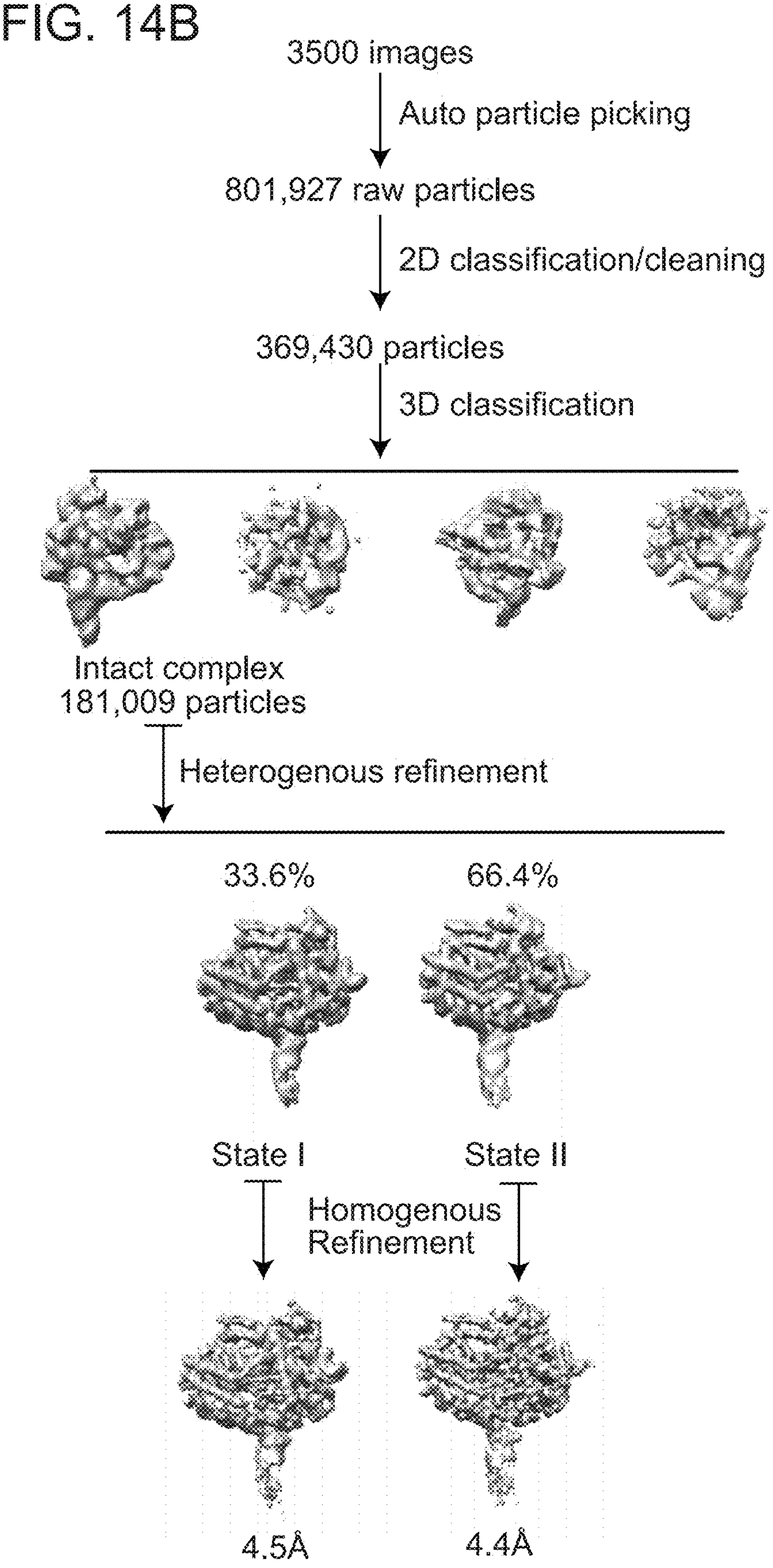
Figure 14C:
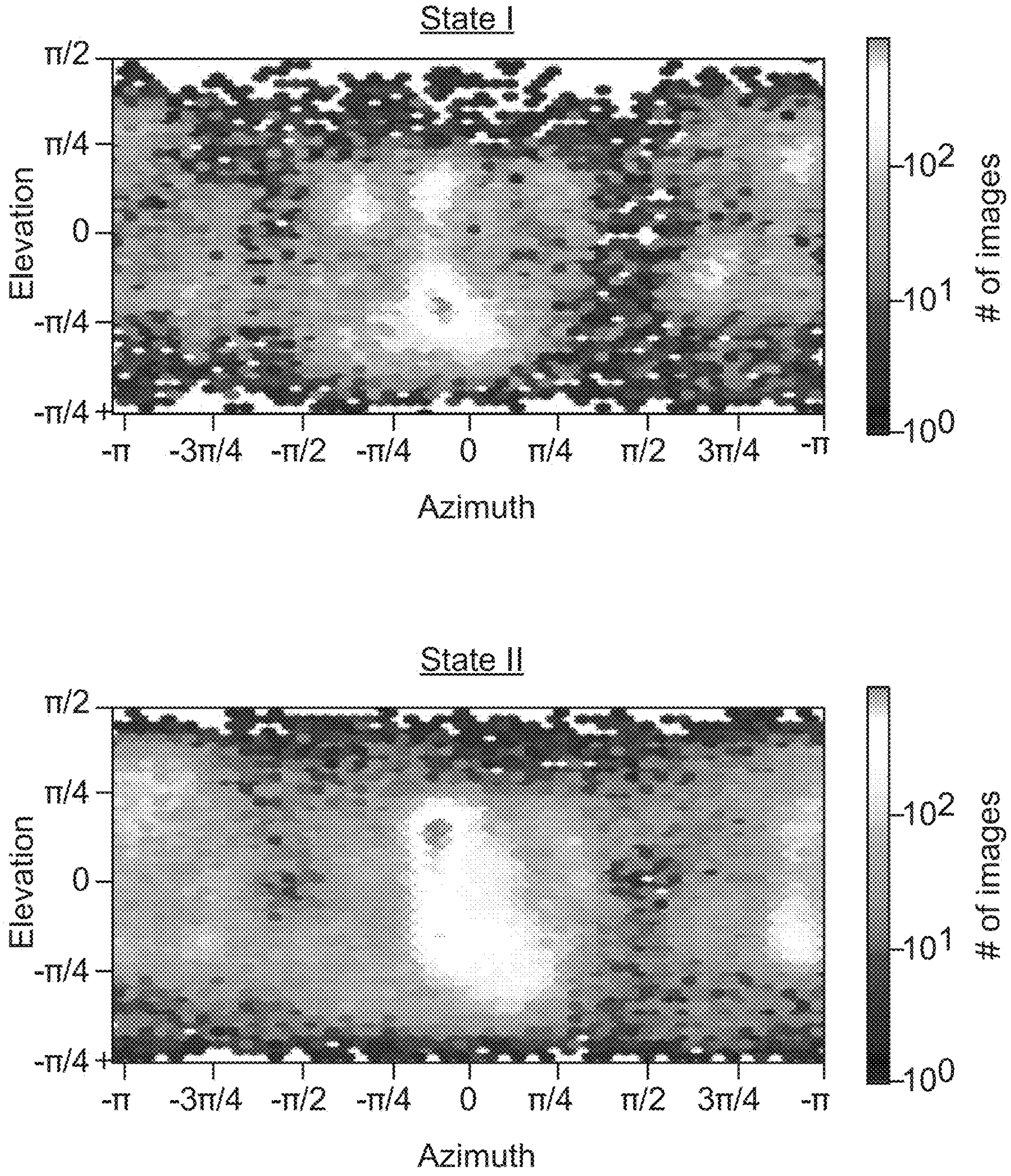
Figure 14D:
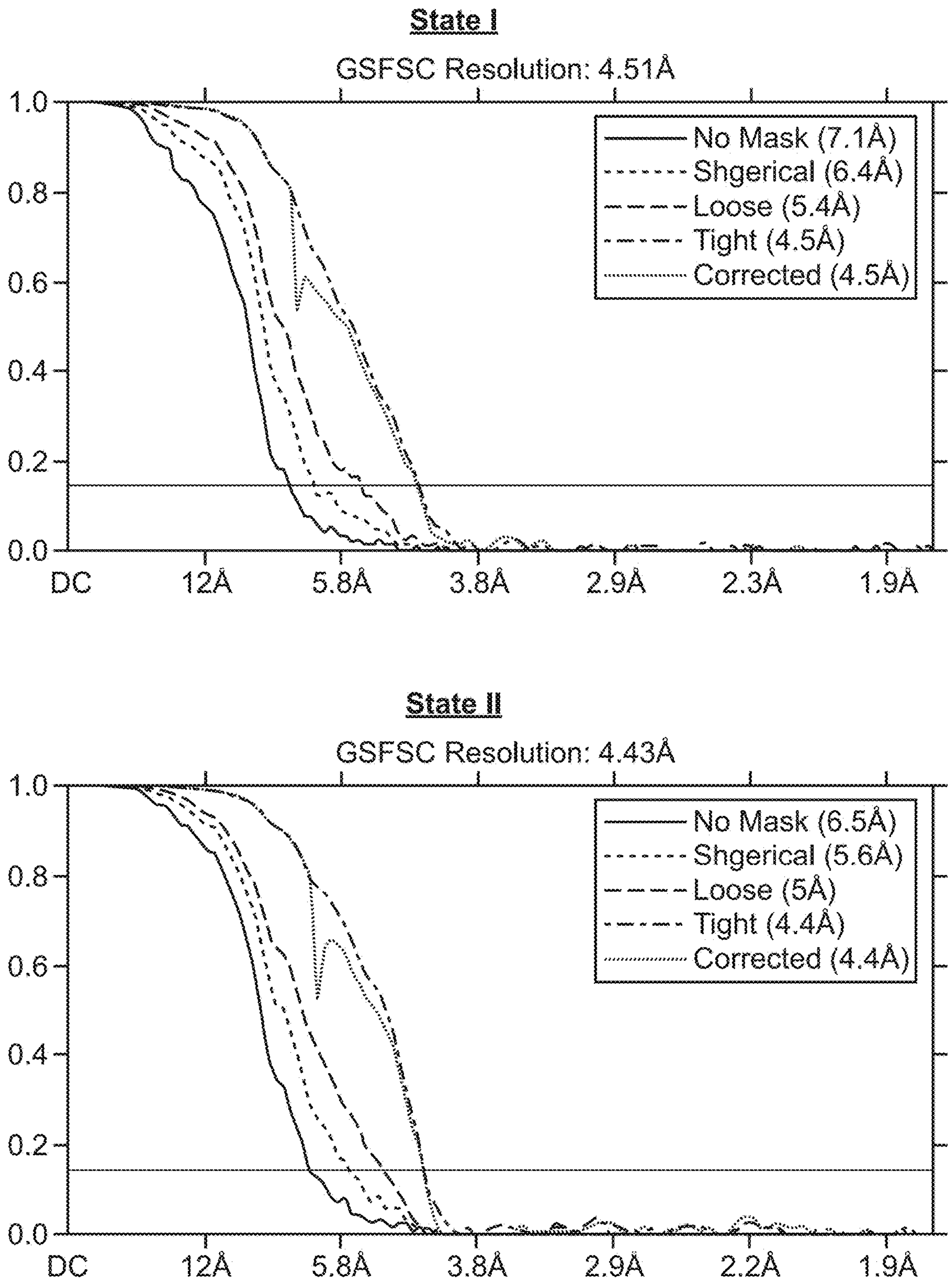
Figure 14E:
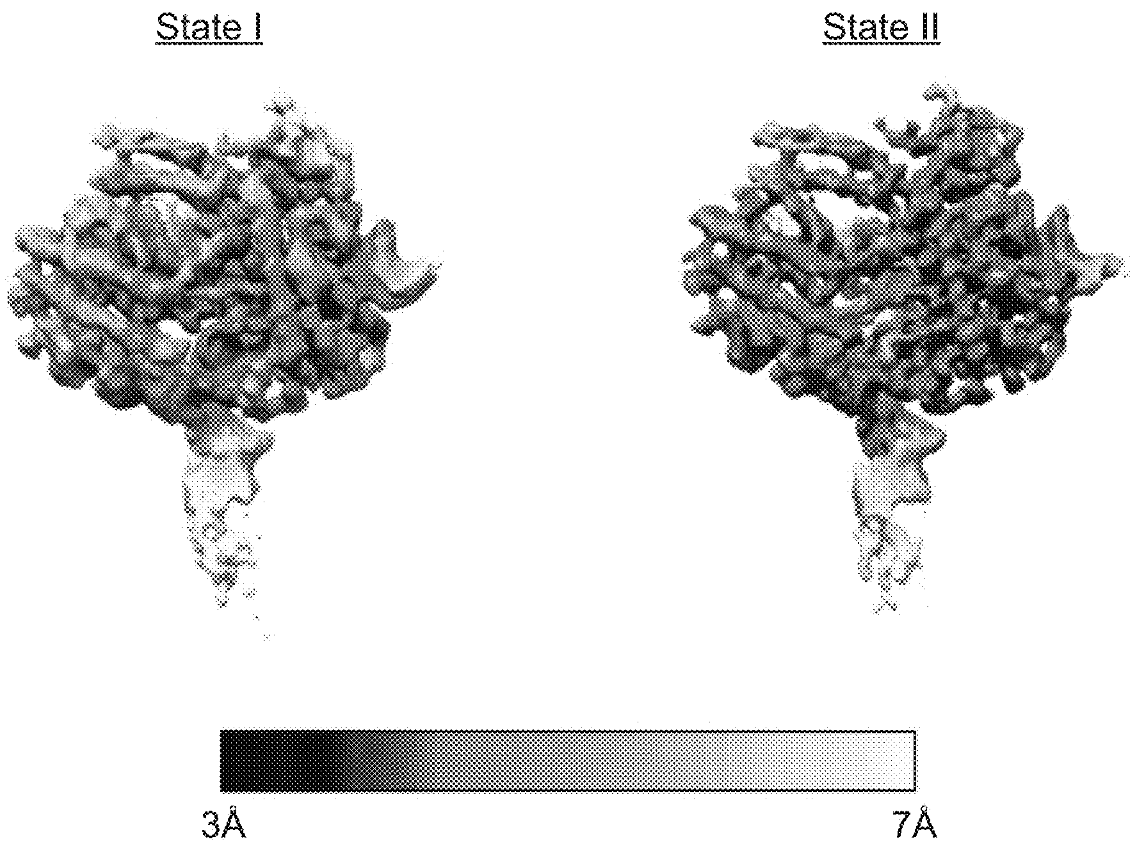

FIG. 5A-5B. Novel domains for target DNA unwinding and loading. a, Electron density map demonstrating the presence of a domain that directly interacts with the non-target DNA strand. Models for CasX ternary complex in State I and II within the cryo-EM map (shown as mesh surface, low-pass filtered to 4.5 Å). CasX is shown in grey with NTSB domain highlighted in red, target strand DNA in purple and non-target strand DNA in magenta. b, Comparison of the cleavage activity of the wild-type CasX and NTSB domain deletion (CasXΔ101-191). The reactions were analyzed at the following time points: 0, 2, 5, 30, 60, 120 minutes. Completely base-paired probe and a bubbled probe were used to test the on-target activity (left half of FIG. 5*b*), and a random 50 nt oligo was used to test the trans-cleavage activity (right half of FIG. 5*b*). P indicates the cleavage product. "Activator" refers to a single stranded DNA target.

FIG. 6A-6E. Proposed model for sequential CasX activation for DNA cleavage. a, Overall architecture of apoCasX. The different protein domains are colored as in FIG. 3. b, Cryo-EM map of gRNA-bound CasX. Upon gRNA binding. CasX undergoes a domain rearrangement. gRNA is shown as a gray solid surface. c, Cryo-EM map of CasX ternary complex in the NTS-loading state (State I). Upon target dsDNA recognition and unwinding by CasX-gRNA complex, the non-target strand is preferentially positioned into the RuvC active site for cleavage. d, Cryo-EM map of CasX ternary complex in the TS-loading state (State II). After non-target strand cleavage, the entire RNA-DNA duplex is bent by the TSL domain, thus positioning the target strand into RuvC active site. e, Cryo-EM of CasX ternary complex in a hypothetical Trans-active state. After the target strand DNA cleavage, the tension within the bent RNA-DNA duplex favors the return of the CasX ternary complex to State I, thus enabling the RuvC domain to cut any accessible single strand DNA. The model shown here is adopted from the CasX ternary complex with a short NTS DNA in State I. To mimic the trans-ssDNA. 5' overhang of TS DNA which folds back to RuvC domain is colored by blue.

FIG. 14A-14E. EM analysis of CasX-gRNA-DNA ternary complex with shortened NTS (20 nt NTS and 45 nt TS). a, Target DNA sequence in this complex. b, Cryo-EM analysis pipeline. 801,927 particles were picked from 3.500 drift-corrected micrographs and then used for 2D classification. By 2D based manual screening, 369,430 good particles were selected for 3D classification into 4 classes. 181,009 particles from the class showing better structure preservation were further used for heterogeneous refinement, which generated two models, state I and state II, with 33.6% and 66.4% of the particles, respectively. State I and State II were then independently refined to 4.5 Å and 4.4 Å by homogenous reconstruction. c, The Euler angle distribution of refined particles belong to State I and State II. d, FSC curve calculated using two independent half maps, indicating an overall resolution of 4.5 Å for state I and 4.4 Å for state II. e, Cryo-EM structures of State I and State II colored by local resolution as calculated in Cryopsarc. Resolution ranges from 3 Å to 7 Å. Panels c and d are directly adopted from the standard outputs of Cryosparc.

Figure 15A:
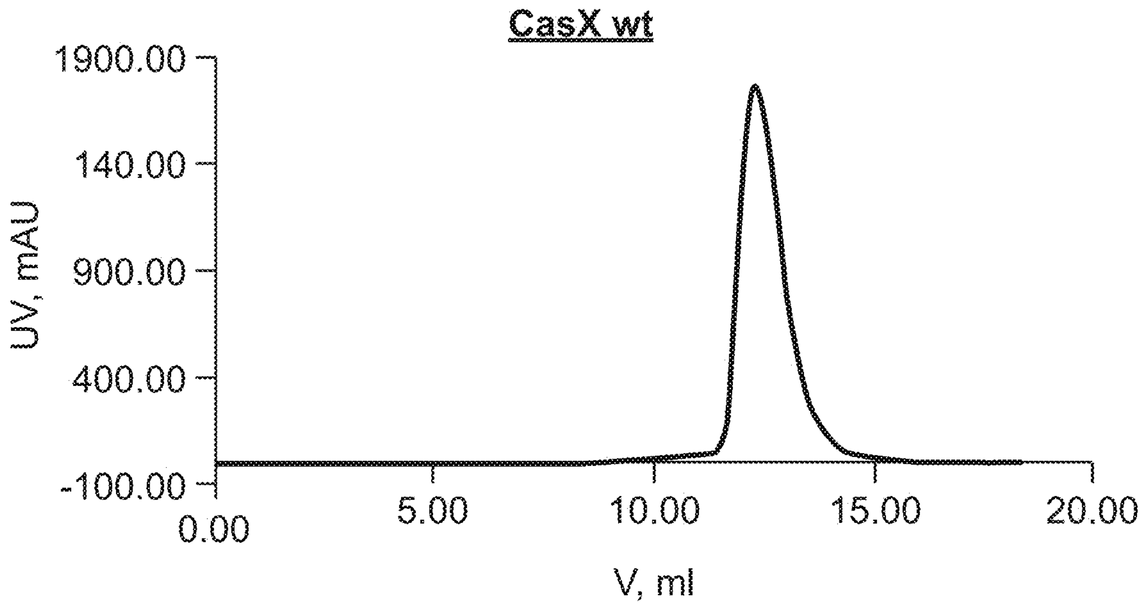
FIG. 15A-15C depict CasX ΔNTSBD purification and substrate cleavage.
Figure 15A:
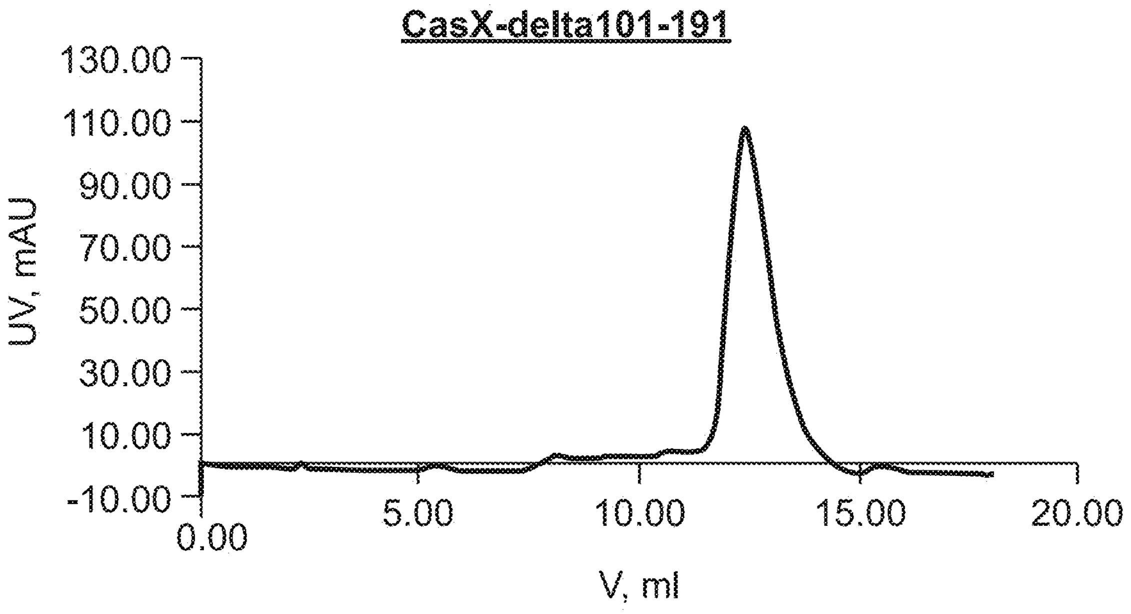
Figure 15B:
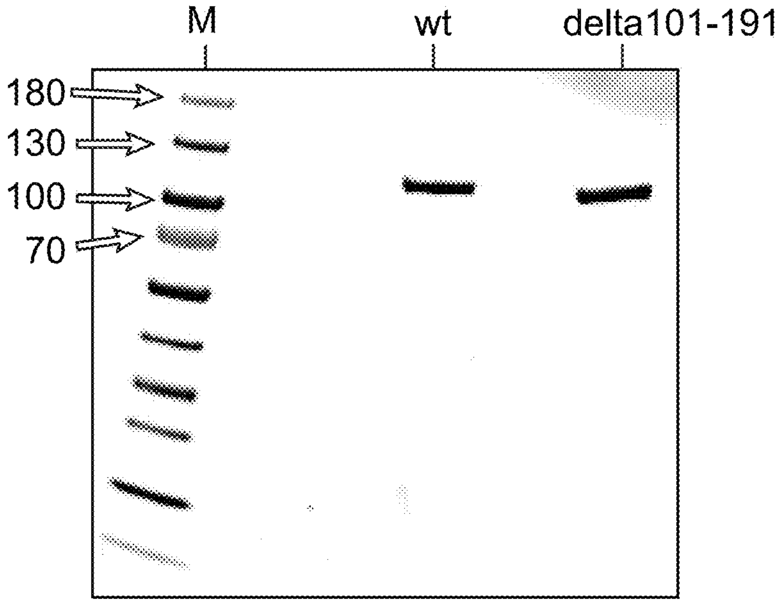
Figure 15C:
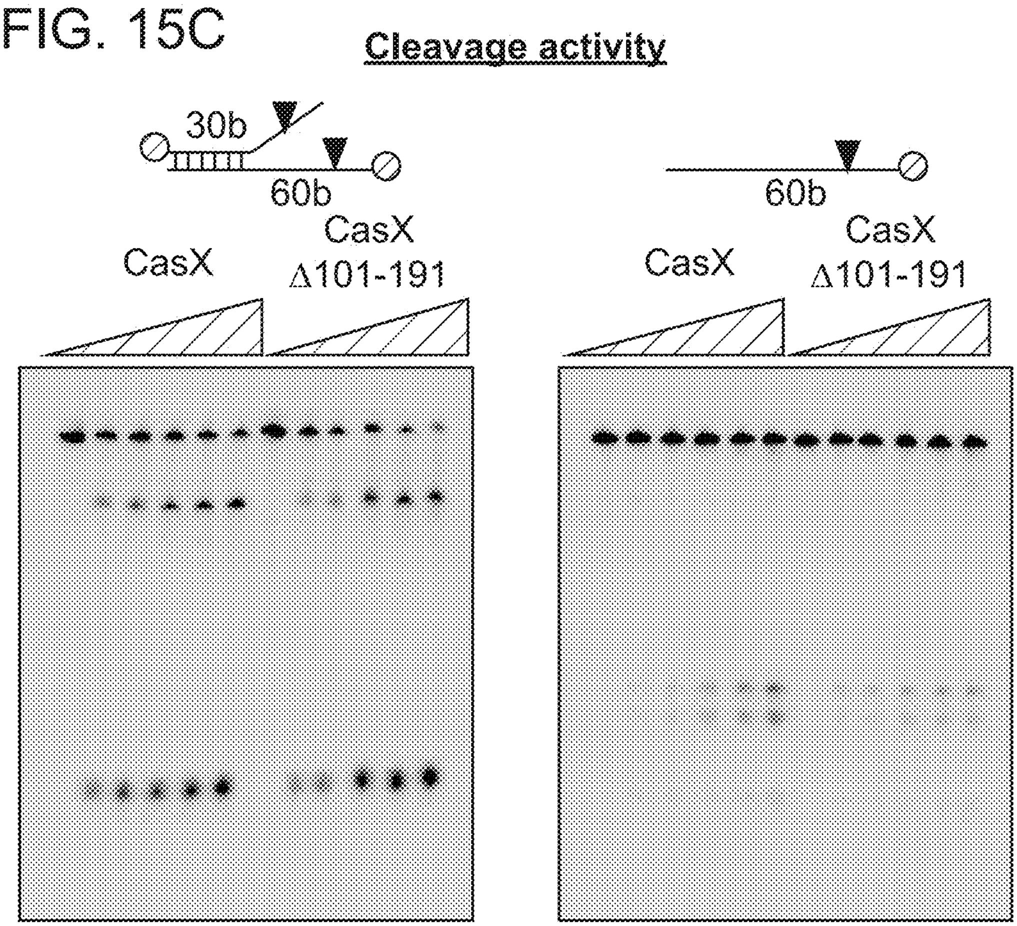

FIG. 15A-15C. CasX ΔNTSBD purification and substrate cleavage. a, The representative S200 size exclusion traces by UV280 absorbance for wt CasX and for CasX with NTSB domain truncation. SDS-PAGE of wt CasX protein and CasX protein with NTSB domain truncation by Coomassie brilliant blue staining is shown on the up-right panel. b, Comparison of the cleavage activities of wt CasX and CasX with NTSB domain truncation on an unwound probe (only the PAM region is base-paired, the rest of the probe is mismatched) and on just a single target DNA strand.

FIG. 7A-7D. Schematic of CasX indicating the sites of mutation in the TSLD. A) Schematic of CasX indicating sites of mutation in the TSLD. B) *E. coli* CRISPRi assays examining the ability of the CasX proteins that completely lacked the TSLD (delta TSLD) to bind and repress GFP. All proteins tested with the nuclease deficient or dead variants. Proteins comprising a deletion of the entire domain do not seem to function in DNA binding likely to enzyme destabilization. (+) Indicates a targeting guide (−) indicates a non-targeting negative control. C) *E. coli* CRISPRi assays examining the ability of the subsection TSLD replacements to repress GFP. The data demonstrates that subsection 2.1 & 2.2, as visualized in A, do not appear to function in DNA binding and repression of gene expression; however, 2.3 appears to function in both DNA binding and GFP repression. (+) Indicates a targeting guide (−) indicates a non-targeting negative control. D) *E. coli* genome cleavage assay using the CasX 2.3 deletion mutants with genome targeting guides and the active ("CasX-2.3") or triple nuclease dead ("dddCasX" and "dddCasX-2.3") versions of the constructs where reduction of CFU/mL indicates genomic cleavage activity. This assay indicates that while the 2.3 swap does bind DNA, it does not cleave both strands of the DNA and lead to cell death of *E. coli*; this is indicative of nicking activity when coupled with the purported function of this domain. All assays were done in biological triplicate, error bars represent S.D.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant CasX polypeptide comprising 85% or more identity to SEQ ID NO: 1 or 2, wherein amino acids 863-873 of SEQ ID NO: 1 or amino acids 850-860 of SEQ ID NO: 2 are replaced with a glycine polymer, a glycine-serine polymer, a glycine-alanine polymer, or an alanine-serine polymer, wherein the variant CasX polypeptide retains DNA binding activity and wherein the variant CasX polypeptide does not exhibit double-stranded DNA cleavage activity.

2. A method of binding, or binding and nicking, a target nucleic acid, the method comprising contacting the target nucleic acid with:

a) the variant CasX polypeptide of claim 1; and b) a CasX guide RNA comprising a guide sequence that hybridizes to a target sequence of the target nucleic acid.

3. A method of modulating transcription from a target DNA, modifying a target nucleic acid, or modifying a protein associated with a target nucleic acid, the method comprising contacting the target nucleic acid with:

a) a CasX fusion polypeptide comprising the variant CasX polypeptide of claim 1 fused to a heterologous polypeptide; and b) a CasX guide RNA comprising a guide sequence that hybridizes to a target sequence of the target nucleic acid.

4. A method of detecting a target single-stranded DNA in a sample, the method comprising:

(a) contacting the sample with:

(i) the variant CasX polypeptide of claim 1;

(ii) a guide RNA comprising: a region that binds to the variant CasX polypeptide, and a guide sequence that hybridizes with the target DNA; and (iii) a detector DNA that is single stranded and does not hybridize with the guide sequence of the guide RNA; and (b) measuring a detectable signal produced by cleavage of the single-stranded detector DNA by the variant CasX polypeptide, thereby detecting the target DNA.

5. The variant CasX polypeptide of claim 1, wherein amino acids 863-873 of SEQ ID NO:1 or amino acids 850-860 of SEQ ID NO:2 are replaced with the glycine-serine polymer.

6. The variant CasX polypeptide of claim 1, wherein amino acids 863-873 of SEQ ID NO:1 or amino acids 850-860 of SEQ ID NO:2 are replaced with GGSGGSGGSG (SEQ ID NO: 100).

7. A CasX fusion polypeptide comprising:

a) the variant CasX polypeptide of claim 1; and b) a heterologous polypeptide.

8. A method of binding, or binding and nicking, a target nucleic acid, the method comprising contacting the target nucleic acid with:

a) the fusion polypeptide of claim 7; and b) a CasX guide RNA comprising a guide sequence that hybridizes to a target sequence of the target nucleic acid.

9. The fusion polypeptide of claim 7, wherein the fusion polypeptide comprises one or more nuclear localization sequences (NLSs).

10. The fusion polypeptide of claim 7, wherein the heterologous polypeptide comprises a targeting polypeptide that provides for binding to a cell surface moiety on a target cell or target cell type.

11. The fusion polypeptide of claim 7, wherein the heterologous polypeptide exhibits an enzymatic activity that modifies target DNA.

12. The fusion polypeptide of claim 7, wherein the heterologous polypeptide exhibits one or more DNA-modifying enzymatic activities selected from: nuclease activity, methyltransferase activity, demethylase activity, deamination activity, depurination activity, integrase activity, transposase activity, and recombinase activity.

13. The fusion polypeptide of claim 7, wherein the heterologous polypeptide exhibits an enzymatic activity that modifies a histone associated with a target nucleic acid.

14. The fusion polypeptide of claim 7, wherein the heterologous polypeptide comprises a protein that increases or decreases transcription.

15. A nucleic acid comprising a nucleotide sequence encoding a variant CasX polypeptide comprising 85% or more identity to SEQ ID NO: 1 or 2, wherein amino acids 863-873 of SEQ ID NO: 1 or amino acids 850-860 of SEQ ID NO: 2 are replaced with a glycine polymer, a glycine-serine polymer, a glycine-alanine polymer, or an alanine-serine polymer, wherein the variant CasX polypeptide retains DNA binding activity and wherein the variant CasX polypeptide does not exhibit double-stranded DNA cleavage activity.

16. A recombinant expression vector comprising the nucleic acid of claim 15.

17. An in vitro cell comprising the nucleic acid of claim 15.

18. The cell of claim 17, wherein the cell is a eukaryotic cell.

19. The nucleic acid of claim 15, further comprising a nucleotide sequence encoding a CasX guide RNA.

20. A nucleic acid comprising a nucleotide sequence encoding a CasX fusion polypeptide, the CasX fusion polypeptide comprising:

a) a variant CasX polypeptide comprising 85% or more identity to SEQ ID NO: 1 or 2, wherein amino acids 863-873 of SEQ ID NO: 1 or amino acids 850-860 of SEQ ID NO: 2 are replaced with a glycine polymer, a glycine-serine polymer, a glycine-alanine polymer, or an alanine-serine polymer, wherein the variant CasX polypeptide retains DNA binding activity and wherein the variant CasX polypeptide does not exhibit double-stranded DNA cleavage activity; and b) a heterologous polypeptide.

21. The nucleic acid of claim 20, further comprising a nucleotide sequence encoding a CasX guide RNA.

22. A composition comprising:

a) the variant CasX polypeptide of claim 1, or the nucleic acid of claim 15; and b) a CasX guide RNA, or one or more DNA molecules comprising a nucleotide sequence encoding the CasX guide RNA.

23. A composition comprising:

a) the fusion polypeptide of claim 7, or the nucleic acid of claim 20; and b) a CasX guide RNA, or one or more DNA molecules comprising a nucleotide sequence encoding the CasX guide RNA.

* * * * *